United States Patent
Aliferis et al.

(10) Patent No.: US 12,325,879 B2
(45) Date of Patent: Jun. 10, 2025

(54) METHODS FOR PREDICTING A RESPONSE TO BEVACIZUMAB OR PLATINUM-BASED CHEMOTHERAPY OR BOTH IN PATIENTS WITH OVARIAN CANCER

(71) Applicant: REGENTS OF THE UNIVERSITY OF MINNESOTA, Minneapolis, MN (US)

(72) Inventors: Konstantinos Aliferis, Minneapolis, MN (US); Boris Jan Nils Winterhoff, Minneapolis, MN (US); Sisi Ma, Minneapolis, MN (US); Jinhua Wang, Edina, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 1017 days.

(21) Appl. No.: 17/290,172

(22) PCT Filed: Oct. 31, 2019

(86) PCT No.: PCT/US2019/059218
§ 371 (c)(1),
(2) Date: Apr. 29, 2021

(87) PCT Pub. No.: WO2020/092808
PCT Pub. Date: May 7, 2020

(65) Prior Publication Data
US 2022/0017965 A1    Jan. 20, 2022

Related U.S. Application Data

(60) Provisional application No. 62/753,274, filed on Oct. 31, 2018.

(51) Int. Cl.
*C12Q 1/6886* (2018.01)
*G16H 10/40* (2018.01)
*G16H 20/10* (2018.01)
*G16H 50/30* (2018.01)

(52) U.S. Cl.
CPC ........... *C12Q 1/6886* (2013.01); *G16H 10/40* (2018.01); *G16H 20/10* (2018.01); *G16H 50/30* (2018.01); *C12Q 2600/118* (2013.01); *C12Q 2600/158* (2013.01)

(58) Field of Classification Search
CPC ........... C12Q 1/6886; C12Q 2600/118; C12Q 2600/158; G16H 10/40; G16H 20/10; G16H 50/30; G01N 33/57449
See application file for complete search history.

(56) References Cited

U.S. PATENT DOCUMENTS

| 8,655,821 | B2 | 2/2014 | Aliferis et al. |
| 8,725,426 | B2 | 5/2014 | Shak et al. |
| 8,805,761 | B2 | 8/2014 | Statnikov et al. |
| 8,868,352 | B2 | 10/2014 | Baker et al. |
| 10,181,018 | B2 | 1/2019 | Shak et al. |
| 2010/0292303 | A1 | 11/2010 | Birrer et al. |
| 2017/0253933 | A1 | 9/2017 | Wang |

FOREIGN PATENT DOCUMENTS

| EP | 3 874 274 B1 | 1/2024 | |
| WO | WO 2015/109234 A1 | 7/2015 | |
| WO | WO 2015/118353 | * 8/2015 | ............ A61P 35/00 |
| WO | WO 2015/118353 A1 | 8/2015 | |
| WO | WO 2020/092808 A1 | 5/2020 | |

OTHER PUBLICATIONS

Wang et al. (Onco Targets and Therapy, 11: 4001-4017, 2018).*
International Patent Application No. PCT/US2019/059218, filed Oct. 31, 2019; International Search Report and Written Opinion issued Apr. 2, 2020; 15 pages.
International Patent Application No. PCT/US2019/059218, filed Oct. 31, 2019; International Preliminary Report on Patentability issued May 14, 2021; 11 pages.
Aliferis et al., Local Causal and Markov Blanket Induction for Causal Discovery and Feature Selection for Classification, Part I: Algorithms and Empirical Evaluation, Journal of Machine Learning Research. 11 (2010) 171-234.
Aliferis et al., Local Causal and Markov Blanket Induction for Causal Discovery and Feature Selection for Classification, Part II: Analysis and Extensions, Journal of Machine Learning Research. 11 (2010) 234-84.
Boser et al., A Training Algorithm for Optimal Margin Classifiers. *Proceedings of the 5th Annual Workshop on Computational Learning Theory* (COLT'92), Pittsburgh, Jul. 27-29, 1992, 144-152.
Clark et al., Survival analysis part I: basic concepts and first analyses. Br J Cancer 89, 232-238 (2003).
Efron, The Efficiency of Cox's Likelihood Function for Censored Data, Am Stat Assoc. 1977; 72(359):557-65.
Heitz et al., Dilution of Molecular-Pathologic Gene Signatures by Medically Associated Factors Might Prevent Prediction of Resection Status After Debulking Surgery in Patients With Advanced Ovarian Cancer. Clin Cancer Res 26, 213-219 (2020).
Kommoss et al., Bevacizumab May Differentially Improve Ovarian Cancer Outcome in Patients with Proliferative and Mesenchymal Molecular Subtypes. Clin Cancer Res 23, 3794-3801 (2017).

(Continued)

*Primary Examiner* — Nelson B Moseley, II
(74) *Attorney, Agent, or Firm* — Mueting Raasch Group

(57) ABSTRACT

This disclosure describes methods of predicting the response of a patient with ovarian cancer to platinum-based chemotherapy and/or treatment with bevacizumab using clinical and molecular tumor characteristics in patients, methods of treating patients with ovarian cancer, and kits for performing all or part of the methods described herein. This disclosure also describes methods that include determining a prediction of an outcome for a patient having ovarian cancer based on one or more signatures and patient test data comprising clinical data, gene expression data, or both.

18 Claims, 4 Drawing Sheets

(56) References Cited

OTHER PUBLICATIONS

Konecny et al., Prognostic and therapeutic relevance of molecular subtypes in high-grade serous ovarian cancer. J Natl Cancer Inst 106, (2014).

Mok et al., A gene signature predictive for outcome in advanced ovarian cancer identifies a survival factor: microfibril-associated glycoprotein 2. Cancer Cell 16, 521-532 (2009).

Oken et al., Toxicity and response criteria of the Eastern Cooperative Oncology Group. Am J Clin Oncol 5, 649-655 (1982).

Perren et al., A phase 3 trial of bevacizumab in ovarian cancer. N Engl J Med 365, 2484-2496 (2011).

Spivey et al., A prognostic gene signature in advanced ovarian cancer reveals a microfibril-associated protein (MAGP2) as a promoter of tumor cell survival and angiogenesis. Cell Adh Migr 4, 169-171 (2010).

Statnikov et al., Analysis and computational dissection of molecular signature multiplicity. PLoS Comput Biol 6, e1000790 (2010).

Statnikov et al., Algorithms for Discovery of Multiple Markov Boundaries. J Mach Learn Res 14, 499-566 (2013).

Statnikov et al., *A Gentle Introduction to Support Vector Machines in Biomedicine: Theory and Methods;* vol. 1. World Scientific Pub. Co. 2011; Title Page, Publisher's Page, and Table of Contents.

Statnikov et al., *A Gentle Introduction to Support Vector Machines in Biomedicine: Case Studies and Benchmarks;* vol. 2. World Scientific Pub. Co. 2013; Title Page, Publisher's Page, and Table of Contents.

Tothill et al., Novel molecular subtypes of serous and endometrioid ovarian cancer linked to clinical outcome. Clin Cancer Res 14, 5198-5208 (2008).

Vapnik, *The Nature of Statistical Learning Theory.* Springer-Verlag, New York; 2000. 168 pages.

Verhaak et al., Prognostically relevant gene signatures of high-grade serous ovarian carcinoma. J Clin Invest 123, 517-525 (2013).

Winterhoff et al., Molecular classification of high grade endometrioid and clear cell ovarian cancer using TCGA gene expression signatures. Gynecol Oncol 141, 95-100 (2016).

Winterhoff et al., Developing a Clinico-Molecular Test for Individualized Treatment of Ovarian Cancer: The interplay of Precision Medicine Informatics with Clinical and Health Economics Dimensions. AMIA Annu Symp Proc 2018, 1093-1102 (2018).

* cited by examiner

METHODS FOR PREDICTING A RESPONSE TO BEVACIZUMAB OR PLATINUM-BASED CHEMOTHERAPY OR BOTH IN PATIENTS WITH OVARIAN CANCER

CONTINUING APPLICATION DATA

This application is the § 371 U.S. National Stage of International Application No. PCT/US2019/059218, filed Oct. 31, 2019, which claims priority to U.S. Provisional Patent Application No. 62/753,274 filed Oct. 31, 2018, each of which is incorporated herein by reference in its entirety.

GOVERNMENT FUNDING

This invention was made with government support under CA077598 and TR002494 awarded by the National Institutes of Health. The government has certain rights in the invention.

BACKGROUND

Epithelial ovarian cancer has the highest mortality rate of all gynecologic cancers with most patients diagnosed with stage III or IV disease. Additionally, up to one-third of patients will not respond to standard initial treatment including cytoreductive surgery and platinum-based chemotherapy. Although significant improvements in median progression-free survival (PFS) have been observed when bevacizumab was added to standard therapy, a subgroup of patients do not benefit from the treatment.

SUMMARY OF THE INVENTION

This disclosure describes methods of predicting the response of a patient with ovarian cancer to platinum-based chemotherapy and/or treatment with a monoclonal antibody against VEGF-A, bevacizumab (also referred to by the brand name AVASTIN), using clinical and molecular tumor characteristics in patients. This disclosure further provides methods of treating patients with ovarian cancer based on those predictions.

In one aspect, this disclosure describes a method for treating a patient suffering from ovarian cancer following removal of a tumor. In some embodiments, the method includes determining whether the patient is predicted to benefit from the administration of bevacizumab and, if the patient is predicted to benefit from the administration of bevacizumab, administering bevacizumab. Determining whether the patient is predicted to benefit from the administration of bevacizumab may include determining whether the patient is predicted to benefit from the administration of bevacizumab in addition to the administration of platinum-based chemotherapy.

Determining whether the patient is predicted to benefit from the administration of bevacizumab may include determining the patient's gene expression level of microfibril associated protein 2 (MFAP2) and determining the patient's gene expression level of vascular endothelial growth factor A (VEGFA). Determining whether the patient is predicted to benefit from the administration of bevacizumab may further include at least one of determining the patient's International Federation of Gynecology and Obstetrics (FIGO) stage; determining the patient's Eastern Cooperative Oncology Group (ECOG) performance status; and determining the size of the tumor tissue remaining post-removal of the tumor.

In another aspect, this disclosure describes a method for treating a patient suffering from ovarian cancer following removal of a tumor, the method comprising determining whether the patient is predicted to benefit from the administration of a platinum-based chemotherapy and, if the patient is predicted to benefit from the administration of platinum-based chemotherapy, administering platinum-based chemotherapy.

In some embodiments, determining whether the patient is predicted to respond to the administration a platinum-based chemotherapy includes determining the patient's gene expression level of microfibril associated protein 2 (MFAP2); determining the patient's International Federation of Gynecology and Obstetrics (FIGO) stage; determining the patient's Eastern Cooperative Oncology Group (ECOG) performance status; and determining the size of the tumor tissue remaining post-removal of the tumor. In some embodiments, determining whether the patient is predicted to benefit from the administration of a platinum-based chemotherapy further includes determining the patient's gene expression level of vascular endothelial growth factor A (VEGFA).

In a further aspect, this disclosure describes a method that includes identifying a patient with ovarian cancer, and determining the patient's gene expression levels of microfibril associated protein 2 (MFAP2) and vascular endothelial growth factor A (VEGFA) in a biological sample containing cancer cells obtained from the patient, determining the patient's International Federation of Gynecology and Obstetrics (FIGO) stage, determining the patient's Eastern Cooperative Oncology Group (ECOG) performance status, determining the size of the tumor tissue remaining post-removal of a tumor, and calculating a patient risk score for the patient.

In another aspect, this disclosure describes a method for predicting the response of a patient with ovarian cancer to treatment with bevacizumab. In some embodiments, the method includes: determining gene expression levels of VEGFA and MFAP2; calculating a FIGO numeric score, wherein the FIGO stage is coded as an integer; calculating a surgical outcome score, wherein the score is −1 if the surgical outcome was suboptimal; 0 if the surgical outcome was optimal but tumor tissue smaller than 1 cm remained; or +1 if the surgical outcome was optimal and no visible macroscopic tumor tissue remained; calculating an ECOG score of 0 to 2, based on ECOG performance status; and applying the expression levels, FIGO numeric score, surgical outcome score, and ECOG score to a predictive model that relates the variables with progression-free survival of ovarian cancer; and evaluating an output of the predictive model to predict progression-free survival of the patient.

In yet another aspect, this disclosure describes a method for predicting the response of a patient with ovarian cancer to treatment with bevacizumab wherein the method includes determining gene expression levels of a collection of genes taken from a biological sample of the patient, applying the expression levels to a predictive model that relates the expression levels of the collection of genes the likelihood of progression-free survival of the patient; and evaluating an output of the predictive model to predict the likelihood of progression-free survival of the patient. In some embodiments, the collection of genes comprises at least 80%, at least 90%, at least 95%, at least 98%, or 100% of the genes of any one of Tables 9-12 In some embodiments, the collection of genes comprises the genes of any one of Tables 9-12. In some embodiments, the method further includes applying at least one of FIGO stage, surgical outcome, ECOG score, and tumor histology to the predictive model.

In a further aspect, this disclosure provides a method for predicting progression-free survival of a patient with ovarian cancer. In some embodiment the method includes determining gene expression levels of a collection of genes taken from a biological sample of the patient, applying the expression levels to a predictive model that relates the expression levels of the collection of genes with progression-free survival of ovarian cancer; and evaluating an output of the predictive model to predict progression-free survival of the patient.

In some embodiments, the collection of genes includes at least 80%, at least 90%, at least 95%, at least 98%, or 100% of the genes of any one of Tables 6, 7, or 13-68. In some embodiments, the collection of genes includes the genes of any one of Tables 6, 7, or 13-68. In some embodiments, the method further includes applying at least one of FIGO stage, surgical outcome, ECOG score, and tumor histology to the predictive model.

In an additional aspect, this disclosure describes a method for predicting an outcome for a patient, the method including: receiving an identified set of biomarkers determined based on a set of predetermined data comprising clinical data, gene expression data, or both; identifying other sets of biomarkers based on the identified set of biomarkers and remaining data comprising the set of predetermined data excluding the identified set of biomarkers; generating a signature for each set of biomarkers to predict an outcome for a patient having ovarian cancer; and determining a prediction of an outcome for a patient having ovarian cancer based on one or more signatures and patient test data comprising clinical data, gene expression data, or both.

As used herein, the term "ovarian cancer" is used in the broadest sense and refers to all stages and all forms of cancer arising from the ovary.

As used herein, the term "signature" refers to a computational or mathematical model including a set of variables and corresponding coefficients. The variables may include clinical variables or molecular variables (for example, gene expression) or both. A signature may be used to evaluate patient test data.

As used herein, the term "ensemble" refers to a collection of or catalogue of signatures.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (for example, 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

All headings are for the convenience of the reader and should not be used to limit the meaning of the text that follows the heading, unless so specified.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

BRIEF DESCRIPTION OF THE FIGURES

FIG. 4A identifies a "clear benefit" group that should receive bevacizumab; a "no benefit" group; and an intermediate group with "minor/questionable benefit" from bevacizumab. FIG. 4B shows a strategy that combines the "no benefit" and "minor/questionable benefit" subgroups of FIG. 4A.

DETAILED DESCRIPTION OF ILLUSTRATIVE EMBODIMENTS

Figure 1:
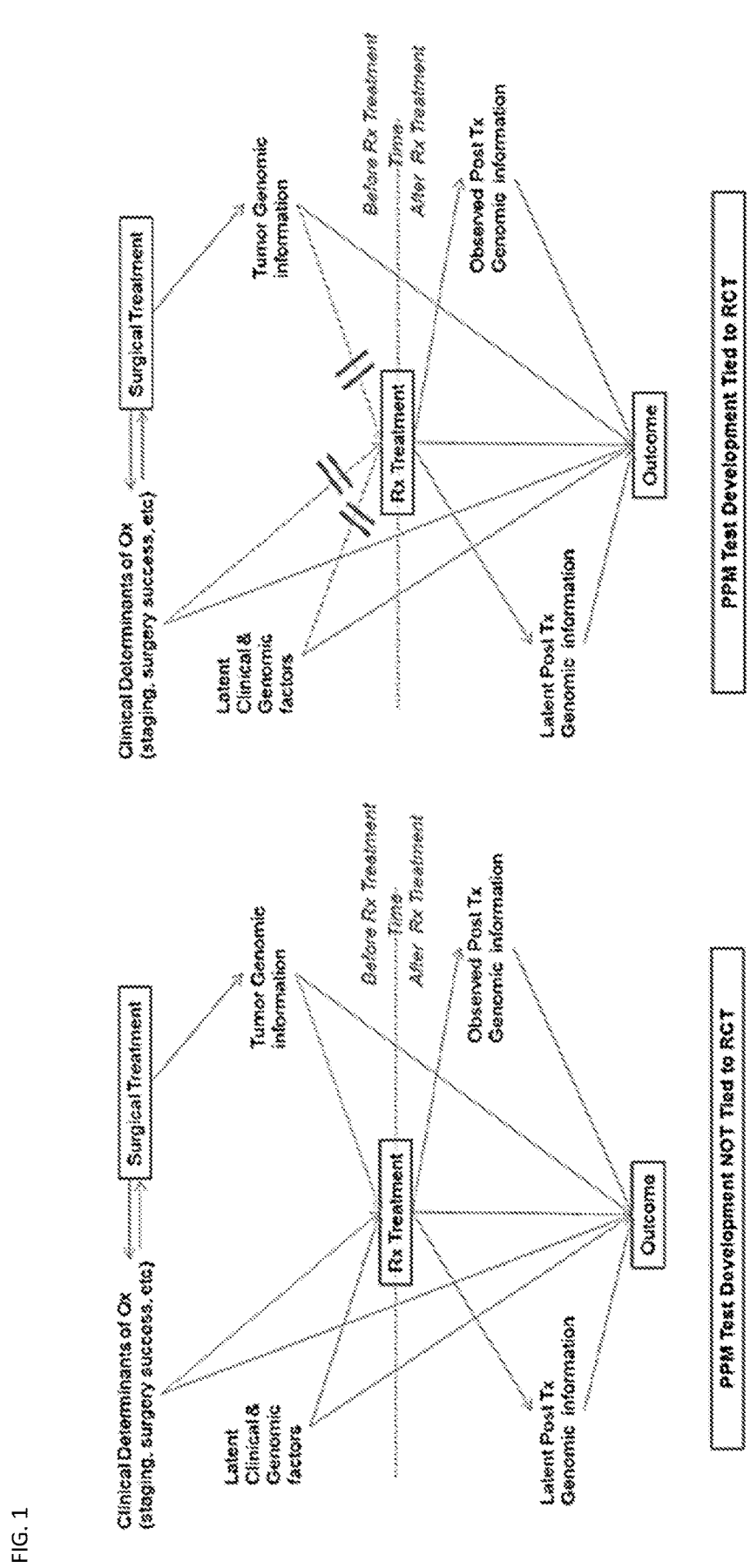
FIG. 1 shows the methodological benefits (for example, computational modeling advantages) of tying development of precision medicine tests to randomized clinical trials (RCTs).

In one aspect, this disclosure describes methods of determining whether a patient with ovarian cancer is predicted to benefit from platinum-based chemotherapy and/or administration of bevacizumab. The prediction may be based on the patient's clinical characteristics or molecular tumor characteristics or both. In another aspect, this disclosure provides methods of treating patients with ovarian cancer. In some embodiments, the patients may be treated based on the predictions. In another aspect, this disclosure describes a method of determining a risk score for a patient with ovarian cancer. In an additional aspect, this disclosure describes predicting progression-free survival of a patient with ovarian cancer. In a further aspect, this disclosure describes an apparatus, a system, and a kit for performing all or part of the methods described herein.

Need for and Benefit of a Predictive Test

Patients are considered platinum-refractory if they progress while on treatment or platinum-resistant if their disease recurs less than six months from completion of the initial platinum-based chemotherapy. Even in patients who have a complete initial response to chemotherapy, 80% will recur and eventually develop resistance to multiple drugs and die from drug-resistant disease. Efforts are ongoing to study novel, targeted agents, including bevacizumab, an antiangiogenic monoclonal antibody against vascular endothelial growth factor (VEGF). Two phase III frontline trials in ovarian cancer (ICON? and GOG 218) showed statistically significant improvements in median progression-free survival (PFS) of 2.3 and 3.8 months, respectively, when bevacizumab was added to standard first-line chemotherapy (Kommoss et al. *Clin Cancer Res Off J Am Assoc Cancer Res.* 2017; 23(14):3794-801; Perren et al. *N Engl J Med.* 2011; 365(26):2484-96.) A subgroup of patients benefits significantly whereas the majority benefit moderately or do not benefit. The problem is further compounded by the high cost of bevacizumab which is currently $400,000 per progression-free life saved in the USA, thus making treatment of all patients economically infeasible. Moreover, the patients who can afford the drug are not necessarily the ones who will benefit from it. These problems underscore the pressing clinical need for more individualized treatment strategies.

At the time of the invention, gene expression analysis of ovarian cancers performed in The Cancer Genome Atlas (TCGA) had led to a molecular classification of ovarian cancer into four subtypes (Tothill et al. *Clin Cancer Res Off J Am Assoc Cancer Res.* 2008; 14(16):5198-208; Konecny et al. *J Natl Cancer Inst.* 2014; 106(10):dju249; Winterhoff et al. *Gynecol Oncol.* 2016; 141(1):95-100.) These four subgroups have some prognostic significance. (Winterhoff et al. *Gynecol Oncol.* 2016; 141(1):95-100; Konecny et al. *J Natl Cancer Inst.* 2014; 106(10):dju249.) Although differential response to bevacizumab and platinum-based chemotherapy within those four molecular subtypes had been demonstrated using formalin-fixed paraffin-embedded (FFPE) tumor samples (Kommoss et al. *Clin Cancer Res Off J Am Assoc Cancer Res.* 2017; 23(14):3794-801), development and statistical validation of a clinico-molecular stratification model with sufficient accuracy was needed to allow these observations to be clinically actionable. Development of such a model is described in the present disclosure (Example 1).

The potential for health economic impact of a precision test based on the predictivity of the models and corresponding clinical strategies described herein is enormous. For example, if only patients who were predicted to strongly benefit from treatment with bevacizumab were treated instead of all patients, up to $90 billion in savings globally could be realized over 10 years. Moreover, the methods described herein may identify patients who will not benefit from either conventional or bevacizumab treatment, allowing them to be routed to alternative experimental treatments, providing additional survival and economic benefits.

Determining Gene Expression Levels

In some embodiments, the methods described herein include determining a gene expression level of a patient.

In some embodiments, a gene expression level may be measured using a standard biochemical technique and/or assay and may be converted to a quantitative gene expression level using an appropriate value transformation for that technology. In some embodiments, the gene expression level may be used as an input in a model, as described herein.

In some embodiments, the gene includes microfibril associated protein 2 (MFAP2) or vascular endothelial growth factor A (VEGFA) or both.

In some embodiments, determining a gene expression level of a patient includes determining the gene expression level of a collection of genes taken from a biological sample of the patient.

In some embodiments, the collection of genes includes the genes of any one of Tables 6, 7, or 9-68. In some embodiments, some of the genes of a table may be excluded from the collection of genes at the cost of some reduction in predictive performance. In some embodiments, the collection of genes includes at least two genes, at least 14 genes, at least 18 genes, at least 20 genes, or at least 30 genes selected from the genes of any one of Tables 6, 7, or 9-68. In some embodiments, the collection of genes includes at least 50%, at least 60%, at least 70%, at least 80%, at least 90%, at least 95%, at least 98%, or 100% of the genes of any one of Tables 6, 7, or 9-68.

In some embodiments, the collection of genes of any one of Tables 6, 7, or 9-68 may be selected by excluding only those genes of that table that do not significantly affect predictivity.

In some embodiments, the collection of genes may be selected by optimizing predictivity with a constraint or a set of constraints. A constraint may include, for example, cost or user convenience.

In some embodiments, determining a gene expression level includes assessing the amount (for example, absolute amount, relative amount, or concentration) of a gene product in a sample. A gene product may include, for example, a protein or RNA transcript encoded by the gene, or a fragment of the protein or RNA transcript. In some embodiments, determining a gene expression level includes receiving the results of such an assessment. In some embodiments, determining a gene expression level includes converting the results of such an assessment to a quantitative gene expression level.

A sample may include a biological sample of the patient. In some embodiments, the sample may be a biological sample containing cancer cells. For example, the sample may include a tissue sample obtained by biopsy of a patient, a bodily fluid (for example, blood, plasma, serum, urine, etc.), a cell that is the progeny of a patient's tumor cell, or a sample enriched for tumor cells.

The sample may be subjected to a variety of well-known post-collection preparative and storage techniques (for example, fixation, storage, freezing, lysis, homogenization, DNA or RNA extraction, ultrafiltration, concentration, evaporation, centrifugation, etc.) prior to assessing the gene expression level in the sample.

The amount of the gene product may be assessed by any suitable method known to a person having skill in the art. For example, gene expression may be identified using sequencing, quantitative RT-PCR, microarray analysis, and/ or immunohistochemistry as described in, for example, U.S. Pat. No. 8,725,426 and WO 2015/109234. Standard assay normalization methods and batch effect correction methods suitable to each type of assay may also be employed.

In some embodiments, the method includes normalizing the gene expression levels including, for example, normalizing the level of the RNA transcripts to obtain normalized gene expression levels.

International Federation of Gynecology and Obstetrics (FIGO) Stage

In some embodiments, the methods of this disclosure include determining a patient's International Federation of Gynecology and Obstetrics (FIGO) stage, as described at, for example, www.cancer.org/cancer/ovarian-cancer/detection-diagnosis-staging/staging.html. In some embodiments, the FIGO stage may be coded as an integer for the purposes of calculating a risk score for a patient. For example, FIGO stage IA=1, FIGO stage IB=2, FIGO stage IC=3, FIGO stage IIA=4, FIGO stage IIB=5, FIGO stage IIC=5, FIGO stage IIIA=7, FIGO stage IIIB=8, FIGO stage IIIC=9, and FIGO stage IV=10.

Eastern Cooperative Oncology Group (ECOG) Performance Status

In some embodiments, the methods of this disclosure include determining a patient's Eastern Cooperative Oncology Group (ECOG) performance status. Oken et al. *Am J Clin Oncol.* 1982; 5:649-655. A patient has an ECOG performance status of 0 if the patient is fully active and able to carry on all pre-disease performance without restriction. A patient has an ECOG performance status of 1 if the patient is restricted in physically strenuous activity but ambulatory and able to carry out work of a light or sedentary nature including, for example, light house work, office work, etc. A patient has an ECOG performance status of 2 if the patient is ambulatory and capable of all selfcare but unable to carry out any work activities and is up and about more than 50% of waking hours. A patient has an ECOG performance status of 3 if the patient is capable of only limited selfcare; confined to bed or chair more than 50% of waking hours. A patient has an ECOG performance status of 4 if the patient is completely disabled.

Removal of the Tumor and Size of the Tumor Tissue

In some embodiments, the methods of this disclosure include treating a patient after removal of a tumor by surgery. In some embodiments, the methods of this disclosure include determining the size of a patient's tumor after removal of the tumor.

Removal of the ovarian cancer (including, for example, the tumor) by surgery may include any surgical method undertaken for the removal of cancerous surgery including, for example, hysterectomy, oophorectomy, salpingo-oophorectomy, omentectomy, and/or removal of any visible cancer within the abdomen including, for example, resection of bowel, parts of the liver spleen, a lymph node, diaphragm, parts of the stomach and or pancreas, gallbladder, and any other involved tissue or organ.

In some embodiments, the tumor may be a primary tumor (for example, from the ovary, fallopian tube or primary peritoneum). In some embodiments, the tumor may be a secondary tumor (for example, a metastatic tumor from a different organ to the ovary and or fallopian tube).

In some embodiments, a patient may be characterized based on whether the surgical outcome was suboptimal (that is, tumor tissue greater than 1 centimeter (cm) remained); the surgical outcome was optimal (that is, no tumor tissue greater than 1 cm remained) but tumor tissue smaller than 1 cm remained; or the surgical outcome was optimal and no visible macroscopic tumor tissue remained. In some embodiments, the patient's surgical outcome may be converted to a score (surg_outcome), where surg_outcome is −1 if the surgical outcome was suboptimal; surg_outcome is 0 if the surgical outcome was optimal but tumor tissue smaller than 1 cm remained; and surg_outcome is +1 if the surgical outcome was optimal and no visible macroscopic tumor tissue remained.

Tumor Histology

In some embodiments, a patient may be characterized based on the histology of the tumor as determined by a pathologist. For example, microscopic examination of tumor tissue by a pathologist may be used to determine whether a patient has a serous borderline ovarian tumor (hist_rev_SBOT) or a metastatic tumor (hist_rev_metastais). If the patient is found to have a tumor (for example, either a serous borderline ovarian tumor or a metastatic tumor), the patient may be assigned a value: 1; if a tumor is present, 0 if a tumor is not present.

Platinum-Based Chemotherapy and Administration of Platinum-Based Chemotherapy

In some embodiments, the methods described herein include determining whether a patient is predicted to benefit from the administration of platinum-based chemotherapy. In some embodiments, the methods described herein include administering platinum-based chemotherapy. In some embodiments, the methods described herein include administering platinum-based chemotherapy if a patient is predicted to benefit from the administration of platinum-based chemotherapy. In some embodiments, the methods described herein include administering platinum-based chemotherapy in combination with bevacizumab.

Platinum-based chemotherapy may include any suitable platinum-based chemotherapy. Platinum-based chemotherapy may include, for example, one or more of cisplatin, carboplatin, oxaliplatin, nedaplatin, lobaplatin, heptaplatin, triplatin tetranitrate, phenanthriplatin, picoplatin, and satraplatin.

Platinum-based chemotherapy may be administered by any suitable method. The selected dosage level will depend upon a variety of factors including the activity of the particular compound of the present disclosure employed, the route of administration, the time of administration, the rate of excretion of the particular compound being employed, the duration of the treatment, other drugs, compounds and/or materials used in combination with the chemotherapy, the age, sex, weight, condition, general health and prior medical history of the subject being treated, and like factors well known in the medical arts.

Bevacizumab and Administration of Bevacizumab

In some embodiments, the methods described herein include determining whether a patient is predicted to benefit from the administration of bevacizumab. In some embodiments, the methods described herein include administering bevacizumab. In some embodiments, the methods described herein include administering bevacizumab if a patient is predicted to benefit from the administration of bevacizumab. In some embodiments, the methods described herein include administering bevacizumab in combination with platinum-based chemotherapy. In some embodiments, the methods described herein include administering bevacizumab in combination with platinum-based chemotherapy if a patient is predicted to benefit from the administration of bevacizumab in combination with platinum-based chemotherapy.

In some embodiments, determining whether a patient is predicted to benefit from the administration of bevacizumab may include using one or more of the sets of variables enumerated in Tables 9-12. In some embodiments, a set of variables (that is the set of genes and other biomarkers) as enumerated in one of Tables 9-12 may be used in combination with the corresponding coefficients described in those tables. In some embodiments, a set of variables (as enumerated in one of Tables 9-12 may be used in combination with alternative coefficients including, for example, coefficients obtained using a fitting protocol and classifier as described herein.

In some embodiments, determining whether a patient is predicted to benefit from the administration of bevacizumab may include using one or more of the sets of genes enumerated in Tables 9-12. In some embodiments, a set of gene as enumerated in one of Tables 9-12 may be used in combination with the corresponding coefficients described in those tables. In some embodiments, a set of genes of one of Tables 9-12 may be used in combination with alternative coefficients including, for example, coefficients obtained using a fitting protocol and classifier as described herein.

In some embodiments, determining whether a patient is predicted to benefit from the administration of bevacizumab may include using one or more of the sets of genes enumerated in Tables 9-12.

Bevacizumab may be administered by any suitable method. The selected dosage level will depend upon a variety of factors including the activity of the particular compound employed, the route of administration, the time of administration, the rate of excretion of bevacizumab, the rate of metabolism of bevacizumab, the duration of the treatment, other drugs, compounds and/or materials used in combination with bevacizumab, the age, sex, weight, condition, general health and prior medical history of the subject being treated, and like factors well known in the medical arts.

Predictive Model

In some embodiments, a method described herein includes determining if a patient is predicted to benefit from the administration of bevacizumab, including the administration of bevacizumab in combination with platinum-based chemotherapy. In some embodiments, a method described herein includes determining if a patient is predicted to benefit from the administration of a platinum-based chemotherapy (for example, a platinum-based chemotherapy with bevacizumab or a platinum-based chemotherapy without bevacizumab). In some embodiments, the method may include determining if a patient is predicted to benefit from the administration of bevacizumab in combination with the administration of platinum-based chemotherapy. In some embodiments, the method may include predicting progression-free survival of the patient or the difference in progression-free survival of the patient depending on which therapy is administered.

In some embodiments, the method includes determining the patient's gene expression level of microfibril associated protein 2 (MFAP2); and/or determining the patient's gene expression level of vascular endothelial growth factor A (VEGFA). In some embodiments, the method may further include one or more of: determining the patient's International Federation of Gynecology and Obstetrics (FIGO) stage; determining the patient's Eastern Cooperative Oncology Group (ECOG) performance status; and determining the size of the tumor tissue remaining post-removal of the tumor.

In some embodiments, a threshold gene expression level of MFAP may be selected based on a clinical outcome (for example, a certain increase in progression free survival), and an expression level greater than that threshold expression may indicate an increased likelihood of benefit from the administration of bevacizumab, In some embodiments, a threshold gene expression level of VEGFA may be selected based on a clinical outcome (for example, a certain increase in progression free survival) and a gene expression level greater than that threshold expression may indicate a decreased likelihood of benefit from the administration of bevacizumab. In some embodiments, a FIGO stage greater than 1 may indicate a decreased likelihood of benefit from the administration of bevacizumab. In some embodiments, an ECOG performance status greater than 0 may indicate an increased likelihood of benefit from the administration of bevacizumab. In some embodiments, a tumor size smaller than 1 cm may indicate an increased likelihood of benefit from the administration of bevacizumab. In some embodiments, a threshold value of the combinations of the MFAP, VEGFA, FIGO stage and ECOG values may be selected based on a clinical outcome (for example, a certain increase in progression free survival) and a value of the combination greater than that threshold expression may indicate a decreased likelihood of benefit from the administration of bevacizumab.

In some embodiments, a threshold gene expression level of MFAP may by selected based on a clinical outcome (for example, a certain increase in progression free survival), and a gene expression level greater than that threshold gene expression level may indicate a decreased likelihood of benefit from the administration of platinum-based chemotherapy. In some embodiments, a threshold gene expression level of VEGFA may by selected based on a clinical outcome (for example, a certain increase in progression free survival) and an expression level greater than that threshold gene expression level may indicate an increased likelihood of benefit from the administration of platinum-based chemotherapy. In some embodiments, a FIGO stage greater than 1 may indicate a decreased likelihood of benefit from the administration of platinum-based chemotherapy. In some embodiments, an ECOG performance status greater than 0 may indicate a decreased likelihood of benefit from the administration of platinum-based chemotherapy. In some embodiments, a tumor size smaller than 1 cm may indicate an increased likelihood of benefit from the administration of platinum-based chemotherapy. In some embodiments, a threshold value of the combinations of the MFAP, VEGFA, FIGO stage and ECOG values may be selected based on a clinical outcome (for example, a certain increase in progression free survival) and a value of the combination greater than that threshold expression may indicate an increased likelihood of benefit from the administration of platinum-based chemotherapy.

In some embodiments, the method may include determining a patient's predicted progression-free survival. For example, the method may include determining if a patient's predicted progression-free survival time with the administration of a platinum-based chemotherapy and bevacizumab and/or determining the patient's predicted progression-free survival time with the administration of a platinum-based chemotherapy without bevacizumab. In some embodiments, the method may include comparing the patient's predicted progression-free survival time with the administration of a platinum-based chemotherapy and bevacizumab and the patient's predicted progression-free survival time with the administration of a platinum-based chemotherapy without bevacizumab.

In some embodiments, determining a patient's predicted progression-free survival may include using one or more of the sets of variables enumerated in Table 6, Table 7, or one or more of the sets of variables described in Example 6 (Tables 13-68). In some embodiments, a set of variables (that is the set of genes and other biomarkers) as enumerated in one of Tables 6, 7, or 13-68 may be used in combination with the corresponding coefficients described in those tables. In some embodiments, a set of variables (as enumerated in one of Tables 6, 7, or 13-68 may be used in combination with alternative coefficients including, for example, coefficients obtained using a fitting protocol and classifier as described herein.

In some embodiments, determining a patient's predicted progression-free survival may include using one or more of the sets of variables enumerated in Table 6, Table 7, or one or more of the sets of variables described in Example 6 (Tables 13-68). In some embodiments, a set of variables (that is the set of genes and other biomarkers) as enumerated in one of Tables 6, 7, or 13-68 may be used in combination with the corresponding coefficients described in those tables. In some embodiments, a set of variables (as enumerated in one of Tables 6, 7, or 13-68 may be used in combination with alternative coefficients including, for example, coefficients obtained using a fitting protocol and classifier as described herein.

In some embodiments, determining a patient's predicted progression-free survival may include using one or more of the sets of genes enumerated in Table 6, Table 7, or one or more of the sets of genes described in Example 6 (Tables 13-68). In some embodiments, a set of gene as enumerated in one of Tables 6, 7, or 13-68 may be used in combination with the corresponding coefficients described in those tables. In some embodiments, a set of genes of one of Tables 6, 7, or 13-68 may be used in combination with alternative coefficients including, for example, coefficients obtained using a fitting protocol and classifier as described herein.

In some embodiments, the method may include determining whether a patient's predicted increase in progression-free survival time with the administration of a platinum-based chemotherapy and bevacizumab compared to the patient's predicted progression-free survival time with the administration of a platinum-based chemotherapy without bevacizumab is clinically meaningful. In some embodiments, a "clinically meaningful" increase in progression-free survival time may be determined by the treating physician. In some embodiments, the method may include defining a benefit threshold.

In some embodiments, a patient may be predicted to benefit from the administration of bevacizumab if the patient's predicted increase in progression-free survival is at least 3 months, at least 4 months, at least 5 months, at least 6 months, at least 7 months, at least 8 months, at least 9 months, or at least 10 months.

In some embodiments, the method may include applying a model for modeling time-to-event outcomes (for example, progression-free survival). Any model suitable for modeling time-to-event outcomes may be used including, for example, a Cox model or an accelerated failure time model. In some embodiments, the method may include applying a model for modeling binary outcomes (for example, progression-free survival up to a certain time point). Any modeling procedure suitable for modeling binary outcomes may be used including, for example, a support vector machine model or another classification method appropriate for biomedical data classification. In some embodiments, the method may include applying Nested N-Fold Cross-Validation (NNFCV).

In some embodiments, the method may include calculating a patient risk score. For example, in some embodiments, a patient's risk score may be calculated as described in Example 3.

In some embodiments, the method may further include calculating a patient's risk of recurrence at time t. For example, in some embodiments, a patient's risk of recurrence at time t may be calculated as described in Example 3.

In some embodiments, a method may include applying a patient's gene expression level (or levels) to a predictive model that relates the expression level (or levels) with progression-free survival of ovarian cancer. In some embodiments, a method may include applying the expression levels of a collection of genes to a predictive model that relates the expression levels of that collection of genes with progression-free survival of ovarian cancer. Examples of such collections of genes are provided herein. In some embodiments, the method may further include determining, applying, or determining and applying one or more of: the patient's International Federation of Gynecology and Obstetrics (FIGO) stage; the patient's Eastern Cooperative Oncology Group (ECOG) performance status; the size of the tumor tissue remaining post-removal of the tumor; tumor histology indicating a serous borderline ovarian tumor (hist_rev_SBOT); and tumor histology indicating a metastatic tumor (hist_rev_metastasis).

In some embodiments, the method includes determining the expression level of a gene or a collection of genes multiple times.

In some embodiments, the method includes detecting an additional biomarker of progression-free survival of the patient. Such biomarkers may include, for example, a germline mutation, a somatic mutation, a DNA methylation marker, and/or a protein marker.

Predictive Ensemble Model

In some embodiments, methods for predicting an outcome for a patient include receiving an identified set of biomarkers determined based on a set of predetermined data including clinical data, gene expression data, or both; identifying other sets of biomarkers based on the identified set of biomarkers and remaining data includes the set of predetermined data excluding the identified set of biomarkers; generating a signature for each set of biomarkers to predict an outcome for a patient having ovarian cancer; and determining a prediction of an outcome for a patient having ovarian cancer based on one or more of the signatures and patient test data including clinical data, gene expression data, or both.

The identified set of biomarkers may be determined to have optimal predictivity. The identified set of biomarkers may also be determined to have non-redundancy and may be described as a "Markov Boundary" biomarker set.

In some embodiments, the outcome relates to progression-free survival for a patient with ovarian cancer. In other embodiments, the outcome relates to benefitting from the administration of bevacizumab, platinum-based chemotherapy, or both for a patient with ovarian cancer.

Any suitable identified set of biomarkers may be used. In some embodiments, the identified set of biomarkers is a member of an ensemble, which is described herein in more detail. In some embodiments, the signatures of the ensemble include some or all genes of any one of Table 6, Table 7, and Tables 9-68.

A TIE* algorithm (or other multiplicity discovery technique) may be used to identify the remaining Markov Boundary sets of biomarkers in the data other than the previously identified set of biomarkers. In some embodiments, identifying other sets of biomarkers includes feeding the previously identified set of biomarkers and remaining data into a TIE* algorithm to provide the other equivalent sets of biomarkers. In particular, the TIE* algorithm may provide equivalent sets of biomarkers to the previously identified set of biomarkers. Any other appropriate biomarker and signature multiplicity discovery technique may be used in place of the TIE* algorithm known to one skilled in the art having the benefit of this disclosure.

Any suitable instantiation of the TIE* algorithm (or algorithms with similar functionality) may be used. (Statnikov and Aliferis. *PLoS Computational Biology* 2010; 6(5), p. e1000790; U.S. Pat. No. 8,805,761; Aliferis et al. *Journal of Machine Learning Research* 2010; 11(January), pp. 171-234; Statnikov et al. *Journal of Machine Learning Research* 2013; 14(February), pp. 499-566; U.S. Pat. No. 8,655,821.)

In some embodiments, the TIE* algorithm systematically examines information equivalences in the "seed" biomarker set (and by extension to all corresponding optimal signatures) with variables in the remainder of the data (for example, full set of variables minus the seed). Replacement of a subset of the "seed" and execution of a subroutine may be performed to identify the Markov Boundary set of biomarkers in the remainder of the data (for example, running the subroutine once for each time a subset of the "seed" is excluded). The replacement of the subset of the "seed" and execution of the subroutine may be repeated recursively until all existing sets of biomarkers have been identified and output by the TIE* algorithm. As the TIE* algorithm, traverses the space of replacement subsets the remainder of the data shrinks. In some embodiments, the TIE* algorithm will terminate when no biomarker replacement can generate new equivalent biomarker sets.

In some embodiments, generating a signature for each set of biomarkers sets identified by TIE* (or other multiplicity algorithm) includes feeding each set of biomarkers into a machine learning classifier fitting and model "pipeline". The pipeline may incorporate model selection and error estimation. The pipeline may apply one or more of the following: a repeated nested n-fold cross validation with grid parameter choice, a support vector machine classifier, a random forest classifier, a lasso classifier, or any other suitable technique in the field of "omics" based classification by molecular signature construction. In some embodiments, the output of the TIE* algorithm provides a catalogue, or database, of biomarker sets.

Each set of biomarkers may be fed into a machine learning classifier fitting and model pipeline that typically incorporates model selection and error estimation. (Statnikov. A gentle introduction to support vector machines in biomedicine: Theory and methods; Vol. 1. World Scientific Pub. Co.; 2011; Statnikov et al. A Gentle Introduction to Support Vector Machines in Biomedicine: Volume 2: Case Studies and Benchmarks. World Scientific Pub. Co.; 2013.) One or more methods for deriving signatures, or models, from datasets may be used. In some embodiments, different models may be generated by the pipeline. In some embodiments, different models can be generated by a machine learning classifier fitting and model pipeline. In some embodiments, different models can have the same underlying sets of biomarkers but with different coefficients for each biomarker in the set. For example, a plurality of classifier models can be produced for each set of biomarkers, each having different coefficients. Although the models may have different coefficients, the models can be constructed so that they will have functional (input-output) equivalency. Further, coefficients in each model may be refit as new data is acquired.

Still further, coefficients may be tuned to a particular measuring platform used to generate the biomarker data, such as clinical or gene expression data. Different measuring platforms may require slightly different coefficients.

The output of the pipeline for each set of biomarkers, or each member of the equivalency catalogue, may be used as a signature for predicting patient outcomes, for example, in response to treatment. Typically, a signature does not include data used for its construction or validation. These signatures may be implemented as a companion test, or companion diagnostic, according to usual methods that combine: assaying of the biomarkers from tumor tissue specimens and processing of the generated measurements via fitting and application of classifiers to create clinical decision guidance and support that is delivered in clinical practice.

In some embodiments, the signatures are statistically indistinguishable from one another for a particular predictivity level. In some embodiments, each signature is a minimal (for example, non-reducible without degradation of predictivity) set of biomarkers for a particular predictivity level.

The catalogue of signatures may be described as an ensemble. In some embodiments, determining a prediction of an outcome for a patient having ovarian cancer is based on an ensemble prediction using a plurality of the signatures. The catalogue of signatures may be used to provide an ensemble prediction. Use of the ensemble prediction may reduce, or even minimize, the variance of prediction accuracy when compared to using single signatures.

In one example, the ensemble prediction may average outputs of each of the signatures. A prediction may be obtained from every signature in the catalogue, and the predictions may be averaged to obtain a consolidated ensemble prediction.

In another example, the ensemble prediction may use a plurality of the signatures based on available patient test data. A prediction may be obtained from only a select number of signatures in the catalogue, or ensemble, and the predictions may be averaged to obtain a consolidated ensemble prediction. The signatures may be selected based on availability. In some embodiments, one or a few signatures (for example, up to the full ensemble) may be used for prediction. Factors contributing to availability, or choice of signature to use, may include one or more of: convenience, cost, and ease of collection. The companion test may be personalized or customized for different patients by means of choice of members of the ensemble of signatures.

Testing Whether a Signature Belongs in the Ensemble

A signature may be tested by a party who does not have a full ensemble to determine whether the signature belongs in an existing ensemble used to predict a particular outcome. In one example, when the full ensemble of signatures is known the inventor simply needs perform a table lookup for the signature against the ensemble. When the ensemble is not disclosed a method may determine whether the signature belongs to the existing ensemble even if all the signatures in the ensemble are unknown to the party. In general, determining the full ensemble (for example, determining all the equivalent sets of biomarkers.

The method may include determining whether the predictivity level of a signature under consideration is statistically indistinguishable from the known predictivity of the existing set of signatures in the ensemble. Any suitable statistical technique for testing differences of predictivity measures of classifiers may be used to compare the predictivity levels to determine whether the predictivity levels are statistically indistinguishable as known to one skilled having the benefit of this disclosure. (Statnikov et al. A Gentle Introduction to Support Vector Machines in Biomedicine: Volume 2: Case Studies and Benchmarks. World Scientific Pub. Co.; 2013.)

The method may also include determining whether new signature is minimal for the related predictivity level. Minimality of the new signature may be established by testing and verifying that removal of at least one subset of markers does not leave the predictivity level intact.

If the signature has a predictivity level that is statistically indistinguishable from the predictivity of signatures in the existing ensemble and the signature is minimal, then the signature may be determined to belong in the existing ensemble.

If the new signature has a predictivity level that is statistically distinguishable, then the signature is not part of the ensemble.

If the new signature has a predictivity level that is statistically indistinguishable from a known signature in the existing ensemble but is not minimal, then the method may determine that the signature includes a signature that is part of the existing ensemble (whether known or unknown) plus some noise, or redundant markers. Noise or redundant markers may be described as adding no predictive value to the signature of the ensemble.

In general, the addition of biomarkers beyond the minimal level required for optimal predictivity should not confer any predictive advantage and thus would not constitute an enhanced or otherwise improved signature. Therefore, any predictively optimal biomarker set and signature that is minimal also corresponds to a large number of biomarker sets and signatures that may be constructed by "padding" essential biomarkers with predictively unnecessary (and potentially costly and cumbersome) biomarkers.

Apparatus and Systems

The present disclosure further provides exemplary apparatuses and systems for executing all or part of the methods described herein. In some embodiments, an apparatus may include, for example, a computer, a processor, or a group of processors. In some embodiments, an apparatus may include a microarray, a sequencer, and/or a device capable of performing PCR. A system may include, for example, a computer program, a computer-readable medium, or an algorithm.

Kits

In another aspect, this disclosure describes a kit that may be used to perform all or part of a method described herein. For example, in some embodiments, a kit may include reagent suitable for determining gene expression levels. In some embodiments, a kit may include a system for executing a computer program described herein.

Exemplary Method Embodiments Including Administration of Bevacizumab

1. A method for treating a patient suffering from ovarian cancer following removal of a tumor, the method comprising:
    determining whether the patient is predicted to benefit from the administration of bevacizumab, wherein such determination comprises:
        determining the patient's gene expression level of microfibril associated protein 2 (MFAP2); and
        determining the patient's gene expression level of vascular endothelial growth factor A (VEGFA); and
    if the patient is predicted to benefit from the administration of bevacizumab, administering bevacizumab.

2. The method of Embodiment 1, wherein determining whether the patient is predicted to benefit from the administration of bevacizumab comprises determining whether the patient is predicted to benefit from the administration of bevacizumab in addition to the administration of platinum-based chemotherapy.

3. The method of Embodiment 1 or 2, wherein determining whether the patient is predicted to benefit from the administration of bevacizumab further comprises at least one of:
    determining the patient's International Federation of Gynecology and Obstetrics (FIGO) stage;
    determining the patient's Eastern Cooperative Oncology Group (ECOG) performance status; and
    determining the size of the tumor tissue remaining post-removal of the tumor.

4. The method of Embodiment 3, wherein
    a gene expression level of MFAP greater than a threshold gene expression level indicates a decreased likelihood of benefit from platinum-based chemotherapy, wherein the threshold gene expression level is selected based on a clinical outcome;
    a gene expression level of VEGFA greater than a threshold gene expression level indicates an increased likelihood of benefit from the administration of platinum-based chemotherapy, wherein the threshold gene expression level is selected based on a clinical outcome;
    a FIGO stage greater than 1 indicates a decreased likelihood of benefit from the administration of bevacizumab,
    an ECOG performance status greater than 0 indicates an increased likelihood of benefit from the administration of bevacizumab, and
    a tumor size smaller than 1 cm indicates an increased likelihood of benefit from the administration of bevacizumab.

5. The method of Embodiment 4, wherein the clinical outcome comprises increased time of progression-free survival.

6. The method of Embodiment 5, wherein the patient's predicted increase in progression-free survival is at least 3 months, at least 4 months, at least 5 months, at least 6 months, at least 7 months, at least 8 months, at least 9 months, or at least 10 months.

7. The method of any one of the preceding Embodiments, wherein determining whether the patient is predicted to benefit from the administration of bevacizumab further comprises determining the patient's predicted progression-free survival time with the administration of a platinum-based chemotherapy without bevacizumab.

8. The method of Embodiment 7, wherein determining whether the patient is predicted to benefit from a platinum-based chemotherapy without bevacizumab comprises:
    determining the patient's gene expression level of microfibril associated protein 2 (MFAP2);
    determining the patient's gene expression level of vascular endothelial growth factor A (VEGFA);
    determining the patient's International Federation of Gynecology and Obstetrics (FIGO) stage;
    determining the patient's Eastern Cooperative Oncology Group (ECOG) performance status; and
    determining the size of the tumor tissue remaining post-removal of the tumor.

9. The method of Embodiment 8, wherein
a gene expression level of MFAP greater than a threshold gene expression level indicates a decreased likelihood of benefit from platinum-based chemotherapy, wherein the threshold gene expression level is selected based on a clinical outcome;
a gene expression level of VEGFA greater than a threshold gene expression level indicates an increased likelihood of benefit from the administration of platinum-based chemotherapy, wherein the threshold gene expression level is selected based on a clinical outcome;
a FIGO stage greater than 1 indicates a decreased likelihood of benefit from platinum-based chemotherapy,
an ECOG performance status greater than 0 indicates a decreased likelihood of benefit from platinum-based chemotherapy, and
a tumor size smaller than 1 cm indicates an increased likelihood of benefit from platinum-based chemotherapy.
10. The method of Embodiment 9, wherein the clinical outcome comprises increased time of progression-free survival.
11. The method of Embodiment 10, wherein the patient's predicted increase in progression-free survival is at least 3 months, at least 4 months, at least 5 months, at least 6 months, at least 7 months, at least 8 months, at least 9 months, or at least 10 months.
12. The method of any one of Embodiments 7 to 11, wherein determining whether the patient is predicted to benefit from the administration of bevacizumab further comprises determining if the patient's predicted progression-free survival time with the administration of a platinum-based chemotherapy and bevacizumab is greater than the patient's predicted progression-free survival time with the administration of a platinum-based chemotherapy without bevacizumab.
13. The method of Embodiment 12, wherein the patient is predicted to benefit from the administration of bevacizumab if the patient's predicted increase in progression-free survival is clinically meaningful.
14. The method of Embodiment 13, wherein the patient is predicted to benefit from the administration of bevacizumab if the patient's predicted increase in progression-free survival is at least 3 months, at least 4 months, at least 5 months, at least 6 months, at least 7 months, at least 8 months, at least 9 months, or at least 10 months.
15. The method of any one of the preceding Embodiments, wherein determining whether the patient is predicted to benefit from the administration of bevacizumab comprises defining a benefit threshold.
16. The method of any one of the preceding Embodiments, wherein determining whether the patient is predicted to benefit from the administration of bevacizumab comprises applying a Cox model.
17. The method of any one of the preceding Embodiments, wherein the method comprises administering platinum-based chemotherapy.
18. The method of any one of the preceding Embodiments, wherein the tumor comprises a primary tumor.
19. The method of any one of the preceding Embodiments, wherein the tumor comprises a secondary tumor.
18. The method of any one of the preceding Embodiments, wherein the tumor comprises a primary tumor or a secondary tumor.
20. The method of any one of the preceding Embodiments, further comprising:
receiving an identified set of biomarkers determined based on a set of predetermined data comprising clinical data, gene expression data, or both, wherein the identified set of biomarkers comprises at least MFAP2 and VEGFA;
identifying other sets of biomarkers based on the identified set of biomarkers and remaining data comprising the set of predetermined data excluding the identified set of biomarkers; and
generating a signature for each set of biomarkers to predict an outcome for a patient having ovarian cancer,
wherein determining whether the patient is predicted to benefit from the administration of bevacizumab is based on an ensemble prediction using a plurality of signatures and patient test data comprising clinical data, gene expression data, or both.

Exemplary Method Embodiments Including Administration of a Platinum-Based Chemotherapy 1. A method for treating a patient suffering from ovarian cancer following removal of a tumor, the method comprising:
determining whether the patient is predicted to benefit from the administration of a platinum-based chemotherapy, wherein such determination comprises:
determining the patient's gene expression level of microfibril associated protein 2 (MFAP2);
determining the patient's International Federation of Gynecology and Obstetrics (FIGO) stage;
determining the patient's Eastern Cooperative Oncology Group (ECOG) performance status; and
determining the size of the tumor tissue remaining post-removal of the tumor; and
if the patient is predicted to benefit from the administration of platinum-based chemotherapy, administering platinum-based chemotherapy.
2. The method of Embodiment 1, wherein determining whether the patient is predicted to benefit from the administration of a platinum-based chemotherapy further comprises:
determining the patient's gene expression level of vascular endothelial growth factor A (VEGFA).
3. The method of Embodiment 2, wherein
a gene expression level of MFAP greater than a threshold gene expression level indicates a decreased likelihood of benefit from the administration of platinum-based chemotherapy, wherein the threshold gene expression level is selected based on a clinical outcome;
a gene expression level of VEGFA greater than a threshold gene expression level indicates an increased likelihood of benefit from the administration of platinum-based chemotherapy, wherein the threshold gene expression level is selected based on a clinical outcome;
a FIGO stage greater than 1 indicates a decreased likelihood of benefit from platinum-based chemotherapy,
an ECOG performance status greater than 0 indicates aa decreased likelihood of benefit from platinum-based chemotherapy, and
a tumor size smaller than 1 cm indicates an increased likelihood of benefit from platinum-based chemotherapy.

4. The method of Embodiment 3, wherein the clinical outcome comprises increased time of progression-free survival.
5. The method of Embodiment 4, wherein the patient's predicted increase in progression-free survival is at least 3 months, at least 4 months, at least 5 months, at least 6 months, at least 7 months, at least 8 months, at least 9 months, or at least 10 months.
6. The method of any one of the preceding Embodiments, wherein determining whether the patient is predicted to benefit from the administration of a platinum-based chemotherapy further comprises determining the patient's predicted progression-free survival time.
7. The method of any one of the preceding Embodiments, wherein determining whether the patient is predicted to benefit from the administration of a platinum-based chemotherapy comprises applying a Cox model.
8. The method of any one of the preceding Embodiments, wherein the method comprises administering bevacizumab.
9. The method of any one of the preceding Embodiments, wherein the tumor is a primary tumor.

Exemplary Method Embodiments Including Calculating a Quantitative Score

1. A method comprising:
    identifying a patient with ovarian cancer;
    determining a patient's gene expression levels of microfibril associated protein 2 (MFAP2) and vascular endothelial growth factor A (VEGFA) in a biological sample containing cancer cells obtained from the patient,
    determining the patient's International Federation of Gynecology and Obstetrics (FIGO) stage,
    determining the patient's Eastern Cooperative Oncology Group (ECOG) performance status,
    determining the size of the tumor tissue remaining post-removal of a tumor, and
    calculating a patient risk score for the patient.
2. The method of Embodiment 1, wherein the patient risk score (recurrence_score) is calculated as follows:

recurrence_score=0.31*figo_numeric−0.35*surg_outcome+0.23*MFAP2+0.48*ECOG+
    0.19*VEGFA*Bevacizumab−
    0.15*MFAP2*Bevacizumab−
    0.44*ECOG*Bevacizumab wherein figo_numeric=FIGO stage coded as integers,
    wherein surg_outcome is −1 if the surgical outcome was suboptimal; 0 if the surgical outcome was optimal but tumor tissue smaller than 1 cm remained; or +1 if the surgical outcome was optimal and no visible macroscopic tumor tissue remained;
    wherein MFAP2=gene expression level of MFAP2;
    wherein ECOG=ECOG performance status; and
    wherein VEGFA=gene expression level of VEGFA.
3. The method of Embodiment 1 or 2, the method further comprising calculating the patient's risk of recurrence at time t ($\lambda(t)$) wherein $$\lambda(t)=A_0(t)e^{recurrence\_score}$$

wherein $\lambda_0(t)$ is the baseline hazard function estimated with a non-parametric strategy.
4. The method of any one of the preceding Embodiments, wherein determining the expression levels of MFAP2 and VEGFA comprises measuring levels of RNA transcripts
5. The method of Embodiment 4, wherein the method further comprises normalizing the level of the RNA transcripts to obtain normalized gene expression levels.
6. The method of any one of the preceding Embodiments, wherein the biological sample containing cancer cells is fixed, paraffin-embedded, fresh, or frozen.
7. The method of any one of the preceding Embodiments, wherein the method further comprises computing the patient's risk of recurrence at time t if the patient receives platinum-based therapy.
8. The method of any one of the preceding Embodiments, wherein the method further comprises computing the patient's risk of recurrence at time t if the patient receives bevacizumab.
9. The method of Embodiment 8, wherein the method comprises calculating the benefit of the patient receiving bevacizumab and platinum-based therapy versus platinum-based therapy without bevacizumab.
10. The method of any one of the preceding Embodiments, wherein the method further comprises administering bevacizumab or platinum-based therapy or both.
11. The method of Embodiment 10, wherein the method comprises administering bevacizumab only if the patient's risk of recurrence at time t of the patient receiving bevacizumab is greater than the patient's risk of recurrence at time t of the patient receiving platinum-based therapy without bevacizumab.
12. The method of Embodiment 11, wherein the difference in the patient's risk of recurrence at time t is at least 1 month, at least 2 months, at least 3 months, at least 4 months, at least 5 months, or at least 6 months.

Exemplary Method Embodiments for Predicting the Response of a Patient with Ovarian Cancer to Treatment with Bevacizumab 1. A method for predicting the response of a patient with ovarian cancer to treatment with bevacizumab, the method comprising:
    determining gene expression levels of VEGFA and MFAP2;
    calculating a FIGO numeric score, wherein the FIGO stage is coded as an integer;
    calculating a surgical outcome score, wherein the score is −1 if the surgical outcome was suboptimal; 0 if the surgical outcome was optimal but tumor tissue smaller than 1 cm remained; or +1 if the surgical outcome was optimal and no visible macroscopic tumor tissue remained;
    calculating an ECOG score of 0 to 2, based on ECOG performance status;
    applying the expression levels, FIGO numeric score, surgical outcome score, and ECOG score to a predictive model that relates the variables with progression-free survival of ovarian cancer; and
    evaluating an output of the predictive model to predict progression-free survival of the patient.
2. The method of Embodiment 1, wherein the method further comprises applying the expression levels, FIGO numeric score, surgical outcome score, and ECOG score to a predictive model that relates the variables with progression-free survival of a patient with ovarian cancer if the patient is given platinum-based therapy or with progression-free survival of a patient with ovarian cancer if the patient is given platinum-based therapy and bevacizumab.
3. The method of any one of the preceding Embodiments, wherein the predictive model comprises a Cox model.

4. A method for predicting the response of a patient with ovarian cancer to treatment with bevacizumab, the method comprising:
   determining gene expression levels of a collection of genes taken from a biological sample of the patient, wherein the collection of genes comprises at least 80%, at least 90%, at least 95%, at least 98%, or 100% of the genes of any one of Tables 9-12;
   applying the expression levels to a predictive model that relates the expression levels of the collection of genes the likelihood of progression-free survival of the patient; and
   evaluating an output of the predictive model to predict the likelihood of progression-free survival of the patient.
5. The method of Embodiment 4, wherein the collection of genes is selected from the genes of any one of Tables 9-12 by optimizing the predictive performance with a constraint.
6. The method of Embodiment 4 or 5, the method further comprising applying at least one of FIGO stage, surgical outcome, ECOG score, and tumor histology to the predictive model.
7. The method of any one of Embodiments 4 to 6, wherein the expression levels of the collection of genes are determined at multiple times.
8. The method of any one of Embodiments 4 to 7, wherein the biological sample is fixed, paraffin-embedded, fresh, or frozen.
9. The method of any one of the preceding Embodiments, wherein the predictive model calculates progression-free survival of a patient with ovarian cancer if the patient is given platinum-based therapy and progression-free survival of a patient with ovarian cancer if the patient is given platinum-based therapy and bevacizumab.
10. The method of any one of the preceding Embodiments, wherein the predictive model comprises a support vector machine model.
11. A method comprising the method of any one of the preceding Embodiments and further comprising administering platinum-based therapy or bevacizumab or both to the patient.

Exemplary Method Embodiments for Predicting the Progression-Free Survival of a Patient with Ovarian Cancer 1. A method for predicting progression-free survival of a patient with ovarian cancer, the method comprising:
   determining gene expression levels of a collection of genes taken from a biological sample of the patient, wherein the collection of genes comprises at least 80%, at least 90%, at least 95%, at least 98%, or 100% of the genes of any one of Tables 6, 7, or 13-68;
   applying the expression levels to a predictive model that relates the expression levels of the collection of genes with progression-free survival of ovarian cancer; and
   evaluating an output of the predictive model to predict progression-free survival of the patient.
2. The method of Embodiment 1, wherein the collection of genes is selected from the genes of any one of Tables 6, 7, or 13-68 by optimizing the predictive performance with a constraint.
3. The method of Embodiments 1 or 2, the method further comprising applying at least one of FIGO stage, surgical outcome, and tumor histology to progression-free survival of a patient with ovarian cancer.
4. The method of any one of the preceding Embodiments, the method further comprising detecting an additional biomarker of progression-free survival of the patient.
5. The method of Embodiment 4, wherein the additional biomarker of progression-free survival comprises a germline mutation, a somatic mutation, a DNA methylation marker, a protein marker, or a combination thereof.
6. The method of any one of the preceding Embodiments, wherein the expression levels of the collection of genes are determined at multiple times.
7. The method of any one of the preceding Embodiments, wherein the predictive model comprises a support vector machine model.
8. The method of any one of the preceding Embodiments, wherein the biological sample is fixed, paraffin-embedded, fresh, or frozen.
9. A method comprising the method of any one of the preceding Embodiments and further comprising administering platinum-based therapy or bevacizumab or both to the patient.

Exemplary Method Embodiments for Predicting an Outcome for a Patient with Ovarian Cancer 1. A method for predicting an outcome for a patient, the method comprising:
   receiving an identified set of biomarkers determined based on a set of predetermined data comprising clinical data, gene expression data, or both;
   identifying other sets of biomarkers based on the identified set of biomarkers and remaining data comprising the set of predetermined data excluding the identified set of biomarkers;
   generating a signature for each set of biomarkers to predict an outcome for a patient having ovarian cancer; and
   determining a prediction of an outcome for a patient having ovarian cancer based on one or more signatures and patient test data comprising clinical data, gene expression data, or both.
2. The method of Embodiment 1, wherein the outcome relates to progression-free survival for a patient with ovarian cancer.
3. The method of Embodiment 1, wherein the outcome relates to benefitting from the administration of bevacizumab, platinum-based chemotherapy, or both for a patient with ovarian cancer.
4. The method of any one of the preceding Embodiments, wherein generating a signature for each set of biomarkers comprises feeding each set of biomarkers into a machine learning classifier fitting and model pipeline.
5. The method of Embodiment 4, wherein the machine learning classifier fitting and model pipeline incorporates model selection and error estimation.
6. The method of Embodiment 4 or 5, wherein the machine learning classifier fitting and model pipeline applies one or more of the following: a repeated nested n-fold cross validation with grid parameter choice, a support vector machine classifier, a random forest classifier, or a lasso classifier.
7. The method of any one of the preceding Embodiments, wherein determining a prediction of an outcome for a patient having ovarian cancer is based on an ensemble prediction using one or more signatures.
8. The method of Embodiment 7, wherein the ensemble prediction averages outputs of each signature.

9. The method of Embodiment 7, wherein the ensemble prediction uses one or more signatures or each signature based on available patient test data.

10. The method of any one of the preceding Embodiments, wherein each signature is statistically indistinguishable from another signature for a particular predictivity level.

11. The method of any one of the preceding Embodiments, wherein each signature is a minimal set of biomarkers for a particular predictivity level.

12. The method of any one of the preceding Embodiments, wherein each signature comprises some or all genes of any of Tables 6, 7, or 9-68.

13. The method of any one of the preceding Embodiments, wherein identifying other sets of biomarkers comprises feeding the identified set of biomarkers and remaining data into a TIE* algorithm to provide the other sets of biomarkers.

14. The method of Embodiment 13, wherein the TIE* algorithm identifies the Markov Boundary set of biomarkers in the remaining data.

15. The method of Embodiment 13 or 14, wherein the TIE* algorithm recursively identifies the Markov Boundary sets of biomarkers for different subsets of remaining data.

16. A method for predicting an outcome for a patient, the method comprising:
    determining a prediction of an outcome for a patient having ovarian cancer based on one or more signatures and patient test data comprising clinical data, gene expression data, or both, wherein the one or more signatures are generated to be statistically indistinguishable from a signature of any one of Tables 6, 7, or 9-68 for predicting a clinical response to bevacizumab, platinum-based chemotherapy, or both.

17. A method comprising the method of any one of the preceding Embodiments and further comprising administering platinum-based therapy or bevacizumab or both to the patient.

The present invention is illustrated by the following examples. It is to be understood that the particular examples, materials, amounts, and procedures are to be interpreted broadly in accordance with the scope and spirit of the invention as set forth herein.

EXAMPLES

Example 1

To address which ovarian cancer patients will benefit from bevacizumab and which ovarian cancer patients will benefit from conventional platinum-based chemotherapy, predictive and causal models attributing treatment benefit and predicting benefit from alternate treatment paths were developed. The development included determining the relative information value of clinical and of molecular information and how to optimally combine them with the goal of creating viable clinical strategies that incorporate health economics constraints so that all patients who benefit from bevacizumab will receive it and those who will not benefit, will not burden the health care system and will not suffer adverse reactions and toxicities.

A. Tying modeling to Randomized Clinical Trials (RCTs) facilitates estimating clinical benefits of alternative treatments.

In designs where treatments are not randomized (left panel of FIG. 1) the effects of the treatment post-surgery are confounded by observed and latent (unmeasured) clinical and genomic factors. Whereas a variety of design and analytic solutions exist (including matching to known confounders, analytical control of known and suspected confounders, propensity scoring, and causal graph-based do-calculous), they leave open the possibility of residual confounding (matching, analytical controls), are subject to bias (propensity scoring), are subject to undetectable latent confounding (all methods), or are not practical to apply in genome-wide scale (do-calculous).

In contrast, development of a precision test based on a randomized clinical trial (RCT) design eliminates confounding both from measured and latent variables. The causal effects of post-treatment factors regardless of observed or latent status are incorporated into the total estimated causal effect of the treatment variables. When factors co-determining the outcome are observed, they can be used a covariates in models that individualize the predicted effect on outcome on the basis of these measured factors.

B. Nested N-Fold Cross-Validation (NNFCV) model selection and error estimation design allows for sequential (phased) modeling without overfitting of model error estimates.

Figure 2:
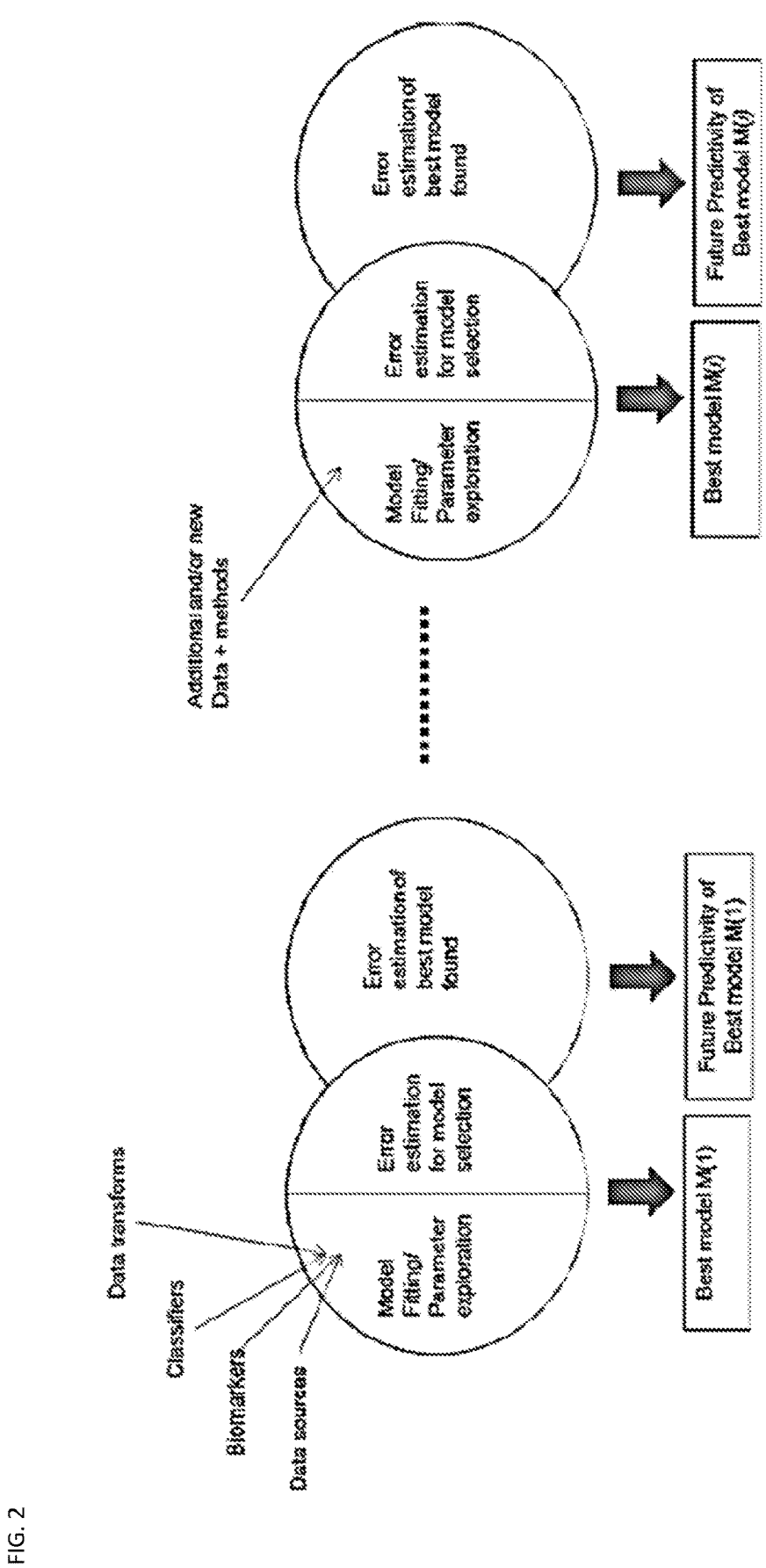
FIG. 2 shows sequential Nested N-Fold Cross-Validation model selection and error estimation design (NNFCV) used for overfitting-resistant multi-stage analysis as new methods and new data become available.

Nested N-Fold Cross-Validation (NNFCV) is an established state-of-the-art design for powerful model selection and unbiased error estimation. But an aspect of this design that is not widely recognized is its ability to perform an analysis in stages as new data and methods become available without overfitting the error estimates of the best models. (See FIG. 2.) This ability is achieved because each time the new models or data compete with the older ones against multiple internal validation tests, without ever accessing the final test set. Only after a winning model has been found, the error estimates are produced up to that round of analysis. This estimate never affects the choice of best model(s) thus avoiding overfitting. In a multi-center, multi-investigator, multi-modality, setting with data obtained in discrete stages, with evolving analytical methods, and with expanding molecular assays, the ability for ongoing, sequential analyses is very important.

C. Data & Specimens

Specimens and clinical data for the present study come from the OVAR-11 (German part of the ICON-7 phase III RCT). (Kommoss et al. *Clin Cancer Res Off J Am Assoc Cancer Res.* 2017; 23(14):3794-801; Perren et al. *N Engl J Med.* 2011; 365(26):2484-96.) Clinical data used for analysis were: age, race, International Federation of Gynecology and Obstetrics (FIGO) stage, histology, treatment, progression-free survival (PFS), overall survival (OS), surgical outcome (for example, debulking status), Eastern Cooperative Oncology Group (ECOG) performance status, independent path review diagnosis and visits.

Specimens were randomly allocated to RNA extraction and assay run order. In brief, 200 ng of RNA was analyzed using the Illumina Whole-Genome DASL array with the HumanRef-8 Bead Chip with 29K gene transcripts or 21K unique genes according to the manufacturer's protocol. (Kommoss et al. *Clin Cancer Res Off J Am Assoc Cancer Res.* 2017; 23(14):3794-801.) Gene expression data quality was assessed via residual minus vs average plots, box plots and jitter plots, to detect experimental artifacts such as batch effects. In addition, numerical measures such as stress and dfbeta, and measures of the magnitude of change due to normalization, were utilized. (Kommoss et al. *Clin Cancer Res Off J Am Assoc Cancer Res.* 2017; 23(14):3794-801; Konecny et al. *J Natl Cancer Inst.* 2014; 106(10):dju249.)

D. Classifiers and Causal effect modeling—Supervised dichotomous prediction models for PFS.

Models were built that predict whether patients would relapse within 12, 24, 36, 48, and 60 months from entering the trial and receiving treatment. This analysis excluded patients that dropped out before each prediction point and they were relapse negative. Support Vector Machines (SVMs) (Vapnik V. The Nature of Statistical Learning Theory. 2nd ed. New York: Springer-Verlag; 2000; Boser et al. A Training Algorithm for Optimal Margin Classifiers. In: Proceedings of the Fifth Annual Workshop on Computational Learning Theory. New York, NY, USA: ACM; 1992. p. 144-152. (COLT '92)) with polynomial kernel of degree from 1 to 3, c parameter from 0.1, 1 and 10 optimized with a nested 10-fold cross-validation (NNFCV, that is, inner fold performing grid model selection and outer fold providing unbiased estimates of generalization error measure via ROC AUC) were used.

Features entering the analysis included: clinical variables (n=20), and gene expression microarray variables (n=29, 000).

Feature selectors for binary prediction models explored: all features, Markov Boundary induction (via HITON-PC (Aliferis et al. *J Mach Learn Res.* 2010; 11:171-234; Aliferis et al. *J Mach Learn Res.* 2010; 11:235-284) with fixed k parameter to 1), and the 106 ovarian cancer genes from the CLOVAR signature obtained by TCGA analysis and previously reported (Konecny et al. *J Natl Cancer Inst.* 2014; 106(10):dju249; Verhaak et al. *J Clin Invest.* 2013; 123(1): 517-25).

Multi-modal data combination strategies for clinical+ gene expression data included: clinical only, gene expression only and clinical+gene expression in a single input vector. Feature selection and multi-modal combinations evaluation were fully nested in the NNFCV to avoid overfitting the genes selected to the data.

E. Classifiers and Causal effect modeling—Time-to-event models that predict risk of relapse under different treatments and identify the patients that will benefit from bevacizumab.

Cox modeling combined with Markov Boundary induction (Aliferis et al. *J Mach Learn Res.* 2010; 11:171-234; Aliferis et al. *J Mach Learn Res.* 2010; 11:235-284) was used for feature selection to model the risk for relapse as a function of treatment and of other measured possible determinants of relapse. Cox modeling uses all available information whereas dichotomous prediction at a fixed time point methods discard information due to censoring. (Efron *J Am Stat Assoc.* 1977; 72(359):557-65.) Because the data came from a randomized trial, all possible confounders effects relating treatment and outcome were eliminating by randomization, thus the estimation of the treatment effect does not require an adjustment for confounders. The multivariate analysis separates the effect of treatment from the effect of other measured co-determinants of relapse, however. The interaction terms were constructed between potential co-determinants of relapse and the treatment. A significant interaction effect indicates a differential treatment effect for different values/levels of a co-determinant, thus results in differential treatment response from patients.

Once a model was fit, the model setting bevacizumab=yes was used as a prognostic model for the group receiving bevacizumab to estimate the outcome in that group. Similar for bevacizumab=no. The difference between the model risk predictions for individual patients setting bevacizumab=yes and then bevacizumab=no was calculated to estimate the benefit of receiving bevacizumab (for example, patients for which the estimated risk difference is negative will benefit from bevacizumab). 100-repeated 20-fold nested cross-validation was used. Treatment effects were then estimated for every subject in the testing set. Different threshold values were applied on the estimated treatment effect to group people into three groups: (1) predicted to strongly benefit; (2) predicted to achieve minor benefit; or (3) predict to not benefit. For patients in each of the three groups, the actual observed benefit in terms of relapse between the treated and untreated patients was compared. The relapse outcome was evaluated with Hazard Ratio (HR) and median survival difference between treatment and control. (Clark et al. *Br J Cancer.* 2003; 89(2):232-8.)

Markov Boundary induction (GLL-PC instantiated with a Cox regression model as the conditional independent test used by the algorithm (Aliferis et al. *J Mach Learn Res.* 2010; 11:171-234; Aliferis et al. *J Mach Learn Res.* 2010; 11:235-284), referred to as GLL-PC-Cox) combined with a knowledge-driven gene selection strategy was used for knowledge-driven and de novo feature selection for Cox modeling as follows: genes related to VEGF were selected from the literature and pathway databases strictly based on literature support without reference to the data in hand.

The following genes were selected: VEGFA, VEGFR2, VEGFB, VEGFC, VEGFR1, VEGFR3, CLDN6, TUBB2B, FGF12, MFAP2, and KIF1A. In the dataset, there are 16 probes measuring 9 of the above genes. A candidate set comprising the 16 gene probes+clinical data variables was formed, and Markov Boundary induction was applied on that set using Cox as a conditional independence test when performing feature selection, and then the selected features were fitted with a Cox model. All these steps were fully embedded inside the inner loop of the NNFCV design.

F. Results

1. Prognostic Models (Binarized Time Points)

Models predicting Progression-Free Survival (PFS) with predictivities and selected feature types/numbers are shown in Table 1. In bold are models with sufficient predictivity to be potentially clinically actionable. The best models have sufficient predictivity to support for clinically actionable prognosis since they match the predictivity of other FDA-approved precision tests. The de novo feature selection resulted in the models having the AUCs indicated in Table 1 and outperformed the predictivity of the 106 genes (CLOVAR signature) previously reported in literature (AUC=0.63). Also notable for this type of model, just 3 clinical variables achieved an AUC of 0.75 (as shown in row 1 of Table 1, column 6). A slightly less predictive model (AUC of 0.74) can be obtained with gene expression only (as shown in row 2 of Table 1, column 6). Because clinical variables are highly subjective, however, these factors may not translate to other providers and could be biased to favor decisions towards specific treatment options. For example, residual disease after surgical cytoreduction is determined by the surgeon and may not translate to other surgeons. This bias could be overcome by using an objective gene expression models. Predictivity was observed to drop after 48 months because many patients had exited the trial at that time.

2. Time to Event Model.

The final Cox Model (complete model) is shown in Table 2. Out of 16 genes+clinical variables and their interaction with the treatment, 7 variables remained in the final model after feature selection with GLL-PC-Cox.

VEGFA, MFAP2, and ECOG have a significant interaction effect with the treatment, indicating that the effects of these variables on progression-free survival depends on if the treatment was administered. For example, MFAP2 show a significant main effect with coefficient of 0.23, a significant interaction with treatment with coefficient of −0.15. In the treatment group, MFAP2 have an overall coefficient of 0.23+(−0.15)*1=0.08 (HR=1.08). In the control group, MRAP2 have an overall coefficient of 0.23+(−0.15)*0=0.23 (HR=1.25).

TABLE 1

Dichotomous prognostic models.

| Time point: | | 12 mo | 24 mo | 36 mo | 48 mo | 60 mo |
|---|---|---|---|---|---|---|
| Models with clinical features only | AUC | 0.71 ± 0.03 | 0.75 ± 0.03 | 0.73 ± 0.02 | 0.75 ± 0.02 | 0.71 ± 0.04 |
| | # of features | 5 | 4 | 4 | 3 | 3 |
| Models with gene expression only | AUC | 0.56 ± 0.03 | 0.58 ± 0.03 | 0.68 ± 0.03 | 0.74 ± 0.03 | 0.42 ± 0.05 |
| | # of features | 149 | 153 | 222 | 215 | 94 |
| Models with clinical + gene expression | AUC | 0.62 ± 0.02 | 0.65 ± 0.03 | 0.72 ± 0.03 | 0.77 ± 0.02 | 0.57 ± 6.03 |
| | # of features | 4 + 149 | 3 + 142 | 3 + 202 | 3 + 176 | 3 + 79 |
| Models with 106 genes from prior work (CLOVAR signature) | AUC | 0.62 ± 0.04 | 0.59 ± 0.03 | 0.62 ± 0.03 | 0.62 ± 0.02 | 0.47 ± 0.06 |
| | # of features | 8 | 4 | 6 | 7 | 2 |

TABLE 3

Examples of using the Cox models to identify patient subgroups that will benefit the most and the least from bevacizumab

| | | Predict to Not Benefit | | | | Gray Zone | | | | Predict to Benefit | | | |
|---|---|---|---|---|---|---|---|---|---|---|---|---|---|
| | | Median Surv Diff | | HR | | Median Surv Diff | | HR | | Median Surv Diff | | HR | |
| Perc. | Thre. | mean | sd | mean | sd | mean | sd | mean | sd | mean | sd | mean | sd |
| 40% | 60% | 1.28 | 1.45 | 0.95 | 0.07 | 7.99 | 4.60 | 0.82 | 0.13 | 7.74 | 0.86 | 0.62 | 0.05 |
| 40% | 80% | 1.28 | 1.45 | 0.95 | 0.07 | 5.79 | 2.12 | 0.77 | 0.06 | 9.95 | 1.53 | 0.49 | 0.07 |
| 60% | 80% | 3.34 | 0.77 | 0.90 | 0.04 | 5.63 | 2.49 | 0.73 | 0.12 | 9.95 | 1.53 | 0.49 | 0.07 |

TABLE 2

Time-to-event causal effect and prognostic models.

| Variables | Coef | exp(Coef) | se exp(Coef) | z | pval |
|---|---|---|---|---|---|
| figo_numeric: figo stage coded as integers, 10 levels, 1 = IA, 2 = IB, . . . , 9 = IIIC, and 10 = IV | 0.31 | 1.37 | 0.06 | 5.58 | 2.39E−08 |
| surg_outcome: 3 levels, −1 = suboptimal; 0 = optimal but remaining tissue smaller than 1 cm; +1 = optimal or no macroscopic tissue remaining | −0.35 | 0.71 | 0.08 | −4.61 | 3.98E−06 |
| MFAP2: gene expression level of MFAP2, Microfibril Associated Protein 2, ranges from 6.7 to 15.9 with mean of 13.1 | 0.23 | 1.26 | 0.06 | 3.70 | 0.000215 |
| ECOG: ECOG performance status, 3 levels,0 = Fully active, able to carry on all pre-disease performance without restriction; 1 = Restricted in physically strenuous activity but ambulatory and able to carry out work of a light or sedentary nature, 2 = Ambulatory and capable of all selfcare but unable to carry out any work activities; up and about more than 50% of waking hours. | 0.48 | 1.61 | 0.14 | 3.34 | 0.000851 |
| VEGFAxrndid VEGFA: gene expression level of MFAP2, Vascular Endothelial Growth Factor A, ranges from 4.9 to 13.3 with mean of 10.5 Rndid: 1 = bevacizumab + Carboplatin; 0 = Carboplatin, VEGFAxrndid, MFAP2xrndid, ECOGxrndid indicate interaction effects. | 0.19 | 1.20 | 0.07 | 2.76 | 0.005818 |
| MFAP2xrndid | −0.15 | 0.86 | 0.05 | −2.83 | 0.004651 |
| ECOGxrndid | −0.44 | 0.64 | 0.19 | −2.26 | 0.023707 |

Concordance = 0.693 (se = 0.019), Rsquare = 0.281 (max possible = 0.999), Likelihood ratio test = 125.2 on 7 df, p = 0, Wald test = 97.88 on 7 df, p = 0, and Score (logrank) test = 108.7 on 7 df, p = 0.

3. Identifying subpopulations who benefit from bevacizumab.

By exploring different thresholds on the PFS risk produced by the Cox models, individual patients and subpopulations that will benefit the most, the least, and in between can be identified. Table 3 shows examples of subpopulation identification.

Figure 3:
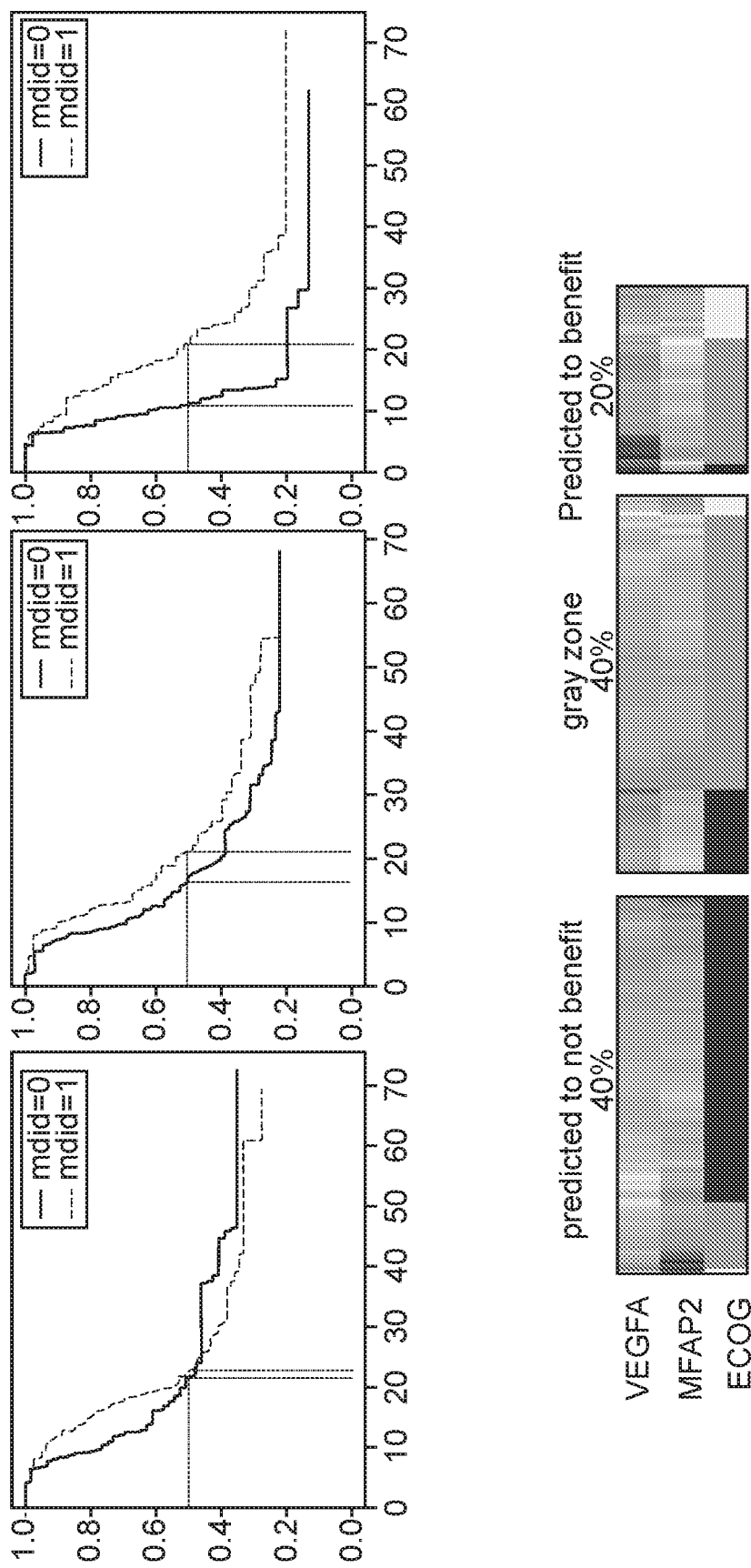
FIG. 3 shows Kaplan-Meier curves (top) and heatmaps (bottom) corresponding to subgroups and predictor variables in the reduced model identifying patients and subgroups that will benefit the most or the least from bevacizumab, as further described in Example 1.

For example, the second row of Table 3 (bolded) depicts separation of a subgroup equal to 20% of the total patient population that will benefit (approximately 10 months for survival), or on the other end a subgroup equal to 40% of the total population without benefit (nominal benefit of 1.3 months which is not statistically significant). FIG. 3 depicts Kaplan-Meier curves (top) and heatmaps (bottom) corresponding to these subgroups and predictor variables in the reduced model. Kaplan-Meier curves (top) and heatmaps (bottom) corresponding to subgroups and predictor variables in the reduced model identifying patients and subgroups that will benefit the most or the least from Bevacizumab. Patients that benefit more from the addition of bevacizumab have lower expression level of VEGF-A, higher expression level of MFAP2 and worse EGOC performance status. Each column in the lower panel indicates a patient. Yellow indicates higher value, green indicates intermediate value and blue indicates lower value. All variables were scaled between 0 to 1 to assist visualization.

4. Construction of Treatment Strategies

Figure 4A:
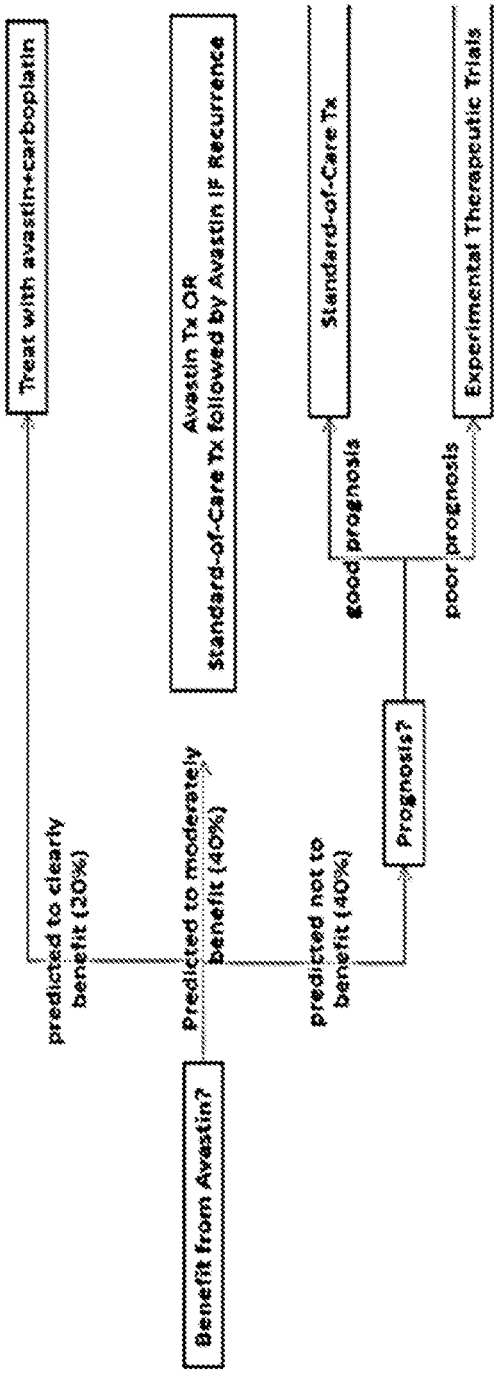
FIG. 4A-FIG. 4B shows exemplary clinical strategies using precision treatment models/tests as described herein.
Figure 4B:
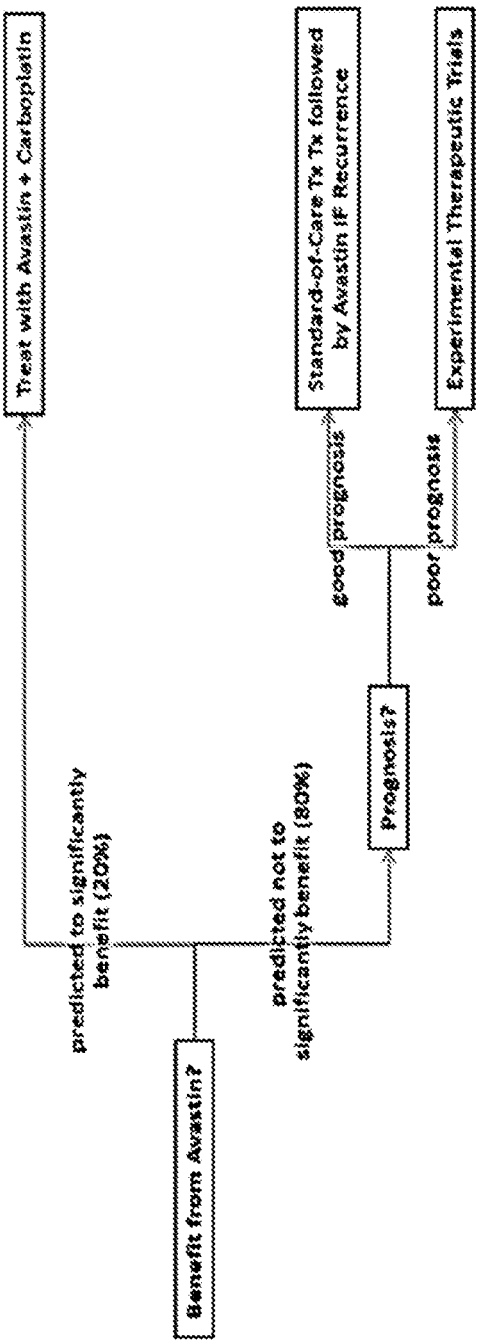

By using the analytical models described in this Example, clinical treatment strategies can be constructed and evaluated. Two possible strategies are depicted in FIG. 4A-FIG. 4B. FIG. 4A identifies a "clear benefit" group that should receive bevacizumab, a "no benefit" group that should receive standard treatment if the dichotomous prognosis models predict good response to Carboplatin or should be routed to experimental therapeutics if predicted response is not good. An intermediate group with "minor/questionable benefit" from bevacizumab may receive standard care plus bevacizumab in case of recurrence. An alternative binary strategy is depicted in FIG. 4B where the "no benefit" and "minor/questionable benefit" groups are merged.

Example 2

As shown in Example 1 and Table 1, models predicting Progression-Free Survival (PFS) were developed. The models exhibiting an AUC of 0.75 or greater are further described in this Example.

Determination of figo_numeric and urg_outcome are described in Table 2. hist_rev_SBOT was determined by microscopic examination of tumor tissue by a pathologist: a patient determined to have a serous borderline ovarian tumor was assigned a value of 1; a patient without a serous borderline ovarian tumor was assigned a value of 0. hist_rev_metastais was determined by microscopic examination of tumor tissue by a pathologist: a patient determined to have a metastatic tumor was assigned a value of 1; a patient without a metastatic tumor was assigned a value of 0.

The model with 4 clinical features providing an AUC of 0.75±0.03 (row 1, 24 months column of Table 1) included the clinical factors and coefficients shown in Table 4.

TABLE 4

| Clinical Factor | Coefficient |
| --- | --- |
| figo_numeric | 0.499594 |
| surg_outcome | 0.000775 |
| hist_rev_SBOT | 2.497971 |
| hist_rev_metastasis | 2.998709 |

The model with 3 clinical features providing an AUC of 0.75±0.02 (row 1, 48 months column of Table 1) included the clinical factors and coefficients shown in Table 5.

TABLE 5

| Clinical Factor | Coefficient |
| --- | --- |
| figo_numeric | 0.400073 |
| surg_outcome | 0.00005 |
| hist_rev_SBOT | 2.000265 |

The model with 215 genes (and no clinical features) providing an AUC of 0.74±0.02 (row 2, 48 months column of Table 1) included the genes and coefficients shown in Table 6.

The model with 3 clinical features and 176 genes providing an AUC of 0.77±0.02 (row 3, 48 months column of Table 1) included the genes and coefficients shown in Table 7 and the clinical factors and coefficients shown in Table 8.

TABLE 8

| Clinical Factor | Coefficient |
| --- | --- |
| figo_numeric | 0.231416 |
| hist_rev_SBOT | 0.173699 |
| surg_outcome | 0.068338 |

TABLE 6

| Gene Name | Coefficient | Gene Name | Coefficient | Gene Name | Coefficient | Gene Name | Coefficient |
| --- | --- | --- | --- | --- | --- | --- | --- |
| SERPINB2 | 0.03622 | EEF1E1 | 0.173467 | RNF7 | 0.01282 | IQCA1 | 0.116866 |
| C1orf168 | 0.138901 | PITX2 | 0.115383 | PCSK6 | 0.101694 | TPM2 | 0.069739 |
| MIDN | 0.041086 | ZNF75D | 0.025308 | ABHD3 | 0.054748 | EDN3 | 0.086092 |
| HBA2 | 0.175207 | RARG | 0.190947 | AXL | 0.038725 | ADAMTS1 | 0.000471 |
| MCAM | 0.051688 | UPK3B | 0.106369 | KCNIP3 | 0.171931 | NFATC4 | 0.096882 |
| PLAC9 | 0.076069 | RAD54B | 0.026128 | DSC3 | 0.113964 | EPYC | 0.122943 |
| SELENBP1 | 0.025843 | GAD1 | 0.086734 | C17orf106 | 0.062762 | CD34 | 0.092926 |
| HCFC1R1 | 0.102289 | PPAPDC1A | 0.020161 | KIF3C | 0.018418 | DUT | 0.201835 |
| FAM70A | 0.053427 | MYOHD1 | 0.14274 | PKN1 | 0.147588 | ORC1L | 0.340407 |
| IGSF9 | 0.04932 | FLJ33360 | 0.130302 | TMEM52 | 0.114855 | YARS2 | 0.071752 |
| METRNL | 0.149908 | CALD1 | 0.059619 | KCNQ2 | 0.003826 | OTUD7A | 0.224324 |
| NYX | 0.073665 | C10orf116 | 0.090491 | HPRT1 | 0.155877 | CASP8AP2 | 0.001789 |
| MMP12 | 0.049893 | LBH | 0.055515 | GRIN3A | 0.065821 | PNMA5 | 0.009767 |
| SFN | 0.120181 | KRT80 | 0.005235 | ADORA1 | 0.202699 | NR6A1 | 0.038371 |
| FBXO48 | 0.155071 | ODF2 | 0.035257 | SFRS4 | 0.040789 | NLRP9 | 0.161918 |

TABLE 6-continued

| Gene Name | Coefficient | Gene Name | Coefficient | Gene Name | Coefficient | Gene Name | Coefficient |
| --- | --- | --- | --- | --- | --- | --- | --- |
| ENPEP | 0.204423 | HIC1 | 0.056785 | PSMC6 | 0.08759 | TAF15 | 0.039363 |
| GJA5 | 0.115978 | HDAC7 | 0.062167 | TCEAL8 | 0.087723 | CLDN6 | 0.073599 |
| C17orf58 | 0.161763 | UBR7 | 0.013314 | FAM187B | 0.058209 | CXCL13 | 0.07641 |
| GSR | 0.001917 | BTF3 | 0.148726 | ICAM4 | 0.119818 | WARS | 0.011903 |
| SATB2 | 0.157891 | C11orf24 | 0.033189 | MIR212 | 0.048242 | TESC | 0.064945 |
| TRIM58 | 0.140981 | NTRK2 | 0.02828 | ALS2CL | 0.015398 | CYP1A2 | 0.052665 |
| DNAH11 | 0.0699 | DBNDD2 | 0.228329 | ICAM2 | 0.080758 | TM2D3 | 0.246656 |
| HLXB9 | 0.058337 | VANGL2 | 0.003238 | RARA | 0.027594 | SNORD93 | 0.081411 |
| JUNB | 0.025915 | SERPINB5 | 0.060212 | NFATC3 | 0.103829 | TNFRSF18 | 0.165332 |
| CCL13 | 0.049223 | PRKAA2 | 0.210635 | IL1RAP | 0.10806 | RASGEF1C | 0.124793 |
| FKBP10 | 0.057389 | C8orf79 | 0.081366 | NET1 | 0.032067 | CCR2 | 0.019484 |
| ADAM17 | 0.074427 | XBP1 | 0.119153 | LGI3 | 0.038461 | GMNN | 0.115653 |
| FOSB | 0.011615 | EZH2 | 0.107034 | ARL6IP1 | 0.101664 | ROD1 | 0.073321 |
| EMP1 | 0.014821 | THBS3 | 0.027919 | C17orf58 | 0.092084 | BDNF | 0.033912 |
| C18orf56 | 0.00339 | PLSCR4 | 0.100974 | SHC1 | 0.086425 | NP | 0.150271 |
| MFSD11 | 0.03905 | CDC42BPA | 0.004402 | C11orf49 | 0.195174 | SBSN | 0.15035 |
| TMEM62 | 0.044461 | ERI2 | 0.070412 | GBP7 | 0.052231 | ARMCX3 | 0.072789 |
| TNNT2 | 0.122743 | FMNL3 | 0.207885 | RAP1A | 0.001336 | SPANXD | 0.080842 |
| LRRTM4 | 0.11724 | DNMT3L | 0.194431 | PLEKHG5 | 0.142552 | CRYBA1 | 0.095109 |
| NUP155 | 0.027639 | ZSWIM4 | 0.107025 | ALX3 | 0.017065 | TOMM20L | 0.042679 |
| PRSS27 | 0.063727 | HPS4 | 0.079177 | SLC9A10 | 0.038537 | | |
| BMPR1A | 0.124556 | MFRP | 0.094868 | HCG9 | 0.106585 | | |
| HDLBP | 0.050078 | EPHB1 | 0.062946 | LRRC14B | 0.108694 | | |
| SLC25A34 | 0.086934 | SLC23A1 | 0.025963 | DOCK7 | 0.096171 | | |
| PRAMEF5 | 0.19769 | C1orf64 | 0.172403 | RNASEK | 0.061792 | | |
| SYTL3 | 0.006225 | PMEPA1 | 0.079342 | ATXN10 | 0.191254 | | |
| ASB5 | 0.06092 | CECR4 | 0.145267 | FOXN1 | 0.068077 | | |
| STC2 | 0.028435 | FBXO43 | 0.014442 | MYCN | 0.007338 | | |
| BCAS1 | 0.063785 | NRXN3 | 0.117417 | UBR7 | 0.081387 | | |
| HR | 0.218781 | MACC1 | 0.104212 | SEC22C | 0.233998 | | |
| ADAMTS9 | 0.051007 | PDLIM2 | 0.105603 | FLJ43752 | 0.084094 | | |
| GBE1 | 0.125008 | HOOK1 | 0.104046 | LOC441150 | 0.075526 | | |
| ESPNL | 0.026457 | CYB5R3 | 0.044329 | MIR654 | 0.132396 | | |
| ZNF114 | 0.11843 | SLC4A5 | 0.080003 | LENEP | 0.035236 | | |
| STC1 | 0.066473 | SOX2 | 0.088092 | MIR571 | 0.142624 | | |
| MANSC1 | 0.114537 | STYX | 0.030971 | HSD11B1 | 0.016267 | | |
| NT5DC1 | 0.194833 | MIR942 | 0.062775 | C14orf102 | 0.085657 | | |
| MCART6 | 0.064187 | MIA2 | 0.099157 | MIR1914 | 0.133341 | | |
| PANK4 | 0.046483 | KRTAP10.10 | 0.203315 | KIAA0773 | 0.016884 | | |
| GLDN | 0.06358 | XRN2 | 0.110497 | CREB5 | 0.14742 | | |
| BAI1 | 0.067673 | SERPINB6 | 0.163358 | OTOP1 | 0.012675 | | |
| RBP4 | 0.042606 | MIR576 | 0.066863 | EIF2C2 | 0.041661 | | |
| ENO1 | 0.028603 | LOC492303 | 0.107718 | ANO7 | 0.153893 | | |
| FAM13AOS | 0.299714 | GFRA3 | 0.039813 | ANKRD30A | 0.133547 | | |
| SCXB | 0.054135 | LRRC37A4 | 0.16319 | ZNF599 | 0.121019 | | |

TABLE 7

| Gene Name | Coefficient | Gene Name | Coefficient | Gene Name | Coefficient |
| --- | --- | --- | --- | --- | --- |
| C1orf168 | 0.142046 | GAD1 | 0.050425 | TMEM52 | 0.003004 |
| MIDN | 0.0359 | PPAPDC1A | 0.002159 | KCNQ2 | 0.020539 |
| HBA2 | 0.108688 | MYOHD1 | 0.180576 | HPRT1 | 0.086891 |
| MCAM | 0.04625 | FLJ33360 | 0.205058 | SFRS4 | 0.15813 |
| PLAC9 | 0.124332 | CALD1 | 0.022523 | PSMC6 | 0.083801 |
| SELENBP1 | 0.010922 | C10orf116 | 0.126446 | TCEAL8 | 0.083907 |
| HCFC1R1 | 0.044686 | LBH | 0.026799 | FAM187B | 0.066754 |
| FAM70A | 0.050927 | KRT80 | 0.101739 | ICAM4 | 0.101648 |
| SERPINB2 | 0.025977 | ODF2 | 0.061025 | MIR212 | 0.050117 |
| NYX | 0.033832 | HIC1 | 0.044034 | FOSL2 | 0.041694 |
| MMP12 | 0.009991 | HDAC7 | 0.157829 | ALS2CL | 0.082645 |
| SFN | 0.135709 | UBR7 | 0.046341 | ICAM2 | 0.033457 |
| FBXO48 | 0.188484 | BTF3 | 0.132272 | RARA | 0.019454 |
| ENPEP | 0.290998 | C11orf24 | 0.068234 | NFATC3 | 0.122866 |
| GJA5 | 0.200544 | NTRK2 | 0.007944 | IL1RAP | 0.126467 |
| C17orf58 | 0.108486 | DBNDD2 | 0.139397 | LGI3 | 0.062777 |
| GSR | 0.00945 | SERPINB5 | 0.072663 | ARL6IP1 | 0.107493 |
| SATB2 | 0.117074 | PRKAA2 | 0.214928 | C17orf58 | 0.032018 |
| TRIM58 | 0.153599 | C8orf79 | 0.087576 | SHC1 | 0.0814 |
| DNAH11 | 0.074143 | XBP1 | 0.148784 | IQCA1 | 0.179486 |
| CCL13 | 0.027153 | EZH2 | 0.08015 | TPM2 | 0.125612 |
| FKBP10 | 0.043095 | THBS3 | 0.008082 | ADAMTS1 | 0.030315 |
| ADAM17 | 0.06098 | PLSCR4 | 0.130711 | NFATC4 | 0.096009 |
| FOSB | 0.023202 | RNF7 | 0.063844 | EPYC | 0.070795 |
| EMP1 | 0.037216 | ABHD3 | 0.106972 | CD34 | 0.113475 |

TABLE 7-continued

| Gene Name | Coefficient | Gene Name | Coefficient | Gene Name | Coefficient |
|---|---|---|---|---|---|
| C18orf56 | 0.028461 | AXL | 0.107418 | DUT | 0.186273 |
| EEF1E1 | 0.135893 | KCNIP3 | 0.109267 | ORC1L | 0.238539 |
| PITX2 | 0.028185 | DSC3 | 0.120844 | YARS2 | 0.016456 |
| ZNF75D | 0.057275 | C17orf106 | 0.037081 | OTUD7A | 0.201115 |
| RARG | 0.216165 | KIF3C | 0.034227 | CASP8AP2 | 0.016062 |
| RAD54B | 0.045267 | PKN1 | 0.170888 | PNMA5 | 0.135075 |
| NR6A1 | 0.006141 | STC1 | 0.006462 | XRN2 | 0.161955 |
| NLRP9 | 0.152894 | MANSC1 | 0.218641 | MIR576 | 0.136067 |
| TAF15 | 0.057532 | NT5DC1 | 0.174405 | LOC492303 | 0.166097 |
| CLDN6 | 0.075814 | MCART6 | 0.067483 | LRRC37A4 | 0.138503 |
| CXCL13 | 0.110036 | PANK4 | 0.003817 | C11orf49 | 0.236135 |
| WARS | 0.000433 | BAI1 | 0.112174 | GBP7 | 0.039005 |
| CYP1A2 | 0.025302 | CDC42SE2 | 0.021331 | RAP1A | 0.062414 |
| L3MBTL2 | 0.113922 | ENO1 | 0.033418 | PLEKHG5 | 0.124847 |
| NOVA2 | 0.097248 | FAM13AOS | 0.265658 | SLC9A10 | 0.001898 |
| TM2D3 | 0.263952 | SCXB | 0.005665 | LRRC14B | 0.120427 |
| SNORD93 | 0.130103 | PIGA | 0.259665 | DOCK7 | 0.086846 |
| TNFRSF18 | 0.176799 | CDC42BPA | 0.018359 | RNASEK | 0.058433 |
| CCR2 | 0.019608 | ERI2 | 0.048111 | ATXN10 | 0.328539 |
| GMNN | 0.056982 | FMNL3 | 0.268819 | FOXN1 | 0.130011 |
| ROD1 | 0.00363 | DNMT3L | 0.11955 | MYCN | 0.05342 |
| BDNF | 0.033034 | ZSWIM4 | 0.00694 | UBR7 | 0.130303 |
| NP | 0.185919 | HPS4 | 0.054637 | SEC22C | 0.198633 |
| TMEM62 | 0.042722 | MFRP | 0.105931 | FU43752 | 0.025543 |
| TNNT2 | 0.11036 | EPHB1 | 0.038068 | MIR654 | 0.141295 |
| LRRTM4 | 0.017028 | SLC23A1 | 0.082779 | LENEP | 0.016182 |
| NUP155 | 0.030303 | C1orf64 | 0.132788 | MIR571 | 0.1286 |
| BMPR1A | 0.179979 | PMEPA1 | 0.010494 | HSD11B1 | 0.054315 |
| HDLBP | 0.063327 | NRXN3 | 0.047603 | C14orf102 | 0.045687 |
| SLC25A34 | 0.160687 | MACC1 | 0.132316 | MIR1914 | 0.11015 |
| PRAMEF5 | 0.179546 | PDLIM2 | 0.092791 | CREB5 | 0.18562 |
| SYTL3 | 0.101981 | CYB5R3 | 0.042923 | ANO7 | 0.204686 |
| STC2 | 0.004501 | SLC4A5 | 0.079908 | SBSN | 0.192868 |
| C14orf109 | 0.025836 | SOX2 | 0.048221 | ARMCX3 | 0.028017 |
| BCAS1 | 0.101035 | STYX | 0.038973 | CRYBA1 | 0.063877 |
| HR | 0.275219 | MIR942 | 0.093471 | TOMM20L | 0.060286 |
| GBE1 | 0.097187 | PHYH | 0.02152 | | |
| ESPNL | 0.011079 | KRTAP10.10 | 0.226854 | | |

Example 3

Example 3 provides further information about the Time to Event Model (Cox model) of Example 2, Table 2.

A. Definitions

Patient risk score function is defined as:

recurrence_score=0.31*figo_numeric−0.35*surg_outcome+0.23*MFAP2+0.48*ECOG+ 0.19*VEGFA*Bevacizumab− 0.15*MFAP2*Bevacizumab− 0.44*ECOG*Bevacizumab     Equation (1)

wherein figo_numeric=FIGO stage coded as integers,
wherein surg_outcome is −1 if the surgical outcome was suboptimal; 0 if the surgical outcome was optimal but tumor tissue smaller than 1 cm remained; or +1 if the surgical outcome was optimal and no visible macroscopic tumor tissue remained;
wherein MFAP2=gene expression level of MFAP2;
wherein ECOG=ECOG performance status; and
wherein VEGFA=gene expression level of VEGFA.
The Cox proportional hazard function is defined as:

$$\lambda(t)=\lambda_0(t)e^{recurrence\_score}$$     Equation (2)

Where $\lambda(t)$ is the risk of recurrence at time t and $\lambda_0(t)$ is the baseline hazard function estimated with a non-parametric strategy, describing how the risk of event per time unit changes over time at baseline levels of covariates. recurrence_score is computed from Equation (1).

B. Compute Patient Risk of Death at Time t if Platin Based Therapy is Given

1. Compute risk score using equation (1): use equation in (1), plug in Bevacizumab=0 and patient value for figo_numeric, surg_outcome, MFAP2, ECOG, VEGFA, MFAP2
2. Compute risk at time t: plug score obtained in step B.1 into recurrence_score in Equation (2), plug in t (time when risk need to be estimated).
3. Compute time to reach a given risk: use step B.2 to compute risk at a series of time points, look up time that correspond to the risk in questions.

C. Compute Patient Risk of Death at Time t if Platin Based Therapy+Bevacizumab is Given 1. Compute risk score using Equation (1): use Equation in (1), plug in Bevacizumab=1 and patient value for figo_numeric, surg_outcome, MFAP2, ECOG, VEGFA, MFAP2
2. Compute risk at time t: plug score obtained in step C.1 into recurrence_score in Equation (2), plug in t (time when risk need to be estimated).
3. Compute time to reach a given risk: use step C.2 to compute risk at a series of time points, look up time that correspond to the risk in questions.

D. Compute Benefit from Platin Based Therapy+Bevacizumab

1. Subtract probability obtained in C.2 from probability obtained in B.2, resulting estimated difference in risk of death if Bevacizumab were given in addition to platin based therapy.
2. Pick a risk value, compare time to reach the risk computed from C.2 and B.2, the difference between the two estimated time represents the estimated improvement in/reducing of recurrence.

Example 4

Example 4 provides a procedure for creating an ensemble of signatures for ovarian cancer. In particular, an ensemble of signatures were created for both dichotomous outcomes and survival analysis (Cox) signatures.
  Step 1. The procedure included identifying a single best set of biomarkers, or "seed," produced by Example 1 from predetermined data including clinical data only, gene expression data only, or clinical and gene expression data.
  Step 2. The set of biomarkers were fed into a TIE* algorithm with the remainder of the predetermined data. The TIE* algorithm was used with GLL-PC as a subroutine (parameter X=GLL-PC) with the seed provided by GLL-PC and conditional independence criterion (Y=IGS) and Z=INDEPENDENCE. (Statnikov and Aliferis. *PLoS Computational Biology* 2010; 6(5), p. e1000790; U.S. Pat. No. 8,805,761; Aliferis et al. *Journal of Machine Learning Research* 2010; 11(January), pp. 171-234; Statnikov et al. *Journal of Machine Learning Research* 2013; 14(February), pp. 499-566; U.S. Pat. No. 8,655,821.)
  The TIE* algorithm systematically examined information equivalences in the "seed" with variables in the remainder of the data (for example, full set of variables minus the seed). Replacement of a subset of the "seed" and execution of a subroutine was performed to identify the Markov Boundary set of biomarkers in the remainder of the data (for example, running the subroutine once for each time a subset of the "seed" is excluded).
  Step 3. The replacement of the subset of the "seed" and execution of the subroutine was repeated recursively until all existing sets of biomarkers were identified and output by the TIE* algorithm. The TIE* algorithm was then terminated.
  Step 4. The output of the TIE* algorithm provided a catalogue, or database, of biomarker sets. Each set of biomarkers was fed into a machine learning classifier fitting and model pipeline that incorporated model selection and error estimation. (Statnikov. A gentle introduction to support vector machines in biomedicine: Theory and methods; Vol. 1. World Scientific Pub. Co.; 2011; Statnikov et al. A Gentle Introduction to Support Vector Machines in Biomedicine: Volume 2: Case Studies and Benchmarks. World Scientific Pub. Co.; 2013.) A plurality of methods for deriving signatures from datasets were used. In particular, one or more of the following methods were used be used: a repeated nested n-fold cross validation with grid parameter choice, a support vector machine (SVM) classifier, a random forest (RF) classifier, and a lasso classifier.
  Step 5. The output of the pipeline for each set of biomarkers, or each member of the equivalency catalogue, was a signature for predicting patient outcomes, for example, in response to treatment. The catalogue of signatures may be described as an ensemble.
  Step 6. The catalogue of signatures may be used to provide an ensemble prediction. In a first example, a prediction would be obtained from every signature in the catalogue, and the predictions would be averaged to obtain a consolidated ensemble prediction. The ensemble prediction may minimize variance of prediction accuracy. In a second example, a prediction would be obtained from only a select number of signatures in the catalogue, and the predictions would be averaged to obtain a consolidated ensemble prediction. The signatures would be selected based on availability. Factors contributing to availability would include one or more of: convenience, cost, and ease of collection. In the second example, the companion test may be personalized or customized for different patients.

Example 5

This Example describes the identification of sets of variables and signatures (that is, the set of variables and their coefficients) that predict a response to bevacizumab, developed as described in Example 4.
Methods
  Predictor Set: Clinical features (21) and Gene expression features (29377)
  Target: time to relapse
  N: 380; N events: 269
  Performance estimation: 20 fold 5 repeat cross validation
  Performance Metric: c-index
  Method: TIE with max-k=1, max-card=1, p=0.05, seeded with original MB.
Results:
  Final Model: 4 TIE signatures
  CV performance estimation:
    With lasso cox:
      Original MB (Seed): 0.68+/−0.08
      TIE signatures: 0.64+/−0.08
    With regular cox:
      Original MB (Seed): 0.68+/−0.10
      TIE signature: 0.56+/−0.10
  Exemplary results are shown in Tables 9-12, wherein figo_numeric and surg_outcome are described in Table 2; hist_rev_SBOT and hist_rev_metastais are determined as described in Example 2; ECOG=ECOG performance status. "xrndid" after a variable name indicates interaction with treatment. For example, if the variables include MFAP2_3 and MFAP2_3xrndid, MFAP2_3 indicates expression of MFAP2_3 and MFAP2_3xrndid indicates expression of MFAP2_3, wherein the coefficient is only applied when the patient is treated

TABLE 9

| Variable Name | Coefficient |
| --- | --- |
| surg_outcome | −0.44082714 |
| figo_numeric | 0.31301932 |
| ECOG | 0.45061864 |
| MFAP2_3 | 0.16628139 |
| surg_outcomexrndid | 0.18204931 |
| MFAP2_1xrndid | −0.09522372 |
| VEGFA_3xrndid | 0.1375739 |
| ECOGxrndid | −0.42221603 |
| MFAP2_3xrndid | −0.07687417 |

TABLE 10

| Variable Name | Coefficient | Variable Name | Coefficient |
|---|---|---|---|
| figo_numeric | 0.222512662 | ALKBH7 | −0.024312142 |
| MCAM | 0.080289559 | LOC388503_1 | 0.04485732 |
| REG4 | 0.124861797 | PRDM2_3 | 0.000751499 |
| C18orf56 | −0.276812329 | C20orf77 | 0.00869733 |
| PREP | 0.000281229 | C8orf79_1 | −0.070446044 |
| PRRG4_2 | −0.007129649 | LRRIQ4 | 0.070624165 |
| EXOC3L2 | 0.055025506 | RAD54B_2 | −0.041598424 |
| AXL_1 | 0.025469171 | CARD17_1 | 0.131333116 |
| RNF7_1 | 0.034214255 | EIF4E2 | 0.091643106 |
| C1orf168 | −0.072824665 | YARS2 | 0.005687757 |
| RPS27L_2 | −0.024708305 | FBXO48_2 | −0.136651878 |
| TM2D3_2 | −0.209582854 | GZMB | −0.130786174 |
| C11orf24 | 0.1545701 | ZNF550 | −0.06531994 |
| SLC35C2_2 | 0.140504621 | REXO1L1 | −0.051039716 |
| CCDC114 | −0.010359055 | ZSWIM4_1 | 0.243783625 |
| MYOHD1 | −0.146095296 | LOC387720 | −0.104943347 |
| B3GAT1_3 | −0.025250575 | TCTEX1D4 | −0.022025733 |
| PNPLA3 | −0.044912936 | SATB2 | −0.058100575 |
| C12orf39 | 0.063856301 | CCL18 | −0.000428123 |
| EIF4G3 | 0.0376753 | ECOG | 0.00843997 |
| C10orf32_1 | −0.073368282 | surg_outcomexrndid | −0.195468114 |
| ANKRD30A_2 | 0.122310931 | GRIK5xrndid | −0.039724252 |
| PCNP | −0.08554762 | | |
| DNAH9_3 | −0.01715795 | | |

TABLE 11

| Variable Name | Coefficient | Variable Name | Coefficient | Variable Name | Coefficient | Variable Name | Coefficient |
|---|---|---|---|---|---|---|---|
| figo_numeric | 2.97E−01 | NF2_3rndid | −5.53E−02 | ANKRD30A_2xrndid | 5.56E−03 | | |
| surg_outcome | −4.80E−01 | DNAH1_1rndid | −1.65E−01 | GATA6xrndid | 1.54E−01 | | |
| ECOG | 4.93E−01 | TTRxrndid | 4.93E−02 | GAD1_2xrndid | −2.38E−02 | | |
| MFAP2_3 | 2.02E−01 | MRPS11_2xrndid | −1.01E−02 | ADAM5Pxrndid | 4.89E−02 | | |
| surg_outcomexrndid | 3.18E−01 | ZNF530xrndid | 1.86E−01 | XPNPEP2xrndid | 3.24E−03 | | |
| SERPINB2_2xrndid | 1.76E−05 | CLEC2D_3xrndid | −1.33E−01 | TAS2R7xrndid | 3.87E−01 | | |
| BCAS1_1rndid | 7.79E−02 | RAD9Bxrndid | −1.81E−01 | NFATC4xrndid | 3.73E−02 | | |
| ZBTB25_1rndid | −2.46E−02 | TMEM90Axrndid | −1.30E−01 | PDE4DIP_1xrndid | 1.16E−01 | | |
| NNAT_1rndid | 2.31E−01 | ECOGxrndid | −4.16E−01 | SH2D6xrndid | 4.96E−02 | | |
| CD2xrndid | −9.78E−02 | MFAP2_3xrndid | −1.65E−01 | PCDHA7_3xrndid | 1.71E−01 | | |
| CECR1_2xrndid | −3.20E−02 | | | DUT_3xrndid | −1.44E−02 | | |
| PDE3Axrndid | 2.20E−02 | | | PHLDB2_1xrndid | 1.36E−01 | | |
| ENTPD8_2xrndid | 1.19E−01 | | | PAICS_1xrndid | −2.25E−02 | | |
| GUSBL2xrndid | −8.56E−02 | | | CCDC50_2xrndid | 6.59E−02 | | |
| ANKRD30A_1xrndid | 1.13E−01 | | | BHLHA15xrndid | −1.29E−01 | | |
| ENPEP_2xrndid | 1.50E−02 | | | SORBS3_1xrndid | −1.64E−01 | | |
| MIR1914xrndid | 7.58E−02 | | | NAPSAxrndid | −1.26E−01 | | |
| ZNF276xrndid | −3.50E−02 | | | CDC14B_3xrndid | −7.89E−02 | | |
| REEP1xrndid | 4.13E−02 | | | GPR34_2xrndid | 7.45E−03 | | |
| P4HA1_2xrndid | −1.46E−01 | | | PCSK6_1xrndid | −3.92E−02 | | |
| HARBI1_1xrndid | 2.05E−01 | | | C7orf55_2xrndid | −4.43E−02 | | |
| TNFRSF17xrndid | −2.74E−02 | | | | | | |

TABLE 12

| Variable Name | Coefficient | Variable Name | Coefficient |
|---|---|---|---|
| figo_numeric | 0.230997068 | ECOG | 0.02312799 |
| ANKRD30A_2 | 0.125678399 | surg_outcomexrndid | −0.198492853 |
| MCAM | 0.072331724 | GUSBL2xrndid | −0.008814662 |
| REG4 | 0.130660811 | BHLHA15xrndid | −0.045906491 |
| C18orf56 | −0.261439816 | | |
| PREP | 0.007826764 | | |
| PRRG4_2 | −0.011529826 | | |
| EXOC3L2 | 0.05973232 | | |
| AXL_1 | 0.019925605 | | |
| RNF7_1 | 0.025954975 | | |
| C1orf168 | −0.075746531 | | |
| RPS27L_2 | −0.023185125 | | |
| TM2D3_2 | −0.198849821 | | |
| C11orf24 | 0.159456193 | | |
| SLC35C2_2 | 0.135432627 | | |
| CCDC114 | −0.015655845 | | |
| MYOHD1 | −0.158958318 | | |
| B3GAT1_3 | −0.024714285 | | |

TABLE 12-continued

| Variable Name | Coefficient | Variable Name | Coefficient |
|---|---|---|---|
| PNPLA3 | −0.058457746 | | |
| C12orf39 | 0.065472862 | | |
| EIF4G3 | 0.050656249 | | |
| C10orf32_1 | −0.088038114 | | |
| PCNP | −0.13688082 | | |
| DNAH9_3 | −0.025475558 | | |
| ALKBH7 | −0.029561969 | | |
| LOC388503_1 | 0.063993063 | | |
| PRDM2_3 | 0.01079284 | | |
| C20orf77 | 0.022530994 | | |
| FLJ37587 | 0.005155198 | | |
| C8orf79_1 | −0.062888761 | | |
| LRRIQ4 | 0.076642753 | | |
| RAD54B_2 | −0.048442085 | | |
| CARD17_1 | 0.164118694 | | |
| EIF4E2 | 0.102255429 | | |
| YARS2 | 0.021797945 | | |
| FBXO48_2 | −0.142665906 | | |
| GZMB | −0.132781409 | | |
| ZNF550 | −0.071905525 | | |
| REXO1L1 | −0.050514064 | | |
| ZSWIM4_1 | 0.33711993 | | |
| LOC387720 | −0.117252043 | | |
| TCTEX1D4 | −0.032385501 | | |
| SATB2 | −0.056044084 | | |

Example 6

This Example describes the identification of sets of variables and signatures (that is, the set of variables and their coefficients) that predict ovarian cancer 48 month progression free survival, developed as described in Example 4.

Predictor Set: Clinical features (21) and Gene expression features (29377)
Target: 48 month survival binary outcome
N: 351 (265 dead and 86 alive)
Performance estimation: 10 fold 5 repeat cross validation
Method: TIE Independence test
MB: 56
Median(#MB members): 193
min(#MB members): 190
max(#MB members): 198
vars in at least one MB: 215
CV AUC (mean+/−sd)*: 0.76+/−0.02

*mean is taken first over multiple signatures within each cross validation run resulting in 50 values, then averaged across folds resulting in 5 values where computation of CV AUC mean and standard deviation are based on.

Exemplary results are shown in Tables 13-65, wherein figo_numeric and surg_outcome are described in Table 2; hist_rev_SBOT and hist_rev_metastais are determined as described in Example 2; ECOG=ECOG performance status. "xrndid" after a variable name indicates interaction with treatment.

TABLE 13

| | |
|---|---|
| ABHD3 | 0.0683 |
| ADAM17_2 | 0.2314 |
| ADAMTS1 | 0.1737 |
| ALS2CL_3 | 0.107 |
| ANO7_3 | 0.061 |
| ARL6IP1_1 | 0.0303 |
| ARMCX3_2 | 0.0826 |
| ATXN10_1 | 0.2047 |
| AXL_1 | 0.1075 |
| BAI1_3 | 0.028 |
| BCAS1_1 | 0.3285 |

TABLE 13-continued

| | |
|---|---|
| BDNF_2 | 0.1074 |
| BMPR1A | 0.1122 |
| BTF3_3 | 0.101 |
| C10orf116 | 0.033 |
| C11orf24 | 0.18 |
| C11orf49_3 | 0.1323 |
| C14orf102_2 | 0.1264 |
| C14orf109_2 | 0.0682 |
| C17orf106 | 0.2361 |
| C17orf58_2 | 0.0457 |
| C17orf58_3 | 0.0258 |
| C18orf56 | 0.0371 |
| C1orf168 | 0.032 |
| C1orf64 | 0.1085 |
| C8orf79_1 | 0.0285 |
| CALD1_2 | 0.142 |
| CASP8AP2 | 0.1328 |
| CCL13 | 0.0876 |
| CCR2_3 | 0.0225 |
| CD34_1 | 0.0161 |
| CDC42BPA_2 | 0.0272 |
| CDC42SE2_2 | 0.0196 |
| CLDN6 | 0.1135 |
| CREB5_2 | 0.0184 |
| CRYBA1 | 0.0213 |
| CXCL13 | 0.0758 |
| CYB5R3_2 | 0.1856 |
| CYP1A2 | 0.0639 |
| DBNDD2 | 0.11 |
| DNAH11 | 0.0429 |
| DNMT3L_2 | 0.0253 |
| DOCK7_1 | 0.1394 |
| DSC3_1 | 0.0741 |
| DUT_3 | 0.1195 |
| EEF1E1_1 | 0.0868 |
| EMP1 | 0.1208 |
| ENO1 | 0.1863 |
| ENPEP_2 | 0.1359 |
| EPHB1 | 0.0372 |
| EPYC | 0.0334 |
| ERI2_2 | 0.291 |
| ESPNL | 0.0381 |
| EZH2_1 | 0.0708 |
| FAM13AOS | 0.0481 |
| FAM187B_2 | 0.0111 |
| FAM70A_1 | 0.0802 |
| FBXO48_2 | 0.2657 |

TABLE 13-continued

| | |
|---|---|
| FKBP10 | 0.0668 |
| FLJ33360 | 0.0509 |
| FLJ43752 | 0.1885 |
| FMNL3_2 | 0.0431 |
| FOSB | 0.2051 |
| FOSL2 | 0.0255 |
| FOXN1 | 0.2688 |
| GAD1_2 | 0.0232 |
| GBE1 | 0.0417 |
| GBP7 | 0.13 |
| GJA5_1 | 0.0504 |
| GMNN | 0.0972 |
| GSR_2 | 0.039 |
| HBA2 | 0.2005 |
| HCFC1R1_1 | 0.057 |
| HDAC7_2 | 0.0094 |
| HDLBP_3 | 0.1087 |
| HIC1 | 0.0447 |
| HPRT1_1 | 0.1578 |
| HPS4_1 | 0.0633 |
| HR_1 | 0.044 |
| HSD11B1_1 | 0.0869 |
| ICAM2 | 0.0546 |
| ICAM4_1 | 0.2752 |
| IL1RAP_2 | 0.0543 |
| IQCA1_2 | 0.0335 |
| KCNIP3_1 | 0.1016 |
| KCNQ2_1 | 0.1265 |
| KIF3C | 0.1795 |
| KRT80_2 | 0.1093 |
| KRTAP10.10_2 | 0.0205 |
| L3MBTL2_3 | 0.0342 |
| LBH_2 | 0.1017 |
| LENEP | 0.2269 |
| LGI3 | 0.1139 |
| LOC492303 | 0.0268 |
| LRRC14B | 0.0162 |
| LRRC37A4_2 | 0.0628 |
| LRRTM4 | 0.1661 |
| MACC1 | 0.1204 |
| MANSC1_1 | 0.1385 |
| MCAM | 0.017 |
| MCART6_1 | 0.1323 |
| MFRP | 0.2186 |
| MIDN | 0.0462 |
| MIR1914 | 0.0675 |
| MIR212 | 0.1059 |
| MIR571 | 0.0359 |
| MIR576 | 0.1102 |
| MIR654 | 0.0501 |
| MIR942 | 0.1286 |
| MMP12_1 | 0.1361 |
| MYCN_2 | 0.1413 |
| MYOHD1 | 0.0935 |
| NFATC3_5 | 0.01 |
| NFATC4 | 0.0534 |
| NLRP9 | 0.1806 |
| NOVA2 | 0.1229 |
| NP | 0.096 |
| NR6A1_2 | 0.1529 |
| NRXN3_3 | 0.0972 |
| NT5DC1_2 | 0.1859 |
| NTRK2_3 | 0.0061 |
| NUP155_1 | 0.0476 |
| NYX | 0.1744 |
| ODF2_3 | 0.0079 |
| ORC1L | 0.0303 |
| OTUD7A_3 | 0.0338 |
| PANK4 | 0.061 |
| PDLIM2_2 | 0.2385 |
| PHYH_1 | 0.2011 |
| PIGA_1 | 0.0038 |
| PITX2_1 | 0.0928 |
| PKN1_3 | 0.0215 |
| PLAC9 | 0.2597 |
| PLEKHG5_5 | 0.0282 |
| PLSCR4 | 0.1709 |
| PMEPA1_4 | 0.1243 |
| PNMA5 | 0.1248 |
| PPAPDC1A | 0.1307 |
| PRAMEF5 | 0.0105 |
| PRKAA2 | 0.1351 |
| PSMC6_1 | 0.0022 |
| RAD54B_2 | 0.1795 |
| RAP1A_1 | 0.2149 |
| RARA_3 | 0.0838 |
| RARG | 0.0453 |
| RNASEK | 0.0624 |
| RNF7_1 | 0.0195 |
| ROD1_1 | 0.2162 |
| SATB2 | 0.0584 |
| SBSN | 0.0638 |
| SCXB | 0.0036 |
| SEC22C_3 | 0.1171 |
| SELENBP1 | 0.1929 |
| SERPINB2_2 | 0.0057 |
| SERPINB5 | 0.1986 |
| SFN | 0.0109 |
| SFRS4 | 0.026 |
| SHC1_3 | 0.0727 |
| SLC23A1_2 | 0.1357 |
| SLC25A34 | 0.1581 |
| SLC4A5_3 | 0.0814 |
| SLC9A10 | 0.0828 |
| SNORD93 | 0.1607 |
| SOX2_1 | 0.0799 |
| STC1 | 0.0019 |
| STC2 | 0.1301 |
| STYX_2 | 0.0482 |
| SYTL3 | 0.0065 |
| TAF15_1 | 0.0045 |
| TCEAL8_1 | 0.039 |
| THBS3 | 0.102 |
| TM2D3_2 | 0.0575 |
| TMEM52 | 0.0839 |
| TMEM62 | 0.0081 |
| TNFRSF18_1 | 0.264 |
| TNNT2_1 | 0.003 |
| TOMM20L | 0.0427 |
| TPM2_2 | 0.1768 |
| TRIM58 | 0.1104 |
| UBR7_1 | 0.0603 |
| UBR7_2 | 0.1256 |
| WARS_2 | 0.1536 |
| XBP1_2 | 0.1303 |
| XRN2_1 | 0.0463 |
| YARS2 | 0.0004 |
| ZNF75D_2 | 0.1488 |
| ZSWIM4_2 | 0.162 |
| figo_numeric | 0.0165 |
| hist_rev_SBOT | 0.0573 |
| surg_outcome | 0.0069 |

TABLE 14

| | |
|---|---|
| ABHD3 | 0.0691 |
| ADAM17_2 | 0.2301 |
| ADAMTS1 | 0.1681 |
| ALS2CL_3 | 0.1144 |
| ANO7_3 | 0.0721 |
| ARL6IP1_1 | 0.0276 |
| ARMCX3_2 | 0.0869 |
| ATXN10_1 | 0.2027 |
| AXL_1 | 0.1173 |
| BAI1_3 | 0.04 |
| BCAS1_1 | 0.3333 |
| BDNF_2 | 0.1205 |
| BMPR1A | 0.1078 |
| BTF3_3 | 0.1014 |
| C10orf116 | 0.0327 |
| C11orf24 | 0.1899 |
| C11orf49_3 | 0.1274 |
| C14orf102_2 | 0.1343 |
| C14orf109_2 | 0.0732 |
| C17orf106 | 0.244 |
| C17orf58_2 | 0.0461 |
| C17orf58_3 | 0.027 |

TABLE 14-continued

| | |
|---|---|
| C18orf56 | 0.0469 |
| C1orf168 | 0.0365 |
| C1orf64 | 0.1125 |
| C8orf79__1 | 0.0188 |
| CALD1__2 | 0.1376 |
| CASP8AP2 | 0.1369 |
| CCL13 | 0.0982 |
| CCR2__3 | 0.0247 |
| CD34__1 | 0.0027 |
| CDC42BPA__2 | 0.0175 |
| CDC42SE2__2 | 0.0274 |
| CLDN6 | 0.1012 |
| CREB5__2 | 0.022 |
| CRYBA1 | 0.0213 |
| CXCL13 | 0.0802 |
| CYB5R3__2 | 0.1887 |
| CYP1A2 | 0.0623 |
| DBNDD2 | 0.1093 |
| DNAH11 | 0.047 |
| DNMT3L__2 | 0.0249 |
| DOCK7__1 | 0.1356 |
| DSC3__1 | 0.0723 |
| DUT__3 | 0.1209 |
| EEF1E1__1 | 0.1031 |
| EIF4ENIF1 | 0.1243 |
| EMP1 | 0.1714 |
| ENO1 | 0.1384 |
| ENPEP__2 | 0.0147 |
| EPHB1 | 0.0247 |
| EPYC | 0.0331 |
| ERI2__2 | 0.3022 |
| ESPNL | 0.0445 |
| EZH2__1 | 0.069 |
| FAM13AOS | 0.0401 |
| FAM187B__2 | 0.0085 |
| FAM70A__1 | 0.0737 |
| FBXO48__2 | 0.2627 |
| FGF5__1 | 0.0708 |
| FKBP10 | 0.0415 |
| FLJ33360 | 0.2007 |
| FLJ43752 | 0.0712 |
| FMNL3__2 | 0.04 |
| FMOD | 0.2067 |
| FOSB | 0.0195 |
| FOSL2 | 0.275 |
| FOXN1 | 0.0258 |
| GAD1__2 | 0.019 |
| GBE1 | 0.0448 |
| GBP7 | 0.1269 |
| GJA5__1 | 0.0503 |
| GMNN | 0.0934 |
| GSR__2 | 0.0444 |
| HBA2 | 0.2067 |
| HCFC1R1__1 | 0.0574 |
| HDAC7__2 | 0.0057 |
| HDLBP__3 | 0.097 |
| HIC1 | 0.0395 |
| HPRT1__1 | 0.1532 |
| HPS4__1 | 0.0696 |
| HR__1 | 0.0444 |
| HSD11B1__1 | 0.0979 |
| ICAM2 | 0.0583 |
| ICAM4__1 | 0.2757 |
| IL1RAP__2 | 0.0628 |
| IQCA1__2 | 0.0279 |
| KCNIP3__1 | 0.1018 |
| KCNQ2__1 | 0.1292 |
| KIF3C | 0.1922 |
| KRT80__2 | 0.1117 |
| KRTAP10.10__2 | 0.0225 |
| L3MBTL2__3 | 0.032 |
| LBH__2 | 0.0989 |
| LENEP | 0.2252 |
| LGI3 | 0.1244 |
| LOC492303 | 0.0327 |
| LRRC14B | 0.0225 |
| LRRC37A4__2 | 0.0656 |
| LRRTM4 | 0.1751 |
| MACC1 | 0.1365 |
| MANSC1__1 | 0.1403 |
| MCAM | 0.0266 |
| MCART6__1 | 0.1474 |
| MFRP | 0.2211 |
| MIDN | 0.0471 |
| MIR1914 | 0.0636 |
| MIR212 | 0.1054 |
| MIR571 | 0.0396 |
| MIR576 | 0.1071 |
| MIR654 | 0.0564 |
| MIR942 | 0.139 |
| MMP12__1 | 0.1332 |
| MYCN__2 | 0.1428 |
| NFATC3__5 | 0.1025 |
| NFATC4 | 0.0074 |
| NLRP9 | 0.0542 |
| NOVA2 | 0.1234 |
| NP | 0.0859 |
| NR6A1__2 | 0.1562 |
| NRXN3__3 | 0.0972 |
| NT5DC1__2 | 0.1975 |
| NTRK2__3 | 0.0024 |
| NUP155__1 | 0.0631 |
| NYX | 0.1779 |
| ODF2__3 | 0.0096 |
| ORC1L | 0.0229 |
| OTUD7A__3 | 0.0364 |
| PANK4 | 0.0633 |
| PDLIM2__2 | 0.233 |
| PHYH__1 | 0.2002 |
| PIGA__1 | 0.0086 |
| PITX2__1 | 0.0912 |
| PKN1__3 | 0.0198 |
| PLAC9 | 0.2491 |
| PLEKHG5__5 | 0.0182 |
| PLSCR4 | 0.1645 |
| PMEPA1__4 | 0.1301 |
| PNMA5 | 0.1142 |
| PPAPDC1A | 0.1266 |
| PRAMEF5 | 0.0035 |
| PRKAA2 | 0.1445 |
| PSMC6__1 | 0.0097 |
| RAD54B__2 | 0.1778 |
| RAP1A__1 | 0.2138 |
| RARA__3 | 0.0826 |
| RARG | 0.0438 |
| RNASEK | 0.0706 |
| RNF7__1 | 0.0197 |
| ROD1__1 | 0.2173 |
| SATB2 | 0.0606 |
| SBSN | 0.0556 |
| SCXB | 0.0085 |
| SEC22C__3 | 0.1087 |
| SELENBP1 | 0.1865 |
| SERPINB2__2 | 0.0086 |
| SERPINB5 | 0.2043 |
| SFN | 0.0172 |
| SFRS4 | 0.0302 |
| SHC1__3 | 0.0715 |
| SLC23A1__2 | 0.1325 |
| SLC25A34 | 0.1748 |
| SLC4A5__3 | 0.0833 |
| SLC9A10 | 0.0831 |
| SNORD93 | 0.165 |
| SOX2__1 | 0.0776 |
| STC1 | 0.0081 |
| STC2 | 0.1336 |
| STYX__2 | 0.0487 |
| SYTL3 | 0.0061 |
| TAF15__1 | 0.0023 |
| TCEAL8__1 | 0.0419 |
| THBS3 | 0.103 |
| TM2D3__2 | 0.062 |
| TMEM52 | 0.083 |
| TMEM62 | 0.0104 |
| TNFRSF18__1 | 0.2692 |
| TNNT2__1 | 0.0018 |
| TOMM20L | 0.0437 |
| TPM2__2 | 0.1748 |
| TRIM58 | 0.1078 |
| UBR7__1 | 0.0702 |

TABLE 14-continued

| | |
|---|---|
| UBR7_2 | 0.1186 |
| WARS_2 | 0.1435 |
| XBP1_2 | 0.1283 |
| XRN2_1 | 0.0466 |
| YARS2 | 0.0054 |
| ZNF75D_2 | 0.1609 |
| ZSWIM4_2 | 0.1605 |
| figo_numeric | 0.0106 |
| hist_rev_SBOT | 0.0666 |
| surg_outcome | 0.0011 |

TABLE 15

| | |
|---|---|
| ABHD3 | 0.017 |
| ADAM17_2 | 0.2178 |
| ADAMTS1 | 0.1513 |
| ALS2CL_3 | 0.0869 |
| ANO7_3 | 0.0093 |
| ARL6IP1_1 | 0.039 |
| ARMCX3_2 | 0.114 |
| ATXN10_1 | 0.2204 |
| AURKA_1 | 0.107 |
| AXL_1 | 0.0976 |
| BAI1_3 | 0.2864 |
| BCAS1_1 | 0.1898 |
| BDNF_2 | 0.1284 |
| BMPR1A | 0.0733 |
| BTF3_3 | 0.0703 |
| C10orf116 | 0.046 |
| C11orf24 | 0.1475 |
| C11orf49_3 | 0.1114 |
| C14orf102_2 | 0.0717 |
| C14orf109_2 | 0.0896 |
| C17orf106 | 0.2203 |
| C17orf58_2 | 0.0689 |
| C17orf58_3 | 0.0309 |
| C18orf56 | 0.0005 |
| C1orf168 | 0.0392 |
| C1orf64 | 0.1062 |
| C8orf79_1 | 0.0099 |
| CALD1_2 | 0.14 |
| CASP8AP2 | 0.1131 |
| CCL13 | 0.0461 |
| CCR2_3 | 0.03 |
| CD34_1 | 0.0066 |
| CDC42BPA_2 | 0.0174 |
| CDC42SE2_2 | 0.0321 |
| CLDN6 | 0.1156 |
| CREB5_2 | 0.0101 |
| CRYBA1 | 0.0287 |
| CXCL13 | 0.1119 |
| CYB5R3_2 | 0.1371 |
| CYP1A2 | 0.0806 |
| DBNDD2 | 0.1056 |
| DNAH11 | 0.0465 |
| DNMT3L_2 | 0.0109 |
| DOCK7_1 | 0.0962 |
| DSC3_1 | 0.0865 |
| DUT_3 | 0.1196 |
| EEF1E1_1 | 0.1118 |
| EMP1 | 0.1077 |
| ENO1 | 0.2069 |
| ENPEP_2 | 0.1358 |
| EPHB1 | 0.04 |
| EPYC | 0.0359 |
| ERI2_2 | 0.2463 |
| ESPNL | 0.0146 |
| FAM13AOS | 0.0501 |
| FAM187B_2 | 0.0008 |
| FAM70A_1 | 0.0226 |
| FBXO482 | 0.2865 |
| FKBP10 | 0.0455 |
| FLJ33360 | 0.0508 |
| FLJ43752 | 0.1805 |
| FMNL3_2 | 0.0098 |
| FOSB | 0.2 |
| FOSL2 | 0.0571 |

TABLE 15-continued

| | |
|---|---|
| FOXN1 | 0.2266 |
| GAD1_2 | 0.0281 |
| GBE1 | 0.039 |
| GBP7 | 0.095 |
| GJA5_1 | 0.0386 |
| GMNN | 0.077 |
| GSR_2 | 0.0027 |
| HBA2 | 0.1406 |
| HCFC1R1_1 | 0.0402 |
| HDAC7_2 | 0.0238 |
| HDLBP_3 | 0.1024 |
| HIC1 | 0.032 |
| HPRT1_1 | 0.0882 |
| HPS4_1 | 0.0776 |
| HR_1 | 0.0278 |
| HSD11B1_1 | 0.1166 |
| ICAM2 | 0.0296 |
| ICAM4_1 | 0.2485 |
| IL1RAP_2 | 0.0406 |
| IQCA1_2 | 0.0634 |
| KCNIP3_1 | 0.1136 |
| KCNQ2_1 | 0.1423 |
| KIF3C | 0.1857 |
| KRT80_2 | 0.1431 |
| KRTAP10.10_2 | 0.0013 |
| L3MBTL2_3 | 0.0236 |
| LBH_2 | 0.1133 |
| LENEP | 0.1974 |
| LGI3 | 0.1402 |
| LOC492303 | 0.049 |
| LRRC14B | 0.0347 |
| LRRC37A4_2 | 0.0681 |
| LRRTM4 | 0.1938 |
| MACC1 | 0.0885 |
| MANSC1_1 | 0.1009 |
| MCAM | 0.0045 |
| MCART6_1 | 0.142 |
| MFRP | 0.2163 |
| MIDN | 0.0208 |
| MIR1914 | 0.0797 |
| MIR212 | 0.0822 |
| MIR571 | 0.0335 |
| MIR576 | 0.1208 |
| MIR654 | 0.0169 |
| MIR942 | 0.1718 |
| MMP12_1 | 0.0955 |
| MYCN_2 | 0.066 |
| MYOHD1 | 0.082 |
| NFATC3_5 | 0.0152 |
| NFATC4 | 0.0671 |
| NLRP9 | 0.1677 |
| NOVA2 | 0.0844 |
| NP | 0.1041 |
| NR6A1_2 | 0.1279 |
| NRXN3_3 | 0.0986 |
| NT5DC1_2 | 0.1927 |
| NTRK2_3 | 0.007 |
| NUP155_1 | 0.0258 |
| NYX | 0.1517 |
| ODF2_3 | 0.031 |
| ORC1L | 0.0202 |
| OTUD7A_3 | 0.0067 |
| PANKA | 0.0503 |
| PDLIM2_2 | 0.2085 |
| PHYH_1 | 0.1832 |
| PIGA_1 | 0.0184 |
| PITX2_1 | 0.1464 |
| PKN1_3 | 0.0467 |
| PLAC9 | 0.201 |
| PLEKHG5_5 | 0.0054 |
| PLSCR4 | 0.1996 |
| PMEPA1_4 | 0.1614 |
| PNMA5 | 0.1364 |
| PPAPDC1A | 0.1327 |
| PRAMEF5 | 0.0077 |
| PRKAA2 | 0.0733 |
| PSMC6_1 | 0.0126 |
| RAD54B_2 | 0.1822 |
| RAP1A_1 | 0.1883 |
| RARA_3 | 0.0844 |

TABLE 15-continued

| | |
|---|---|
| RARG | 0.0525 |
| RNASEK | 0.0791 |
| RNF7_1 | 0.074 |
| ROD1_1 | 0.1579 |
| SATB2 | 0.0435 |
| SBSN | 0.0119 |
| SCXB | 0.0168 |
| SEC22C_3 | 0.1048 |
| SELENBP1 | 0.1497 |
| SERPINB2_2 | 0.0248 |
| SERPINB5 | 0.1755 |
| SFN | 0.0234 |
| SFRS4 | 0.041 |
| SHC1_3 | 0.0616 |
| SLC23A1_2 | 0.0775 |
| SLC25A34 | 0.1748 |
| SLC4A5_3 | 0.0545 |
| SLC9A10 | 0.0644 |
| SNORD93 | 0.1602 |
| SOX2_1 | 0.0722 |
| STC1 | 0.017 |
| STC2 | 0.1174 |
| STYX_2 | 0.0447 |
| SYTL3 | 0.0231 |
| TAF15_1 | 0.0384 |
| TCEAL8_1 | 0.0641 |
| THBS3 | 0.0535 |
| TM2D3_2 | 0.0597 |
| TMEM52 | 0.0905 |
| TMEM62 | 0.0353 |
| TNFRSF18_1 | 0.2073 |
| TNNT2_1 | 0.0036 |
| TOMM20L | 0.0199 |
| TPM2_2 | 0.1779 |
| TRIM58 | 0.0972 |
| UBR7_1 | 0.0564 |
| UBR7_2 | 0.1055 |
| WARS_2 | 0.1344 |
| WDR76 | 0.1029 |
| XBP1_2 | 0.0411 |
| XRN2_1 | 0.0238 |
| YARS2 | 0.2448 |
| ZNF75D_2 | 0.1373 |
| ZSWIM4_2 | 0.1486 |
| figo_numeric | 0.0116 |
| hist_rev_SBOT | 0.0544 |
| surg_outcome | 0.0173 |

TABLE 16

| | |
|---|---|
| ABHD3 | 0.0747 |
| ADAM17_2 | 0.2317 |
| ADAMTS1 | 0.1658 |
| ALS2CL_3 | 0.0808 |
| ANO7_3 | 0.0363 |
| ARL6IP1_1 | 0.0278 |
| ARMCX3_2 | 0.0847 |
| ATXN10_1 | 0.1749 |
| AXL_1 | 0.1004 |
| BAI1_3 | 0.0291 |
| BCAS1_2 | 0.3377 |
| BDNF_2 | 0.082 |
| BMPR1A | 0.1275 |
| BTF3_3 | 0.1258 |
| C10orf116 | 0.009 |
| C11orf24 | 0.1986 |
| C11orf49_3 | 0.1205 |
| C14orf102_2 | 0.1068 |
| C14orf109_2 | 0.0823 |
| C17orf106 | 0.2146 |
| C17orf58_2 | 0.0416 |
| C17orf58_3 | 0.0174 |
| C18orf56 | 0.0652 |
| C1orf168 | 0.0495 |
| C1orf64 | 0.11 |
| C8orf79_1 | 0.024 |
| CALD1_2 | 0.1349 |

TABLE 16-continued

| | |
|---|---|
| CASP8AP2 | 0.1386 |
| CCL13 | 0.0976 |
| CCR2_3 | 0.042 |
| CD34 | 0.0276 |
| CDC42BPA_2 | 0.0327 |
| CDC42SE2_2 | 0.0358 |
| CLDN6 | 0.1204 |
| CREB5_2 | 0.0007 |
| CRYBA1 | 0.0133 |
| CXCL13 | 0.0859 |
| CYB5R3_2 | 0.1771 |
| CYP1A2 | 0.0533 |
| DBNDD2 | 0.1028 |
| DNAH11 | 0.046 |
| DNMT3L_2 | 0.0307 |
| DOCK7_1 | 0.1517 |
| DSC3_1 | 0.0958 |
| DUT_3 | 0.1344 |
| EEF1E1_1 | 0.1017 |
| EMP1 | 0.1196 |
| ENO1 | 0.1976 |
| ENPEP_2 | 0.1452 |
| EPHB1 | 0.0422 |
| EPYC | 0.0263 |
| ERI2_2 | 0.3104 |
| ESPNL | 0.0371 |
| EZH2_1 | 0.0793 |
| FAM13AOS | 0.0488 |
| FAM187B_2 | 0.003 |
| FAM70A_1 | 0.0692 |
| FBXO48_2 | 0.2424 |
| FKBP10 | 0.0708 |
| FLJ33360 | 0.0337 |
| FLJ43752 | 0.1703 |
| FMNL3_2 | 0.0497 |
| FOSB | 0.1989 |
| FOSL2 | 0.0207 |
| FOXN1 | 0.2588 |
| GAD1_2 | 0.011 |
| GBE1 | 0.052 |
| GBP7 | 0.1297 |
| GJA5_1 | 0.0608 |
| GMNN | 0.0927 |
| GSR_2 | 0.0347 |
| HBA2 | 0.1888 |
| HCFC1R1_1 | 0.0557 |
| HDAC7_2 | 0.0085 |
| HDLBP_3 | 0.08 |
| HIC1 | 0.0079 |
| HPRT1_1 | 0.1413 |
| HPS4_1 | 0.0578 |
| HR_1 | 0.0683 |
| HSD11B1_1 | 0.0791 |
| ICAM2 | 0.0553 |
| ICAM4_1 | 0.2718 |
| IL1RAP_2 | 0.0666 |
| IQCA1_2 | 0.0458 |
| KCNIP3_1 | 0.1062 |
| KCNQ2_1 | 0.1298 |
| KIF3C | 0.1888 |
| KRT80_2 | 0.1043 |
| KRTAP10.10_2 | 0.0252 |
| L3MBTL2_3 | 0.0224 |
| LBH_2 | 0.1201 |
| LENEP | 0.2267 |
| LGI3 | 0.0942 |
| LOC492303 | 0.0283 |
| LRRC14B | 0.002 |
| LRRC37A4_2 | 0.0748 |
| LRRTM4 | 0.1456 |
| MACC1 | 0.1269 |
| MANSC1_1 | 0.1122 |
| MCAM | 0.0051 |
| MCART6_1 | 0.1513 |
| MFRP | 0.2472 |
| MIDN | 0.0353 |
| MIR1914 | 0.0721 |
| MIR212 | 0.1101 |
| MIR571 | 0.0105 |
| MIR576 | 0.1185 |

TABLE 16-continued

| | |
|---|---|
| MIR654 | 0.0532 |
| MIR942 | 0.1205 |
| MMP12_1 | 0.1358 |
| MYCN_2 | 0.1492 |
| MYOHD1 | 0.0898 |
| NFATC3_5 | 0.0112 |
| NFATC4 | 0.0474 |
| NLRP9 | 0.1736 |
| NOVA2 | 0.1253 |
| NP | 0.1082 |
| NR6A1_2 | 0.1415 |
| NRXN3_3 | 0.1 |
| NT5DC1_2 | 0.1905 |
| NTRK2_3 | 0.0049 |
| NUP155_1 | 0.0442 |
| NYX | 0.169 |
| ODF2_3 | 0.0024 |
| ORC1L | 0.0312 |
| OTUD7A_3 | 0.024 |
| PANK4 | 0.0574 |
| PDLIM2_2 | 0.2424 |
| PHYH_1 | 0.2254 |
| PIGA_1 | 0.0076 |
| PITX2_1 | 0.1073 |
| PKN1_3 | 0.0335 |
| PLAC9 | 0.255 |
| PLEKHG5_5 | 0.0223 |
| PLSCR4 | 0.1482 |
| PMEPA1_4 | 0.1317 |
| PNMA5 | 0.1286 |
| PPAPDC1A | 0.1167 |
| PRAMEF5 | 0.0087 |
| PRKAA2 | 0.1363 |
| PSMC6_1 | 0.0136 |
| RAD54B_2 | 0.171 |
| RAP1A_1 | 0.2223 |
| RARA_3 | 0.0814 |
| RARG | 0.0542 |
| RNASEK | 0.0725 |
| RNF7_1 | 0.0007 |
| ROD1_1 | 0.2151 |
| SATB2 | 0.0497 |
| SBSN | 0.0558 |
| SCXB | 0.0084 |
| SEC22C_3 | 0.115 |
| SELENBP1 | 0.1832 |
| SERPINB2_2 | 0.0166 |
| SERPINB5 | 0.2045 |
| SFN | 0.0067 |
| SFRS4 | 0.0454 |
| SHC1_3 | 0.0867 |
| SLC23A1_2 | 0.1344 |
| SLC25A34 | 0.1652 |
| SLC4A5_3 | 0.077 |
| SLC9A10 | 0.0804 |
| SNORD93 | 0.1576 |
| SOX2_1 | 0.0576 |
| STC1 | 0.0072 |
| STC2 | 0.1268 |
| STYX_2 | 0.0469 |
| SYTL3 | 0.0415 |
| TAF15_1 | 0.0093 |
| TCEAL8_1 | 0.0306 |
| THBS3 | 0.1029 |
| TM2D3_2 | 0.0536 |
| TMEM52 | 0.0764 |
| TMEM62 | 0.0115 |
| TNFRSF18_1 | 0.2552 |
| TNNT2_1 | 0.0025 |
| TOMM20L | 0.0431 |
| TPM2_2 | 0.1772 |
| TRIM58 | 0.0949 |
| UBR7_1 | 0.0817 |
| UBR7_2 | 0.1309 |
| WARS_2 | 0.1811 |
| XBP1_2 | 0.1364 |
| XRN2_1 | 0.0408 |
| YARS2 | 0.0021 |
| ZNF75D_2 | 0.1606 |
| ZSWIM4_2 | 0.1737 |
| figo_numeric | 0.0311 |
| hist_rev_SBOT | 0.0587 |
| surg_outcome | 0.0173 |

TABLE 17

| | |
|---|---|
| ABHD3 | 0.0849 |
| ADAM17_2 | 0.2224 |
| ADAMTS1 | 0.1657 |
| ALS2CL_3 | 0.1006 |
| ANO7_3 | 0.0182 |
| ARL6IP1_1 | 0.0285 |
| ARMCX3_2 | 0.0788 |
| ATXN10_1 | 0.145 |
| AXL_1 | 0.0852 |
| BAI1_3 | 0.0498 |
| BCAS1_2 | 0.3253 |
| BDNF_2 | 0.0542 |
| BMPR1A | 0.1279 |
| BTF3_3 | 0.1219 |
| C10orf116 | 0.0347 |
| C11orf24 | 0.135 |
| C11orf49_3 | 0.1129 |
| C14orf102_2 | 0.0886 |
| C14orf109_2 | 0.0653 |
| C17orf106 | 0.186 |
| C17orf58_2 | 0.0173 |
| C17orf58_3 | 0.0224 |
| C18orf56 | 0.069 |
| C1orf168 | 0.0417 |
| C1orf64 | 0.0966 |
| C8orf79_1 | 0.0556 |
| CALD1_2 | 0.1387 |
| CASP8AP2 | 0.1287 |
| CCL13 | 0.129 |
| CCR2_3 | 0.0384 |
| CD34_1 | 0.0467 |
| CDC42BPA_2 | 0.0402 |
| CDC42SE2_2 | 0.0171 |
| CLDN6 | 0.1193 |
| CREB5_2 | 0.0082 |
| CREBBP_1 | 0.0336 |
| CRYBA1 | 0.0946 |
| CXCL13 | 0.1656 |
| CYB5R3_2 | 0.1641 |
| CYP1A2 | 0.0445 |
| DBNDD2 | 0.0769 |
| DFFB_2 | 0.0489 |
| DNAH11 | 0.0361 |
| DNMT3L_2 | 0.1396 |
| DOCK7_1 | 0.0392 |
| DSC3_1 | 0.0815 |
| DUT_3 | 0.1487 |
| EEF1E1_1 | 0.0939 |
| EMP1 | 0.1023 |
| ENO1 | 0.1574 |
| ENPEP_2 | 0.123 |
| EPHB1 | 0.0441 |
| EPYC | 0.0215 |
| ERI2_2 | 0.3043 |
| ESPNL | 0.0812 |
| EZH2_1 | 0.0696 |
| FAM13AOS | 0.0348 |
| FAM187B_2 | 0.0133 |
| FAM70A_1 | 0.1001 |
| FBXO48_2 | 0.1998 |
| FKBP10 | 0.1051 |
| FLJ33360 | 0.0309 |
| FLJ43752 | 0.1597 |
| FMNL3_2 | 0.0093 |
| FOSB | 0.1793 |
| FOSL2 | 0.0245 |
| FOXN1 | 0.2707 |
| GAD1_2 | 0.0169 |
| GBE1 | 0.0579 |
| GBP7 | 0.096 |
| GJA5_1 | 0.0592 |

TABLE 17-continued

| | |
|---|---|
| GMNN | 0.0831 |
| GSR_2 | 0.0323 |
| GUSBL2 | 0.1796 |
| HBA2 | 0.0535 |
| HDAC7_2 | 0.0236 |
| HDLBP_3 | 0.2023 |
| HIC1 | 0.0583 |
| HPRT1_1 | 0.1415 |
| HPS4_1 | 0.0392 |
| HR_1 | 0.0907 |
| HSD11B1_1 | 0.078 |
| ICAM2 | 0.0379 |
| ICAM4_1 | 0.2654 |
| IL1RAP_2 | 0.0582 |
| IQCA1_2 | 0.0154 |
| KCNIP3_1 | 0.0947 |
| KCNQ2_1 | 0.1368 |
| KIF3C | 0.2001 |
| KRT80_2 | 0.0777 |
| KRTAP10.10_2 | 0.017 |
| L3MBTL2_3 | 0.0297 |
| LBH_2 | 0.115 |
| LENEP | 0.227 |
| LGI3 | 0.108 |
| LOC492303 | 0.0652 |
| LRRC14B | 0.0074 |
| LRRC37A4_2 | 0.0756 |
| LRRTM4 | 0.1404 |
| MACC1 | 0.1261 |
| MANSC1_1 | 0.1005 |
| MAPK3_1 | 0.0421 |
| MCAM | 0.1193 |
| MCART6_1 | 0.245 |
| MFRP | 0.0322 |
| MIDN | 0.0405 |
| MIR1914 | 0.0603 |
| MIR212 | 0.105 |
| MIR571 | 0.0175 |
| MIR576 | 0.0932 |
| MIR654 | 0.0046 |
| MIR942 | 0.0898 |
| MMP12_1 | 0.1345 |
| MYCN_2 | 0.1567 |
| MYOHD1 | 0.0838 |
| NFATC3_5 | 0.0215 |
| NFATC4 | 0.0458 |
| NLRP9 | 0.1584 |
| NOVA2 | 0.0925 |
| NP | 0.0944 |
| NR6A1_2 | 0.1293 |
| NRXN3_3 | 0.0854 |
| NT5DC1_2 | 0.2065 |
| NTRK2_3 | 0.0069 |
| NUP155_1 | 0.0424 |
| NYX | 0.1168 |
| ODF2_3 | 0.0324 |
| ORC1L | 0.0686 |
| OTUD7A_3 | 0.0408 |
| PANKA | 0.0531 |
| PDLIM2_2 | 0.2123 |
| PHYH_1 | 0.2441 |
| PIGA_1 | 0.0191 |
| PITX2_1 | 0.1065 |
| PKN1_3 | 0.0469 |
| PLAC9 | 0.2449 |
| PLEKHG5_5 | 0.012 |
| PLSCR4 | 0.1373 |
| PMEPA1_4 | 0.1187 |
| PNMA5 | 0.1309 |
| PPAPDC1A | 0.1066 |
| PRAMEF5 | 0.0252 |
| PRKAA2 | 0.1312 |
| PSMC6_1 | 0.0277 |
| RAD54B_2 | 0.194 |
| RAP1A_1 | 0.2216 |
| RARA_3 | 0.0738 |
| RARG | 0.0353 |
| RNASEK | 0.0754 |
| RNF7_1 | 0.0307 |
| ROD1_1 | 0.215 |

TABLE 17-continued

| | |
|---|---|
| SATB2 | 0.0451 |
| SBSN | 0.0509 |
| SCXB | 0.0046 |
| SEC22C_3 | 0.107 |
| SELENBP1 | 0.187 |
| SERPINB2_2 | 0 |
| SERPINB5 | 0.2241 |
| SFN | 0.0073 |
| SFRS4 | 0.061 |
| SHC1_3 | 0.0821 |
| SLC23A1_2 | 0.0993 |
| SLC25A34 | 0.1422 |
| SLC4A5_3 | 0.0807 |
| SLC9A10 | 0.0695 |
| SNORD93 | 0.1626 |
| SOX2_1 | 0.0384 |
| STC1 | 0.0055 |
| STC2 | 0.0906 |
| STYX_2 | 0.06 |
| SYTL3 | 0.0395 |
| TAF15_1 | 0.0068 |
| TCEAL8_1 | 0.0377 |
| THBS3 | 0.0909 |
| TM2D3_2 | 0.0473 |
| TMEM52 | 0.0514 |
| TMEM62 | 0.0034 |
| TNFRSF18_1 | 0.2597 |
| TNNT2_1 | 0.0028 |
| TOMM20L | 0.0343 |
| TPM2_2 | 0.1535 |
| TRIM58 | 0.0861 |
| UBR7_1 | 0.0507 |
| UBR7_2 | 0.1277 |
| WARS_2 | 0.1917 |
| XBP1_2 | 0.1677 |
| XRN2_1 | 0.0257 |
| YARS2 | 0.0047 |
| ZNF75D_2 | 0.1573 |
| ZSWIM4_2 | 0.1616 |
| figo_numeric | 0.0422 |
| hist_rev_SBOT | 0.0621 |
| surg_outcome | 0.017 |

TABLE 18

| | |
|---|---|
| ABHD3 | 0.0358 |
| ADAM17_2 | 0.2175 |
| ADAMTS1 | 0.1475 |
| ALS2CL_3 | 0.0718 |
| ANO7_3 | 0.0026 |
| ARL6IP1_1 | 0.0301 |
| ARMCX3_2 | 0.1154 |
| ATXN10_1 | 0.2003 |
| AURKA_1 | 0.097 |
| AXL_1 | 0.098 |
| BAI1_3 | 0.2848 |
| BCAS1_2 | 0.1934 |
| BDNF_2 | 0.1042 |
| BMPR1A | 0.0773 |
| BTF3_3 | 0.1061 |
| C10orf116 | 0.0394 |
| C11orf24 | 0.1559 |
| C11orf49_3 | 0.1075 |
| C14orf102_2 | 0.061 |
| C14orf109_2 | 0.0944 |
| C17orf106 | 0.2116 |
| C17orf58_2 | 0.0678 |
| C17orf58_3 | 0.0153 |
| C18orf56 | 0.0143 |
| C1orf168 | 0.0481 |
| C1orf64 | 0.1025 |
| C8orf79_1 | 0.0143 |
| CALD1_2 | 0.1427 |
| CASP8AP2 | 0.1075 |
| CCL13 | 0.0573 |
| CCR2_3 | 0.0416 |
| CD34_1 | 0.0012 |

TABLE 18-continued

| | |
|---|---|
| CDC42BPA__2 | 0.0142 |
| CDC42SE2__2 | 0.0393 |
| CLDN6 | 0.1119 |
| CREB5__2 | 0.0003 |
| CRYBA1 | 0.0128 |
| CXCL13 | 0.1187 |
| CYB5R3__2 | 0.1309 |
| CYP1A2 | 0.0741 |
| DBNDD2 | 0.098 |
| DNAH11 | 0.0412 |
| DNMT3L__2 | 0.0177 |
| DOCK7__1 | 0.1137 |
| DSC3__1 | 0.1013 |
| DUT__3 | 0.1326 |
| EEF1E1__1 | 0.1225 |
| EMP1 | 0.1073 |
| ENO1 | 0.2154 |
| ENPEP__2 | 0.1391 |
| EPHB1 | 0.0.37 |
| EPYC | 0.0317 |
| ERI2__2 | 0.2626 |
| ESPNL | 0.0144 |
| FAM13AOS | 0.0531 |
| FAM187B__2 | 0.0063 |
| FAM70A__1 | 0.0312 |
| FBXO48__2 | 0.2751 |
| FKBP10 | 0.0421 |
| FLJ33360 | 0.0369 |
| FLJ43752 | 0.1619 |
| FMNL3__2 | 0.0038 |
| FOSB | 0.2003 |
| FOSL2 | 0.0605 |
| FOXN1 | 0.2122 |
| GAD1__2 | 0.0339 |
| GBE1 | 0.0371 |
| GBP7 | 0.1079 |
| GJA5__1 | 0.0488 |
| GMNN | 0.0748 |
| GSR__2 | 0.0024 |
| HBA2 | 0.1338 |
| HCFC1R1__1 | 0.0335 |
| HDAC7__2 | 0.0236 |
| HDLBP__3 | 0.0856 |
| HIC1 | 0.0437 |
| HPRT1__1 | 0.0759 |
| HPS4__1 | 0.0729 |
| HR__1 | 0.0355 |
| HSD11B1__1 | 0.1016 |
| ICAM2 | 0.0264 |
| ICAM4__1 | 0.2407 |
| IL1RAP__2 | 0.0502 |
| IQCA1__2 | 0.0688 |
| KCNIP3__1 | 0.121 |
| KCNQ2__1 | 0.1444 |
| KIF3C | 0.1813 |
| KRT80__2 | 0.1373 |
| KRTAP10.10__2 | 0.0006 |
| L3MBTL2__3 | 0.0243 |
| LBH__2 | 0.1357 |
| LENEP | 0.1929 |
| LGI3 | 0.1337 |
| LOC492303 | 0.0623 |
| LRRC14B | 0.0203 |
| LRRC37A4__2 | 0.0692 |
| LRRTM4 | 0.1867 |
| MACC1 | 0.0958 |
| MANSC1__1 | 0.0871 |
| MCAM | 0.0151 |
| MCART6__1 | 0.1587 |
| MFRP | 0.2311 |
| MIDN | 0.0149 |
| MIR1914 | 0.0871 |
| MIR212 | 0.0853 |
| MIR571 | 0.0262 |
| MIR576 | 0.1224 |
| MIR654 | 0.0165 |
| MIR942 | 0.1649 |
| MMP12__1 | 0.0964 |
| MYCN__2 | 0.0799 |
| MYOHD1 | 0.0809 |
| NFATC3__5 | 0.0184 |
| NFATC4 | 0.0587 |
| NLRP9 | 0.1608 |
| NOVA2 | 0.0823 |
| NP | 0.1078 |
| NR6A1__2 | 0.1216 |
| NRXN3__3 | 0.0929 |
| NT5DC1__2 | 0.1956 |
| NTRK2__3 | 0.0019 |
| NUP155__1 | 0.0124 |
| NYX | 0.1302 |
| ODF2__3 | 0.0364 |
| ORC1L | 0.0235 |
| OTUD7A__3 | 0.0004 |
| PANK4 | 0.0478 |
| PDLIM2__2 | 0.2134 |
| PHYH__1 | 0.1987 |
| PIGA__1 | 0.0208 |
| PITX2__1 | 0.1588 |
| PKN1__3 | 0.0585 |
| PLAC9 | 0.1971 |
| PLEKHG5__5 | 0.0088 |
| PLSCR4 | 0.1785 |
| PMEPA1__4 | 0.1644 |
| PNMA5 | 0.1479 |
| PPAPDC1A | 0.1292 |
| PRAMEF5 | 0.0158 |
| PRKAA2 | 0.0749 |
| PSMC6__1 | 0.0165 |
| RAD54B__2 | 0.1786 |
| RAP1A__1 | 0.1964 |
| RARA__3 | 0.0843 |
| RARG | 0.0599 |
| RNASEK | 0.086 |
| RNF7__1 | 0.0603 |
| ROD1__1 | 0.1465 |
| SATB2 | 0.0455 |
| SBSN | 0.0009 |
| SCXB | 0.0096 |
| SEC22C__3 | 0.1034 |
| SELENBP1 | 0.1436 |
| SERPINB2__2 | 0.0398 |
| SERPINB5 | 0.182 |
| SFN | 0.0272 |
| SFRS4 | 0.0202 |
| SHC1__3 | 0.0728 |
| SLC23A1__2 | 0.0726 |
| SLC25A34 | 0.1777 |
| SLC4A5__3 | 0.0493 |
| SLC9A10 | 0.0661 |
| SNORD93 | 0.1527 |
| SOX2__1 | 0.064 |
| STC1 | 0.0261 |
| STC2 | 0.11 |
| STYX__2 | 0.0508 |
| SYTL3 | 0.0402 |
| TAF15__1 | 0.039 |
| TCEAL8__1 | 0.0633 |
| THBS3 | 0.0541 |
| TM2D3__2 | 0.0553 |
| TMEM52 | 0.0882 |
| TMEM62 | 0.0349 |
| TNFRSF18__1 | 0.1996 |
| TNNT2__1 | 0.0012 |
| TOMM20L | 0.0207 |
| TPM2__2 | 0.1747 |
| TRIM58 | 0.0846 |
| UBR7__1 | 0.0724 |
| UBR7__2 | 0.1081 |
| WARS__2 | 0.1504 |
| WDR76 | 0.1055 |
| XBP1__2 | 0.0507 |
| XRN2__1 | 0.0154 |
| YARS2 | 0.2493 |
| ZNF75D__2 | 0.1434 |
| ZSWIM4__2 | 0.1542 |
| figo__numeric | 0.017 |
| hist__rev__SBOT | 0.0598 |
| surg__outcome | 0.0325 |

TABLE 19

| Gene | Value |
|---|---|
| ABHD3 | 0.0867 |
| ADAM17_2 | 0.2243 |
| ADAMTS1 | 0.1794 |
| ALS2CL_3 | 0.1263 |
| ANO7_3 | 0.0411 |
| ARL6IP1_1 | 0.0351 |
| ARMCX3_2 | 0.0851 |
| ATXN10_1 | 0.1618 |
| AXL_1 | 0.0848 |
| BAI1_3 | 0.0502 |
| BCAS1_1 | 0.3153 |
| BDNF_2 | 0.0933 |
| BMPR1A | 0.117 |
| BTF3_3 | 0.1172 |
| C10orf116 | 0.0561 |
| C11orf24 | 0.1261 |
| C11orf49_3 | 0.1216 |
| C14orf102_2 | 0.1004 |
| C14orf109_2 | 0.0679 |
| C17orf106 | 0.2023 |
| C17orf58_2 | 0.0266 |
| C17orf58_3 | 0.0287 |
| C18orf56 | 0.0405 |
| C1orf168 | 0.0309 |
| C1orf64 | 0.1031 |
| C8orf79_1 | 0.0769 |
| CALD1_2 | 0.1442 |
| CASP8AP2 | 0.1236 |
| CCL13 | 0.1216 |
| CCR2_3 | 0.0345 |
| CD34_1 | 0.0393 |
| CDC42BPA_2 | 0.0358 |
| CDC42SE2_2 | 0.0007 |
| CLDN6 | 0.1183 |
| CREB5_2 | 0.0028 |
| CREBBP_1 | 0.0384 |
| CRYBA1 | 0.0852 |
| CXCL13 | 0.1743 |
| CYB5R3_2 | 0.1549 |
| CYP1A2 | 0.0615 |
| DBNDD2 | 0.0776 |
| DFFB_2 | 0.0471 |
| DNAH11 | 0.0366 |
| DNMT3L_2 | 0.1082 |
| DOCK7_1 | 0.0236 |
| DSC3_1 | 0.0613 |
| DUT_3 | 0.1296 |
| EEF1E1_1 | 0.0553 |
| EMP1 | 0.1035 |
| ENO1 | 0.1501 |
| ENPEP_2 | 0.1261 |
| EPHB1 | 0.039 |
| EPYC | 0.0286 |
| ERI2_2 | 0.2795 |
| ESPNL | 0.0821 |
| EZH2_1 | 0.0578 |
| FAM13AOS | 0.0376 |
| FAM187B_2 | 0.0233 |
| FAM70A_1 | 0.1041 |
| FBXO48_2 | 0.2125 |
| FKBP10 | 0.1071 |
| FLJ33360 | 0.0473 |
| FLJ43752 | 0.1767 |
| FMNL3_2 | 0.0002 |
| FOSB | 0.183 |
| FOSL2 | 0.0192 |
| FOXN1 | 0.2739 |
| GAD1_2 | 0.0157 |
| GBE1 | 0.0527 |
| GBP7 | 0.0937 |
| GJA5_1 | 0.0517 |
| GMNN | 0.0868 |
| GSR_2 | 0.0316 |
| GUSBL2 | 0.1966 |
| HBA2 | 0.0744 |
| HDAC7_2 | 0.0462 |
| HDLBP_3 | 0.2167 |
| HIC1 | 0.0817 |
| HPRT1_1 | 0.153 |
| HPS4_1 | 0.0374 |
| HR_1 | 0.0572 |
| HSD11B1_1 | 0.0885 |
| ICAM2 | 0.0476 |
| ICAM4_1 | 0.2756 |
| IL1RAP_2 | 0.0478 |
| IQCA1_2 | 0.0159 |
| KCNIP3_1 | 0.0903 |
| KCNQ2_1 | 0.1439 |
| KIF3C | 0.1887 |
| KRT80_2 | 0.0722 |
| KRTAP10.10_2 | 0.007 |
| L3MBTL2_3 | 0.0389 |
| LBH_2 | 0.1057 |
| LENEP | 0.2159 |
| LGI3 | 0.1292 |
| LOC492303 | 0.054 |
| LRRC14B | 0.0258 |
| LRRC37A4_2 | 0.0709 |
| LRRTM4 | 0.1619 |
| MACC1 | 0.1254 |
| MANSC1_1 | 0.1334 |
| MCAM | 0.0693 |
| MCART6_1 | 0.1011 |
| MFRP | 0.2146 |
| MIDN | 0.0485 |
| MIR1914 | 0.063 |
| MIR212 | 0.0949 |
| MIR571 | 0.007 |
| MIR576 | 0.097 |
| MIR654 | 0.0006 |
| MIR942 | 0.107 |
| MMP12_1 | 0.135 |
| MYCN_2 | 0.1539 |
| MYOHD1 | 0.0868 |
| NFATC3_5 | 0.0261 |
| NFATC4 | 0.0564 |
| NLRP9 | 0.159 |
| NOVA2 | 0.0939 |
| NP | 0.0856 |
| NR6A1_2 | 0.1322 |
| NRXN3_3 | 0.0775 |
| NT5DC1_2 | 0.2081 |
| NTRK2_3 | 0.0021 |
| NUP155_1 | 0.0426 |
| NYX | 0.1089 |
| ODF2_3 | 0.031 |
| ORC1L | 0.0606 |
| OTUD7A_3 | 0.0437 |
| PANK4 | 0.0523 |
| PDLIM2_2 | 0.2126 |
| PHYH_1 | 0.2226 |
| PIGA_1 | 0.0139 |
| PITX2_1 | 0.0894 |
| PKN1_3 | 0.0564 |
| PLAC9 | 0.2581 |
| PLEKHG5_5 | 0.0187 |
| PLSCR4 | 0.16 |
| PMEPA1_4 | 0.112 |
| PNMA5 | 0.1346 |
| PPAPDC1A | 0.1058 |
| PRAMEF5 | 0.0239 |
| PRKAA2 | 0.1246 |
| PSMC6_1 | 0.0096 |
| RAD54B_2 | 0.1877 |
| RAP1A_1 | 0.212 |
| RARA_3 | 0.0857 |
| RARG | 0.017 |
| RNASEK | 0.0678 |
| RNF7_1 | 0.0169 |
| ROD1_1 | 0.2162 |
| SATB2 | 0.054 |
| SBSN | 0.0626 |
| SCXB | 0.002 |
| SEC22C_3 | 0.1031 |
| SELENBP1 | 0.1888 |
| SERPINB2_2 | 0.006 |
| SERPINB5 | 0.2102 |
| SFN | 0.0075 |
| SFRS4 | 0.0402 |
| SHC1_3 | 0.0816 |

TABLE 19-continued

| | |
|---|---|
| SLC23A1__2 | 0.0991 |
| SLC25A34 | 0.1145 |
| SLC4A5__3 | 0.0837 |
| SLC9A10 | 0.0845 |
| SNORD93 | 0.1611 |
| SOX2__1 | 0.0554 |
| STC1 | 0.0034 |
| STC2 | 0.087 |
| STYX__2 | 0.0552 |
| SYTL3 | 0.0023 |
| TAF15__1 | 0.0001 |
| TCEAL8__1 | 0.0511 |
| THBS3 | 0.0877 |
| TM2D3__2 | 0.0459 |
| TMEM52 | 0.0589 |
| TMEM62 | 0.0064 |
| TNFRSF18__1 | 0.2544 |
| TNNT2__1 | 0.0027 |
| TOMM20L | 0.0407 |
| TPM2__2 | 0.1518 |
| TRIM58 | 0.111 |
| UBR7__1 | 0.0246 |
| UBR7__2 | 0.1237 |
| WARS__2 | 0.1836 |
| XBP1__2 | 0.1624 |
| XRN2__1 | 0.0277 |
| YARS2 | 0.0053 |
| ZNF75D__2 | 0.1444 |
| ZSWIM4__2 | 0.157 |
| figo__numeric | 0.0381 |
| hist__rev__SBOT | 0.0579 |
| surg__outcome | 0.0071 |

TABLE 20

| | |
|---|---|
| ABHD3 | 0.0624 |
| ADAM17__2 | 0.2343 |
| ADAMTS1 | 0.1768 |
| ALS2CL__3 | 0.1061 |
| ANO7__3 | 0.0694 |
| ARL6IP1__1 | 0.037 |
| ARMCX3__2 | 0.0811 |
| ATXN10__1 | 0.2064 |
| AXL__1 | 0.1046 |
| BAI1__3 | 0.0284 |
| BCAS1__1 | 0.3214 |
| BDNF__2 | 0.1134 |
| BMPR1A | 0.11 |
| BTF33 | 0.1052 |
| C10orf116 | 0.0302 |
| C11orf24 | 0.1733 |
| C11orf49__3 | 0.1351 |
| C14orf102__2 | 0.1246 |
| C14orf109__2 | 0.0694 |
| C17orf106 | 0.2355 |
| C17orf58__2 | 0.0328 |
| C17orf58__3 | 0.0253 |
| C18orf56 | 0.0356 |
| C1orf168 | 0.0309 |
| C1orf64 | 0.1075 |
| C8orf79__1 | 0.021 |
| CASP8AP2 | 0.141 |
| CCL13 | 0.146 |
| CCR2__3 | 0.0827 |
| CD34__1 | 0.0204 |
| CDC42BPA__2 | 0.0281 |
| CDC42SE2__2 | 0.0175 |
| CLDN6 | 0.1155 |
| CREB5__2 | 0.0101 |
| CRYBA1 | 0.0182 |
| CXCL13 | 0.0736 |
| CYB5R3__2 | 0.1819 |
| CYP1A2 | 0.0568 |
| DBNDD2 | 0.1052 |
| DNAH11 | 0.0467 |
| DNMT3L__2 | 0.0206 |
| DOCK7__1 | 0.1317 |

TABLE 20-continued

| | |
|---|---|
| DSC3__1 | 0.0661 |
| DUT__3 | 0.121 |
| EEF1E1__1 | 0.0871 |
| EMP1 | 0.1112 |
| ENO1 | 0.1821 |
| ENPEP__2 | 0.1326 |
| EPHB1 | 0.0452 |
| EPYC | 0.0338 |
| ERI2__2 | 0.2957 |
| ESPNL | 0.0367 |
| EZH2__1 | 0.0785 |
| FAM13AOS | 0.0433 |
| FAM187B__2 | 0.0131 |
| FAM70A__1 | 0.0792 |
| FBXO48__2 | 0.2631 |
| FKBP10 | 0.0694 |
| FLJ33360 | 0.0483 |
| FLJ43752 | 0.1925 |
| FMNL3__2 | 0.0428 |
| FOSB | 0.1926 |
| FOSL2 | 0.0287 |
| FOXN1 | 0.261 |
| GAD1__2 | 0.0214 |
| GBE1 | 0.0453 |
| GBP7 | 0.133 |
| GJA5__1 | 0.0525 |
| GMNN | 0.0973 |
| GSR__2 | 0.0421 |
| HBA2 | 0.2048 |
| HCFC1R1__1 | 0.0572 |
| HDAC7__2 | 0.0043 |
| HDLBP__3 | 0.1153 |
| HIC1 | 0.0396 |
| HPRT1__1 | 0.1514 |
| HPS4__1 | 0.0653 |
| HR__1 | 0.0434 |
| HSD11B1__1 | 0.0931 |
| ICAM2 | 0.0493 |
| ICAM4__1 | 0.279 |
| IL1RAP__2 | 0.06 |
| IQCA1__2 | 0.0294 |
| KCNIP3__1 | 0.1039 |
| KCNQ2__1 | 0.1248 |
| KIF3C | 0.1802 |
| KRT80__2 | 0.1107 |
| KRTAP10.10__2 | 0.0206 |
| L3MBTL2__3 | 0.034 |
| LBH__2 | 0.0952 |
| LENEP | 0.2321 |
| LGI3 | 0.1201 |
| LOC492303 | 0.0295 |
| LRRC14B | 0.0148 |
| LRRC37A4__2 | 0.0563 |
| LRRTM4 | 0.167 |
| MACC1 | 0.1174 |
| MANSC1__1 | 0.1393 |
| MCAM | 0.0176 |
| MCART6__1 | 0.1302 |
| MFRP | 0.2149 |
| MIDN | 0.0442 |
| MIR1914 | 0.0697 |
| MIR212 | 0.1069 |
| MIR571 | 0.0316 |
| MIR576 | 0.1023 |
| MIR654 | 0.0539 |
| MIR942 | 0.1338 |
| MMP12__1 | 0.1307 |
| MYCN__2 | 0.1396 |
| MYOHD1 | 0.0939 |
| NFATC3__5 | 0.008 |
| NFATC4 | 0.0521 |
| NLRP9 | 0.18 |
| NOVA2 | 0.1202 |
| NP | 0.0885 |
| NR6A1__2 | 0.1446 |
| NRXN3__3 | 0.0999 |
| NT5DC1__2 | 0.1855 |
| NTRK2__3 | 0.0077 |
| NUP155__1 | 0.0488 |
| NYX | 0.1733 |

TABLE 20-continued

| | |
|---|---|
| ODF2_3 | 0.0153 |
| ORC1L | 0.0294 |
| OTUD7A_3 | 0.0342 |
| PANK4 | 0.055 |
| PDLIM2_2 | 0.2387 |
| PHYH_1 | 0.1976 |
| PIGA_1 | 0.0024 |
| PITX2_1 | 0.0924 |
| PKN1_3 | 0.0216 |
| PLAC9 | 0.2492 |
| PLEKHG5_5 | 0.0323 |
| PLSCR4 | 0.1766 |
| PMEPA1_4 | 0.1204 |
| PNMA5 | 0.1295 |
| PPAPDC1A | 0.1315 |
| PRAMEF5 | 0.0165 |
| PRKAA2 | 0.1306 |
| PSMC6_1 | 0.0029 |
| RAD54B_2 | 0.1842 |
| RAP1A_1 | 0.2169 |
| RARA_3 | 0.0856 |
| RARG | 0.0481 |
| RNASEK | 0.064 |
| RNF7_1 | 0.0209 |
| ROD1_1 | 0.2196 |
| SATB2 | 0.057 |
| SBSN | 0.0581 |
| SCXB | 0.0069 |
| SEC22C_3 | 0.1229 |
| SELENBP1 | 0.1943 |
| SERPINB2_2 | 0.0123 |
| SERPINB5 | 0.198 |
| SFN | 0.0091 |
| SFRS4 | 0.0329 |
| SHC1_3 | 0.072 |
| SLC23A1_2 | 0.1388 |
| SLC25A34 | 0.1531 |
| SLC4A5_3 | 0.0803 |
| SLC9A10 | 0.0867 |
| SNORD93 | 0.1624 |
| SOX21 | 0.0764 |
| STC1 | 0.0073 |
| STC2 | 0.1324 |
| STYX_2 | 0.0448 |
| SYTL3 | 0.0108 |
| TAF15_1 | 0.0108 |
| TCEAL8_1 | 0.0417 |
| THBS3 | 0.1047 |
| THY1 | 0.0575 |
| TIMP2_2 | 0.0816 |
| TM2D3_2 | 0.005 |
| TMEM52 | 0.0275 |
| TMEM62 | 0.0704 |
| TNFRSF18_1 | 0.2567 |
| TNNT2_1 | 0.0008 |
| TOMM20L | 0.0434 |
| TPM2_2 | 0.1799 |
| TRIM58 | 0.1137 |
| UBR7_1 | 0.0577 |
| UBR7_2 | 0.1274 |
| WARS_2 | 0.1613 |
| XBP1_2 | 0.1397 |
| XRN2_1 | 0.0525 |
| YARS2 | 0.0062 |
| ZNF75D_2 | 0.1498 |
| ZSWIM4_2 | 0.1618 |
| figo_numeric | 0.021 |
| hist_rev_SBOT | 0.048 |
| surg_outcome | 0.0088 |

TABLE 21

| | |
|---|---|
| ABHD3 | 0.0663 |
| ADAM17_2 | 0.2308 |
| ADAMTS1 | 0.175 |
| ALS2CL_3 | 0.1066 |
| ANO7_3 | 0.0621 |

TABLE 21-continued

| | |
|---|---|
| ARL6IP1_1 | 0.0271 |
| ARMCX3_2 | 0.0823 |
| ATXN10_1 | 0.2065 |
| AXL_1 | 0.1063 |
| BAI1_3 | 0.0239 |
| BCAS1_1 | 0.3215 |
| BDNF_2 | 0.1088 |
| BMPR1A | 0.1123 |
| BTF3_3 | 0.1045 |
| C10orf116 | 0.0333 |
| C11orf24 | 0.1704 |
| C11orf49_3 | 0.1322 |
| C14orf102_2 | 0.1184 |
| C14orf109_2 | 0.0685 |
| C17orf106 | 0.2339 |
| C17orf58_2 | 0.0463 |
| C17orf58_3 | 0.0226 |
| C18orf56 | 0.0371 |
| C1orf168 | 0.0353 |
| C1orf64 | 0.1083 |
| C8orf79_1 | 0.0248 |
| CASP8AP2 | 0.1364 |
| CCL13 | 0.1382 |
| CCR2_3 | 0.083 |
| CD34_1 | 0.015 |
| CDC42BPA_2 | 0.0272 |
| CDC42SE2_2 | 0.0209 |
| CLDN6 | 0.114 |
| CREB5_2 | 0.014 |
| CRYBA1 | 0.0281 |
| CXCL13 | 0.0738 |
| CYB5R3_2 | 0.18 |
| CYP1A2 | 0.0588 |
| DBNDD2 | 0.1084 |
| DNAH11 | 0.0475 |
| DNMT3L_2 | 0.0228 |
| DOCK7_1 | 0.14 |
| DSC3_1 | 0.0737 |
| DUT_3 | 0.1195 |
| EEF1E1_1 | 0.0883 |
| EMP1 | 0.1186 |
| ENO1 | 0.1822 |
| ENPEP_2 | 0.1303 |
| EPHB1 | 0.0369 |
| EPYC | 0.0297 |
| ERI2_2 | 0.2948 |
| ESPNL | 0.0342 |
| EZH2_1 | 0.0734 |
| FAM13AOS | 0.0438 |
| FAM187B_2 | 0.011 |
| FAM70A_1 | 0.081 |
| FBXO48_2 | 0.2591 |
| FKBP10 | 0.0693 |
| FLJ33360 | 0.0537 |
| FLJ43752 | 0.1899 |
| FMNL3_2 | 0.0457 |
| FOSB | 0.2007 |
| FOSL2 | 0.0284 |
| FOXN1 | 0.2708 |
| GAD1_2 | 0.0186 |
| GBE1 | 0.0467 |
| GBP7 | 0.1322 |
| GJA5_1 | 0.0489 |
| GMNN | 0.1011 |
| GSR_2 | 0.0408 |
| HBA2 | 0.1972 |
| HCFC1R1_1 | 0.0584 |
| HDAC7_2 | 0.0084 |
| HDLBP_3 | 0.1136 |
| HIC1 | 0.0397 |
| HPRT1_1 | 0.1549 |
| HPS4_1 | 0.0624 |
| HR_1 | 0.041 |
| HSD11B1_1 | 0.0915 |
| ICAM2 | 0.0608 |
| ICAM4_1 | 0.2742 |
| IL1RAP_2 | 0.0589 |
| IQCA1_2 | 0.0298 |
| KCNIP3_1 | 0.1058 |
| KCNQ2_1 | 0.1317 |

TABLE 21-continued

| | |
|---|---|
| KIF3C | 0.1789 |
| KRT80_2 | 0.1081 |
| KRTAP10.10_2 | 0.0215 |
| L3MBTL2_3 | 0.0311 |
| LBH_2 | 0.0943 |
| LENEP | 0.2325 |
| LGI3 | 0.1111 |
| LOC492303 | 0.0252 |
| LRRC14B | 0.0127 |
| LRRC37A4_2 | 0.061 |
| LRRTM4 | 0.1675 |
| MACC1 | 0.1186 |
| MANSC1_1 | 0.1364 |
| MCAM | 0.013 |
| MCART6_1 | 0.1314 |
| MFRP | 0.2201 |
| MIDN | 0.0394 |
| MIR1914 | 0.0643 |
| MIR212 | 0.1082 |
| MIR571 | 0.0339 |
| MIR576 | 0.104 |
| MIR654 | 0.0504 |
| MIR942 | 0.1245 |
| MMP12_1 | 0.131 |
| MYCN_2 | 0.144 |
| MYL9_2 | 0.0911 |
| MYOHD1 | 0.0077 |
| NFATC3_5 | 0.0536 |
| NFATC4 | 0.0635 |
| NLRP9 | 0.181 |
| NOVA2 | 0.1239 |
| NP | 0.0898 |
| NR6A1_2 | 0.1487 |
| NRXN3_3 | 0.1005 |
| NT5DC1_2 | 0.1878 |
| NTRK2_3 | 0.0059 |
| NUP155_1 | 0.0484 |
| NYX | 0.1782 |
| ODF2_3 | 0.0118 |
| ORC1L | 0.0299 |
| OTUD7A_3 | 0.0332 |
| PANK4 | 0.0559 |
| PDLIM2_2 | 0.2435 |
| PHYH_1 | 0.1998 |
| PIGA_1 | 0.0015 |
| PITX2_1 | 0.0912 |
| PKN1_3 | 0.018 |
| PLAC9 | 0.2485 |
| PLEKHG5_5 | 0.0248 |
| PLSCR4 | 0.1735 |
| PMEPA1_4 | 0.1229 |
| PNMA5 | 0.1265 |
| PPAPDC1A | 0.1353 |
| PRAMEF5 | 0.0079 |
| PRKAA2 | 0.1319 |
| PSMC6_1 | 0.0012 |
| RAD54B_2 | 0.1809 |
| RAP1A_1 | 0.2108 |
| RARA_3 | 0.0834 |
| RARG | 0.0468 |
| RNASEK | 0.0632 |
| RNF7_1 | 0.0209 |
| ROD1_1 | 0.2223 |
| SATB2 | 0.0592 |
| SBSN | 0.0579 |
| SCXB | 0.0053 |
| SEC22C_3 | 0.1148 |
| SELENBP1 | 0.1917 |
| SERPINB2_2 | 0.004 |
| SERPINB5 | 0.1982 |
| SFN | 0.0117 |
| SFRS4 | 0.0329 |
| SHC1_3 | 0.0696 |
| SLC23A1_2 | 0.1397 |
| SLC25A34 | 0.155 |
| SLC4A5_3 | 0.0813 |
| SLC9A10 | 0.0816 |
| SNORD93 | 0.1585 |
| SOX2_1 | 0.0771 |
| STC1 | 0.0091 |

TABLE 21-continued

| | |
|---|---|
| STC2 | 0.1293 |
| STYX_2 | 0.0471 |
| SYTL3 | 0.008 |
| TAF15_1 | 0.0012 |
| TCEAL8_1 | 0.0388 |
| THBS3 | 0.1054 |
| TTMP2_2 | 0.0614 |
| TM2D3_2 | 0.0737 |
| TMEM52 | 0.0072 |
| TMEM62 | 0.0699 |
| TNFRSF18_1 | 0.2674 |
| TNNT2_1 | 0.0025 |
| TOMM20L | 0.0407 |
| TPM2_2 | 0.1772 |
| TRIM58 | 0.1118 |
| UBR7_1 | 0.0622 |
| UBR7_2 | 0.1264 |
| WARS_2 | 0.1566 |
| XBP1_2 | 0.1366 |
| XRN2_1 | 0.0525 |
| YARS2 | 0.0045 |
| ZNF75D_2 | 0.1493 |
| ZSWIM4_2 | 0.1622 |
| figo_numeric | 0.0199 |
| hist_rev_SBOT | 0.0508 |
| surg_outcome | 0.0057 |

TABLE 22

| | |
|---|---|
| ABHD3 | 0.0702 |
| ADAM17_2 | 0.24 |
| ADAMTS1 | 0.1767 |
| ALS2CL_3 | 0.1037 |
| ANO7_3 | 0.0614 |
| ARL6IP1_1 | 0.0381 |
| ARMCX3_2 | 0.082 |
| ATXN10_1 | 0.1984 |
| AXL_1 | 0.1098 |
| BAI1_3 | 0.0235 |
| BCAS1_1 | 0.3327 |
| BDNF_2 | 0.11 |
| BMPR1A | 0.1201 |
| BTF3_3 | 0.1057 |
| C10orf116 | 0.038 |
| C11orf24 | 0.1905 |
| C11orf49_3 | 0.1248 |
| C14orf102_2 | 0.1242 |
| C14orf109_2 | 0.0629 |
| C17orf106 | 0.2391 |
| C17orf58_2 | 0.0316 |
| C17orf58_3 | 0.0302 |
| C18orf56 | 0.0364 |
| C1orf168 | 0.0316 |
| C8orf79_1 | 0.1135 |
| CALD1_2 | 0.0409 |
| CASP8AP2 | 0.1434 |
| CCL13 | 0.0815 |
| CCR2_3 | 0.0319 |
| CD34_1 | 0.0148 |
| CDC42BPA_2 | 0.0307 |
| CDC42SE2_2 | 0.0235 |
| CLDN6 | 0.1084 |
| CREB5_2 | 0.0169 |
| CRYBA1 | 0.0302 |
| CXCL13 | 0.0792 |
| CYB5R3_2 | 0.1878 |
| CYP1A2 | 0.0598 |
| DBNDD2 | 0.1083 |
| DNAH11 | 0.0458 |
| DNMT3L_2 | 0.019 |
| DOCK7_1 | 0.1366 |
| DSC3_1 | 0.0765 |
| DUT3 | 0.1146 |
| EEF1E1_1 | 0.0742 |
| EMP1 | 0.1256 |
| ENO1 | 0.1956 |
| ENPEP_2 | 0.1362 |

TABLE 22-continued

| | |
|---|---|
| EPHB1 | 0.0311 |
| EPYC | 0.0385 |
| ERI2_2 | 0.2922 |
| ESPNL | 0.0338 |
| EZH2_1 | 0.0821 |
| FAM13AOS | 0.0551 |
| FAM187B_2 | 0.0037 |
| FAM70A_1 | 0.1031 |
| FBXO48_2 | 0.2667 |
| FKBP10 | 0.0661 |
| FLJ33360 | 0.048 |
| FLJ43752 | 0.2006 |
| FMNL3_2 | 0.0538 |
| FOSB | 0.2041 |
| FOSL2 | 0.0243 |
| FOXN1 | 0.2702 |
| GAD1_2 | 0.0071 |
| GBE1 | 0.045 |
| GBP7 | 0.1204 |
| GJA5_1 | 0.0543 |
| GMNN | 0.1034 |
| GSR_2 | 0.0442 |
| HBA2 | 0.2027 |
| HCFC1R1_1 | 0.0499 |
| HDAC7_2 | 0.0025 |
| HDLBP_3 | 0.1094 |
| HIC1 | 0.0438 |
| HPRT1_1 | 0.1519 |
| HPS4_1 | 0.0643 |
| HR_1 | 0.0448 |
| HSD11B1_1 | 0.0927 |
| ICAM2 | 0.0457 |
| ICAM4_1 | 0.2788 |
| IL1RAP_2 | 0.0514 |
| IQCA1_2 | 0.0262 |
| KCNIP3_1 | 0.1058 |
| KCNQ2_1 | 0.1243 |
| KIF3C | 0.1741 |
| KRT80_2 | 0.1197 |
| KRTAP10.10_2 | 0.0223 |
| L3MBTL2_3 | 0.032 |
| LBH_2 | 0.0926 |
| LENEP | 0.231 |
| LGI3 | 0.1303 |
| LOC492303 | 0.0326 |
| LRRC14B | 0.0188 |
| LRRC37A4_2 | 0.0536 |
| LRRTM4 | 0.1687 |
| MACC1 | 0.124 |
| MANSC1_1 | 0.1326 |
| MCAM | 0.0075 |
| MCART6_1 | 0.1271 |
| MFRP | 0.2258 |
| MIDN | 0.048 |
| MIR1914 | 0.0695 |
| MIR212 | 0.102 |
| MIR571 | 0.0301 |
| MIR576 | 0.1013 |
| MIR654 | 0.0511 |
| MIR942 | 0.1348 |
| MMP12_1 | 0.1385 |
| MYCN_2 | 0.143 |
| MYOHD1 | 0.089 |
| NFATC3_5 | 0.0118 |
| NFATC4 | 0.0472 |
| NLRP9 | 0.1849 |
| NOVA2 | 0.1147 |
| NP | 0.0941 |
| NR6A1_2 | 0.1439 |
| NRXN3_3 | 0.0945 |
| NT5DC1_2 | 0.1882 |
| NTRK2_3 | 0.0009 |
| NUP155_1 | 0.0572 |
| NYX | 0.1804 |
| ODF2_3 | 0.0208 |
| ORC1L | 0.0268 |
| OTUD7A_3 | 0.0356 |
| PANK4 | 0.0582 |
| PDLIM2_2 | 0.2471 |
| PHYH_1 | 0.1962 |

TABLE 22-continued

| | |
|---|---|
| PIGA_1 | 0.0032 |
| PITX2_1 | 0.0989 |
| PKN1_3 | 0.0161 |
| PLAC9 | 0.2729 |
| PLEKHG5_5 | 0.0299 |
| PLSCR4 | 0.1546 |
| PMEPA1_4 | 0.1226 |
| PNMA5 | 0.1159 |
| PPAPDC1A | 0.1284 |
| PRAMEF5 | 0.0196 |
| PRKAA2 | 0.1281 |
| PSMC6_1 | 0.0134 |
| RAD54B_2 | 0.1807 |
| RAP1A_1 | 0.2136 |
| RARA_3 | 0.0868 |
| RARG | 0.0463 |
| RNASEK | 0.062 |
| RNF7_1 | 0.0136 |
| ROD1_1 | 0.2251 |
| SATB2 | 0.053 |
| SBSN | 0.055 |
| SCXB | 0.0075 |
| SEC22C_3 | 0.1238 |
| SELENBP1 | 0.1967 |
| SERPINA12 | 0.0282 |
| SERPINB2_2 | 0.1935 |
| SERPINB5 | 0.003 |
| SFN | 0.0536 |
| SFRS4 | 0.0298 |
| SHC1_3 | 0.0655 |
| SLC23A1_2 | 0.141 |
| SLC25A34 | 0.1681 |
| SLC4A5_3 | 0.0826 |
| SLC9A10 | 0.0799 |
| SNORD93 | 0.1647 |
| SOX2_1 | 0.0848 |
| STC1 | 0.0087 |
| STC2 | 0.1232 |
| STYX_2 | 0.0512 |
| SYTL3 | 0.0226 |
| TAF15_1 | 0.0036 |
| TCEAL8_1 | 0.0349 |
| THBS3 | 0.0901 |
| TM2D3_2 | 0.058 |
| TMEM52 | 0.0888 |
| TMEM62 | 0.0037 |
| TNFRSF18_1 | 0.2615 |
| TNNT2_1 | 0.0125 |
| TOMM20L | 0.0402 |
| TPM2_2 | 0.1775 |
| IRIM58 | 0.1153 |
| UBR7_1 | 0.0551 |
| UBR7_2 | 0.1342 |
| WARS_2 | 0.1524 |
| XBP1_2 | 0.1231 |
| XRN2_1 | 0.0467 |
| YARS2 | 0.0093 |
| ZNF75D_2 | 0.1453 |
| ZSWIM4_2 | 0.1658 |
| figo_numeric | 0.0134 |
| hist_rev_SBOT | 0.0617 |
| surg_outcome | 0.0173 |

TABLE 23

| | |
|---|---|
| ABHD3 | 0.0752 |
| ADAM17_2 | 0.2422 |
| ADAMTS1 | 0.1531 |
| ADAMTS2_1 | 0.1 |
| ALS2CL_3 | 0.0622 |
| ANO7_3 | 0.0333 |
| ARL6IP1_1 | 0.0222 |
| ARMCX3_2 | 0.0627 |
| ATXN10_1 | 0.1719 |
| AXL_1 | 0.0779 |
| BAI1_3 | 0.0545 |
| BCAS1_1 | 0.316 |

TABLE 23-continued

| | |
|---|---|
| BDNF_2 | 0.0885 |
| BMPR1A | 0.1239 |
| BTF3_3 | 0.1092 |
| C10orf116 | 0.0845 |
| C11orf24 | 0.1233 |
| C11orf49_3 | 0.111 |
| C14orf102_2 | 0.0988 |
| C14orf109_2 | 0.1089 |
| C17orf106 | 0.1557 |
| C17orf58_2 | 0.0009 |
| C17orf58_3 | 0.0262 |
| C18orf56 | 0.0128 |
| C1orf168 | 0.0266 |
| C1orf64 | 0.1011 |
| C8orf79_1 | 0.0411 |
| CALD1_2 | 0.1497 |
| CASP8AP2 | 0.1247 |
| CCL13 | 0.1557 |
| CCR2_3 | 0.0359 |
| CD34_1 | 0.0391 |
| CDC42BPA_2 | 0.0028 |
| CDC42SE2_2 | 0.0014 |
| CIDEC_1 | 0.1111 |
| CLDN6 | 0.0245 |
| CREB5_2 | 0.0192 |
| CREBBP_1 | 0.0576 |
| CRYBA1 | 0.0714 |
| CXCL13 | 0.1734 |
| CYB5R3_2 | 0.1585 |
| CYP1A2 | 0.0603 |
| DBNDD2 | 0.0978 |
| DFFB_2 | 0.0433 |
| DNAH11 | 0.0292 |
| DNMT3L_2 | 0.0881 |
| DOCK7_1 | 0.0205 |
| DSC3_1 | 0.0348 |
| DUT_3 | 0.116 |
| EEF1E1_1 | 0.1036 |
| ELN_2 | 0.118 |
| EMP1 | 0.1789 |
| ENO1 | 0.1485 |
| ENPEP_2 | 0.0537 |
| EPHB1 | 0.03 |
| EPYC | 0.0396 |
| ERI2_2 | 0.2726 |
| ESPNL | 0.0801 |
| EZH2_1 | 0.0464 |
| FAM13AOS | 0.055 |
| FAM187B_2 | 0.0069 |
| FAM70A_1 | 0.1027 |
| FBXO48_2 | 0.1908 |
| FKBP10 | 0.0969 |
| FLJ33360 | 0.0233 |
| FLJ43752 | 0.2125 |
| FMNL3_2 | 0.0269 |
| FOSB | 0.1983 |
| FOSL2 | 0.0424 |
| FOXN1 | 0.2379 |
| GAD1_2 | 0.0249 |
| GBE1 | 0.0517 |
| GBP7 | 0.069 |
| GJA5_1 | 0.0574 |
| GMNN | 0.1028 |
| GSR_2 | 0.011 |
| GUSBL2 | 0.1976 |
| HBA2 | 0.0682 |
| HDAC7_2 | 0.0378 |
| HDLBP_3 | 0.2046 |
| HIC1 | 0.0844 |
| HPRT1_1 | 0.146 |
| HPS4_1 | 0.0335 |
| HR_1 | 0.0376 |
| HSD11B1_1 | 0.1071 |
| ICAM2 | 0.009 |
| ICAM4_1 | 0.2848 |
| IL1RAP_2 | 0.0627 |
| IQCA1_2 | 0.0016 |
| KCNIP3_1 | 0.082 |
| KCNQ2_1 | 0.1277 |
| KIF3C | 0.1765 |
| KRT80_2 | 0.0673 |
| KRTAP10.10_2 | 0.0301 |
| L3MBTL2_3 | 0.0485 |
| LBH_2 | 0.0769 |
| LENEP | 0.2266 |
| LGI3 | 0.1039 |
| LOC340508 | 0.0295 |
| LOC492303 | 0.035 |
| LRRC14B | 0.0695 |
| LRRC37A4_2 | 0.0036 |
| LRRTM4 | 0.1592 |
| MACC1 | 0.1494 |
| MANSC1_1 | 0.1284 |
| MAPK3_1 | 0.0788 |
| MCAM | 0.0948 |
| MCART6_1 | 0.2292 |
| MFRP | 0.0249 |
| MIDN | 0.0441 |
| MIR1914 | 0.0566 |
| MIR212 | 0.0952 |
| MIR571 | 0.0392 |
| MIR576 | 0.0931 |
| MIR654 | 0.0133 |
| MIR942 | 0.0942 |
| MMP12_1 | 0.1263 |
| MYCN_2 | 0.1423 |
| MYOHD1 | 0.0937 |
| NFATC3_5 | 0.0344 |
| NFATC4 | 0.0592 |
| NLRP9 | 0.156 |
| NOVA2 | 0.0483 |
| NP | 0.0783 |
| NR6A1_2 | 0.1239 |
| NRXN3_3 | 0.1232 |
| NT5DC1_2 | 0.1835 |
| NTRK2_3 | 0.0091 |
| NUP155_1 | 0.036 |
| NYX | 0.0826 |
| ODF2_3 | 0.0205 |
| ORC1L | 0.047 |
| OTUD7A_3 | 0.0436 |
| PANK4 | 0.0471 |
| PDLIM2_2 | 0.1911 |
| PDZRN4_2 | 0.2271 |
| PHYH_1 | 0.0097 |
| PIGA_1 | 0.0838 |
| PITX2_1 | 0.1998 |
| PKN1_3 | 0.0372 |
| PLEKHG5_5 | 0.2717 |
| PLSCR4 | 0.0178 |
| PMEPA1_4 | 0.1444 |
| PNMA5 | 0.1694 |
| PPAPDC1A | 0.087 |
| PRAMEF5 | 0.0101 |
| PRKAA2 | 0.1108 |
| PSMC6_1 | 0.0137 |
| RAD54B_2 | 0.1908 |
| RAP1A_1 | 0.1953 |
| RARA_3 | 0.0953 |
| RARG | 0.0276 |
| RNASEK | 0.1092 |
| RNF7_1 | 0.0409 |
| ROD1_1 | 0.1859 |
| SATB2 | 0.0304 |
| SBSN | 0.0903 |
| SCXB | 0.006 |
| SEC22C_3 | 0.0935 |
| SELENBP1 | 0.1544 |
| SERPINB2_2 | 0.0056 |
| SERPINB5 | 0.1869 |
| SFN | 0.0032 |
| SFRS4 | 0.063 |
| SHC1_3 | 0.0786 |
| SLC23A1_2 | 0.0821 |
| SLC25A34 | 0.0944 |
| SLC4A5_3 | 0.0989 |
| SLC9A10 | 0.0687 |
| SNORD93 | 0.1311 |
| SOX2_1 | 0.0498 |
| STC1 | 0.0123 |

TABLE 23-continued

| | |
|---|---|
| STC2 | 0.09 |
| STYX_2 | 0.0308 |
| SYTL3 | 0.0161 |
| TAF15_1 | 0.0182 |
| TCEAL8_1 | 0.0291 |
| THBS3 | 0.0783 |
| TM2D3_2 | 0.0275 |
| TMEM52 | 0.0679 |
| TMEM62 | 0.0014 |
| TNFRSF18_1 | 0.23 |
| TNNT2_1 | 0.0008 |
| TOMM20L | 0.0044 |
| TPM2_2 | 0.1504 |
| TRIM58 | 0.1121 |
| UBR7_1 | 0.0587 |
| UBR7_2 | 0.1435 |
| WARS_2 | 0.2033 |
| XBP1_2 | 0.176 |
| XRN2_1 | 0.0354 |
| YARS2 | 0.0318 |
| ZNF75D_2 | 0.1281 |
| ZSWIM4_2 | 0.1684 |
| figo_numeric | 0.0233 |
| hist_rev_SBOT | 0.0775 |
| surg_outcome | 0.008 |

TABLE 24

| | |
|---|---|
| ABCC9_3 | 0.0684 |
| ABHD3 | 0.2415 |
| ADAM17_2 | 0.1509 |
| ADAMTS1 | 0.077 |
| ADAMTS2_1 | 0.1042 |
| ALS2CL_3 | 0.0566 |
| ANO7_3 | 0.0462 |
| ARL6IP1_1 | 0.0085 |
| ARMCX3_2 | 0.0652 |
| ATXN10_1 | 0.1727 |
| AXL_1 | 0.072 |
| BAI1_3 | 0.0458 |
| BCAS1_1 | 0.3113 |
| BDNF_2 | 0.1029 |
| BMPR1A | 0.1241 |
| BTF3_3 | 0.1138 |
| C10orf116 | 0.0767 |
| C11orf24 | 0.1289 |
| C11orf49_3 | 0.1095 |
| C14orf102_2 | 0.0891 |
| C14orf109_2 | 0.114 |
| C17orf106 | 0.1586 |
| C17orf58_2 | 0.0052 |
| C17orf58_3 | 0.0216 |
| C18orf56 | 0.0081 |
| C1orf168 | 0.0357 |
| C1orf64 | 0.1059 |
| C8orf79_1 | 0.0398 |
| CALD1_2 | 0.1445 |
| CASP8AP2 | 0.126 |
| CCL13 | 0.1388 |
| CCR2_3 | 0.038 |
| CD34_1 | 0.0492 |
| CDC42BPA_2 | 0.0116 |
| CDC42SE2_2 | 0.0038 |
| CIDEC_1 | 0.1085 |
| CLDN6 | 0.0179 |
| CREB5_2 | 0.0244 |
| CREBBP_1 | 0.0478 |
| CRYBA1 | 0.0722 |
| CXCL13 | 0.1738 |
| CYB5R3_2 | 0.1632 |
| CYP1A2 | 0.0538 |
| DBNDD2 | 0.0963 |
| DFFB_2 | 0.0411 |
| DNAH11 | 0.0364 |
| DNMT3L_2 | 0.0966 |
| DOCK7_1 | 0.0181 |
| DSC3_1 | 0.0424 |

TABLE 24-continued

| | |
|---|---|
| DUT_3 | 0.1173 |
| EEF1E1_1 | 0.0994 |
| EMP1 | 0.1047 |
| ENO1 | 0.1697 |
| ENPEP_2 | 0.1446 |
| EPHB1 | 0.0415 |
| EPYC | 0.0292 |
| ERI2_2 | 0.2792 |
| ESPNL | 0.0781 |
| EZH2_1 | 0.0508 |
| FAM13AOS | 0.0616 |
| FAM187B_2 | 0.0118 |
| FAM70A_1 | 0.0982 |
| FBXO48_2 | 0.1891 |
| FKBP10 | 0.1123 |
| FLJ33360 | 0.0243 |
| FLJ43752 | 0.2297 |
| FMNL3_2 | 0.0231 |
| FOSB | 0.1828 |
| FOSL2 | 0.0439 |
| FOXN1 | 0.2469 |
| GAD1_2 | 0.0292 |
| GBE1 | 0.0479 |
| GBP7 | 0.0792 |
| GJA5_1 | 0.065 |
| GMNN | 0.1116 |
| GSR_2 | 0.0206 |
| GUSBL2 | 0.2016 |
| HBA2 | 0.0675 |
| HDAC7_2 | 0.0442 |
| HDLBP_3 | 0.1963 |
| HIC1 | 0.0948 |
| HPRT1_1 | 0.1329 |
| HPS4_1 | 0.035 |
| HR_1 | 0.0463 |
| HSD11B1_1 | 0.1014 |
| ICAM2 | 0.0074 |
| ICAM4_1 | 0.2673 |
| IL1RAP_2 | 0.0556 |
| IQCA1_2 | 0.0019 |
| KCNIP3_1 | 0.0898 |
| KCNQ2_1 | 0.135 |
| KIF3C | 0.1711 |
| KRT802 | 0.0795 |
| KRTAP10.10_2 | 0.0249 |
| L3MBTL2_3 | 0.0536 |
| LBH_2 | 0.0829 |
| LENEP | 0.2326 |
| LGI3 | 0.1066 |
| LOC340508 | 0.0496 |
| LOC492303 | 0.0275 |
| LRRC14B | 0.0657 |
| LRRC37A4_2 | 0.0104 |
| LRRTM4 | 0.1747 |
| MACC1 | 0.1582 |
| MANSC1_1 | 0.128 |
| MAPK3_1 | 0.059 |
| MCAM | 0.1059 |
| MCART6_1 | 0.2265 |
| MFRP | 0.023 |
| MIDN | 0.0172 |
| MIR1914 | 0.0434 |
| MIR212 | 0.0923 |
| MIR571 | 0.0389 |
| MIR576 | 0.0846 |
| MIR654 | 0.0019 |
| MIR942 | 0.0906 |
| MMP12_1 | 0.1295 |
| MYCN_2 | 0.15 |
| MYOHD1 | 0.0934 |
| NFATC3_5 | 0.0162 |
| NFATC4 | 0.0518 |
| NLRP9 | 0.1645 |
| NOVA2 | 0.0652 |
| NP | 0.0917 |
| NR6A1_2 | 0.1183 |
| NRXN3_3 | 0.1265 |
| NT5DC1_2 | 0.1841 |
| NTRK2_3 | 0.0117 |
| NUP155_1 | 0.0354 |

TABLE 24-continued

| | |
|---|---|
| NYX | 0.0627 |
| ODF2__3 | 0.0347 |
| ORC1L | 0.0411 |
| OTUD7A__3 | 0.0579 |
| PANK4 | 0.0507 |
| PDLIM2__2 | 0.1883 |
| PDZRN4__2 | 0.2332 |
| PHYH__1 | 0.0127 |
| PIGA__1 | 0.0899 |
| PITX2__1 | 0.1944 |
| PKN1__3 | 0.0315 |
| PLEKHG5__5 | 0.2484 |
| PLSCR4 | 0.019 |
| PMEPA1__4 | 0.1389 |
| PNMA5 | 0.172 |
| PPAPDC1A | 0.0878 |
| PRAMEF5 | 0.0026 |
| PRKAA2 | 0.1149 |
| PSMC6__1 | 0.0193 |
| RAD54B__2 | 0.1881 |
| RAP1A__1 | 0.2007 |
| RARA__3 | 0.0887 |
| RARG | 0.0307 |
| RNASEK | 0.1066 |
| RNF7__1 | 0.0492 |
| ROD1__1 | 0.193 |
| SATB2 | 0.0326 |
| SBSN | 0.0699 |
| SCXB | 0.0074 |
| SEC22C__3 | 0.0918 |
| SELENBP1 | 0.1492 |
| SERPINB2__2 | 0.0194 |
| SERPINB5 | 0.1876 |
| SFN | 0.0072 |
| SFRS4 | 0.0706 |
| SHC1__3 | 0.0852 |
| SLC23A1__2 | 0.0937 |
| SLC25A34 | 0.1048 |
| SLC4A5__3 | 0.0947 |
| SLC9A10 | 0.0692 |
| SNORD93 | 0.1264 |
| SOX2__1 | 0.0569 |
| STC1 | 0.0117 |
| STC2 | 0.0978 |
| STYX__2 | 0.0393 |
| SYTL3 | 0.0208 |
| TAF15__1 | 0.0158 |
| TCEAL8__1 | 0.0333 |
| THBS3 | 0.0884 |
| TM2D3__2 | 0.0378 |
| TMEM52 | 0.0732 |
| TMEM62 | 0.0112 |
| TNFRSF18__1 | 0.2304 |
| TNNT2__1 | 0.0086 |
| TOMM20L | 0.0048 |
| TPM2__2 | 0.155 |
| TRIM58 | 0.0944 |
| UBR7__1 | 0.0538 |
| UBR7__2 | 0.139 |
| WARS__2 | 0.1959 |
| XBP1__2 | 0.1609 |
| XRN2__1 | 0.043 |
| YARS2 | 0.0284 |
| ZNF75D__2 | 0.1318 |
| ZSWIM4__2 | 0.1659 |
| figo__numeric | 0.0217 |
| hist__rev__SBOT | 0.0682 |
| surg__outcome | 0.003 |

TABLE 25

| | |
|---|---|
| ABCC9__3 | 0.0682 |
| ABHD3 | 0.2443 |
| ADAM17__2 | 0.1454 |
| ADAMTS1 | 0.0824 |
| ALS2CL__3 | 0.1078 |
| ANO7__3 | 0.0537 |

TABLE 25-continued

| | |
|---|---|
| ARL6IP1__1 | 0.0393 |
| ARMCX3__2 | 0.061 |
| ATXN10__1 | 0.1742 |
| AXL | 0.0704 |
| BAI1__3 | 0.0545 |
| BCAS1__1 | 0.3079 |
| BDNF__2 | 0.0952 |
| BMPR1A | 0.1185 |
| BTF3__3 | 0.1115 |
| C10orf116 | 0.0781 |
| C11orf24 | 0.1297 |
| C11orf49__3 | 0.1091 |
| C14orf102__2 | 0.0892 |
| C14orf109__2 | 0.1107 |
| C17orf106 | 0.1527 |
| C17orf58__2 | 0.0055 |
| C17orf58__3 | 0.0287 |
| C18orf56 | 0.0055 |
| C1orf168 | 0.0317 |
| C1orf64 | 0.1038 |
| C8orf79__1 | 0.0412 |
| CALD1__2 | 0.1514 |
| CASP8AP2 | 0.1197 |
| CCL13 | 0.1514 |
| CCR2__3 | 0.0338 |
| CD34__1 | 0.0492 |
| CDC42BPA__2 | 0.0003 |
| CDC42SE2__2 | 0 |
| CIDEC__1 | 0.1061 |
| CLDN6 | 0.0199 |
| CREB5__2 | 0.0184 |
| CREBBP__1 | 0.0514 |
| CRYBA1 | 0.0675 |
| CXCL13 | 0.1712 |
| CYB5R3__2 | 0.1603 |
| CYP1A2 | 0.0663 |
| DBNDD2 | 0.1017 |
| DEEB__2 | 0.0413 |
| DNAH11 | 0.0317 |
| DNMT3L__2 | 0.0967 |
| DOCK7__1 | 0.0128 |
| DSC3__1 | 0.0401 |
| DUT__3 | 0.122 |
| EEF1E1__1 | 0.1049 |
| ELN__2 | 0.1082 |
| EMP1 | 0.1789 |
| ENO1 | 0.1426 |
| ENPEP__2 | 0.0575 |
| EPHB1 | 0.0434 |
| EPYC | 0.031 |
| ERI2__2 | 0.2677 |
| ESPNL | 0.0833 |
| EZH2__1 | 0.0402 |
| FAM13AOS | 0.0554 |
| FAM187B__2 | 0.0103 |
| FAM70A__1 | 0.1018 |
| FBXO48__2 | 0.1877 |
| FKBP10 | 0.1051 |
| FLJ33360 | 0.0249 |
| FLJ43752 | 0.2266 |
| FMNL3__2 | 0.0365 |
| FOSB | 0.1925 |
| FOSL2 | 0.0394 |
| FOXN1 | 0.2509 |
| GAD1__2 | 0.0272 |
| GBE1 | 0.0517 |
| GBP7 | 0.0794 |
| GJA5__1 | 0.0623 |
| GMNN | 0.1058 |
| GSR__2 | 0.0111 |
| GUSBL2 | 0.193 |
| HBA2 | 0.069 |
| HDAC7__2 | 0.0304 |
| HDLBP__3 | 0.1922 |
| HIC1 | 0.0854 |
| HPRT1__1 | 0.1421 |
| HPS4__1 | 0.029 |
| HR__1 | 0.0414 |
| HSD11B1__1 | 0.104 |
| ICAM2 | 0.0109 |

TABLE 25-continued

| | |
|---|---|
| ICAM4_1 | 0.2758 |
| IL1RAP_2 | 0.0583 |
| IQCA1_2 | 0.0014 |
| KCNIP3_1 | 0.0838 |
| KCNQ2_1 | 0.1263 |
| KIF3C | 0.182 |
| KRT80_2 | 0.0691 |
| KRTAP10.10_2 | 0.0228 |
| L3MBTL2_3 | 0.0495 |
| LBH_2 | 0.0787 |
| LENEP | 0.2331 |
| LGI3 | 0.1062 |
| LOC340508 | 0.042 |
| LOC492303 | 0.0288 |
| LRRC14B | 0.0692 |
| LRRC37A4_2 | 0.0079 |
| LRRTM4 | 0.1633 |
| MACC1 | 0.1624 |
| MANSC1_1 | 0.1213 |
| MAPK3_1 | 0.0602 |
| MCAM | 0.103 |
| MCART6_1 | 0.2245 |
| MFRP | 0.0236 |
| MIDN | 0.0246 |
| MIR1914 | 0.0441 |
| MIR212 | 0.0936 |
| MIR571 | 0.0381 |
| MIR576 | 0.0926 |
| MIR654 | 0.0013 |
| MIR942 | 0.0829 |
| MMP12_1 | 0.132 |
| MYCN_2 | 0.1408 |
| MYOHD1 | 0.0938 |
| NFATC3_5 | 0.0259 |
| NFATC4 | 0.0532 |
| NLRP9 | 0.1573 |
| NOVA2 | 0.0573 |
| NP | 0.0799 |
| NR6A1_2 | 0.1194 |
| NRXN3_3 | 0.1309 |
| NT5DC1_2 | 0.1804 |
| NTRK2_3 | 0.0104 |
| NUP155_1 | 0.0276 |
| NYX | 0.0582 |
| ODF2_3 | 0.0258 |
| ORC1L | 0.0454 |
| OTUD7A_3 | 0.0526 |
| PANK4 | 0.0511 |
| PDLIM2_2 | 0.1911 |
| PDZRN4_2 | 0.2309 |
| PHYH_1 | 0.0191 |
| PIGA_1 | 0.0892 |
| PITX2_1 | 0.1958 |
| PKN1_3 | 0.0308 |
| PLEKHG5_5 | 0.2591 |
| PLSCR4 | 0.0174 |
| PMEPA1_4 | 0.1368 |
| PNMA5 | 0.1731 |
| PPAPDC1A | 0.093 |
| PRAMEF5 | 0.0086 |
| PRKAA2 | 0.1125 |
| PSMC6_1 | 0.018 |
| RAD54B_2 | 0.1885 |
| RAP1A_1 | 0.1957 |
| RARA_3 | 0.0886 |
| RARG | 0.0401 |
| RNASEK | 0.1013 |
| RNF7_1 | 0.0468 |
| ROD1_1 | 0.1929 |
| SATB2 | 0.0271 |
| SBSN | 0.0761 |
| SCXB | 0.0089 |
| SEC22C_3 | 0.0921 |
| SELENBP1 | 0.1486 |
| SERPINB2_2 | 0.0165 |
| SERPINB5 | 0.1847 |
| SFN | 0.0132 |
| SFRS4 | 0.0678 |
| SHC1_3 | 0.0831 |
| SLC23A1_2 | 0.0904 |

TABLE 25-continued

| | |
|---|---|
| SLC25A34 | 0.0975 |
| SLC4A5_3 | 0.0945 |
| SLC9A10 | 0.0638 |
| SNORD93 | 0.1306 |
| SOX2_1 | 0.0626 |
| STC1 | 0.0084 |
| STC2 | 0.0892 |
| STYX_2 | 0.0331 |
| SYTL3 | 0.0208 |
| TAF15_1 | 0.0086 |
| TCEAL8_1 | 0.0316 |
| THBS3 | 0.0873 |
| TM2D3_2 | 0.0322 |
| TMEM52 | 0.0723 |
| TMEM62 | 0.0051 |
| TNFRSF18_1 | 0.2355 |
| TNNT2_1 | 0.0045 |
| TOMM20L | 0.0044 |
| TPM2_2 | 0.1559 |
| TRIM58 | 0.1018 |
| UBR7_1 | 0.0572 |
| UBR7_2 | 0.1508 |
| WARS_2 | 0.1977 |
| XBP1_2 | 0.161 |
| XRN2_1 | 0.026 |
| YARS2 | 0.0281 |
| ZNF75D_2 | 0.1315 |
| ZSWIM4_2 | 0.1654 |
| figo_numeric | 0.0208 |
| hist_rev_SBOT | 0.0748 |
| surg_outcome | 0.0014 |

TABLE 26

| | |
|---|---|
| ABCC9_3 | 0.0476 |
| ABHD3 | 0.2469 |
| ADAM17_2 | 0.16 |
| ADAMTS1 | 0.0982 |
| ADAMTS2_1 | 0.1272 |
| ALS2CL_3 | 0.05 |
| ANO7_3 | 0.0392 |
| ARL6IP1_1 | 0.0192 |
| ARMCX32 | 0.0755 |
| ATXN10_1 | 0.1707 |
| AXL_1 | 0.0883 |
| BAI1_3 | 0.0608 |
| BCAS1_1 | 0.3288 |
| BDNF_2 | 0.104 |
| BMPR1A | 0.1257 |
| BTF3_3 | 0.1173 |
| C10orf116 | 0.044 |
| C11orf24 | 0.1453 |
| C11orf49_3 | 0.1311 |
| C14orf102_2 | 0.0888 |
| C14orf109_2 | 0.0692 |
| C17orf106 | 0.1665 |
| C17orf58_2 | 0.01 |
| C17orf58_3 | 0.0344 |
| C18orf56 | 0.0318 |
| C1orf168 | 0.0381 |
| C1orf64 | 0.1247 |
| C8orf79_1 | 0.0568 |
| CALD1_2 | 0.1613 |
| CASP8AP2 | 0.1143 |
| CCL13 | 0.1617 |
| CCR2_3 | 0.0119 |
| CD34_1 | 0.0599 |
| CDC42BPA_2 | 0.0156 |
| CDC42SE2_2 | 0.017 |
| CIDEC_1 | 0.1153 |
| CLDN6 | 0.0052 |
| CREB5_2 | 0.0516 |
| CREBBP_1 | 0.0369 |
| CRYBA1 | 0.0801 |
| CXCL13 | 0.1697 |
| CYB5R3_2 | 0.1687 |
| CYP1A2 | 0.0699 |

TABLE 26-continued

| | |
|---|---|
| DBNDD2 | 0.084 |
| DFFB__2 | 0.037 |
| DNAH11 | 0.0235 |
| DNMT3L__2 | 0.1057 |
| DOCK7__1 | 0.0147 |
| DSC3__1 | 0.0535 |
| DUT__3 | 0.1181 |
| EEF1E1__1 | 0.0877 |
| ELN__2 | 0.1041 |
| EMP1 | 0.1731 |
| ENO1 | 0.1271 |
| ENPEP__2 | 0.0578 |
| EPHB1 | 0.0574 |
| EPYC | 0.0271 |
| ERI2__2 | 0.2777 |
| ESPNL | 0.0816 |
| EZH2__1 | 0.0374 |
| FAM13AOS | 0.0287 |
| FAM187B__2 | 0.0124 |
| FAM70A__1 | 0.0974 |
| FBXO48__2 | 0.1976 |
| FKBP10 | 0.0997 |
| FLJ33360 | 0.0363 |
| FLJ43752 | 0.2224 |
| FMNL3__2 | 0.0145 |
| FOSB | 0.1895 |
| FOSL2 | 0.0201 |
| FOXN1 | 0.2817 |
| GAD1__2 | 0.0171 |
| GBE1 | 0.0639 |
| GBP7 | 0.1032 |
| GJA5__1 | 0.051 |
| GMNN | 0.0776 |
| GSR__2 | 0.0245 |
| GUSBL2 | 0.188 |
| HBA2 | 0.0817 |
| HDAC7__2 | 0.0295 |
| HDLBP__3 | 0.2006 |
| HIC1 | 0.0848 |
| HPRT1__1 | 0.1553 |
| HPS4__1 | 0.0392 |
| HR__1 | 0.0504 |
| HSD11B1__1 | 0.0967 |
| ICAM2 | 0.0054 |
| ICAM4__1 | 0.2676 |
| IL1RAP__2 | 0.0356 |
| IQCA1__2 | 0.0114 |
| KCNIP3__1 | 0.0805 |
| KCNQ2__1 | 0.1399 |
| KIF3C | 0.2155 |
| KRT80__2 | 0.0639 |
| KRTAP10.10__2 | 0.0151 |
| L3MBTL2__3 | 0.0464 |
| LBH__2 | 0.0991 |
| LENEP | 0.2429 |
| LGI3 | 0.1157 |
| LOC340508 | 0.0435 |
| LOC492303 | 0.0199 |
| LRRC14B | 0.0696 |
| LRRC37A4__2 | 0.0045 |
| LRRTM4 | 0.1548 |
| MACC1 | 0.1409 |
| MANSC1__1 | 0.1432 |
| MAPK3__1 | 0.0687 |
| MCAM | 0.1114 |
| MCART6__1 | 0.2171 |
| MFRP | 0.0204 |
| MIDN | 0.0342 |
| MIR1914 | 0.0392 |
| MIR212 | 0.0991 |
| MIR571 | 0.0311 |
| MIR576 | 0.0854 |
| MIR654 | 0.0168 |
| MIR942 | 0.0906 |
| MMP12__1 | 0.1239 |
| MYCN__2 | 0.1542 |
| MYOHD1 | 0.0972 |
| NFATC3__5 | 0.0407 |
| NFATC4 | 0.0513 |
| NLRP9 | 0.1502 |
| NOVA2 | 0.085 |
| NP | 0.0834 |
| NR6A1__2 | 0.1261 |
| NRXN3__3 | 0.0891 |
| NT5DC1__2 | 0.1823 |
| NTRK2__3 | 0.0252 |
| NUP155__1 | 0.0146 |
| NYX | 0.0789 |
| ODF2__3 | 0.0283 |
| ORC1L | 0.0571 |
| OTUD7A__3 | 0.045 |
| PANKA | 0.0423 |
| PDLIM2__2 | 0.2005 |
| PHYH__1 | 0.2122 |
| PIGA__1 | 0.012 |
| PITX2__1 | 0.0764 |
| PKN1__3 | 0.0519 |
| PLEKHG5__5 | 0.2777 |
| PLSCR4 | 0.0333 |
| PMEPA1__4 | 0.1482 |
| PNMA5 | 0.1554 |
| PPAPDC1A | 0.1215 |
| PRAMEF5 | 0.0287 |
| PRKAA2 | 0.1182 |
| PSMC6__1 | 0.0133 |
| RAD54B__2 | 0.1973 |
| RAP1A__1 | 0.2038 |
| RARA__3 | 0.0831 |
| RARG | 0.0136 |
| RNASEK | 0.0596 |
| RNF7__1 | 0.066 |
| ROD1__1 | 0.2187 |
| SATB2 | 0.0385 |
| SBSN | 0.0849 |
| SCXB | 0.0097 |
| SEC22C__3 | 0.0968 |
| SELENBP1 | 0.174 |
| SERPINB2__2 | 0.017 |
| SERPINB5 | 0.203 |
| SFN | 0.0329 |
| SFRS4 | 0.0619 |
| SHC1__3 | 0.0753 |
| SLC23A1__2 | 0.1103 |
| SLC25A34 | 0.0851 |
| SLC4A5__3 | 0.083 |
| SLC9A10 | 0.0945 |
| SNORD93 | 0.1705 |
| SOX2__1 | 0.0489 |
| STC1 | 0.001 |
| STC2 | 0.0976 |
| STYX__2 | 0.0549 |
| SYTL3 | 0.003 |
| TAF15__1 | 0.0041 |
| TCEAL8__1 | 0.0288 |
| THBS3 | 0.0823 |
| TM2D3__2 | 0.0461 |
| TMEM52 | 0.0834 |
| TMEM62 | 0.0011 |
| TNFRSF18__1 | 0.2512 |
| TNNT2__1 | 0.0037 |
| TOMM20L | 0.0464 |
| TPM2__2 | 0.1557 |
| TRIM58 | 0.106 |
| UBR7__1 | 0.0139 |
| UBR7__2 | 0.1407 |
| WARS__2 | 0.1709 |
| XBP1__2 | 0.1367 |
| XRN2__1 | 0.0079 |
| YARS2 | 0.0026 |
| ZNF75D__2 | 0.1368 |
| ZSWIM4__2 | 0.1669 |
| figo__numeric | 0.0267 |
| hist__rev__SBOT | 0.0627 |
| surg__outcome | 0.0132 |

TABLE 27

| | |
|---|---|
| ABCC9_3 | 0.065 |
| ABHD3 | 0.2364 |
| ADAM17_2 | 0.1517 |
| ADAMTS1 | 0.1015 |
| ADAMTS2_1 | 0.111 |
| ALS2CL_3 | 0.0631 |
| ANO7_3 | 0.0177 |
| ARL6IP1_1 | 0.0002 |
| ARMCX3_2 | 0.0492 |
| ATXN10_1 | 0.1864 |
| AXL_1 | 0.0812 |
| BAI1_3 | 0.0399 |
| BCAS1_1 | 0.2986 |
| BDNF_2 | 0.0907 |
| BMPR1A | 0.1242 |
| BTF3_3 | 0.11 |
| C10orf116 | 0.0759 |
| C11orf24 | 0.1217 |
| C11orf49_3 | 0.1088 |
| C14orf102_2 | 0.0804 |
| C14orf109_2 | 0.1262 |
| C17orf106 | 0.1575 |
| C17orf58_2 | 0.0313 |
| C17orf58_3 | 0.0388 |
| C18orf56 | 0.0067 |
| C1orf168 | 0.0427 |
| C1orf64 | 0.1084 |
| C8orf79_1 | 0.0602 |
| CALD1_2 | 0.1315 |
| CASP8AP2 | 0.1172 |
| CCL13 | 0.1255 |
| CCR2_3 | 0.0423 |
| CD34_1 | 0.0422 |
| CDC42BPA_2 | 0.015 |
| CDC42SE2_2 | 0.0232 |
| CLDN6 | 0.1183 |
| CREB5_2 | 0.0239 |
| CREBBP_1 | 0.0347 |
| CRYBA1 | 0.0762 |
| CXCL13 | 0.1625 |
| CYB5R3_2 | 0.1798 |
| CYP1A2 | 0.0773 |
| DBNDD2 | 0.0986 |
| DFFB_2 | 0.0369 |
| DNAH11 | 0.0356 |
| DNMT3L_2 | 0.113 |
| DOCK7_1 | 0.0058 |
| DSC3_1 | 0.0561 |
| DUT_3 | 0.1277 |
| EEF1E1_1 | 0.1034 |
| ELN_2 | 0.109 |
| EMP1 | 0.1754 |
| ENO1 | 0.1403 |
| ENPEP_2 | 0.0449 |
| EPHB1 | 0.0394 |
| EPYC | 0.0314 |
| ERI2_2 | 0.2791 |
| ESPNL | 0.0955 |
| EZH2_1 | 0.0336 |
| FAM13AOS | 0.0556 |
| FAM187B_2 | 0.0291 |
| FAM70A_1 | 0.094 |
| FBXO48_2 | 0.1923 |
| FKBP10 | 0.1219 |
| FLJ33360 | 0.0077 |
| FLJ43752 | 0.2354 |
| FMNL3_2 | 0.0352 |
| FOSB | 0.2097 |
| FOSL2 | 0.0224 |
| FOXN1 | 0.2375 |
| GAD1_2 | 0.0205 |
| GBE1 | 0.07 |
| GBP7 | 0.0943 |
| GJA5_1 | 0.0504 |
| GMNN | 0.0833 |
| GSR_2 | 0.0126 |
| GUSBL2 | 0.2013 |
| HBA2 | 0.0841 |
| HDAC7_2 | 0.023 |
| HDLBP_3 | 0.1929 |

TABLE 27-continued

| | |
|---|---|
| HIC1 | 0.1045 |
| HPRT1_1 | 0.1451 |
| HPS4_1 | 0.004 |
| HR_1 | 0.045 |
| HSD11B1_1 | 0.1073 |
| ICAM2 | 0.0219 |
| ICAM4_1 | 0.2635 |
| IL1RAP_2 | 0.0726 |
| IQCA1_2 | 0.0176 |
| KCNIP3_1 | 0.0945 |
| KCNQ2_1 | 0.1335 |
| KIF3C | 0.193 |
| KRT80_2 | 0.0765 |
| KRTAP10.10_2 | 0.0138 |
| L3MBTL2_3 | 0.0427 |
| LBH_2 | 0.0826 |
| LENEP | 0.2258 |
| LGI3 | 0.1079 |
| LOC340508 | 0.0632 |
| LOC492303 | 0.0294 |
| LRRC14B | 0.0808 |
| LRRC37A4_2 | 0.0079 |
| LRRTM4 | 0.181 |
| MACC1 | 0.1689 |
| MANSC1_1 | 0.1203 |
| MAPK3_1 | 0.0447 |
| MCAM | 0.1012 |
| MCART6_1 | 0.2168 |
| MFRP | 0.0342 |
| MIDN | 0.0277 |
| MIR1914 | 0.0621 |
| MIR212 | 0.0887 |
| MIR571 | 0.0229 |
| MIR576 | 0.0855 |
| MIR654 | 0.0092 |
| MIR942 | 0.0891 |
| MMP12_1 | 0.1221 |
| MYCN_2 | 0.1217 |
| MYOHD1 | 0.0882 |
| NFATC3_5 | 0.0152 |
| NFATC4 | 0.058 |
| NLRP9 | 0.1587 |
| NOVA2 | 0.0556 |
| NP | 0.0842 |
| NR6A1_2 | 0.1202 |
| NRXN3_3 | 0.1317 |
| NT5DC1_2 | 0.1844 |
| NTRK2_3 | 0.0283 |
| NUP155_1 | 0.0382 |
| NYX | 0.0625 |
| ODF2_3 | 0.0315 |
| ORC1L | 0.0513 |
| OTUD7A_3 | 0.073 |
| PANK4 | 0.0475 |
| PDLIM2_2 | 0.1872 |
| PDZRN4_2 | 0.2358 |
| PHYH_1 | 0.0063 |
| PIGA_1 | 0.1012 |
| PITX2_1 | 0.1804 |
| PKN1_3 | 0.0399 |
| PLEKHG5_5 | 0.2662 |
| PLSCR4 | 0.027 |
| PMEPA1_4 | 0.1375 |
| PNMA5 | 0.1794 |
| PPAPDC1A | 0.0921 |
| PRAMEF5 | 0.003 |
| PRKAA2 | 0.0835 |
| PSMC6_1 | 0.001 |
| RAD54B_2 | 0.1935 |
| RAP1A_1 | 0.208 |
| RARA_3 | 0.0748 |
| RARG | 0.0289 |
| RNASEK | 0.098 |
| RNF7_1 | 0.0311 |
| ROD1_1 | 0.2203 |
| SATB2 | 0.0192 |
| SBSN | 0.0578 |
| SCXB | 0.012 |
| SEC22C_3 | 0.0927 |
| SELENBP1 | 0.137 |

TABLE 27-continued

| | |
|---|---|
| SERPINB2__2 | 0.0345 |
| SERPINB5 | 0.1967 |
| SFN | 0.0191 |
| SFRS4 | 0.061 |
| SHC1__3 | 0.089 |
| SLC23A1__2 | 0.0882 |
| SLC25A34 | 0.0937 |
| SLC4A5__3 | 0.0897 |
| SLC9A10 | 0.0675 |
| SNORD93 | 0.1369 |
| SOX2__1 | 0.0599 |
| STC1 | 0.0115 |
| STC2 | 0.0823 |
| STYX__2 | 0.0391 |
| SYTL3 | 0.0069 |
| TAF15__1 | 0.0071 |
| TCEAL8__1 | 0.0398 |
| THBS3 | 0.0768 |
| TM2D3__2 | 0.0367 |
| TMEM52 | 0.0746 |
| TMEM62 | 0.0034 |
| TNFRSF18__1 | 0.2372 |
| TNNT2__1 | 0.0008 |
| TOMM20L | 0.0068 |
| TPM2__2 | 0.1513 |
| TRIM58 | 0.102 |
| UBR7__1 | 0.0338 |
| UBR7__2 | 0.1467 |
| WARS__2 | 0.1962 |
| XBP1__2 | 0.1619 |
| XRN2__1 | 0.0064 |
| YARS2 | 0.0057 |
| ZNF75D__2 | 0.1134 |
| ZSWIM4__2 | 0.1535 |
| figo__numeric | 0.0079 |
| hist__rev__SBOT | 0.0662 |
| surg__outcome | 0.0034 |

TABLE 28

| | |
|---|---|
| ABCC9__3 | 0.0685 |
| ABHD3 | 0.244 |
| ADAM17__2 | 0.1456 |
| ADAMTS1 | 0.0804 |
| ADAMTS2__1 | 0.1088 |
| ALS2CL__3 | 0.0534 |
| ANO7__3 | 0.0387 |
| ARL6IP1__1 | 0.0062 |
| ARMCX3__2 | 0.0603 |
| ATXN10__1 | 0.1744 |
| AXL__1 | 0.0709 |
| BAI1__3 | 0.0546 |
| BCAS1__1 | 0.307 |
| BDNF__2 | 0.0947 |
| BMPR1A | 0.1185 |
| BTF3__3 | 0.1107 |
| C10orf116 | 0.0779 |
| C11orf24 | 0.1292 |
| C11orf49__3 | 0.1097 |
| C14orf102__2 | 0.0891 |
| C14orf109__2 | 0.11 |
| C17orf106 | 0.1543 |
| C17orf58__2 | 0.0053 |
| C17orf58__3 | 0.028 |
| C18orf56 | 0.0048 |
| C1orf168 | 0.0315 |
| C1orf64 | 0.1037 |
| C8orf79__1 | 0.042 |
| CALD1__2 | 0.1513 |
| CASP8AP2 | 0.1192 |
| CCL13 | 0.151 |
| CCR2__3 | 0.034 |
| CD34__1 | 0.0494 |
| CDC42BPA__2 | 0.0004 |
| CDC42SE2__2 | 0.0005 |
| CIDEC__1 | 0.1068 |
| CLDN6 | 0.0201 |

TABLE 28-continued

| | |
|---|---|
| CREB5__2 | 0.0193 |
| CREBBP__1 | 0.0516 |
| CRYBA1 | 0.0675 |
| CXCL13 | 0.1724 |
| CYB5R3__2 | 0.16 |
| CYP1A2 | 0.0667 |
| DBNDD2 | 0.1008 |
| DFFB__2 | 0.0414 |
| DNAH11 | 0.0309 |
| DNMT3L__2 | 0.0979 |
| DOCK7__1 | 0.0132 |
| DSC3__1 | 0.0382 |
| DUT__3 | 0.1216 |
| EEF1E1__1 | 0.1052 |
| ELN__2 | 0.1082 |
| EMP1 | 0.1791 |
| ENO1 | 0.1418 |
| ENPEP__2 | 0.0594 |
| EPHB1 | 0.0427 |
| EPYC | 0.0308 |
| ERI2__2 | 0.2675 |
| ESPNL | 0.0834 |
| EZH2__1 | 0.0414 |
| FAM13AOS | 0.055 |
| FAM187B__2 | 0.0098 |
| FAM70A__1 | 0.1018 |
| FBXO48__2 | 0.1878 |
| FKBP10 | 0.1057 |
| FLJ33360 | 0.0249 |
| FLJ43752 | 0.226 |
| FMNL3__2 | 0.0365 |
| FOSB | 0.1933 |
| FOSL2 | 0.0384 |
| FOXN1 | 0.2511 |
| GAD1__2 | 0.0273 |
| GBE1 | 0.0526 |
| GBP7 | 0.0796 |
| GJA5__1 | 0.0627 |
| GMNN | 0.106 |
| GSR__2 | 0.0097 |
| GUSBL2 | 0.1927 |
| HBA2 | 0.0699 |
| HDAC7__2 | 0.0315 |
| HDLBP__3 | 0.1918 |
| HIC1 | 0.0858 |
| HPRT1__1 | 0.1429 |
| HPS4__1 | 0.0275 |
| HR__1 | 0.0396 |
| HSD11B1__1 | 0.1048 |
| ICAM2 | 0.0101 |
| ICAM4__1 | 0.2764 |
| IL1RAP__2 | 0.0589 |
| IQCA1__2 | 0.0019 |
| KCNIP3__1 | 0.0836 |
| KCNQ2__1 | 0.1263 |
| KIF3C | 0.1822 |
| KRT80__2 | 0.0699 |
| KRTAP10.10__2 | 0.0235 |
| L3MBTL2__3 | 0.0499 |
| LBH__2 | 0.0784 |
| LENEP | 0.2324 |
| LGI3 | 0.1069 |
| LOC492303 | 0.0413 |
| LRRC14B | 0.0286 |
| LRRC37A4__2 | 0.069 |
| LRRTM4 | 0.1636 |
| MACC1 | 0.1621 |
| MANSC1__1 | 0.1209 |
| MAPK3__1 | 0.0616 |
| MCAM | 0.1033 |
| MCART6__1 | 0.2257 |
| MFRP | 0.0231 |
| MIDN | 0.0249 |
| MIR1914 | 0.0424 |
| MIR212 | 0.0931 |
| MIR571 | 0.0375 |
| MIR576 | 0.0931 |
| MIR654 | 0.0012 |
| MIR942 | 0.0823 |
| MMP12__1 | 0.1315 |

TABLE 28-continued

| | |
|---|---|
| MYCN_2 | 0.1405 |
| MYOHD1 | 0.0938 |
| NFATC3_5 | 0.0265 |
| NFATC4 | 0.0531 |
| NLRP9 | 0.1566 |
| NOVA2 | 0.0572 |
| NP | 0.0798 |
| NR6A1_2 | 0.1202 |
| NRXN3_3 | 0.1303 |
| NT5DC1_2 | 0.1811 |
| NTRK2_3 | 0.0106 |
| NUP155_1 | 0.0284 |
| NYX | 0.0589 |
| ODF2_3 | 0.0259 |
| ORC1L | 0.0456 |
| OTUD7A_3 | 0.0528 |
| PANK4 | 0.0518 |
| PDLIM2_2 | 0.1921 |
| PDZRN4_2 | 0.2307 |
| PHYH_1 | 0.0186 |
| PIGA_1 | 0.0892 |
| PITX2_1 | 0.1948 |
| PKN1_3 | 0.0313 |
| PLEKHG5_5 | 0.2595 |
| PLSCR4 | 0.0171 |
| PMEPA1_4 | 0.1383 |
| PNMA5 | 0.1722 |
| PPAPDC1A | 0.093 |
| PRAMEF5 | 0.0075 |
| PRKAA2 | 0.1133 |
| PSMC6_1 | 0.0177 |
| RAD54B_2 | 0.1882 |
| RAP1A_1 | 0.194 |
| RARA_3 | 0.0881 |
| RARG | 0.0404 |
| RNASEK | 0.1022 |
| RNF7_1 | 0.0459 |
| ROD1_1 | 0.1934 |
| SATB2 | 0.0276 |
| SBSN | 0.0758 |
| SCXB | 0.009 |
| SEC22C_3 | 0.0927 |
| SELENBP1 | 0.1487 |
| SERPINB2_2 | 0.0152 |
| SERPINB5 | 0.1862 |
| SFN | 0.014 |
| SFRS4 | 0.0682 |
| SHC1_3 | 0.0832 |
| SLC23A1_2 | 0.0905 |
| SLC25A34 | 0.097 |
| SLC4A5_3 | 0.0945 |
| SLC9A10 | 0.0638 |
| SNORD93 | 0.1296 |
| SOX2_1 | 0.0626 |
| STC1 | 0.0083 |
| STC2 | 0.0902 |
| STYX_2 | 0.0325 |
| SYTL3 | 0.0211 |
| TAF15_1 | 0.0091 |
| TCEAL8_1 | 0.0323 |
| THBS3 | 0.0868 |
| TM2D3_2 | 0.0321 |
| TMEM52 | 0.0706 |
| TMEM62 | 0.0054 |
| TNFRSF18_1 | 0.2353 |
| TNNT2_1 | 0.005 |
| TOMM20L | 0.0051 |
| TPM2_2 | 0.1559 |
| TRIM58 | 0.1018 |
| UBR7_1 | 0.0569 |
| UBR7_2 | 0.1509 |
| WARS_2 | 0.197 |
| XBP1_2 | 0.1612 |
| XRN2_1 | 0.0263 |
| YARS2 | 0.0284 |
| ZNF75D_2 | 0.1315 |
| ZSWIM4_2 | 0.1654 |
| figo_numeric | 0.0217 |
| hist_rev_SBOT | 0.0745 |
| surg_outcome | 0.0002 |

TABLE 29

| | |
|---|---|
| ABHD3 | 0.0618 |
| ADAM17_2 | 0.2475 |
| ADAMTS1 | 0.1461 |
| ADAMTS2_1 | 0.0871 |
| ALS2CL_3 | 0.077 |
| ANO7_3 | 0.0212 |
| ARL6IP1_1 | 0.0217 |
| ARMCX3_2 | 0.0673 |
| ATXN10_1 | 0.2132 |
| AXL_1 | 0.095 |
| BAI1_3 | 0.0392 |
| BCAS1_1 | 0.3166 |
| BDNF_2 | 0.1039 |
| BMPR1A | 0.1113 |
| BTF3_3 | 0.099 |
| C10orf116 | 0.0686 |
| C11orf24 | 0.1691 |
| C11orf49_3 | 0.1217 |
| C14orf102_2 | 0.1211 |
| C14orf109_2 | 0.1057 |
| C17orf106 | 0.1712 |
| C17orf58_2 | 0.0212 |
| C17orf58_3 | 0.0262 |
| C18orf56 | 0.0087 |
| C1orf168 | 0.0234 |
| C1orf64 | 0.1021 |
| C8orf79_1 | 0.005 |
| CASP8AP2 | 0.1346 |
| CCL13 | 0.1363 |
| CCR2_3 | 0.1265 |
| CD34_1 | 0.012 |
| CDC42BPA_2 | 0.0006 |
| CDC42SE2_2 | 0.0196 |
| CIDEC_1 | 0.0995 |
| CLDN6 | 0.0116 |
| CREB5_2 | 0.0031 |
| CRYBA1 | 0.0607 |
| CXCL13 | 0.0615 |
| CYB5R3_2 | 0.1912 |
| CYP1A2 | 0.0598 |
| DBNDD2 | 0.1261 |
| DNAH11 | 0.0454 |
| DNMT3L_2 | 0.0123 |
| DOCK7_1 | 0.1005 |
| DSC3_1 | 0.0364 |
| DUT_3 | 0.1169 |
| EEF1E1_1 | 0.1311 |
| ELN_2 | 0.1234 |
| EMP1 | 0.2053 |
| ENO1 | 0.1684 |
| ENPEP_2 | 0.0695 |
| EPHB1 | 0.0221 |
| EPYC | 0.0518 |
| ERI2_2 | 0.281 |
| ESPNL | 0.0508 |
| EZH2_1 | 0.0486 |
| FAM13AOS | 0.0603 |
| FAM187B_2 | 0.0061 |
| FAM70A_1 | 0.0744 |
| FBXO48_2 | 0.2395 |
| FKBP10 | 0.0433 |
| FLJ33360 | 0.0163 |
| FLJ43752 | 0.2253 |
| FMNL3_2 | 0.0011 |
| FOSB | 0.2168 |
| FOSL2 | 0.0488 |
| FOXN1 | 0.2391 |
| GAD1_2 | 0.0218 |
| GBE1 | 0.0402 |
| GBP7 | 0.1302 |
| GJA5_1 | 0.0633 |
| GMNN | 0.1023 |

TABLE 29-continued

| | |
|---|---|
| GSR_2 | 0.019 |
| HBA2 | 0.2143 |
| HCFC1R1_1 | 0.0428 |
| HDAC7_2 | 0.003 |
| HDLBP_3 | 0.0974 |
| HIC1 | 0.0161 |
| HPRT1_1 | 0.1425 |
| HPS4_1 | 0.0712 |
| HR_1 | 0.0199 |
| HSD11B1_1 | 0.0988 |
| ICAM2 | 0.0189 |
| ICAM4_1 | 0.3077 |
| IL1RAP_2 | 0.0827 |
| IQCA1_2 | 0.014 |
| KCNIP3_1 | 0.0954 |
| KCNQ2_1 | 0.1123 |
| KIF3C | 0.1782 |
| KRT80_2 | 0.0941 |
| KRTAP10.10_2 | 0.0339 |
| L3MBTL2_3 | 0.0422 |
| LBH_2 | 0.0695 |
| LENEP | 0.2316 |
| LGI3 | 0.0948 |
| LOC340508 | 0.0133 |
| LOC492303 | 0.037 |
| LRRC14B | 0.072 |
| LRRC37A4_2 | 0.0148 |
| LRRTM4 | 0.1616 |
| MACC1 | 0.1462 |
| MANSC1_1 | 0.1217 |
| MCAM | 0.0331 |
| MCART6_1 | 0.114 |
| MFRP | 0.2341 |
| MIDN | 0.0273 |
| MIR1914 | 0.0737 |
| MIR212 | 0.105 |
| MIR571 | 0.0079 |
| MIR576 | 0.1016 |
| MIR654 | 0.0606 |
| MIR942 | 0.1115 |
| MMP12_1 | 0.114 |
| MYCN_2 | 0.1289 |
| MYL9_2 | 0.1078 |
| MYOHD1 | 0.0231 |
| NFATC3_5 | 0.0414 |
| NFATC4 | 0.0648 |
| NLRP9 | 0.1888 |
| NOVA2 | 0.0538 |
| NP | 0.0742 |
| NR6A1_2 | 0.1413 |
| NRXN3_3 | 0.1729 |
| NT5DC1_2 | 0.1804 |
| NTRK2_3 | 0.0071 |
| NUP155_1 | 0.0366 |
| NYX | 0.1525 |
| ODF2_3 | 0.0055 |
| ORC1L | 0.0279 |
| OTUD7A_3 | 0.0312 |
| PANK4 | 0.0578 |
| PDLIM2_2 | 0.2134 |
| PDZRN4_2 | 0.1932 |
| PHYH_1 | 0.0049 |
| PIGA_1 | 0.0808 |
| PITX2_1 | 0.2057 |
| PKN1_3 | 0.0038 |
| PLEKHG5_5 | 0.2623 |
| PLSCR4 | 0.0168 |
| PMEPA1_4 | 0.1561 |
| PNMA5 | 0.1577 |
| PPAPDC1A | 0.1222 |
| PRAMEF5 | 0.0044 |
| PRKAA2 | 0.1197 |
| PSMC6_1 | 0.0273 |
| RAD54B_2 | 0.1907 |
| RAP1A_1 | 0.1828 |
| RARA_3 | 0.0998 |
| RARG | 0.065 |
| RNASEK | 0.0781 |
| RNF7_1 | 0.0041 |
| ROD1_1 | 0.1907 |
| SATB2 | 0.0351 |
| SBSN | 0.102 |
| SCXB | 0.0184 |
| SEC22C_3 | 0.1137 |
| SELENBP1 | 0.1525 |
| SERPINB2_2 | 0.0294 |
| SERPINB5 | 0.1806 |
| SFN | 0.0045 |
| SFRS4 | 0.0628 |
| SHC1_3 | 0.0513 |
| SLC23A1_2 | 0.1159 |
| SLC25A34 | 0.1291 |
| SLC4A5_3 | 0.0937 |
| SLC9A10 | 0.0669 |
| SNORD93 | 0.134 |
| SOX2_1 | 0.0735 |
| STC1 | 0.0015 |
| STC2 | 0.1212 |
| STYX_2 | 0.0093 |
| SYTL3 | 0.0182 |
| TAF15_1 | 0.0303 |
| TCEAL8_1 | 0.0055 |
| THBS3 | 0.0788 |
| THY1 | 0.0272 |
| TIMP2_2 | 0.0904 |
| TM2D3_2 | 0.0107 |
| TMEM52 | 0.0317 |
| TMEM62 | 0.0753 |
| TNFRSF18_1 | 0.2291 |
| TNNT2_1 | 0.0027 |
| TOMM20L | 0.0123 |
| TPM2_2 | 0.1782 |
| TRIM58 | 0.1209 |
| UBR7_1 | 0.0869 |
| UBR7_2 | 0.1318 |
| WARS_2 | 0.1787 |
| XBP1_2 | 0.1588 |
| XRN2_1 | 0.0623 |
| YARS2 | 0.0364 |
| ZCCHC24 | 0.1336 |
| ZNF75D_2 | 0.178 |
| ZSWIM4_2 | 0.005 |
| figo_numeric | 0.042 |
| hist_rev_SBOT | 0.0462 |
| surg_outcome | 0.0032 |

TABLE 30

| | |
|---|---|
| ABHD3 | 0.0616 |
| ADAM17_2 | 0.2471 |
| ADAMTS1 | 0.1489 |
| ADAMTS2_1 | 0.0826 |
| ALS2CL_3 | 0.0755 |
| ANO7_3 | 0.0368 |
| ARL6IP1_1 | 0.0047 |
| ARMCX3_2 | 0.075 |
| ATXN10_1 | 0.2066 |
| AXL_1 | 0.0994 |
| BAI1_3 | 0.0299 |
| BCAS1_1 | 0.3377 |
| BDNF_2 | 0.1184 |
| BMPR1A | 0.1141 |
| BTF3_3 | 0.1065 |
| C10orf116 | 0.0741 |
| C11orf24 | 0.1923 |
| C11orf49_3 | 0.107 |
| C14orf102_2 | 0.1262 |
| C14orf109_2 | 0.1112 |
| C17orf106 | 0.1828 |
| C17orf58_2 | 0.0177 |
| C17orf58_3 | 0.0241 |
| C18orf56 | 0.0112 |
| C1orf168 | 0.0283 |
| C1orf64 | 0.1091 |
| C8orf79_1 | 0.0087 |
| CALD1_2 | 0.1208 |
| CASP8AP2 | 0.1425 |

TABLE 30-continued

| | |
|---|---|
| CCL13 | 0.127 |
| CCR2__3 | 0.0256 |
| CD34__1 | 0.0151 |
| CDC42BPA__2 | 0.0088 |
| CDC42SE2__2 | 0.0086 |
| CIDEC__1 | 0.0993 |
| CLDN6 | 0.0009 |
| CREB5__2 | 0.0038 |
| CRYBA1 | 0.0576 |
| CXCL13 | 0.0679 |
| CYB5R3__2 | 0.1925 |
| CYP1A2 | 0.0545 |
| DBNDD2 | 0.1222 |
| DNAH11 | 0.043 |
| DNMT3L__2 | 0.0228 |
| DOCK7__1 | 0.1114 |
| DSC3__1 | 0.05 |
| DUT__3 | 0.0994 |
| EEF1E1__1 | 0.1284 |
| EMP1 | 0.1304 |
| ENO1 | 0.207 |
| ENPEP__2 | 0.1684 |
| EPHB1 | 0.0222 |
| EPYC | 0.0453 |
| ERI2__2 | 0.2904 |
| ESPNL | 0.0471 |
| EZH2__1 | 0.0561 |
| FAM13AOS | 0.066 |
| FAM187B__2 | 0.0127 |
| FAM70A__1 | 0.0735 |
| FBXO48__2 | 0.2406 |
| FKBP10 | 0.0634 |
| FLJ33360 | 0.0159 |
| FLJ43752 | 0.2325 |
| FMNL3__2 | 0.0124 |
| FOSB | 0.2212 |
| FOSL2 | 0.0487 |
| FOXN1 | 0.2383 |
| GAD1__2 | 0.0286 |
| GBE1 | 0.0374 |
| GBP7 | 0.1255 |
| GJA5__1 | 0.0629 |
| GMNN | 0.1049 |
| GSR__2 | 0.0323 |
| HBA2 | 0.2133 |
| HCFC1R1__1 | 0.0402 |
| HDAC7__2 | 0.0084 |
| HDLBP__3 | 0.1079 |
| HIC1 | 0.0192 |
| HPRT1__1 | 0.1315 |
| HPS4__1 | 0.0742 |
| HR__1 | 0.0307 |
| HSD11B1__1 | 0.0998 |
| ICAM2 | 0.0132 |
| ICAM4__1 | 0.2908 |
| IL1RAP__2 | 0.0712 |
| IQCA1__2 | 0.0221 |
| KCNIP3__1 | 0.102 |
| KCNQ2__1 | 0.1221 |
| KIF3C | 0.158 |
| KRT80__2 | 0.1047 |
| KRTAP10.10__2 | 0.0351 |
| L3MBTL2__3 | 0.0462 |
| LBH__2 | 0.0773 |
| LENEP | 0.2262 |
| LGI3 | 0.0872 |
| LOC340508 | 0.0228 |
| LOC492303 | 0.04 |
| LRRC14B | 0.077 |
| LRRC37A4__2 | 0.0128 |
| LRRTM4 | 0.1688 |
| MACC1 | 0.1328 |
| MANSC1__1 | 0.1301 |
| MCAM | 0.0322 |
| MCART6__1 | 0.1191 |
| MFRP | 0.2311 |
| MIDN | 0.0232 |
| MIR1914 | 0.0637 |
| MIR212 | 0.0967 |
| MIR571 | 0.0043 |
| MIR576 | 0.1015 |
| MIR654 | 0.0586 |
| MIR942 | 0.1229 |
| MMP12__1 | 0.1182 |
| MYCN__2 | 0.1248 |
| MYOHD1 | 0.1121 |
| NFATC3__5 | 0.0145 |
| NFATC4 | 0.0439 |
| NLRP9 | 0.1998 |
| NOVA2 | 0.0714 |
| NP | 0.084 |
| NR6A1__2 | 0.1442 |
| NRXN3__3 | 0.1708 |
| NT5DC1__2 | 0.1851 |
| NTRK2__3 | 0.0054 |
| NUP155__1 | 0.0373 |
| NYX | 0.1587 |
| ODF2__3 | 0.0093 |
| ORC1L | 0.0107 |
| OTUD7A__3 | 0.0394 |
| PANK4 | 0.0564 |
| PDLIM2__2 | 0.2098 |
| PDZRN4__2 | 0.205 |
| PHYH__1 | 0.0038 |
| PIGA__1 | 0.0836 |
| PITX2__1 | 0.216 |
| PKN1__3 | 0.0099 |
| PLEKHG5__5 | 0.2613 |
| PLSCR4 | 0.0138 |
| PMEPA1__4 | 0.1447 |
| PNMA5 | 0.1631 |
| PPAPDC1A | 0.1032 |
| PRAMEF5 | 0.0098 |
| PRKAA2 | 0.1284 |
| PSMC6__1 | 0.0248 |
| RAD54B__2 | 0.1832 |
| RAP1A__1 | 0.1961 |
| RARA__3 | 0.1 |
| RARG | 0.0489 |
| RNASEK | 0.0889 |
| RNF7__1 | 0.0022 |
| ROD1__1 | 0.1789 |
| SATB2 | 0.0348 |
| SBSN | 0.0947 |
| SCXB | 0.0091 |
| SEC22C__3 | 0.1053 |
| SELENBP1 | 0.1512 |
| SERPINB2__2 | 0.0096 |
| SERPINB5 | 0.1899 |
| SFN | 0.0083 |
| SFRS4 | 0.0566 |
| SHC1__3 | 0.0563 |
| SLC23A1__2 | 0.1265 |
| SLC25A34 | 0.1342 |
| SLC4A5__3 | 0.0946 |
| SLC9A10 | 0.0674 |
| SNORD93 | 0.1338 |
| SOX2__1 | 0.0749 |
| STC1 | 0.0153 |
| STC2 | 0.1306 |
| STYX__2 | 0.0142 |
| SYTL3 | 0.0214 |
| TAF15__1 | 0.0329 |
| TCEAL8__1 | 0.012 |
| THBS3 | 0.0896 |
| TM2D3__2 | 0.0347 |
| TMEM52 | 0.0974 |
| TMEM62 | 0.0064 |
| TNFRSF18__1 | 0.23 |
| TNNT2__1 | 0.0087 |
| TOMM20L | 0.0148 |
| TPM2__2 | 0.1766 |
| TRIM58 | 0.1201 |
| UBR7__1 | 0.0894 |
| UBR7__2 | 0.1281 |
| WARS__2 | 0.1675 |
| XBP1__2 | 0.1486 |
| XRN2__1 | 0.067 |
| YARS2 | 0.0371 |
| ZNF75D__2 | 0.1348 |

TABLE 30-continued

| | |
|---|---|
| ZSWIM4_2 | 0.1814 |
| figo_numeric | 0.0002 |
| hist_rev_SBOT | 0.0543 |
| surg_outcome | 0.006 |

TABLE 31

| | |
|---|---|
| ABHD3 | 0.0611 |
| ADAM17_2 | 0.2467 |
| ADAMTS1 | 0.1481 |
| ADAMTS2_1 | 0.0878 |
| ALS2CL_3 | 0.0732 |
| ANO7_3 | 0.026 |
| ARL6IP1_1 | 0.0234 |
| ARMCX3_2 | 0.0699 |
| ATXN10_1 | 0.2139 |
| AXL_1 | 0.0988 |
| BAI1_3 | 0.0483 |
| BCAS1_1 | 0.3278 |
| BDNF_2 | 0.1097 |
| BMPR1A | 0.1125 |
| BTF3_3 | 0.0995 |
| C10orf116 | 0.0784 |
| C11orf24 | 0.1862 |
| C11orf49_3 | 0.1119 |
| C14orf102_2 | 0.1243 |
| C14orf109_2 | 0.1031 |
| C17orf106 | 0.1714 |
| C17orf58_2 | 0.0228 |
| C17orf58_3 | 0.03 |
| C18orf56 | 0.0098 |
| C1orf168 | 0.0231 |
| C1orf64 | 0.106 |
| C8orf79_1 | 0.002 |
| CALD1_2 | 0.1331 |
| CASP8AP2 | 0.1365 |
| CCL13 | 0.14 |
| CCR2_3 | 0.0175 |
| CD34_1 | 0.0126 |
| CDC42BPA_2 | 0.0028 |
| CDC42SE2_2 | 0.0138 |
| CIDEC_1 | 0.0988 |
| CLDN6 | 0.0011 |
| CREB5_2 | 0.003 |
| CRYBA1 | 0.0657 |
| CXCL13 | 0.0628 |
| CYB5R3_2 | 0.19 |
| CYP1A2 | 0.0702 |
| DBNDD2 | 0.1289 |
| DNAH11 | 0.0438 |
| DNMT3L_2 | 0.0171 |
| DOCK7_1 | 0.1044 |
| DSC3_1 | 0.0436 |
| DUT_3 | 0.103 |
| EEF1E1_1 | 0.1359 |
| ELN_2 | 0.1332 |
| EMP1 | 0.2134 |
| ENO1 | 0.1671 |
| ENPEP_2 | 0.0697 |
| EPHB1 | 0.0203 |
| EPYC | 0.0499 |
| ERI2_2 | 0.276 |
| ESPNL | 0.0502 |
| EZH2_1 | 0.0405 |
| FAM13AOS | 0.0591 |
| FAM187B_2 | 0.0072 |
| FAM70A_1 | 0.0775 |
| FBXO48_2 | 0.2457 |
| FKBP10 | 0.0488 |
| FLJ33360 | 0.0155 |
| FLJ43752 | 0.2301 |
| FMNL3_2 | 0.0004 |
| FOSB | 0.2262 |
| FOSL2 | 0.0439 |
| FOXN1 | 0.2459 |
| GAD1_2 | 0.0267 |
| GBE1 | 0.0406 |
| GBP7 | 0.1254 |
| GJA5_1 | 0.0606 |
| GMNN | 0.1019 |
| GSR_2 | 0.0222 |
| HBA2 | 0.2105 |
| HCFC1R1_1 | 0.0388 |
| HDAC7_2 | 0.0036 |
| HDLBP_3 | 0.1 |
| HIC1 | 0.0148 |
| HPRT1_1 | 0.1453 |
| HPS4_1 | 0.0659 |
| HR_1 | 0.0255 |
| HSD11B1_1 | 0.1035 |
| ICAM2 | 0.0171 |
| ICAM4_1 | 0.3048 |
| IL1RAP_2 | 0.0743 |
| IQCA1_2 | 0.014 |
| KCNIP3_1 | 0.0921 |
| KCNQ2_1 | 0.1057 |
| KIF3C | 0.1706 |
| KRT80_2 | 0.0934 |
| KRTAP10.10_2 | 0.0361 |
| L3MBTL2_3 | 0.0435 |
| LBH_2 | 0.0715 |
| LENEP | 0.2254 |
| LGI3 | 0.0879 |
| LOC492303 | 0.0159 |
| LRRC14B | 0.0399 |
| LRRC37A4_2 | 0.0755 |
| LRRTM4 | 0.1586 |
| MACC1 | 0.1379 |
| MANSC1_1 | 0.1215 |
| MCAM | 0.0381 |
| MCART6_1 | 0.1141 |
| MFRP | 0.23 |
| MIDN | 0.0298 |
| MIR1914 | 0.0671 |
| MIR212 | 0.0994 |
| MIR571 | 0.0046 |
| MIR576 | 0.1041 |
| MIR654 | 0.0554 |
| MIR942 | 0.1137 |
| MMP12_1 | 0.1168 |
| MYCN_2 | 0.1202 |
| MYOHD1 | 0.1078 |
| NFATC3_5 | 0.0247 |
| NFATC4 | 0.0433 |
| NLRP9 | 0.1932 |
| NOVA2 | 0.0611 |
| NP | 0.0779 |
| NR6A1_2 | 0.1484 |
| NRXN3_3 | 0.1753 |
| NT5DC1_2 | 0.1814 |
| NTRK2_3 | 0.0048 |
| NUP155_1 | 0.0327 |
| NYX | 0.1538 |
| ODF2_3 | 0.0051 |
| ORC1L | 0.0197 |
| OTUD7A_3 | 0.0402 |
| PANK4 | 0.0561 |
| PDLIM2_2 | 0.2129 |
| PDZRN4_2 | 0.1996 |
| PHYH_1 | 0.0036 |
| PIGA_1 | 0.0841 |
| PITX2_1 | 0.2154 |
| PKN1_3 | 0.0059 |
| PLEKHG5_5 | 0.2748 |
| PLSCR4 | 0.0108 |
| PMEPA1_4 | 0.1442 |
| PNMA5 | 0.1597 |
| PPAPDC1A | 0.1134 |
| PRAMEF5 | 0.0017 |
| PRKAA2 | 0.1194 |
| PSMC6_1 | 0.0261 |
| RAD54B_2 | 0.194 |
| RAP1A_1 | 0.1843 |
| RARA_3 | 0.099 |
| RARG | 0.0566 |
| RNASEK | 0.0867 |
| RNF7_1 | 0.0004 |

TABLE 31-continued

| | |
|---|---|
| ROD1_1 | 0.1804 |
| SATB2 | 0.0317 |
| SBSN | 0.1026 |
| SCXB | 0.016 |
| SEC22C_3 | 0.1117 |
| SELENBP1 | 0.1501 |
| SERPINB2_2 | 0.0195 |
| SERPINB5 | 0.184 |
| SFN | 0.0013 |
| SFRS4 | 0.0584 |
| SHC1_3 | 0.0549 |
| SLC23A1_2 | 0.1183 |
| SLC25A34 | 0.1292 |
| SLC4A5_3 | 0.0944 |
| SLC9A10 | 0.0613 |
| SNORD93 | 0.1383 |
| SOX2_1 | 0.0796 |
| STC1 | 0.0062 |
| STC2 | 0.1198 |
| STYX_2 | 0.0119 |
| SYTL3 | 0.0268 |
| TAF15_1 | 0.0313 |
| TCEAL8_1 | 0.0042 |
| THBS3 | 0.0851 |
| TM2D3_2 | 0.0269 |
| TMEM52 | 0.0942 |
| TMEM62 | 0.0135 |
| TNFRSF18_1 | 0.2313 |
| TNNT2_1 | 0.012 |
| TOMM20L | 0.0136 |
| TPM2_2 | 0.1755 |
| TRIM58 | 0.1229 |
| UBR7_1 | 0.0884 |
| UBR7_2 | 0.1352 |
| WARS_2 | 0.1689 |
| XBP1_2 | 0.1514 |
| XRN2_1 | 0.0559 |
| YARS2 | 0.037 |
| ZNF75D_2 | 0.1337 |
| ZSWIM4_2 | 0.1807 |
| figo_numeric | 0.0053 |
| hist_rev_SBOT | 0.0588 |
| surg_outcome | 0.0047 |

TABLE 32

| | |
|---|---|
| ABCC9_3 | 0.0529 |
| ABHD3 | 0.2424 |
| ADAM17_2 | 0.1512 |
| ADAMTS1 | 0.1088 |
| ADAMTS2_1 | 0.0942 |
| ALS2CL_3 | 0.065 |
| ANO7_3 | 0.0491 |
| ARL6IP1_1 | 0.0162 |
| ARMCX3_2 | 0.0691 |
| ATXN10_1 | 0.198 |
| AXL_1 | 0.0809 |
| BAI1_3 | 0.0175 |
| BCAS1_1 | 0.3169 |
| BDNF_2 | 0.1303 |
| BMPR1A | 0.1153 |
| BTF3_3 | 0.1156 |
| C10orf116 | 0.0674 |
| C11orf24 | 0.1849 |
| C11orf49_3 | 0.1023 |
| C14orf102_2 | 0.1041 |
| C14orf109_2 | 0.1215 |
| C17orf106 | 0.1711 |
| C17orf58_2 | 0.009 |
| C17orf58_3 | 0.0117 |
| C18orf56 | 0.001 |
| C1orf168 | 0.0387 |
| C1orf64 | 0.1176 |
| C8orf79_1 | 0.0116 |
| CASP8AP2 | 0.1278 |
| CCL13 | 0.1316 |
| CCR2_3 | 0.1087 |

TABLE 32-continued

| | |
|---|---|
| CD34_1 | 0.0323 |
| CDC42BPA_2 | 0.0092 |
| CDC42SE2_2 | 0.0096 |
| CIDEC_1 | 0.1047 |
| CLDN6 | 0.0159 |
| CREB5_2 | 0.0147 |
| CRYBA1 | 0.0504 |
| CXCL13 | 0.0645 |
| CYB5R3_2 | 0.1864 |
| CYP1A2 | 0.0554 |
| DBNDD2 | 0.1234 |
| DNAH11 | 0.0447 |
| DNMT3L_2 | 0.0282 |
| DOCK7_1 | 0.1119 |
| DSC3_1 | 0.0486 |
| DUT_3 | 0.1142 |
| EEF1E1_1 | 0.1242 |
| EMP1 | 0.1118 |
| ENO1 | 0.1908 |
| ENPEP_2 | 0.166 |
| EPHB1 | 0.0417 |
| EPYC | 0.0312 |
| ERI2_2 | 0.2846 |
| ESPNL | 0.0526 |
| EZH2_1 | 0.0598 |
| FAM13AOS | 0.0796 |
| FAM187B_2 | 0.0084 |
| FAM70A_1 | 0.0708 |
| FBXO48_2 | 0.2201 |
| FKBP10 | 0.0794 |
| FLJ33360 | 0.0187 |
| FLJ43752 | 0.2468 |
| FMNL3_2 | 0.0007 |
| FOSB | 0.2028 |
| FOSL2 | 0.0376 |
| FOXN1 | 0.2508 |
| GAD1_2 | 0.0232 |
| GBE1 | 0.0526 |
| GBP7 | 0.1402 |
| GJA5_1 | 0.0714 |
| GMNN | 0.1076 |
| GSR_2 | 0.0338 |
| HBA2 | 0.2092 |
| HCFC1R1_1 | 0.0619 |
| HDAC7_2 | 0.0084 |
| HDLBP_3 | 0.1015 |
| HIC1 | 0.0072 |
| HPRT1_1 | 0.1231 |
| HPS4_1 | 0.076 |
| HR_1 | 0.0256 |
| HSD11B1_1 | 0.0858 |
| ICAM2 | 0.0136 |
| ICAM4_1 | 0.285 |
| IL1RAP_2 | 0.0786 |
| IQCA1_2 | 0.0276 |
| KCNIP3_1 | 0.1029 |
| KCNQ2_1 | 0.1189 |
| KIF3C | 0.1695 |
| KRT80_2 | 0.1099 |
| KRTAP10.10_2 | 0.0252 |
| L3MBTL2_3 | 0.0478 |
| LBH_2 | 0.0792 |
| LENEP | 0.2379 |
| LGI3 | 0.0883 |
| LOC340508 | 0.0366 |
| LOC492303 | 0.0211 |
| LRRC14B | 0.0744 |
| LRRC37A4_2 | 0.0238 |
| LRRTM4 | 0.179 |
| MACC1 | 0.1569 |
| MANSC1_1 | 0.1193 |
| MCAM | 0.0131 |
| MCART6_1 | 0.1301 |
| MFRP | 0.2287 |
| MIDN | 0.0079 |
| MIR1914 | 0.0582 |
| MIR212 | 0.0976 |
| MIR571 | 0.0029 |
| MIR576 | 0.1028 |
| MIR654 | 0.0464 |

TABLE 32-continued

| | |
|---|---|
| MIR942 | 0.1057 |
| MMP12__1 | 0.1202 |
| MYCN__2 | 0.1352 |
| MYL9__2 | 0.104 |
| MYOHD1 | 0.0049 |
| NFATC3__5 | 0.0374 |
| NFATC4 | 0.0738 |
| NLRP9 | 0.1861 |
| NOVA2 | 0.0865 |
| NP | 0.0832 |
| NR6A1__2 | 0.1279 |
| NRXN3__3 | 0.1643 |
| NT5DC1__2 | 0.186 |
| NTRK2__3 | 0.0092 |
| NUP155__1 | 0.0304 |
| NYX | 0.1206 |
| ODF2__3 | 0.0217 |
| ORC1L | 0.0297 |
| OTUD7A__3 | 0.0403 |
| PANK4 | 0.0439 |
| PDLIM2__2 | 0.2151 |
| PDZRN4__2 | 0.2076 |
| PHYH__1 | 0.0078 |
| PIGA__1 | 0.0915 |
| PITX2__1 | 0.2042 |
| PKN1__3 | 0.0078 |
| PLEKHG5__5 | 0.2383 |
| PLSCR4 | 0.0206 |
| PMEPA1__4 | 0.1431 |
| PNMA5 | 0.1693 |
| PPAPDC1A | 0.114 |
| PRAMEF5 | 0.0136 |
| PRKAA2 | 0.1277 |
| PSMC6__1 | 0.0415 |
| RAD54B__2 | 0.1692 |
| RAP1A__1 | 0.2019 |
| RARA__3 | 0.0999 |
| RARG | 0.0712 |
| RNASEK | 0.0808 |
| RNF7__1 | 0.0279 |
| ROD1__1 | 0.2035 |
| SATB2 | 0.0406 |
| SBSN | 0.0642 |
| SCXB | 0.0067 |
| SEC22C__3 | 0.1018 |
| SELENBP1 | 0.1488 |
| SERPINB2__2 | 0.0031 |
| SERPINB5 | 0.1804 |
| SFN | 0.0011 |
| SFRS4 | 0.0689 |
| SHC1__3 | 0.0778 |
| SLC23A1__2 | 0.1388 |
| SLC25A34 | 0.1157 |
| SLC4A5__3 | 0.0883 |
| SLC9A10 | 0.0756 |
| SNORD93 | 0.1274 |
| SOX2__1 | 0.0692 |
| STC1 | 0.0055 |
| STC2 | 0.1273 |
| STYX__2 | 0.0154 |
| SYTL3 | 0.0196 |
| TAF15__1 | 0.0258 |
| TCEAL8__1 | 0.0227 |
| THBS3 | 0.1018 |
| THY1 | 0.0426 |
| TIMP2__2 | 0.0947 |
| TM2D3__2 | 0.0076 |
| TMEM52 | 0.0201 |
| TMEM62 | 0.0621 |
| TNFRSF18__1 | 0.2192 |
| TNNT2__1 | 0.0004 |
| TOMM20L | 0.0057 |
| TPM2__2 | 0.1835 |
| TRIM58 | 0.1045 |
| UBR7__1 | 0.0805 |
| UBR7__2 | 0.1223 |
| WARS__2 | 0.1854 |
| XBP1__2 | 0.144 |
| XRN2__1 | 0.0651 |
| YARS2 | 0.0288 |
| ZNF75D__2 | 0.1394 |
| ZSWIM4__2 | 0.1758 |
| figo__numeric | 0.0182 |
| hist__rev__SBOT | 0.0331 |
| surg__outcome | 0.0106 |

TABLE 33

| | |
|---|---|
| ABCC9__3 | 0.0769 |
| ABHD3 | 0.2263 |
| ADAM17__2 | 0.135 |
| ADAMTS1 | 0.1107 |
| ALS2CL__3 | 0.0981 |
| ANO7__3 | 0.0694 |
| ARL6IP1__1 | 0.0407 |
| ARMCX3__2 | 0.0676 |
| ATXN10__1 | 0.1977 |
| AXL__1 | 0.0805 |
| BAI1__3 | 0.0393 |
| BCAS1__1 | 0.3046 |
| BDNF__2 | 0.1224 |
| BMPR1A | 0.115 |
| BTF33 | 0.1162 |
| C10orf116 | 0.074 |
| C11orf24 | 0.1755 |
| C11orf49__3 | 0.109 |
| C14orf102__2 | 0.1056 |
| C14orf109__2 | 0.1252 |
| C17orf106 | 0.1576 |
| C17orf58__2 | 0.0012 |
| C17orf58__3 | 0.0209 |
| C18orf56 | 0.0072 |
| C1orf168 | 0.0443 |
| C1orf64 | 0.1247 |
| C8orf79__1 | 0.0056 |
| CASP8AP2 | 0.1365 |
| CCL13 | 0.1089 |
| CCR2__3 | 0.1056 |
| CD34__1 | 0.0216 |
| CDC42BPA__2 | 0.0082 |
| CDC42SE2__2 | 0.0016 |
| CIDEC__1 | 0.1023 |
| CLDN6 | 0.0187 |
| CREB5__2 | 0.0012 |
| CRYBA1 | 0.0604 |
| CXCL13 | 0.0559 |
| CYB5R3__2 | 0.1876 |
| CYP1A2 | 0.0567 |
| DBNDD2 | 0.1382 |
| DNAH11 | 0.041 |
| DNMT3L__2 | 0.0247 |
| DOCK7__1 | 0.1187 |
| DSC3__1 | 0.0468 |
| DUT__3 | 0.1219 |
| EEF1E1__1 | 0.1415 |
| ELN__2 | 0.1253 |
| EMP1 | 0.2016 |
| ENO1 | 0.1534 |
| ENPEP__2 | 0.0998 |
| EPHB1 | 0.0503 |
| EPYC | 0.0358 |
| ERI2__2 | 0.2572 |
| ESPNL | 0.0616 |
| EZH2__1 | 0.0412 |
| FAM13AOS | 0.0663 |
| FAM187B__2 | 0.0012 |
| FAM70A__1 | 0.078 |
| FBXO48__2 | 0.2295 |
| FKBP10 | 0.0568 |
| FLJ33360 | 0.0175 |
| FLJ43752 | 0.2249 |
| FMNL3__2 | 0.008 |
| FOSB | 0.2095 |
| FOSL2 | 0.0203 |
| FOXN1 | 0.2606 |
| FRMD6__3 | 0.0299 |
| GAD1__2 | 0.0692 |

TABLE 33-continued

| | |
|---|---|
| GBE1 | 0.1563 |
| GBP7 | 0.0956 |
| GJA5_1 | 0.0806 |
| GMNN | 0.0938 |
| GSR_2 | 0.0251 |
| HBA2 | 0.2097 |
| HCFC1R1_1 | 0.0701 |
| HDAC7_2 | 0.0164 |
| HDLBP_3 | 0.0931 |
| HIC1 | 0.0231 |
| HPRT1_1 | 0.1342 |
| HPS4_1 | 0.0585 |
| HR_1 | 0.0251 |
| HSD11B1_1 | 0.0913 |
| ICAM2 | 0.0182 |
| ICAM4_1 | 0.2767 |
| IL1RAP_2 | 0.1004 |
| IQCA1_2 | 0.0196 |
| KCNIP3_1 | 0.0938 |
| KCNQ2_1 | 0.1103 |
| KIF3C | 0.1884 |
| KRT80_2 | 0.0985 |
| KRTAP10.10_2 | 0.0313 |
| L3MBTL2_3 | 0.0356 |
| LBH_2 | 0.068 |
| LENEP | 0.2277 |
| LGI3 | 0.0652 |
| LOC340508 | 0.0296 |
| LOC492303 | 0.0031 |
| LRRC14B | 0.0766 |
| LRRC37A4_2 | 0.0115 |
| LRRTM4 | 0.1479 |
| MACC1 | 0.1498 |
| MANSC1_1 | 0.1195 |
| MCAM | 0.0017 |
| MCART6_1 | 0.1391 |
| MFRP | 0.2329 |
| MIDN | 0.0063 |
| MIR1914 | 0.0619 |
| MIR212 | 0.0944 |
| MIR571 | 0.0076 |
| MIR576 | 0.1135 |
| MIR654 | 0.047 |
| MIR942 | 0.1085 |
| MMP12_1 | 0.109 |
| MYCN_2 | 0.1288 |
| MYL9_2 | 0.0939 |
| MYOHD1 | 0.0301 |
| NFATC3_5 | 0.0334 |
| NFATC4 | 0.0658 |
| NLRP9 | 0.1667 |
| NOVA2 | 0.0742 |
| NP | 0.0703 |
| NR6A1_2 | 0.1314 |
| NRXN3_3 | 0.1686 |
| NT5DC1_2 | 0.1646 |
| NTRK2_3 | 0.0005 |
| NUP155_1 | 0.054 |
| NYX | 0.1204 |
| ODF2_3 | 0.0096 |
| ORC1L | 0.0388 |
| OTUD7A_3 | 0.0475 |
| PANK4 | 0.0329 |
| PDLIM2_2 | 0.214 |
| PDZRN4_2 | 0.2201 |
| PHYH_1 | 0.0164 |
| PIGA_1 | 0.0739 |
| PITX2_1 | 0.194 |
| PKN1_3 | 0.0126 |
| PLEKHG5_5 | 0.2702 |
| PLSCR4 | 0.0288 |
| PMEPA1_4 | 0.1262 |
| PNMA5 | 0.1737 |
| PPAPDC1A | 0.1265 |
| PRAMEF5 | 0.0046 |
| PRKAA2 | 0.11 |
| PSMC6_1 | 0.0405 |
| RAD54B_2 | 0.1786 |
| RAP1A_1 | 0.187 |
| RARA_3 | 0.0946 |

TABLE 33-continued

| | |
|---|---|
| RARG | 0.0879 |
| RNASEK | 0.0679 |
| RNF7_1 | 0.0185 |
| ROD1_1 | 0.2005 |
| SATB2 | 0.0383 |
| SBSN | 0.0809 |
| SCXB | 0.0124 |
| SEC22C_3 | 0.0852 |
| SELENBP1 | 0.1419 |
| SERPINB2_2 | 0.0033 |
| SERPINB5 | 0.1761 |
| SFN | 0.016 |
| SFRS4 | 0.062 |
| SHC1_3 | 0.085 |
| SLC23A1_2 | 0.144 |
| SLC25A34 | 0.1005 |
| SLC4A5_3 | 0.0911 |
| SLC9A10 | 0.0636 |
| SNORD93 | 0.123 |
| SOX2_1 | 0.0597 |
| STC1 | 0.001 |
| STC2 | 0.1239 |
| STYX_2 | 0.0093 |
| SYTL3 | 0.0194 |
| TAF15_1 | 0.022 |
| TCEAL8_1 | 0.0003 |
| THBS3 | 0.0974 |
| THY1 | 0.0381 |
| TTMP2_2 | 0.0828 |
| TM2D3_2 | 0.0051 |
| TMEM52 | 0.0268 |
| TMEM62 | 0.0673 |
| TNFRSF18_1 | 0.2093 |
| TNNT2_1 | 0.0013 |
| TOMM20L | 0.0085 |
| TPM2_2 | 0.1867 |
| TRIM58 | 0.1035 |
| UBR7_1 | 0.0714 |
| UBR7_2 | 0.1268 |
| WARS_2 | 0.1952 |
| XBP1_2 | 0.1465 |
| XRN2_1 | 0.0487 |
| YARS2 | 0.0242 |
| ZNF75D_2 | 0.136 |
| ZSWIM4_2 | 0.1701 |
| figo_numeric | 0.0381 |
| hist_rev_SBOT | 0.0496 |
| surg_outcome | 0.0085 |

TABLE 34

| | |
|---|---|
| ABCC9_3 | 0.0388 |
| ABHD3 | 0.2506 |
| ADAM17_2 | 0.1571 |
| ADAMTS1 | 0.1332 |
| ADAMTS2_1 | 0.1159 |
| ALS2CL_3 | 0.0613 |
| ANO7_3 | 0.0327 |
| ARL6IP1_1 | 0.0201 |
| ARMCX3_2 | 0.0782 |
| ATXN10_1 | 0.2094 |
| AXL_1 | 0.0928 |
| BAI1_3 | 0.0418 |
| BCAS1_1 | 0.3188 |
| BDNF_2 | 0.1466 |
| BMPR1A | 0.126 |
| BTF33 | 0.1093 |
| C10orf116 | 0.0292 |
| C11orf24 | 0.1893 |
| C11orf49_3 | 0.152 |
| C14orf102_2 | 0.1004 |
| C14orf109_2 | 0.0715 |
| C17orf106 | 0.1828 |
| C17orf58_2 | 0.0149 |
| C17orf58_3 | 0.0274 |
| C18orf56 | 0.0323 |
| C1orf168 | 0.0413 |

TABLE 34-continued

| | |
|---|---|
| C1orf64 | 0.1345 |
| C8orf79__1 | 0.026 |
| CASP8AP2 | 0.1526 |
| CCL13 | 0.1129 |
| CCR2__3 | 0.1358 |
| CD34__1 | 0.0399 |
| CDC42BPA__2 | 0.0086 |
| CDC42SE2__2 | 0.0018 |
| CIDEC__1 | 0.123 |
| CLDN6 | 0.0096 |
| CREB5__2 | 0.0464 |
| CRYBA1 | 0.0438 |
| CXCL13 | 0.0717 |
| CYB5R3__2 | 0.1762 |
| CYP1A2 | 0.0849 |
| DBNDD2 | 0.1068 |
| DNAH11 | 0.0327 |
| DNMT3L2 | 0.0097 |
| DOCK7__1 | 0.1207 |
| DSC3__1 | 0.0423 |
| DUT__3 | 0.126 |
| EEF1E1__1 | 0.1036 |
| ELN2 | 0.1072 |
| EMP1 | 0.1975 |
| ENO1 | 0.1405 |
| ENPEP__2 | 0.0842 |
| EPHB1 | 0.0612 |
| EPYC | 0.0344 |
| ERI2__2 | 0.2807 |
| ESPNL | 0.0421 |
| EZH2__1 | 0.0512 |
| FAM13AOS | 0.0246 |
| FAM187B__2 | 0.0024 |
| FAM70A__1 | 0.0769 |
| FBXO48__2 | 0.2347 |
| FKBP10 | 0.05 |
| FLJ33360 | 0.029 |
| FLJ43752 | 0.2396 |
| FMNL3__2 | 0.0106 |
| FOSB | 0.207 |
| FOSL2 | 0.0321 |
| FOXN1 | 0.2979 |
| GAD1__2 | 0.0116 |
| GBE1 | 0.0538 |
| GBP7 | 0.1576 |
| GJA5__1 | 0.0537 |
| GMNN | 0.0806 |
| GSR__2 | 0.0328 |
| HBA2 | 0.1962 |
| HCFC1R1__1 | 0.0691 |
| HDAC7__2 | 0.0115 |
| HDLBP__3 | 0.1051 |
| HIC1 | 0.001 |
| HPRT1__1 | 0.1534 |
| HPS4__1 | 0.0639 |
| HR__1 | 0.0406 |
| HSD11B1__1 | 0.0851 |
| ICAM2 | 0.0185 |
| ICAM4__1 | 0.2705 |
| IL1RAP__2 | 0.0475 |
| IQCA1__2 | 0.0304 |
| KCNIP3__1 | 0.0917 |
| KCNQ21 | 0.1162 |
| KIF3C | 0.2075 |
| KRT80__2 | 0.0952 |
| KRTAP10.10__2 | 0.0191 |
| L3MBTL2__3 | 0.0438 |
| LBH__2 | 0.083 |
| LENEP | 0.2523 |
| LGI3 | 0.101 |
| LOC340508 | 0.0218 |
| LOC492303 | 0.0057 |
| LRRC14B | 0.0674 |
| LRRC37A4__2 | 0.0004 |
| LRRTM4 | 0.165 |
| MACC1 | 0.1471 |
| MANSC1__1 | 0.1409 |
| MCAM | 0.0217 |
| MCART6__1 | 0.1374 |
| MFRP | 0.2239 |
| MIDN | 0.0195 |
| MIR1914 | 0.0494 |
| MIR212 | 0.1098 |
| MIR571 | 0.0105 |
| MIR576 | 0.1182 |
| MIR654 | 0.0259 |
| MIR942 | 0.0974 |
| MMP12__1 | 0.1164 |
| MYCN__2 | 0.1565 |
| MYL9__2 | 0.1105 |
| MYOHD1 | 0.0317 |
| NFATC3__5 | 0.0367 |
| NFATC4 | 0.0743 |
| NLRP9 | 0.1684 |
| NOVA2 | 0.1038 |
| NP | 0.0773 |
| NR6A1__2 | 0.1333 |
| NRXN3__3 | 0.1292 |
| NT5DC1__2 | 0.1712 |
| NTRK2__3 | 0.0184 |
| NUP155__1 | 0.0066 |
| NYX | 0.1169 |
| ODF2__3 | 0.0103 |
| ORC1L | 0.0351 |
| OTUD7A__3 | 0.0408 |
| PANK4 | 0.0451 |
| PDLIM2__2 | 0.2294 |
| PHYH__1 | 0.1882 |
| PIGA__1 | 0.0089 |
| PITX2__1 | 0.0681 |
| PKN1__3 | 0.0189 |
| PLEKHG5__5 | 0.2635 |
| PLSCR4 | 0.0429 |
| PMEPA1__4 | 0.1604 |
| PNMA5 | 0.1476 |
| PPAPDC1A | 0.1517 |
| PRAMEF5 | 0.0077 |
| PRKAA2 | 0.1146 |
| PSMC6__1 | 0.0375 |
| RAD54B__2 | 0.2 |
| RAP1A__1 | 0.2053 |
| RARA__3 | 0.0872 |
| RARG | 0.0514 |
| RNASEK | 0.0322 |
| RNF7__1 | 0.0384 |
| ROD1__1 | 0.2271 |
| SATB2 | 0.0413 |
| SBSN | 0.0873 |
| SCXB | 0.0201 |
| SEC22C__3 | 0.1031 |
| SELENBP1 | 0.1728 |
| SERPINB2__2 | 0.0012 |
| SERPINB5 | 0.1955 |
| SFN | 0.0434 |
| SFRS4 | 0.0657 |
| SHC1__3 | 0.0652 |
| SLC23A1__2 | 0.1524 |
| SLC25A34 | 0.1104 |
| SLC4A5__3 | 0.0766 |
| SLC9A10 | 0.0965 |
| SNORD93 | 0.1544 |
| SOX2__1 | 0.0813 |
| STC1 | 0.0126 |
| STC2 | 0.1178 |
| STYX__2 | 0.0347 |
| SYTL3 | 0.008 |
| TAF15__1 | 0.0138 |
| TCEAL8__1 | 0.0059 |
| THBS3 | 0.0953 |
| THY1 | 0.0587 |
| TIMP2__2 | 0.1112 |
| TM2D3__2 | 0.0069 |
| TMEM52 | 0.014 |
| TMEM62 | 0.0758 |
| TNFRSF18__1 | 0.2563 |
| TNNT2__1 | 0.0088 |
| TOMM20L | 0.0428 |
| TPM2__2 | 0.1822 |
| TRIM58 | 0.1079 |
| UBR7__1 | 0.0384 |

TABLE 34-continued

| | |
|---|---|
| UBR7_2 | 0.1276 |
| WARS_2 | 0.1626 |
| XBP1_2 | 0.115 |
| XRN2_1 | 0.0221 |
| YARS2 | 0.0034 |
| ZNF75D_2 | 0.1379 |
| ZSWIM4_2 | 0.1762 |
| figo_numeric | 0.0245 |
| hist_rev_SBOT | 0.0407 |
| surg_outcome | 0.0258 |

TABLE 35

| | |
|---|---|
| ABCC9_3 | 0.0381 |
| ABHD3 | 0.2338 |
| ADAM17_2 | 0.1493 |
| ADAMTS1 | 0.126 |
| ADAMTS2_1 | 0.1136 |
| ALS2CL_3 | 0.0775 |
| ANO7_3 | 0.0196 |
| ARL6IP1_1 | 0.0044 |
| ARMCX3_2 | 0.0442 |
| ATXN10_1 | 0.2144 |
| AXL_1 | 0.0856 |
| BAI1_3 | 0.0267 |
| BCAS1_1 | 0.2954 |
| BDNF_2 | 0.1234 |
| BMPR1A | 0.111 |
| BTF3_3 | 0.1047 |
| C10orf116 | 0.0513 |
| C11orf24 | 0.1669 |
| C11orf49_3 | 0.1181 |
| C14orf102_2 | 0.0933 |
| C14orf109_2 | 0.1256 |
| C17orf106 | 0.1735 |
| C17orf58_2 | 0.0433 |
| C17orf58_3 | 0.0244 |
| C18orf56 | 0.0027 |
| C1orf168 | 0.0418 |
| C1orf64 | 0.1164 |
| C8orf79_1 | 0.0363 |
| CASP8AP2 | 0.1313 |
| CCL13 | 0.1206 |
| CCR2_3 | 0.1162 |
| CD34_1 | 0.0218 |
| CDC42BPA_2 | 0.0145 |
| CDC42SE2_2 | 0.0079 |
| CLDN6 | 0.122 |
| CREB5_2 | 0.0284 |
| CRYBA1 | 0.02 |
| CXCL13 | 0.0631 |
| CYB5R3_2 | 0.177 |
| CYP1A2 | 0.0825 |
| DBNDD2 | 0.1175 |
| DNAH11 | 0.0373 |
| DNMT3L_2 | 0.0276 |
| DOCK71 | 0.1329 |
| DSC3_1 | 0.0472 |
| DUT_3 | 0.1334 |
| EEF1E1_1 | 0.117 |
| ELN_2 | 0.1039 |
| EMP1 | 0.1967 |
| ENO1 | 0.1639 |
| ENPEP_2 | 0.0613 |
| EPHB1 | 0.0444 |
| EPYC | 0.0412 |
| ERI2_2 | 0.28 |
| ESPNL | 0.0741 |
| EZH2_1 | 0.0341 |
| FAM13AOS | 0.071 |
| FAM187B_2 | 0.0159 |
| FAM70A_1 | 0.0643 |
| FBXO48_2 | 0.2243 |
| FKBP10 | 0.0743 |
| FLJ33360 | 0.0105 |
| FLJ43752 | 0.2547 |
| FMNL3_2 | 0.0115 |

TABLE 35-continued

| | |
|---|---|
| FOSB | 0.2183 |
| FOSL2 | 0.021 |
| FOXN1 | 0.2436 |
| GAD1_2 | 0.0205 |
| GBE1 | 0.068 |
| GBP7 | 0.1563 |
| GJA5_1 | 0.0484 |
| GMNN | 0.093 |
| GSR_2 | 0.0154 |
| HBA2 | 0.2014 |
| HCFC1R1_1 | 0.0703 |
| HDAC7_2 | 0.0006 |
| HDLBP_3 | 0.1085 |
| HIC1 | 0.0162 |
| HPRT1_1 | 0.1394 |
| HPS4_1 | 0.0437 |
| HR_1 | 0.0274 |
| HSD11B1_1 | 0.092 |
| ICAM2 | 0.0318 |
| ICAM4_1 | 0.2845 |
| IL1RAP_2 | 0.0946 |
| IQCA1_2 | 0.044 |
| KCNIP3_1 | 0.098 |
| KCNQ2_1 | 0.1143 |
| KIF3C | 0.1992 |
| KRT80_2 | 0.1022 |
| KRTAP10.10_2 | 0.0127 |
| L3MBTL2_3 | 0.0412 |
| LBH_2 | 0.0802 |
| LENEP | 0.2283 |
| LGI3 | 0.1008 |
| LOC340508 | 0.0476 |
| LOC492303 | 0.0142 |
| LRRC14B | 0.0846 |
| LRRC37A4_2 | 0.0184 |
| LRRTM4 | 0.1877 |
| MACC1 | 0.1835 |
| MANSC1_1 | 0.1151 |
| MCAM | 0.001 |
| MCART6_1 | 0.1265 |
| MFRP | 0.2273 |
| MIDN | 0.0193 |
| MIR1914 | 0.0793 |
| MIR212 | 0.0977 |
| MIR571 | 0.0082 |
| MIR576 | 0.1163 |
| MIR654 | 0.0305 |
| MIR942 | 0.1017 |
| MMP12_1 | 0.1097 |
| MYCN_2 | 0.1174 |
| MYL9_2 | 0.0971 |
| MYOHD1 | 0.0014 |
| NFATC3_5 | 0.0364 |
| NFATC4 | 0.0707 |
| NLRP9 | 0.1794 |
| NOVA2 | 0.0714 |
| NP | 0.0712 |
| NR6A1_2 | 0.1267 |
| NRXN3_3 | 0.1699 |
| NT5DC1_2 | 0.1809 |
| NTRK2_3 | 0.0264 |
| NUP155_1 | 0.0358 |
| NYX | 0.1102 |
| ODF2_3 | 0.018 |
| ORC1L | 0.0475 |
| OTUD7A_3 | 0.0533 |
| PANKA | 0.0492 |
| PDLIM2_2 | 0.2254 |
| PDZRN4_2 | 0.2058 |
| PHYH_1 | 0.0062 |
| PIGA_1 | 0.0959 |
| PITX2_1 | 0.1918 |
| PKN1_3 | 0.0113 |
| PLEKHG5_5 | 0.2537 |
| PLSCR4 | 0.0363 |
| PMEPA1_4 | 0.1511 |
| PNMA5 | 0.1668 |
| PPAPDC1A | 0.1206 |
| PRAMEF5 | 0.0026 |
| PRKAA2 | 0.0848 |

TABLE 35-continued

| | |
|---|---|
| PSMC6__1 | 0.0149 |
| RAD54B__2 | 0.1833 |
| RAP1A__1 | 0.2022 |
| RARA__3 | 0.0878 |
| RARG | 0.0786 |
| RNASEK | 0.0689 |
| RNF7__1 | 0.0148 |
| ROD1__1 | 0.2262 |
| SATB2 | 0.0257 |
| SBSN | 0.0632 |
| SCXB | 0.0105 |
| SEC22C__3 | 0.1011 |
| SELENBP1 | 0.1474 |
| SERPINB2__2 | 0.0031 |
| SERPINB5 | 0.1959 |
| SFN | 0.0091 |
| SFRS4 | 0.0625 |
| SHC1__3 | 0.0771 |
| SLC23A1__2 | 0.1334 |
| SLC25A34 | 0.1103 |
| SLC4A5__3 | 0.0823 |
| SLC9A10 | 0.0738 |
| SNORD93 | 0.1401 |
| SOX2__1 | 0.0698 |
| STC1 | 0.0054 |
| STC2 | 0.1166 |
| STYX__2 | 0.0168 |
| SYTL3 | 0.0068 |
| TAF15__1 | 0.0143 |
| TCEAL8__1 | 0.0282 |
| THBS3 | 0.0785 |
| THY1 | 0.0361 |
| TIMP2__2 | 0.091 |
| TM2D3__2 | 0.0068 |
| TMEM52 | 0.0479 |
| TMEM62 | 0.062 |
| TNFRSF18__1 | 0.2197 |
| TNNT2__1 | 0.0015 |
| TOMM20L | 0.0009 |
| TPM2__2 | 0.1812 |
| TRIM58 | 0.1108 |
| UBR7__1 | 0.0573 |
| UBR7__2 | 0.127 |
| WARS__2 | 0.1946 |
| XBP1__2 | 0.1632 |
| XRN2__1 | 0.025 |
| YARS2 | 0.0083 |
| ZNF75D__2 | 0.1132 |
| ZSWIM4__2 | 0.1604 |
| figo__numeric | 0.0078 |
| hist__rev__SBOT | 0.0391 |
| surg__outcome | 0.01 |

TABLE 36

| | |
|---|---|
| ABCC9__3 | 0.0545 |
| ABHD3 | 0.2415 |
| ADAM17__2 | 0.1477 |
| ADAMTS1 | 0.1122 |
| ADAMTS2__1 | 0.1032 |
| ALS2CL__3 | 0.0595 |
| ANO7__3 | 0.0362 |
| ARL6IP1__1 | 0.0031 |
| ARMCX3__2 | 0.0618 |
| ATXN10__1 | 0.2047 |
| AXL__1 | 0.0783 |
| BAI1__3 | 0.0391 |
| BCAS1__1 | 0.3048 |
| BDNF__2 | 0.1216 |
| BMPR1A | 0.1123 |
| BTF3__3 | 0.1074 |
| C10orf116 | 0.0716 |
| C11orf24 | 0.1755 |
| C11orf49__3 | 0.1114 |
| C14orf102__2 | 0.0991 |
| C14orf109__2 | 0.1138 |
| C17orf106 | 0.1603 |

TABLE 36-continued

| | |
|---|---|
| C17orf58__2 | 0.0148 |
| C17orf58__3 | 0.0157 |
| C18orf56 | 0.0002 |
| C1orf168 | 0.0365 |
| C1orf64 | 0.1172 |
| C8orf79__1 | 0.0041 |
| CASP8AP2 | 0.142 |
| CCL13 | 0.1245 |
| CCR2__3 | 0.1264 |
| CD34__1 | 0.0294 |
| CDC42BPA__2 | 0.0043 |
| CDC42SE2__2 | 0.0164 |
| CIDEC__1 | 0.1042 |
| CLDN6 | 0.0173 |
| CREB5__2 | 0.0142 |
| CRYBA1 | 0.0574 |
| CXCL13 | 0.0592 |
| CYB5R3__2 | 0.1837 |
| CYP1A2 | 0.0737 |
| DBNDD2 | 0.1287 |
| DNAH11 | 0.0425 |
| DNMT3L__2 | 0.0196 |
| DOCK7__1 | 0.1078 |
| DSC3__1 | 0.0417 |
| DUT__3 | 0.124 |
| EEF1E1__1 | 0.1334 |
| ELN__2 | 0.1181 |
| EMP1 | 0.2003 |
| ENO1 | 0.1596 |
| ENPEP__2 | 0.0809 |
| EPHB1 | 0.0459 |
| EPYC | 0.036 |
| ERI2__2 | 0.2708 |
| ESPNL | 0.0581 |
| EZH2__1 | 0.0371 |
| FAM13AOS | 0.0679 |
| FAM187B__2 | 0.0032 |
| FAM70A__1 | 0.0779 |
| FBXO48__2 | 0.2245 |
| FKBP10 | 0.0641 |
| FLJ33360 | 0.0162 |
| FLJ43752 | 0.2442 |
| FMNL3__2 | 0.0149 |
| FOSB | 0.2147 |
| FOSL2 | 0.0302 |
| FOXN1 | 0.2586 |
| GAD1__2 | 0.0218 |
| GBE1 | 0.0561 |
| GBP7 | 0.1392 |
| GJA5__1 | 0.0684 |
| GMNN | 0.1047 |
| GSR__2 | 0.0197 |
| HBA2 | 0.2087 |
| HCFC1R1__1 | 0.0644 |
| HDAC7__2 | 0.0055 |
| HDLBP__3 | 0.0954 |
| HIC1 | 0.0018 |
| HPRT1__1 | 0.1332 |
| HPS4__1 | 0.0653 |
| HR__1 | 0.0203 |
| HSD11B1__1 | 0.0894 |
| ICAM2 | 0.0173 |
| ICAM4__1 | 0.2972 |
| IL1RAP__2 | 0.0791 |
| IQCA1__2 | 0.0194 |
| KCNIP3__1 | 0.0924 |
| KCNQ2__1 | 0.1029 |
| KIF3C | 0.1825 |
| KRT80__2 | 0.095 |
| KRTAP10.10__2 | 0.0274 |
| L3MBTL2__3 | 0.044 |
| LBH__2 | 0.0721 |
| LENEP | 0.2393 |
| LGI3 | 0.0934 |
| LOC492303 | 0.0266 |
| LRRC14B | 0.0216 |
| LRRC37A4__2 | 0.0734 |
| LRRTM4 | 0.1707 |
| MACC1 | 0.1633 |
| MANSC1__1 | 0.1122 |

TABLE 36-continued

| | |
|---|---|
| MCAM | 0.0193 |
| MCART6__1 | 0.1262 |
| MFRP | 0.2249 |
| MIDN | 0.0023 |
| MIR1914 | 0.0565 |
| MIR212 | 0.0981 |
| MIR571 | 0.0046 |
| MIR576 | 0.1079 |
| MIR654 | 0.0442 |
| MIR942 | 0.0995 |
| MMP12__1 | 0.1168 |
| MYCN__2 | 0.133 |
| MYL9__2 | 0.1032 |
| MYOHD1 | 0.0204 |
| NFATC3__5 | 0.0384 |
| NFATC4 | 0.0676 |
| NLRP9 | 0.1737 |
| NOVA2 | 0.0681 |
| NP | 0.0763 |
| NR6A1__2 | 0.1269 |
| NRXN3__3 | 0.171 |
| NT5DC1__2 | 0.1813 |
| NTRK2__3 | 0.0073 |
| NUP155__1 | 0.0266 |
| NYX | 0.1089 |
| ODF2__3 | 0.0152 |
| ORC1L | 0.0419 |
| OTUD7A__3 | 0.0423 |
| PANK4 | 0.0448 |
| PDLIM2__2 | 0.2176 |
| PDZRN4__2 | 0.2035 |
| PHYH__1 | 0.0109 |
| PIGA__1 | 0.0904 |
| PITX2__1 | 0.1997 |
| PKN1__3 | 0.0013 |
| PLEKHG5__5 | 0.2547 |
| PLSCR4 | 0.021 |
| PMEPA1__4 | 0.1405 |
| PNMA5 | 0.1713 |
| PPAPDC1A | 0.1249 |
| PRAMEF5 | 0.0061 |
| PRKAA2 | 0.1218 |
| PSMC6__1 | 0.0398 |
| RAD54B__2 | 0.1753 |
| RAP1A__1 | 0.1949 |
| RARA__3 | 0.0966 |
| RARG | 0.0824 |
| RNASEK | 0.0752 |
| RNF7__1 | 0.0274 |
| ROD1__1 | 0.2054 |
| SATB2 | 0.0387 |
| SBSN | 0.0728 |
| SCXB | 0.014 |
| SEC22C__3 | 0.1054 |
| SELENBP1 | 0.1467 |
| SERPINB2__2 | 0.0143 |
| SERPINB5 | 0.1786 |
| SFN | 0.0177 |
| SFRS4 | 0.0685 |
| SHC1__3 | 0.0692 |
| SLC23A1__2 | 0.1305 |
| SLC25A34 | 0.1051 |
| SLC4A5__3 | 0.0889 |
| SLC9A10 | 0.0683 |
| SNORD93 | 0.1272 |
| SOX2__1 | 0.0728 |
| STC1 | 0.0058 |
| STC2 | 0.1154 |
| STYX__2 | 0.0132 |
| SYTL3 | 0.0257 |
| TAF15__1 | 0.0251 |
| TCEAL8__1 | 0.0139 |
| THBS3 | 0.0963 |
| THY1 | 0.0386 |
| TIMP2__2 | 0.0924 |
| TM2D3__2 | 0.0004 |
| TMEM52 | 0.02 |
| TMEM62 | 0.0682 |
| TNFRSF18__1 | 0.2167 |
| TNNT2__1 | 0.0065 |
| TOMM20L | 0.0036 |
| TPM2__2 | 0.1791 |
| TRIM58 | 0.1121 |
| UBR7__1 | 0.0797 |
| UBR7__2 | 0.1337 |
| WARS__2 | 0.1886 |
| XBP1__2 | 0.1499 |
| XRN2__1 | 0.0436 |
| YARS2 | 0.0291 |
| ZNF75D__2 | 0.1336 |
| ZSWIM4__2 | 0.1728 |
| figo__numeric | 0.0272 |
| hist__rev__SBOT | 0.0364 |
| surg__outcome | 0.0109 |

TABLE 37

| | |
|---|---|
| ABCC9__3 | 0.053 |
| ABHD3 | 0.2403 |
| ADAM17__2 | 0.1493 |
| ADAMTS1 | 0.1085 |
| ALS2CL__3 | 0.0948 |
| ANO7__3 | 0.0613 |
| ARL6IP1__1 | 0.0511 |
| ARMCX3__2 | 0.0684 |
| ATXN10__1 | 0.1976 |
| AXL__1 | 0.0838 |
| BAI1__3 | 0.0217 |
| BCAS1__1 | 0.3211 |
| BDNF__2 | 0.1348 |
| BMPR1A | 0.1172 |
| BTF3__3 | 0.1122 |
| C10orf116 | 0.0744 |
| C11orf24 | 0.1946 |
| C11orf49__3 | 0.1039 |
| C14orf102__2 | 0.1077 |
| C14orf109__2 | 0.1196 |
| C17orf106 | 0.1789 |
| C17orf58__2 | 0.0085 |
| C17orf58__3 | 0.0167 |
| C18orf56 | 0.0009 |
| C1orf168 | 0.038 |
| C1orf64 | 0.1189 |
| C8orf79__1 | 0.0219 |
| CALD1__2 | 0.1263 |
| CASP8AP2 | 0.1316 |
| CCL13 | 0.1129 |
| CCR2__3 | 0.0422 |
| CD34__1 | 0.0328 |
| CDC42BPA__2 | 0.0062 |
| CDC42SE2__2 | 0.0047 |
| CIDEC__1 | 0.1007 |
| CLDN6 | 0.0092 |
| CREB5__2 | 0.0117 |
| CRYBA1 | 0.0523 |
| CXCL13 | 0.0657 |
| CYB5R3__2 | 0.1934 |
| CYP1A2 | 0.0619 |
| DBNDD2 | 0.1231 |
| DNAH11 | 0.0407 |
| DNMT3L__2 | 0.0273 |
| DOCK7__1 | 0.1244 |
| DSC3__1 | 0.0458 |
| DUT__3 | 0.1107 |
| EEF1E1__1 | 0.1213 |
| EMP1 | 0.1142 |
| ENOI | 0.1996 |
| ENPEP__2 | 0.1619 |
| EPHB1 | 0.0395 |
| EPYC | 0.0303 |
| ERI2__2 | 0.2787 |
| ESPNL | 0.0527 |
| EZH2__1 | 0.0572 |
| FAM13AOS | 0.0779 |
| FAM187B__2 | 0.0084 |
| FAM70A__1 | 0.0738 |
| FBXO48__2 | 0.2285 |

TABLE 37-continued

| | |
|---|---|
| FKBP10 | 0.0816 |
| FLJ33360 | 0.0127 |
| FLJ43752 | 0.2482 |
| FMNL3__2 | 0.001 |
| FOSB | 0.2151 |
| FOSL2 | 0.0328 |
| FOXN1 | 0.2578 |
| GAD1__2 | 0.0252 |
| GBE1 | 0.0495 |
| GBP7 | 0.1388 |
| GJA5__1 | 0.0702 |
| GMNN | 0.1019 |
| GSR__2 | 0.0348 |
| HBA2 | 0.2093 |
| HCFC1R1__1 | 0.0638 |
| HDAC7__2 | 0.0111 |
| HDLBP__3 | 0.1043 |
| HIC1 | 0.007 |
| HPRT1__1 | 0.123 |
| HPS4__1 | 0.0684 |
| HR__1 | 0.0267 |
| HSD11B1__1 | 0.0858 |
| ICAM2 | 0.0091 |
| ICAM4__1 | 0.285 |
| IL1RAP__2 | 0.0733 |
| IQCA1__2 | 0.0312 |
| KCNIP3__1 | 0.1025 |
| KCNQ2__1 | 0.1155 |
| KIF3C | 0.1607 |
| KRT80__2 | 0.1105 |
| KRTAP10.10__2 | 0.0262 |
| L3MBTL2__3 | 0.0524 |
| LBH__2 | 0.0853 |
| LENEP | 0.2303 |
| LGI3 | 0.0888 |
| LOC340508 | 0.0384 |
| LOC492303 | 0.0229 |
| LRRC14B | 0.0792 |
| LRRC37A4__2 | 0.0204 |
| LRRTM4 | 0.1778 |
| MACC1 | 0.1575 |
| MANSC1__1 | 0.1242 |
| MCAM | 0.0185 |
| MCART6__1 | 0.1265 |
| MFRP | 0.2275 |
| MIDN | 0.0068 |
| MIR1914 | 0.0485 |
| MIR212 | 0.0913 |
| MIR571 | 0.003 |
| MIR576 | 0.1087 |
| MIR654 | 0.0426 |
| MIR942 | 0.1113 |
| MMP12__1 | 0.1231 |
| MYCN__2 | 0.1306 |
| MYOHD1 | 0.1081 |
| NFATC3__5 | 0.0114 |
| NFATC4 | 0.0383 |
| NLRP9 | 0.189 |
| NOVA2 | 0.0873 |
| NP | 0.0869 |
| NR6A1__2 | 0.1324 |
| NRXN3__3 | 0.1628 |
| NT5DC1__2 | 0.1884 |
| NTRK2__3 | 0.0071 |
| NUP155__1 | 0.0294 |
| NYX | 0.1243 |
| ODF2__3 | 0.0249 |
| ORC1L | 0.024 |
| OTUD7A__3 | 0.0485 |
| PANK4 | 0.0507 |
| PDLIM2__2 | 0.215 |
| PDZRN4__2 | 0.2106 |
| PHYH__1 | 0.0083 |
| PIGA__1 | 0.0914 |
| PITX2__1 | 0.2038 |
| PKN1__3 | 0.0132 |
| PLEKHG5__5 | 0.247 |
| PLSCR4 | 0.0201 |
| PMEPA1__4 | 0.1369 |
| PNMA5 | 0.1684 |

TABLE 37-continued

| | |
|---|---|
| PPAPDC1A | 0.1058 |
| PRAMEF5 | 0.016 |
| PRKAA2 | 0.1326 |
| PSMC6__1 | 0.038 |
| RAD54B__2 | 0.1625 |
| RAP1A__1 | 0.2013 |
| RARA__3 | 0.0969 |
| RARG | 0.0689 |
| RNASEK | 0.0856 |
| RNF7__1 | 0.0228 |
| ROD1__1 | 0.1961 |
| SATB2 | 0.0377 |
| SBSN | 0.0676 |
| SCXB | 0.0075 |
| SEC22C__3 | 0.1025 |
| SELENBP1 | 0.1466 |
| SERPINB2__2 | 0.0008 |
| SERPINB5 | 0.1879 |
| SFN | 0.0016 |
| SFRS4 | 0.0695 |
| SHC1__3 | 0.0757 |
| SLC23A1__2 | 0.1359 |
| SLC25A3__4 | 0.117 |
| SLC4A5__3 | 0.0875 |
| SLC9A10 | 0.0723 |
| SNORD93 | 0.1242 |
| SOX2__1 | 0.0772 |
| STC1 | 0.005 |
| STC2 | 0.1287 |
| STYX__2 | 0.0175 |
| SYTL3 | 0.0242 |
| TAF15__1 | 0.0297 |
| TCEAL8__1 | 0.024 |
| THBS3 | 0.1003 |
| TM2D3__2 | 0.0396 |
| TMEM52 | 0.099 |
| TMEM62 | 0.0101 |
| TNFRSF18__1 | 0.2172 |
| TNNT2__1 | 0.0065 |
| TOMM20L | 0.0067 |
| TPM22 | 0.1822 |
| TRIM58 | 0.1077 |
| UBR7__1 | 0.0832 |
| UBR7__2 | 0.1286 |
| WARS__2 | 0.1735 |
| XBP1__2 | 0.1339 |
| XRN2__1 | 0.0576 |
| YARS2 | 0.0344 |
| ZNF75D__2 | 0.1385 |
| ZSWIM4__2 | 0.1769 |
| figo__numeric | 0.012 |
| hist__rev__SBOT | 0.0396 |
| surg__outcome | 0.0149 |

TABLE 38

| | |
|---|---|
| ABCC93 | 0.0424 |
| ABHD3 | 0.2496 |
| ADAM17__2 | 0.1599 |
| ADAMTS1 | 0.1341 |
| ADAMTS2__1 | 0.1074 |
| ALS2CL__3 | 0.0646 |
| ANO7__3 | 0.0491 |
| ARL6IP1__1 | 0.0019 |
| ARMCX3__2 | 0.0757 |
| ATXN10__1 | 0.2048 |
| AXL__1 | 0.0987 |
| BAI1__3 | 0.0324 |
| BCAS1__1 | 0.3401 |
| BDNF__2 | 0.1591 |
| BMPR1A | 0.1264 |
| BTF3__3 | 0.1119 |
| C10orf116 | 0.0343 |
| C11orf24 | 0.2059 |
| C11orf49__3 | 0.1412 |
| C14orf102__2 | 0.1018 |
| C14orf109__2 | 0.0736 |

TABLE 38-continued

| | |
|---|---|
| C17orf106 | 0.1945 |
| C17orf58_2 | 0.0062 |
| C17orf58_3 | 0.0227 |
| C18orf56 | 0.0333 |
| C1orf168 | 0.0383 |
| C1orf64 | 0.1355 |
| C8orf79_1 | 0.0285 |
| CALD1_2 | 0.1427 |
| CASP8AP2 | 0.1302 |
| CCL13 | 0.1286 |
| CCR2_3 | 0.0076 |
| CD34_1 | 0.0375 |
| CDC42BPA_2 | 0.0167 |
| CDC42SE2_2 | 0.0106 |
| CIDEC_1 | 0.1188 |
| CLDN6 | 0.0114 |
| CREB5_2 | 0.0509 |
| CRYBA1 | 0.0391 |
| CXCL13 | 0.0744 |
| CYB5R3_2 | 0.188 |
| CYP1A2 | 0.0735 |
| DBNDD2 | 0.1055 |
| DNAH11 | 0.033 |
| DNMT3L_2 | 0.0192 |
| DOCK7_1 | 0.1234 |
| DSC3_1 | 0.0459 |
| DUT_3 | 0.1053 |
| EEF1E1_1 | 0.1021 |
| EMP1 | 0.1095 |
| ENO1 | 0.1947 |
| ENPEP_2 | 0.148 |
| EPHB1 | 0.0575 |
| EPYC | 0.0338 |
| ERI2_2 | 0.298 |
| ESPNL | 0.048 |
| EZH2_1 | 0.0645 |
| FAM13AOS | 0.0394 |
| FAM187B_2 | 0.0083 |
| FAM70A_1 | 0.0736 |
| FBXO48_2 | 0.2346 |
| FKBP10 | 0.0639 |
| FLJ33360 | 0.0259 |
| FLJ43752 | 0.2398 |
| FMNL3_2 | 0.0212 |
| FOSB | 0.202 |
| FOSL2 | 0.0377 |
| FOXN1 | 0.2908 |
| GAD1_2 | 0.0145 |
| GBE1 | 0.0505 |
| GBP7 | 0.1583 |
| GJA5_1 | 0.0568 |
| GMNN | 0.0856 |
| GSR_2 | 0.0439 |
| HBA2 | 0.2032 |
| HCFC1R1_1 | 0.0689 |
| HDAC7_2 | 0.007 |
| HDLBP_3 | 0.107 |
| HIC1 | 0.0015 |
| HPRT1_1 | 0.1391 |
| HPS4_1 | 0.0719 |
| HR_1 | 0.0492 |
| HSD11B1_1 | 0.08 |
| ICAM2 | 0.0001 |
| ICAM4_1 | 0.2621 |
| IL1RAP_2 | 0.0496 |
| IQCA1_2 | 0.0424 |
| KCNIP3_1 | 0.0947 |
| KCNQ2_1 | 0.1222 |
| KIF3C | 0.1963 |
| KRT80_2 | 0.1123 |
| KRTAP10.10_2 | 0.0199 |
| L3MBTL2_3 | 0.0511 |
| LBH_2 | 0.0973 |
| LENEP | 0.2515 |
| LGI3 | 0.1002 |
| LOC340508 | 0.0293 |
| LOC492303 | 0.0123 |
| LRRC14B | 0.0733 |
| LRRC37A4_2 | 0.0007 |
| LRRTM4 | 0.1658 |
| MACC1 | 0.1345 |
| MANSC1_1 | 0.146 |
| MCAM | 0.0157 |
| MCART6_1 | 0.1389 |
| MFRP | 0.2154 |
| MIDN | 0.0075 |
| MIR1914 | 0.0498 |
| MIR212 | 0.1042 |
| MIR571 | 0.0109 |
| MIR576 | 0.1081 |
| MIR654 | 0.029 |
| MIR942 | 0.111 |
| MMP12_1 | 0.1258 |
| MYCN_2 | 0.1659 |
| MYOHD1 | 0.115 |
| NFATC3_5 | 0.0204 |
| NFATC4 | 0.0371 |
| NLRP9 | 0.1828 |
| NOVA2 | 0.1187 |
| NP | 0.0913 |
| NR6A1_2 | 0.1321 |
| NRXN3_3 | 0.121 |
| NT5DC1_2 | 0.1775 |
| NTRK2_3 | 0.0178 |
| NUP155_1 | 0.0047 |
| NYX | 0.1288 |
| ODF2_3 | 0.0161 |
| ORC1L | 0.0232 |
| OTUD7A_3 | 0.0454 |
| PANKA | 0.0492 |
| PDLIM2_2 | 0.2231 |
| PHYH_1 | 0.1936 |
| PIGA_1 | 0.0078 |
| PITX2_1 | 0.0748 |
| PKN1_3 | 0.0305 |
| PLEKHG5_5 | 0.26 |
| PLSCR4 | 0.0469 |
| PMEPA1_4 | 0.1514 |
| PNMA5 | 0.1499 |
| PPAPDC1A | 0.136 |
| PRAMEF5 | 0.0069 |
| PRKAA2 | 0.126 |
| PSMC6_1 | 0.0339 |
| RAD54B_2 | 0.1854 |
| RAP1A_1 | 0.2213 |
| RARA_3 | 0.0912 |
| RARG | 0.043 |
| RNASEK | 0.0424 |
| RNF7_1 | 0.0342 |
| ROD1_1 | 0.2221 |
| SATB2 | 0.0456 |
| SBSN | 0.0832 |
| SCXB | 0.0132 |
| SEC22C_3 | 0.106 |
| SELENBP1 | 0.1769 |
| SERPINB2_2 | 0.0047 |
| SERPINB5 | 0.1987 |
| SFN | 0.0351 |
| SFRS4 | 0.0644 |
| SHC1_3 | 0.0707 |
| SLC23A1_2 | 0.1554 |
| SLC25A34 | 0.1192 |
| SLC4A5_3 | 0.0757 |
| SLC9A10 | 0.1008 |
| SNORD93 | 0.1567 |
| SOX2_1 | 0.0798 |
| STC1 | 0.0106 |
| STC2 | 0.1382 |
| STYX_2 | 0.0405 |
| SYTL3 | 0.0078 |
| TAF15_1 | 0.0154 |
| TCEAL8_1 | 0.0147 |
| THBS3 | 0.1018 |
| TM2D3_2 | 0.058 |
| TMEM52 | 0.1205 |
| TMEM62 | 0.0022 |
| TNFRSF18_1 | 0.246 |
| TNNT2_1 | 0.0012 |
| TOMM20L | 0.0383 |
| TPM2_2 | 0.1829 |

TABLE 38-continued

| | |
|---|---|
| TRIM58 | 0.1059 |
| UBR7_1 | 0.0435 |
| UBR7_2 | 0.1202 |
| WARS_2 | 0.1523 |
| XBP1_2 | 0.1057 |
| XRN2_1 | 0.0367 |
| YARS2 | 0.0092 |
| ZNF75D_2 | 0.1434 |
| ZSWIM4_2 | 0.1799 |
| figo_numeric | 0.0132 |
| hist_rev_SBOT | 0.0424 |
| surg_outcome | 0.0264 |

TABLE 39

| | |
|---|---|
| ABCC9_3 | 0.0437 |
| ABHD3 | 0.2335 |
| ADAM17_2 | 0.1471 |
| ADAMTS1 | 0.125 |
| ADAMTS2_1 | 0.1082 |
| ALS2CL_3 | 0.0673 |
| ANO7_3 | 0.028 |
| ARL6IP1_1 | 0.0196 |
| ARMCX3_2 | 0.0532 |
| ATXN10_1 | 0.2092 |
| AXL_1 | 0.0898 |
| BAI1_3 | 0.0149 |
| BCAS1_1 | 0.3127 |
| BDNF_2 | 0.1379 |
| BMPR1A | 0.1149 |
| BTF3_3 | 0.107 |
| C10orf116 | 0.0559 |
| C11orf24 | 0.1941 |
| C11orf49_3 | 0.1089 |
| C14orf102_2 | 0.0951 |
| C14orf109_2 | 0.1318 |
| C17orf106 | 0.1848 |
| C17orf58_2 | 0.0402 |
| C17orf58_3 | 0.0224 |
| C18orf56 | 0.003 |
| C1orf168 | 0.047 |
| C1orf64 | 0.1194 |
| C8orf79_1 | 0.0394 |
| CALD1_2 | 0.1148 |
| CASP8AP2 | 0.122 |
| CCL13 | 0.1135 |
| CCR2_3 | 0.0454 |
| CD34_1 | 0.0186 |
| CDC42BPA_2 | 0.0209 |
| CDC42SE2_2 | 0.0152 |
| CLDN6 | 0.1179 |
| CREB5_2 | 0.0171 |
| CRYBA1 | 0.0193 |
| CXCL13 | 0.068 |
| CYB5R3_2 | 0.1779 |
| CYP1A2 | 0.0781 |
| DBNDD2 | 0.1158 |
| DNAH11 | 0.0338 |
| DNMT3L_2 | 0.035 |
| DOCK7_1 | 0.1459 |
| DSC3_1 | 0.0563 |
| DUT_3 | 0.1267 |
| EEF1E1_1 | 0.1117 |
| EMP1 | 0.11 |
| ENO1 | 0.2058 |
| ENPEP_2 | 0.1652 |
| EPHB1 | 0.032 |
| EPYC | 0.0339 |
| ERI2_2 | 0.2901 |
| ESPNL | 0.0731 |
| EZH2_1 | 0.0436 |
| FAM13AOS | 0.0793 |
| FAM187B_2 | 0.0196 |
| FAM70A_1 | 0.0644 |
| FBXO48_2 | 0.2315 |
| FKBP10 | 0.0873 |
| FLJ33360 | 0.0106 |

TABLE 39-continued

| | |
|---|---|
| FLJ43752 | 0.2561 |
| FMNL3_2 | 0.0038 |
| FOSB | 0.2306 |
| FOSL2 | 0.025 |
| FOXN1 | 0.2475 |
| GAD1_2 | 0.0174 |
| GBE1 | 0.0637 |
| GBP7 | 0.1588 |
| GJA5_1 | 0.0467 |
| GMNN | 0.0908 |
| GSR_2 | 0.028 |
| HBA2 | 0.2021 |
| HCFC1R1_1 | 0.0685 |
| HDAC7_2 | 0.0048 |
| HDLBP_3 | 0.1149 |
| HIC1 | 0.0175 |
| HPRT1_1 | 0.1297 |
| HPS4_1 | 0.0428 |
| HR_1 | 0.0359 |
| HSD11B1_1 | 0.0878 |
| ICAM2 | 0.0247 |
| ICAM4_1 | 0.2693 |
| IL1RAP_2 | 0.084 |
| IQCA1_2 | 0.053 |
| KCNIP3_1 | 0.1079 |
| KCNQ2_1 | 0.1233 |
| KIF3C | 0.1757 |
| KRT80_2 | 0.114 |
| KRTAP10.10_2 | 0.0114 |
| L3MBTL2_3 | 0.0448 |
| LBH_2 | 0.092 |
| LENEP | 0.2239 |
| LGI3 | 0.0908 |
| LOC340508 | 0.0562 |
| LOC492303 | 0.02 |
| LRRC14B | 0.0937 |
| LRRC37A4_2 | 0.0203 |
| LRRTM4 | 0.198 |
| MACC1 | 0.1688 |
| MANSC1_1 | 0.1222 |
| MCAM | 0.0005 |
| MCART6_1 | 0.1271 |
| MFRP | 0.2211 |
| MIDN | 0.008 |
| MIR1914 | 0.0703 |
| MIR212 | 0.0928 |
| MIR571 | 0.0125 |
| MIR576 | 0.114 |
| MIR654 | 0.0306 |
| MIR942 | 0.1136 |
| MMP12_1 | 0.1152 |
| MYCN_2 | 0.1162 |
| MYOHD1 | 0.1035 |
| NFATC3_5 | 0.0005 |
| NFATC4 | 0.0387 |
| NLRP9 | 0.1917 |
| NOVA2 | 0.0861 |
| NP | 0.0807 |
| NR6A1_2 | 0.1299 |
| NRXN3_3 | 0.1635 |
| NT5DC1_2 | 0.1893 |
| NTRK2_3 | 0.0237 |
| NUP155_1 | 0.0329 |
| NYX | 0.1176 |
| ODF2_3 | 0.0268 |
| ORC1L | 0.0328 |
| OTUD7A_3 | 0.0567 |
| PANK4 | 0.0489 |
| PDLIM2_2 | 0.2186 |
| PDZRN4_2 | 0.2162 |
| PHYH_1 | 0.0042 |
| PIGA_1 | 0.1044 |
| PITX2_1 | 0.1952 |
| PKN1_3 | 0.0181 |
| PLEKHG5_5 | 0.2534 |
| PLSCR4 | 0.031 |
| PMEPA1_4 | 0.1353 |
| PNMA5 | 0.1673 |
| PPAPDC1A | 0.1097 |
| PRAMEF5 | 0.0097 |

TABLE 39-continued

| | |
|---|---|
| PRKAA2 | 0.0972 |
| PSMC6_1 | 0.0129 |
| RAD54B_2 | 0.1676 |
| RAP1A_1 | 0.2097 |
| RARA_3 | 0.0864 |
| RARG | 0.0705 |
| RNASEK | 0.0784 |
| RNF7_1 | 0.0122 |
| ROD1_1 | 0.2194 |
| SATB2 | 0.0246 |
| SBSN | 0.0546 |
| SCXB | 0.0042 |
| SEC22C_3 | 0.0938 |
| SELENBP1 | 0.1442 |
| SERPINB2_2 | 0.0145 |
| SERPINB5 | 0.2 |
| SFN | 0.0027 |
| SFRS4 | 0.0606 |
| SHC1_3 | 0.0783 |
| SLC23A1_2 | 0.1316 |
| SLC25A34 | 0.1141 |
| SLC4A5_3 | 0.0799 |
| SLC9A10 | 0.0728 |
| SNORD93 | 0.1344 |
| SOX2_1 | 0.0773 |
| STC1 | 0.0038 |
| STC2 | 0.1182 |
| STYX_2 | 0.0238 |
| SYTL3 | 0.0103 |
| TAF15_1 | 0.0148 |
| TCEAL8_1 | 0.033 |
| THBS3 | 0.0835 |
| TM2D3_2 | 0.0401 |
| IMEM52 | 0.099 |
| IMEM62 | 0.0043 |
| TNFRSF18_1 | 0.2257 |
| TNNT2_1 | 0.0041 |
| TOMM20L | 0.0004 |
| TPM2_2 | 0.1766 |
| TRIM58 | 0.1115 |
| UBR7_1 | 0.0699 |
| UBR7_2 | 0.1313 |
| WARS_2 | 0.1744 |
| XBP1_2 | 0.1496 |
| XRN2_1 | 0.0279 |
| YARS2 | 0.012 |
| ZNF75D_2 | 0.1209 |
| ZSWIM4_2 | 0.1681 |
| figo_numeric | 0.0044 |
| hist_rev_SBOT | 0.0511 |
| surg_outcome | 0.0121 |

TABLE 40

| | |
|---|---|
| ABCC9_3 | 0.0533 |
| ABHD3 | 0.2416 |
| ADAM17_2 | 0.148 |
| ADAMTS1 | 0.112 |
| ADAMTS2_1 | 0.0961 |
| ALS2CL_3 | 0.0628 |
| ANO7_3 | 0.0498 |
| ARL6IP1_1 | 0.0137 |
| ARMCX3_2 | 0.0685 |
| ATXN10_1 | 0.1957 |
| AXL_1 | 0.0829 |
| BAI1_3 | 0.0209 |
| BCAS1_1 | 0.3223 |
| BDNF_2 | 0.1353 |
| BMPR1A | 0.1158 |
| BTF3_3 | 0.1138 |
| C10orf116 | 0.0743 |
| C11orf24 | 0.1957 |
| C11orf49_3 | 0.102 |
| C14orf102_2 | 0.1078 |
| C14orf109_2 | 0.1201 |
| C17orf106 | 0.1726 |
| C17orf58_2 | 0.0099 |

TABLE 40-continued

| | |
|---|---|
| C17orf58_3 | 0.0145 |
| C18orf56 | 0.0003 |
| C1orf168 | 0.0389 |
| C1orf64 | 0.1191 |
| C8orf79_1 | 0.0166 |
| CALD1_2 | 0.1284 |
| CASP8AP2 | 0.1304 |
| CCL13 | 0.1154 |
| CCR2_3 | 0.0417 |
| CD34_1 | 0.0328 |
| CDC42BPA_2 | 0.0034 |
| CDC42SE2_2 | 0.0074 |
| CIDEC_1 | 0.1011 |
| CLDN6 | 0.0107 |
| CREB5_2 | 0.0106 |
| CRYBA1 | 0.0538 |
| CXCL13 | 0.0652 |
| CYB5R3_2 | 0.1903 |
| CYP1A2 | 0.0627 |
| DBNDD2 | 0.1258 |
| DNAH11 | 0.0411 |
| DNMT3L_2 | 0.0282 |
| DOCK7_1 | 0.1161 |
| DSC3_1 | 0.0478 |
| DUT_3 | 0.1115 |
| EEF1E1_1 | 0.1222 |
| EMP1 | 0.116 |
| ENO1 | 0.1972 |
| ENPEP_2 | 0.1664 |
| EPHB1 | 0.0401 |
| EPYC | 0.0303 |
| ERI2_2 | 0.2829 |
| ESPNL | 0.0543 |
| EZH2_1 | 0.0546 |
| FAM13AOS | 0.0791 |
| FAM187B_2 | 0.0105 |
| FAM70A_1 | 0.0714 |
| FBXO48_2 | 0.2243 |
| FKBP10 | 0.081 |
| FLJ33360 | 0.0135 |
| FLJ43752 | 0.2485 |
| FMNL3_2 | 0.0005 |
| FOSB | 0.2147 |
| FOSL2 | 0.0333 |
| FOXN1 | 0.2566 |
| GAD1_2 | 0.0249 |
| GBE1 | 0.0473 |
| GBP7 | 0.1373 |
| GJA5_1 | 0.0723 |
| GMNN | 0.1036 |
| GSR_2 | 0.0336 |
| HBA2 | 0.2112 |
| HCFC1R1 1 | 0.061 |
| HDAC7_2 | 0.0082 |
| HDLBP_3 | 0.102 |
| HIC1 | 0.0059 |
| HPRT1_1 | 0.123 |
| HPS4_1 | 0.0724 |
| HR_1 | 0.0282 |
| HSD11B1_1 | 0.0849 |
| ICAM2 | 0.0088 |
| ICAM4_1 | 0.2845 |
| IL1RAP_2 | 0.0729 |
| IQCA1_2 | 0.0317 |
| KCNIP3_1 | 0.102 |
| KCNQ2_1 | 0.1156 |
| KIF3C | 0.1639 |
| KRT80_2 | 0.11 |
| KRTAP10.10_2 | 0.0243 |
| L3MBTL2_3 | 0.0525 |
| LBH_2 | 0.0857 |
| LENEP | 0.233 |
| LGI3 | 0.0878 |
| LOC492303 | 0.0373 |
| LRRC14B | 0.025 |
| LRRC37A4_2 | 0.0794 |
| LRRTM4 | 0.179 |
| MACC1 | 0.1568 |
| MANSC1_1 | 0.1233 |
| MCAM | 0.0164 |

TABLE 40-continued

| | |
|---|---|
| MCART6__1 | 0.1279 |
| MFRP | 0.2234 |
| MIDN | 0.008 |
| MIR1914 | 0.0516 |
| MIR212 | 0.0933 |
| MIR571 | 0.0013 |
| MIR576 | 0.1094 |
| MIR654 | 0.0443 |
| MIR942 | 0.1108 |
| MMP12__1 | 0.1245 |
| MYCN__2 | 0.1301 |
| MYOHD1 | 0.1094 |
| NFATC3__5 | 0.0121 |
| NFATC4 | 0.0385 |
| NLRP9 | 0.1901 |
| NOVA2 | 0.0877 |
| NP | 0.0868 |
| NR6A1__2 | 0.1293 |
| NRXN3__3 | 0.163 |
| NT5DC1__2 | 0.1897 |
| NTRK2__3 | 0.0079 |
| NUP155__1 | 0.0268 |
| NYX | 0.1178 |
| ODF2__3 | 0.0219 |
| ORC1L | 0.0235 |
| OTUD7A__3 | 0.0497 |
| PANK4 | 0.0507 |
| PDLIM2__2 | 0.2123 |
| PDZRN4__2 | 0.2088 |
| PHYH__1 | 0.0108 |
| PIGA__1 | 0.0936 |
| PITX2__1 | 0.2057 |
| PKN1__3 | 0.0116 |
| PLEKHG5__5 | 0.2467 |
| PLSCR4 | 0.0204 |
| PMEPA1__4 | 0.1344 |
| PNMA5 | 0.1709 |
| PPAPDC1A | 0.1055 |
| PRAMEF5 | 0.0152 |
| PRKAA2 | 0.133 |
| PSMC6__1 | 0.04 |
| RAD54B__2 | 0.1622 |
| RAP1A__1 | 0.2022 |
| RARA__3 | 0.0968 |
| RARG | 0.0719 |
| RNASEK | 0.0821 |
| RNF7__1 | 0.0257 |
| ROD1__1 | 0.1967 |
| SATB2 | 0.0371 |
| SBSN | 0.0678 |
| SCXB | 0.0068 |
| SEC22C__3 | 0.1023 |
| SELENBP1 | 0.1462 |
| SERPINB2__2 | 0.0024 |
| SERPINB5 | 0.1847 |
| SFN | 0.0027 |
| SFRS4 | 0.0691 |
| SHC1__3 | 0.0782 |
| SLC23A1__2 | 0.1364 |
| SLC25A34 | 0.1162 |
| SLC4A5__3 | 0.0874 |
| SLC9A10 | 0.0726 |
| SNORD93 | 0.1248 |
| SOX2__1 | 0.0778 |
| STC1 | 0.0055 |
| STC2 | 0.1283 |
| STYX__2 | 0.0171 |
| SYTL3 | 0.0246 |
| TAF15__1 | 0.0303 |
| TCEAL8__1 | 0.0237 |
| THBS3 | 0.102 |
| TM2D3__2 | 0.0399 |
| TMEM52 | 0.1032 |
| TMEM62 | 0.0084 |
| TNFRSF18__1 | 0.2162 |
| TNNT2__1 | 0.0037 |
| TOMM20L | 0.0051 |
| TPM2__2 | 0.1824 |
| TRIM58 | 0.1067 |
| UBR7__1 | 0.084 |
| UBR7__2 | 0.1307 |
| WARS__2 | 0.176 |
| XBP1__2 | 0.1358 |
| XRN2__1 | 0.0599 |
| YARS2 | 0.034 |
| ZNF75D__2 | 0.1361 |
| ZSWIM4__2 | 0.1774 |
| figo__numeric | 0.0096 |
| hist__rev__SBOT | 0.0385 |
| surg__outcome | 0.0116 |

TABLE 41

| | |
|---|---|
| ABCC9__3 | 0.0397 |
| ABHD3 | 0.2499 |
| ADAM17__2 | 0.1539 |
| ADAMTS1 | 0.142 |
| ALS2CL__3 | 0.1129 |
| ANO7__3 | 0.059 |
| ARL6IP1__1 | 0.0407 |
| ARMCX3__2 | 0.0754 |
| ATXN10__1 | 0.2072 |
| AXL__1 | 0.0942 |
| BAI1__3 | 0.0426 |
| BCAS1__1 | 0.3299 |
| BDNF__2 | 0.1511 |
| BMPR1A | 0.1229 |
| BTF3__3 | 0.108 |
| C10orf116 | 0.0296 |
| C11orf24 | 0.2047 |
| C11orf49__3 | 0.1498 |
| C14orf102__2 | 0.1044 |
| C14orf109__2 | 0.0708 |
| C17orf106 | 0.1763 |
| C17orf58__2 | 0.0123 |
| C17orf58__3 | 0.0281 |
| C18orf56 | 0.029 |
| C1orf168 | 0.0419 |
| C1orf64 | 0.1374 |
| C8orf79__1 | 0.0234 |
| CALD1__2 | 0.1552 |
| CASP8AP2 | 0.1138 |
| CCL13 | 0.1448 |
| CCR2__3 | 0.0026 |
| CD34__1 | 0.037 |
| CDC42BPA__2 | 0.0056 |
| CDC42SE2__2 | 0.0015 |
| CIDEC__1 | 0.1194 |
| CLDN6 | 0.013 |
| CREB5__2 | 0.0427 |
| CRYBA1 | 0.0429 |
| CXCL13 | 0.0699 |
| CYB5R3__2 | 0.1766 |
| CYP1A2 | 0.0889 |
| DBNDD2 | 0.108 |
| DNAH11 | 0.0306 |
| DNMT3L__2 | 0.0143 |
| DOCK7__1 | 0.1172 |
| DSC3__1 | 0.0472 |
| DUT__3 | 0.1225 |
| EEF1E1__1 | 0.1071 |
| ELN__2 | 0.1114 |
| EMP1 | 0.2017 |
| ENO1 | 0.1477 |
| ENPEP__2 | 0.0718 |
| EPHB1 | 0.0599 |
| EPYC | 0.0354 |
| ERI2__2 | 0.2846 |
| ESPNL | 0.0508 |
| EZH2__1 | 0.0488 |
| FAM13AOS | 0.0304 |
| FAM187B__2 | 0.0104 |
| FAM70A__1 | 0.0757 |
| FBXO48__2 | 0.2353 |
| FKBP10 | 0.0533 |
| FLJ33360 | 0.0322 |
| FLJ43752 | 0.2425 |

TABLE 41-continued

| | |
|---|---|
| FMNL3_2 | 0.0113 |
| FOSB | 0.2125 |
| FOSL2 | 0.0292 |
| FOXN1 | 0.2988 |
| GAD1_2 | 0.0126 |
| GBE1 | 0.0504 |
| GBP7 | 0.1549 |
| GJA5_1 | 0.0538 |
| GMNN | 0.082 |
| GSR_2 | 0.0361 |
| HBA2 | 0.1962 |
| HCFC1R1_1 | 0.0678 |
| HDAC7_2 | 0.0126 |
| HDLBP_3 | 0.0981 |
| HIC1 | 0.0001 |
| HPRT1_1 | 0.1525 |
| HPS4_1 | 0.0655 |
| HR_1 | 0.0481 |
| HSD11B1_1 | 0.083 |
| ICAM2 | 0.012 |
| ICAM4_1 | 0.2696 |
| IL1RAP_2 | 0.0469 |
| IQCA1_2 | 0.0363 |
| KCNIP3_1 | 0.0911 |
| KCNQ2_1 | 0.1135 |
| KIF3C | 0.2112 |
| KRT80_2 | 0.1004 |
| KRTAP10.10_2 | 0.0162 |
| L3MBTL2_3 | 0.0447 |
| LBH_2 | 0.0936 |
| LENEP | 0.2514 |
| LGI3 | 0.1011 |
| LOC340508 | 0.0265 |
| LOC492303 | 0.0131 |
| LRRC14B | 0.0724 |
| LRRC37A4_2 | 0.0026 |
| LRRTM4 | 0.1641 |
| MACC1 | 0.1444 |
| MANSC1_1 | 0.1437 |
| MCAM | 0.0178 |
| MCART6_1 | 0.1369 |
| MFRP | 0.2153 |
| MIDN | 0.0203 |
| MIR1914 | 0.0513 |
| MIR212 | 0.1066 |
| MIR571 | 0.0077 |
| MIR576 | 0.1208 |
| MIR654 | 0.024 |
| MIR942 | 0.1037 |
| MMP12_1 | 0.1228 |
| MYCN_2 | 0.1558 |
| MYOHD1 | 0.1153 |
| NFATC3_5 | 0.0349 |
| NFATC4 | 0.0346 |
| NLRP9 | 0.1737 |
| NOVA2 | 0.104 |
| NP | 0.077 |
| NR6A1_2 | 0.1329 |
| NRXN3_3 | 0.1299 |
| NT5DC1_2 | 0.1761 |
| NTRK2_3 | 0.0155 |
| NUP155_1 | 0.0032 |
| NYX | 0.1139 |
| ODF2_3 | 0.0109 |
| ORC1L | 0.0328 |
| OTUD7A_3 | 0.0381 |
| PANK4 | 0.0477 |
| PDLIM2_2 | 0.2231 |
| PHYH_1 | 0.1928 |
| PIGA_1 | 0.0149 |
| PITX2_1 | 0.0749 |
| PKN1_3 | 0.0208 |
| PLEKHG5_5 | 0.2748 |
| PLSCR4 | 0.0429 |
| PMEPA1_4 | 0.1469 |
| PNMA5 | 0.1504 |
| PPAPDC1A | 0.1486 |
| PRAMEF5 | 0.0147 |
| PRKAA2 | 0.1132 |
| PSMC6_1 | 0.0322 |
| RAD54B_2 | 0.192 |
| RAP1A_1 | 0.2103 |
| RARA_3 | 0.0895 |
| RARG | 0.0525 |
| RNASEK | 0.0326 |
| RNF7_1 | 0.0412 |
| ROD1_1 | 0.2198 |
| SATB2 | 0.0405 |
| SBSN | 0.0882 |
| SCXB | 0.0176 |
| SEC22C_3 | 0.105 |
| SELENBP1 | 0.173 |
| SERPINB2_2 | 0.0034 |
| SERPINB5 | 0.1921 |
| SFN | 0.0433 |
| SFRS4 | 0.0632 |
| SHC1_3 | 0.0668 |
| SLC23A1_2 | 0.1474 |
| SLC25A34 | 0.1086 |
| SLC4A5_3 | 0.0741 |
| SLC9A10 | 0.098 |
| SNORD93 | 0.1599 |
| SOX2_1 | 0.0826 |
| STC1 | 0.0136 |
| STC2 | 0.1175 |
| STYX_2 | 0.0395 |
| SYTL3 | 0.0075 |
| TAF15_1 | 0.0141 |
| TCEAL8_1 | 0.0075 |
| THBS3 | 0.0959 |
| TM2D3_2 | 0.055 |
| TMEM52 | 0.1215 |
| TMEM62 | 0.0099 |
| TNFRSF18_1 | 0.256 |
| TNNT2_1 | 0.0068 |
| TOMM20L | 0.0466 |
| TPM2_2 | 0.1813 |
| TRIM58 | 0.1118 |
| UBR7_1 | 0.0387 |
| UBR7_2 | 0.1325 |
| WARS_2 | 0.1551 |
| XBP1_2 | 0.1108 |
| XRN2_1 | 0.0171 |
| YARS2 | 0.0048 |
| ZNF75D_2 | 0.1391 |
| ZSWIM4_2 | 0.1784 |
| figo_numeric | 0.0128 |
| hist_rev_SBOT | 0.0481 |
| surg_outcome | 0.0218 |

TABLE 42

| | |
|---|---|
| ABCC9_3 | 0.0425 |
| ABHD3 | 0.2305 |
| ADAM17_2 | 0.1466 |
| ADAMTS1 | 0.1315 |
| ALS2CL_3 | 0.1149 |
| ANO7_3 | 0.0659 |
| ARL6IP1_1 | 0.0178 |
| ARMCX3_2 | 0.0467 |
| ATXN10_1 | 0.216 |
| AXL_1 | 0.0883 |
| BAI1_3 | 0.0263 |
| BCAS1_1 | 0.3029 |
| BDNF_2 | 0.1326 |
| BMPR1A | 0.1149 |
| BTF3_3 | 0.1015 |
| C10orf116 | 0.0584 |
| C11orf24 | 0.1867 |
| C11orf49_3 | 0.1161 |
| C14orf102_2 | 0.0909 |
| C14orf109_2 | 0.1302 |
| C17orf106 | 0.1793 |
| C17orf58_2 | 0.0493 |
| C17orf58_3 | 0.0259 |
| C18orf56 | 0.0048 |
| C1orf168 | 0.046 |

TABLE 42-continued

| | |
|---|---|
| C1orf64 | 0.1192 |
| C8orf79__1 | 0.0404 |
| CALD1__2 | 0.1241 |
| CASP8AP2 | 0.1146 |
| CCL13 | 0.1245 |
| CCR2__3 | 0.0408 |
| CD34__1 | 0.0143 |
| CDC42BPA__2 | 0.0129 |
| CDC42SE2__2 | 0.0115 |
| CLDN6 | 0.1193 |
| CREB5__2 | 0.0185 |
| CRYBA1 | 0.0202 |
| CXCL13 | 0.0644 |
| CYB5R3__2 | 0.1752 |
| CYP1A2 | 0.0925 |
| DBNDD2 | 0.1199 |
| DNAH11 | 0.0324 |
| DNMT3L__2 | 0.0295 |
| DOCK7__1 | 0.1454 |
| DSC3__1 | 0.0494 |
| DUT__3 | 0.1321 |
| EEF1E1__1 | 0.1159 |
| ELN__2 | 0.1108 |
| EMP1 | 0.2116 |
| ENO1 | 0.1609 |
| ENPEP__2 | 0.0584 |
| EPHB1 | 0.0334 |
| EPYC | 0.0371 |
| ERI2__2 | 0.2778 |
| ESPNL | 0.0754 |
| EZH2__1 | 0.0275 |
| FAM13AOS | 0.074 |
| FAM187B__2 | 0.0166 |
| FAM70A__1 | 0.0699 |
| FBXO48__2 | 0.2364 |
| FKBP10 | 0.0782 |
| FLJ33360 | 0.0094 |
| FLJ43752 | 0.253 |
| FMNL3__2 | 0.0067 |
| FOSB | 0.2377 |
| FOSL2 | 0.0173 |
| FOXN1 | 0.2532 |
| GAD1__2 | 0.0134 |
| GBE1 | 0.0693 |
| GBP7 | 0.1589 |
| GJA5__1 | 0.0434 |
| GMNN | 0.0865 |
| GSR__2 | 0.0197 |
| HBA2 | 0.1984 |
| HCFC1R1__1 | 0.0748 |
| HDAC7__2 | 0.0025 |
| HDLBP__3 | 0.1123 |
| HIC1 | 0.0216 |
| HPRT1__1 | 0.141 |
| HPS4__1 | 0.0305 |
| HR__1 | 0.0314 |
| HSD11B1__1 | 0.09 |
| ICAM2 | 0.0303 |
| ICAM4__1 | 0.2776 |
| IL1RAP__2 | 0.0888 |
| IQCA1__2 | 0.0508 |
| KCNIP3__1 | 0.0998 |
| KCNQ2__1 | 0.1103 |
| KIF3C | 0.1865 |
| KRT80__2 | 0.1084 |
| KRTAP10.10__2 | 0.0109 |
| L3MBTL2__3 | 0.0423 |
| LBH__2 | 0.0868 |
| LENEP | 0.2223 |
| LGI3 | 0.0912 |
| LOC340508 | 0.0526 |
| LOC492303 | 0.0173 |
| LRRC14B | 0.0959 |
| LRRC37A4__2 | 0.0175 |
| LRRTM4 | 0.191 |
| MACC1 | 0.1757 |
| MANSC1__1 | 0.1188 |
| MCAM | 0.004 |
| MCART6__1 | 0.1223 |
| MFRP | 0.2198 |
| MIDN | 0.0121 |
| MIR1914 | 0.0731 |
| MIR212 | 0.0946 |
| MIR571 | 0.0141 |
| MIR576 | 0.12 |
| MIR654 | 0.026 |
| MIR942 | 0.1063 |
| MMP12__1 | 0.113 |
| MYCN__2 | 0.112 |
| MYOHD1 | 0.1003 |
| NFATC3__5 | 0.0061 |
| NFATC4 | 0.0379 |
| NLRP9 | 0.1836 |
| NOVA2 | 0.0788 |
| NP | 0.0729 |
| NR6A1__2 | 0.132 |
| NRXN3__3 | 0.1687 |
| NT5DC1__2 | 0.1873 |
| NTRK2__3 | 0.0257 |
| NUP155__1 | 0.03 |
| NYX | 0.1113 |
| ODF2__3 | 0.023 |
| ORC1L | 0.0393 |
| OTUD7A__3 | 0.0605 |
| PANK4 | 0.0488 |
| PDLIM2__2 | 0.224 |
| PDZRN4__2 | 0.2142 |
| PHYH__1 | 0.0013 |
| PIGA__1 | 0.1039 |
| PITX2__1 | 0.1916 |
| PKN1__3 | 0.0171 |
| PLEKHG5__5 | 0.2654 |
| PLSCR4 | 0.0321 |
| PMEPA1__4 | 0.1345 |
| PNMA5 | 0.1658 |
| PPAPDC1A | 0.1172 |
| PRAMEF5 | 0.0033 |
| PRKAA2 | 0.0835 |
| PSMC6__1 | 0.0085 |
| RAD54B__2 | 0.1735 |
| RAP1A__1 | 0.202 |
| RARA__3 | 0.0836 |
| RARG | 0.0752 |
| RNASEK | 0.0797 |
| RNF7__1 | 0.0084 |
| ROD1__1 | 0.2238 |
| SATB2 | 0.0195 |
| SBSN | 0.0599 |
| SCXB | 0.0079 |
| SEC22C__3 | 0.0985 |
| SELENBP1 | 0.141 |
| SERPINB2__2 | 0.0093 |
| SERPINB5 | 0.1985 |
| SFN | 0.0125 |
| SFRS4 | 0.0619 |
| SHC1__3 | 0.0786 |
| SLC23A1__2 | 0.1282 |
| SLC25A34 | 0.1047 |
| SLC4A5__3 | 0.0788 |
| SLC9A10 | 0.0695 |
| SNORD93 | 0.1365 |
| SOX2__1 | 0.0821 |
| STC1 | 0.0002 |
| STC2 | 0.1076 |
| STYX__2 | 0.0213 |
| SYTL3 | 0.0124 |
| TAF15__1 | 0.0116 |
| TCEAL8__1 | 0.0282 |
| THBS3 | 0.0768 |
| TM2D3__2 | 0.035 |
| TMEM52 | 0.0977 |
| TMEM62 | 0.0098 |
| TNFRSF18__1 | 0.2255 |
| TNNT2__1 | 0.0087 |
| TOMM20L | 0.0036 |
| TPM2__2 | 0.1748 |
| TRIM58 | 0.1149 |
| UBR7__1 | 0.0621 |
| UBR7__2 | 0.1383 |
| WARS__2 | 0.1778 |

TABLE 42-continued

| | |
|---|---|
| XBP1_2 | 0.1525 |
| XRN2_1 | 0.0126 |
| YARS2 | 0.0089 |
| ZNF75D_2 | 0.1155 |
| ZSWIM4_2 | 0.165 |
| figo_numeric | 0.0013 |
| hist_rev_SBOT | 0.0539 |
| surg_outcome | 0.0123 |

TABLE 43

| | |
|---|---|
| ABCC9_3 | 0.0518 |
| ABHD3 | 0.2416 |
| ADAM17_2 | 0.1421 |
| ADAMTS1 | 0.1163 |
| ALS2CL_3 | 0.1032 |
| ANO7_3 | 0.0577 |
| ARL6IP1_1 | 0.0383 |
| ARMCX3_2 | 0.0621 |
| ATXN10_1 | 0.2002 |
| AXL_1 | 0.0787 |
| BAI1_3 | 0.039 |
| BCAS1_1 | 0.3125 |
| BDNF_2 | 0.1249 |
| BMPR1A | 0.1127 |
| BTF3_3 | 0.1074 |
| C10orf116 | 0.0764 |
| C11orf24 | 0.1919 |
| C11orf49_3 | 0.1101 |
| C14orf102_2 | 0.1056 |
| C14orf109_2 | 0.1151 |
| C17orf106 | 0.1628 |
| C17orf58_2 | 0.0165 |
| C17orf58_3 | 0.0188 |
| C18orf56 | 0.0014 |
| C1orf168 | 0.0362 |
| C1orf64 | 0.117 |
| C8orf79_1 | 0.0116 |
| CALD1_2 | 0.1444 |
| CASP8AP2 | 0.1208 |
| CCL13 | 0.1339 |
| CCR2_3 | 0.0306 |
| CD34_1 | 0.0302 |
| CDC42BPA_2 | 0.008 |
| CDC42SE2_2 | 0.0158 |
| CIDEC_1 | 0.1023 |
| CLDN6 | 0.0101 |
| CREB5_2 | 0.0087 |
| CRYBA1 | 0.0583 |
| CXCL13 | 0.0606 |
| CYB5R3_2 | 0.1875 |
| CYP1A2 | 0.0788 |
| DBNDD2 | 0.1281 |
| DNAH11 | 0.0391 |
| DNMT3L_2 | 0.0233 |
| DOCK7_1 | 0.1142 |
| DSC3_1 | 0.0421 |
| DUT_3 | 0.1213 |
| EEF1E1_1 | 0.1304 |
| ELN_2 | 0.1203 |
| EMP1 | 0.2038 |
| ENO1 | 0.1612 |
| ENPEP_2 | 0.0755 |
| EPHB1 | 0.0435 |
| EPYC | 0.0353 |
| ERI2_2 | 0.2661 |
| ESPNL | 0.0618 |
| EZH2_1 | 0.0349 |
| FAM13AOS | 0.0713 |
| FAM187B_2 | 0.0061 |
| FAM70A_1 | 0.0763 |
| FBXO48_2 | 0.2271 |
| FKBP10 | 0.0694 |
| FLJ33360 | 0.015 |
| FLJ43752 | 0.2482 |
| FMNL3_2 | 0.0148 |
| FOSB | 0.2242 |

TABLE 43-continued

| | |
|---|---|
| FOSL2 | 0.027 |
| FOXN1 | 0.2632 |
| GAD1_2 | 0.022 |
| GBE1 | 0.0515 |
| GBP7 | 0.1337 |
| GJA5_1 | 0.0692 |
| GMNN | 0.1028 |
| GSR_2 | 0.0217 |
| HBA2 | 0.2072 |
| HCFC1R1_1 | 0.0608 |
| HDAC7_2 | 0.006 |
| HDLBP_3 | 0.0941 |
| HIC1 | 0.0032 |
| HPRT1_1 | 0.1353 |
| HPS4_1 | 0.0631 |
| HR_1 | 0.0243 |
| HSD11B1_1 | 0.0892 |
| ICAM2 | 0.0138 |
| ICAM4_1 | 0.2951 |
| IL1RAP_2 | 0.0741 |
| IQCA1_2 | 0.0244 |
| KCNIP3_1 | 0.0938 |
| KCNQ2_1 | 0.1005 |
| KIF3C | 0.1804 |
| KRT80_2 | 0.0974 |
| KRTAP10.10_2 | 0.0251 |
| L3MBTL2_3 | 0.047 |
| LBH_2 | 0.0788 |
| LENEP | 0.2352 |
| LGI3 | 0.0898 |
| LOC492303 | 0.0287 |
| LRRC14B | 0.0258 |
| LRRC37A4_2 | 0.0805 |
| LRRTM4 | 0.171 |
| MACC1 | 0.1667 |
| MANSC1_1 | 0.1147 |
| MCAM | 0.0177 |
| MCART6_1 | 0.1242 |
| MFRP | 0.2218 |
| MIDN | 0.0017 |
| MIR1914 | 0.0521 |
| MIR212 | 0.0938 |
| MIR571 | 0.0018 |
| MIR576 | 0.1152 |
| MIR654 | 0.0402 |
| MIR942 | 0.1028 |
| MMP12_1 | 0.1231 |
| MYCN_2 | 0.1288 |
| MYOHD1 | 0.1095 |
| NFATC3_5 | 0.0257 |
| NFATC4 | 0.0391 |
| NLRP9 | 0.1795 |
| NOVA2 | 0.0707 |
| NP | 0.0758 |
| NR6A1_2 | 0.1303 |
| NRXN3_3 | 0.1671 |
| NT5DC1_2 | 0.1835 |
| NTRK2_3 | 0.0065 |
| NUP155_1 | 0.0235 |
| NYX | 0.1072 |
| ODF2_3 | 0.0161 |
| ORC1L | 0.0346 |
| OTUD7A_3 | 0.0453 |
| PANK4 | 0.0512 |
| PDLIM2_2 | 0.2133 |
| PDZRN4_2 | 0.2065 |
| PHYH_1 | 0.0138 |
| PIGA_1 | 0.0954 |
| PITX2_1 | 0.2052 |
| PKN1_3 | 0.0055 |
| PLEKHG5_5 | 0.2631 |
| PLSCR4 | 0.0174 |
| PMEPA1_4 | 0.1317 |
| PNMA5 | 0.1709 |
| PPAPDC1A | 0.1182 |
| PRAMEF5 | 0.0079 |
| PRKAA2 | 0.1228 |
| PSMC6_1 | 0.0374 |
| RAD54B_2 | 0.17 |
| RAP1A_1 | 0.1931 |

TABLE 43-continued

| | |
|---|---|
| RARA_3 | 0.0943 |
| RARG | 0.0835 |
| RNASEK | 0.0781 |
| RNF7_1 | 0.0263 |
| ROD1_1 | 0.1957 |
| SATB2 | 0.0337 |
| SBSN | 0.0787 |
| SCXB | 0.0128 |
| SEC22C_3 | 0.1033 |
| SELENBP1 | 0.1464 |
| SERPINB2_2 | 0.0054 |
| SERPINB5 | 0.1773 |
| SFN | 0.0126 |
| SFRS4 | 0.0664 |
| SHC1_3 | 0.0738 |
| SLC23A1_2 | 0.1263 |
| SLC25A34 | 0.109 |
| SLC4A5_3 | 0.0866 |
| SLC9A10 | 0.0661 |
| SNORD93 | 0.1261 |
| SOX2_1 | 0.0782 |
| STC1 | 0.0047 |
| STC2 | 0.1147 |
| STYX_2 | 0.0145 |
| SYTL3 | 0.0265 |
| TAF15_1 | 0.0283 |
| TCEAL8_1 | 0.0151 |
| THBS3 | 0.0969 |
| TM2D3_2 | 0.0344 |
| TMEM52 | 0.1012 |
| TMEM62 | 0.0003 |
| TNFRSF18_1 | 0.22 |
| TNNT2_1 | 0.0095 |
| TOMM20L | 0.0031 |
| TPM2_2 | 0.1789 |
| TRIM58 | 0.1141 |
| UBR7_1 | 0.0813 |
| UBR7_2 | 0.1399 |
| WARS_2 | 0.1788 |
| XBP1_2 | 0.1423 |
| XRN2_1 | 0.0391 |
| YARS2 | 0.032 |
| ZNF75D_2 | 0.1331 |
| ZSWIM4_2 | 0.1751 |
| figo_numeric | 0.0156 |
| hist_rev_SBOT | 0.0427 |
| surg_outcome | 0.0116 |

TABLE 44

| | |
|---|---|
| ABCC9_3 | 0.036 |
| ABHD3 | 0.2418 |
| ADAM17_2 | 0.1594 |
| ADAMTS1 | 0.1413 |
| ADAMTS2_1 | 0.121 |
| ALS2CL_3 | 0.0649 |
| ANO7_3 | 0.0213 |
| ARL6IP1_1 | 0.0213 |
| ARMCX3_2 | 0.0681 |
| ATXN10_1 | 0.2199 |
| AXL_1 | 0.0968 |
| BAI1_3 | 0.0412 |
| BCAS1_1 | 0.3202 |
| BDNF_2 | 0.1502 |
| BMPR1A | 0.1275 |
| BTF3_3 | 0.1045 |
| C10orf116 | 0.028 |
| C11orf24 | 0.2 |
| C11orf49_3 | 0.1503 |
| C14orf102_2 | 0.083 |
| C14orf109_2 | 0.0921 |
| C17orf106 | 0.1908 |
| C17orf58_2 | 0.039 |
| C17orf58_3 | 0.0287 |
| C18orf56 | 0.0321 |
| C1orf168 | 0.0489 |
| C1orf64 | 0.135 |

TABLE 44-continued

| | |
|---|---|
| C8orf79_1 | 0.036 |
| CALD1_2 | 0.1435 |
| CASP8AP2 | 0.1065 |
| CCL13 | 0.1338 |
| CCR2_3 | 0.017 |
| CD34_1 | 0.0292 |
| CDC42BPA_2 | 0.0121 |
| CDC42SE2_2 | 0.0321 |
| CLDN6 | 0.1355 |
| CREB5_2 | 0.0068 |
| CRYBA1 | 0.065 |
| CXCL13 | 0.0787 |
| CYB5R3_2 | 0.1712 |
| CYP1A2 | 0.0968 |
| DBNDD2 | 0.1126 |
| DNAH11 | 0.0285 |
| DNMT3L_2 | 0.0232 |
| DOCK7_1 | 0.1391 |
| DSC3_1 | 0.0513 |
| DUT_3 | 0.1196 |
| EEF1E1_1 | 0.0951 |
| ELN_2 | 0.1071 |
| EMP1 | 0.2002 |
| ENO1 | 0.1533 |
| ENPEP_2 | 0.0677 |
| EPHB1 | 0.0571 |
| EPYC | 0.0355 |
| ERI2_2 | 0.285 |
| ESPNL | 0.0581 |
| EZH2_1 | 0.0411 |
| FAM13AOS | 0.0424 |
| FAM187B_2 | 0.0158 |
| FAM70A_1 | 0.0593 |
| FBXO48_2 | 0.2378 |
| FKBP10 | 0.0718 |
| FLJ33360 | 0.019 |
| FLJ43752 | 0.2474 |
| FMNL3_2 | 0.0143 |
| FOSB | 0.2264 |
| FOSL2 | 0.02 |
| FOXN1 | 0.2808 |
| GAD1_2 | 0.0056 |
| GBE1 | 0.0656 |
| GBP7 | 0.1639 |
| GJA5_1 | 0.0425 |
| GMNN | 0.0697 |
| GSR_2 | 0.0249 |
| HBA2 | 0.1999 |
| HCFC1R1_1 | 0.0751 |
| HDAC7_2 | 0.0136 |
| HDLBP_3 | 0.1099 |
| HIC1 | 0.0256 |
| HPRT1_1 | 0.1566 |
| HPS4_1 | 0.0459 |
| HR_1 | 0.0402 |
| HSD11B1_1 | 0.087 |
| ICAM2 | 0.0205 |
| ICAM4_1 | 0.2616 |
| IL1RAP_2 | 0.0513 |
| IQCA1_2 | 0.0447 |
| KCNIP3_1 | 0.1012 |
| KCNQ2_1 | 0.1135 |
| KIF3C | 0.2104 |
| KRT80_2 | 0.1038 |
| KRTAP10.10_2 | 0.0058 |
| L3MBTL2_3 | 0.0483 |
| LBH_2 | 0.092 |
| LENEP | 0.2431 |
| LGI3 | 0.0848 |
| LOC340508 | 0.0351 |
| LOC492303 | 0.001 |
| LRRC14B | 0.0865 |
| LRRC37A4_2 | 0.0078 |
| LRRTM4 | 0.1788 |
| MACC1 | 0.1593 |
| MANSC1_1 | 0.1468 |
| MCAM | 0.0017 |
| MCART6_1 | 0.1422 |
| MFRP | 0.2188 |
| MIDN | 0.0097 |

TABLE 44-continued

| | |
|---|---|
| MIR1914 | 0.0589 |
| MIR212 | 0.112 |
| MIR571 | 0.0143 |
| MIR576 | 0.1222 |
| MIR654 | 0.0199 |
| MIR942 | 0.1114 |
| MMP12__1 | 0.1088 |
| MYCN__2 | 0.1385 |
| MYOHD1 | 0.1035 |
| NFATC3__5 | 0.0304 |
| NFATC4 | 0.0453 |
| NLRP9 | 0.1706 |
| NOVA2 | 0.1107 |
| NP | 0.0876 |
| NR6A1__2 | 0.1312 |
| NRXN3__3 | 0.1303 |
| NT5DC1__2 | 0.184 |
| NTRK2__3 | 0.044 |
| NUP155__1 | 0.0115 |
| NYX | 0.1203 |
| ODF2__3 | 0.0224 |
| ORC1L | 0.034 |
| OTUD7A__3 | 0.0543 |
| PANK4 | 0.037 |
| PDLIM2__2 | 0.2288 |
| PHYH__1 | 0.194 |
| PIGA__1 | 0.0048 |
| PITX2__1 | 0.0845 |
| PKN1__3 | 0.0306 |
| PLEKHG5__5 | 0.2787 |
| PLSCR4 | 0.0479 |
| PMEPA1__4 | 0.1626 |
| PNMA5 | 0.1467 |
| PPAPDC1A | 0.1399 |
| PRAMEF5 | 0.0122 |
| PRKAA2 | 0.0937 |
| PSMC6__1 | 0.0073 |
| RAD54B__2 | 0.1946 |
| RAP1A__1 | 0.2211 |
| RARA__3 | 0.0827 |
| RARG | 0.0498 |
| RNASEK | 0.0463 |
| RNF7__1 | 0.027 |
| ROD1__1 | 0.2439 |
| SATB2 | 0.0247 |
| SBSN | 0.0737 |
| SCXB | 0.0121 |
| SEC22C__3 | 0.0979 |
| SELENBP1 | 0.1641 |
| SERPINB2__2 | 0.0109 |
| SERPINB5 | 0.2042 |
| SFN | 0.0343 |
| SFRS4 | 0.0627 |
| SHC1__3 | 0.0789 |
| SLC23A1__2 | 0.1388 |
| SLC25A34 | 0.1082 |
| SLC4A5__3 | 0.0717 |
| SLC9A10 | 0.1028 |
| SNORD93 | 0.1652 |
| SOX2__1 | 0.0838 |
| STC1 | 0.0093 |
| STC2 | 0.1172 |
| STYX__2 | 0.0436 |
| SYTL3 | 0.0048 |
| TAF15__1 | 0.002 |
| TCEAL8__1 | 0.0188 |
| THBS3 | 0.0896 |
| TM2D3__2 | 0.0517 |
| TMEM52 | 0.1115 |
| TMEM62 | 0.0171 |
| TNFRSF18__1 | 0.2479 |
| TNNT2__1 | 0.0053 |
| TOMM20L | 0.049 |
| TPM2__2 | 0.18 |
| TRIM58 | 0.1134 |
| UBR7__1 | 0.0324 |
| UBR7__2 | 0.1357 |
| WARS__2 | 0.1513 |
| XBP1__2 | 0.1115 |
| XRN2__1 | 0.0002 |
| YARS2 | 0.016 |
| ZNF75D__2 | 0.1219 |
| ZSWIM4__2 | 0.1727 |
| figo__numeric | 0.0137 |
| hist__rev__SBOT | 0.0484 |
| surg__outcome | 0.0353 |

TABLE 45

| | |
|---|---|
| ABCC9__3 | 0.0405 |
| ABHD3 | 0.248 |
| ADAM17__2 | 0.1551 |
| ADAMTS1 | 0.1361 |
| ADAMTS2__1 | 0.114 |
| ALS2CL__3 | 0.0574 |
| ANO7__3 | 0.0398 |
| ARL6IP1__1 | 0.0203 |
| ARMCX3__2 | 0.0756 |
| ATXN10__1 | 0.2101 |
| AXL__1 | 0.0947 |
| BAI1__3 | 0.0448 |
| BCAS1__1 | 0.3265 |
| BDNF__2 | 0.1484 |
| BMPR1A | 0.1254 |
| BTF3__3 | 0.1066 |
| C10orf116 | 0.032 |
| C11orf24 | 0.2036 |
| C11orf49__3 | 0.1528 |
| C14orf102__2 | 0.1049 |
| C14orf109__2 | 0.0692 |
| C17orf106 | 0.183 |
| C17orf58__2 | 0.0131 |
| C17orf58__3 | 0.0296 |
| C18orf56 | 0.0308 |
| C1orf168 | 0.0421 |
| C1orf64 | 0.1371 |
| C8orf79__1 | 0.0283 |
| CALD1__2 | 0.1557 |
| CASP8AP2 | 0.1118 |
| CCL13 | 0.1418 |
| CCR2__3 | 0.0027 |
| CD34__1 | 0.0382 |
| CDC42BPA__2 | 0.0056 |
| CDC42SE2__2 | 0.002 |
| CIDEC__1 | 0.1189 |
| CLDN6 | 0.0145 |
| CREB5__2 | 0.0443 |
| CRYBA1 | 0.0424 |
| CXCL13 | 0.0712 |
| CYB5R3__2 | 0.1805 |
| CYP1A2 | 0.0895 |
| DBNDD2 | 0.1079 |
| DNAH11 | 0.0306 |
| DNMT3L__2 | 0.0125 |
| DOCK7__1 | 0.1253 |
| DSC3__1 | 0.0446 |
| DUT__3 | 0.1217 |
| EEF1E1__1 | 0.1053 |
| ELN__2 | 0.1093 |
| EMP1 | 0.2013 |
| ENO1 | 0.1433 |
| ENPEP__2 | 0.0787 |
| EPHB1 | 0.0585 |
| EPYC | 0.0343 |
| ERI2__2 | 0.2792 |
| ESPNL | 0.0496 |
| EZH2__1 | 0.0506 |
| FAM13AOS | 0.0286 |
| FAM187B__2 | 0.0083 |
| FAM70A__1 | 0.077 |
| FBXO48__2 | 0.2388 |
| FKBP10 | 0.0553 |
| FLJ33360 | 0.0312 |
| FLJ43752 | 0.2411 |
| FMNL3__2 | 0.0121 |
| FOSB | 0.2136 |
| FOSL2 | 0.0265 |

TABLE 45-continued

| | |
|---|---|
| FOXN1 | 0.3005 |
| GAD1_2 | 0.0126 |
| GBE1 | 0.0533 |
| GBP7 | 0.1547 |
| GJA5_1 | 0.0544 |
| GMNN | 0.0815 |
| GSR_2 | 0.0369 |
| HBA2 | 0.1941 |
| HCFC1R1_1 | 0.0692 |
| HDAC7_2 | 0.0102 |
| HDLBP_3 | 0.1009 |
| HIC1 | 0.0023 |
| HPRT1_1 | 0.1547 |
| HPS4_1 | 0.0617 |
| HR_1 | 0.042 |
| HSD11B1_1 | 0.0838 |
| ICAM2 | 0.0132 |
| ICAM4_1 | 0.2725 |
| IL1RAP_2 | 0.047 |
| IQCA1_2 | 0.0335 |
| KCNIP3_1 | 0.0906 |
| KCNQ2_1 | 0.1123 |
| KIF3C | 0.2087 |
| KRT80_2 | 0.1016 |
| KRTAP10.10_2 | 0.0184 |
| L3MBTL2_3 | 0.0458 |
| LBH_2 | 0.0914 |
| LENEP | 0.2476 |
| LGI3 | 0.1018 |
| LOC492303 | 0.0262 |
| LRRC14B | 0.0105 |
| LRRC37A4_2 | 0.0724 |
| LRRTM4 | 0.162 |
| MACC1 | 0.147 |
| MANSC1_1 | 0.1434 |
| MCAM | 0.0203 |
| MCART6_1 | 0.1354 |
| MFRP | 0.2209 |
| MIDN | 0.0197 |
| MIR1914 | 0.0461 |
| MIR212 | 0.1054 |
| MIR571 | 0.0122 |
| MIR576 | 0.1217 |
| MIR654 | 0.0234 |
| MIR942 | 0.104 |
| MMP12_1 | 0.1214 |
| MYCN_2 | 0.1555 |
| MYOHD1 | 0.1145 |
| NFATC3_5 | 0.0357 |
| NFATC4 | 0.0353 |
| NLRP9 | 0.1721 |
| NOVA2 | 0.1049 |
| NP | 0.0776 |
| NR6A1_2 | 0.1366 |
| NRXN3_3 | 0.1304 |
| NT5DC1_2 | 0.1769 |
| NTRK2_3 | 0.0182 |
| NUP155_1 | 0.0071 |
| NYX | 0.1181 |
| ODF2_3 | 0.0143 |
| ORC1L | 0.0339 |
| OTUD7A_3 | 0.0389 |
| PANK4 | 0.0493 |
| PDLIM2_2 | 0.2253 |
| PHYH_1 | 0.1925 |
| PIGA_1 | 0.0109 |
| PITX2_1 | 0.0726 |
| PKN1_3 | 0.0238 |
| PLEKHG5_5 | 0.275 |
| PLSCR4 | 0.0404 |
| PMEPA1_4 | 0.1528 |
| PNMA5 | 0.1469 |
| PPAPDC1A | 0.1491 |
| PRAMEF5 | 0.0133 |
| PRKAA2 | 0.1131 |
| PSMC6_1 | 0.0295 |
| RAD54B_2 | 0.1927 |
| RAP1A_1 | 0.2064 |
| RARA_3 | 0.0877 |
| RARG | 0.0507 |
| RNASEK | 0.0392 |
| RNF7_1 | 0.0375 |
| ROD1_1 | 0.2204 |
| SATB2 | 0.0409 |
| SBSN | 0.0881 |
| SCXB | 0.0192 |
| SEC22C_3 | 0.1055 |
| SELENBP1 | 0.1717 |
| SERPINB2_2 | 0.0002 |
| SERPINB5 | 0.1947 |
| SFN | 0.0443 |
| SFRS4 | 0.064 |
| SHC1_3 | 0.0668 |
| SLC23A1_2 | 0.1452 |
| SLC25A34 | 0.1091 |
| SLC4A5_3 | 0.0736 |
| SLC9A10 | 0.0977 |
| SNORD93 | 0.1568 |
| SOX2_1 | 0.0829 |
| STC1 | 0.0155 |
| STC2 | 0.1165 |
| STYX_2 | 0.0385 |
| SYTL3 | 0.008 |
| TAF15_1 | 0.0146 |
| TCEAL8_1 | 0.0078 |
| THBS3 | 0.0944 |
| TM2D3_2 | 0.0534 |
| TMEM52 | 0.1154 |
| TMEM62 | 0.0076 |
| TNFRSF18_1 | 0.2551 |
| TNNT2_1 | 0.0097 |
| TOMM20L | 0.0442 |
| TPM2_2 | 0.1828 |
| TRIM58 | 0.1129 |
| UBR7_1 | 0.0366 |
| UBR7_2 | 0.1311 |
| WARS_2 | 0.152 |
| XBP1_2 | 0.1099 |
| XRN2_1 | 0.0157 |
| YARS2 | 0.0047 |
| ZNF75D_2 | 0.1409 |
| ZSWIM4_2 | 0.1781 |
| figo_numeric | 0.0154 |
| hist_rev_SBOT | 0.0474 |
| surg_outcome | 0.026 |

TABLE 46

| | |
|---|---|
| ABCC9_3 | 0.0433 |
| ABHD3 | 0.2313 |
| ADAM17_2 | 0.1463 |
| ADAMTS1 | 0.1324 |
| ADAMTS2_1 | 0.1156 |
| ALS2CL_3 | 0.0663 |
| ANO7_3 | 0.0165 |
| ARL6IP1_1 | 0.005 |
| ARMCX3_2 | 0.0473 |
| ATXN10_1 | 0.2153 |
| AXL_1 | 0.0883 |
| BAI1_3 | 0.0263 |
| BCAS1_1 | 0.303 |
| BDNF_2 | 0.1325 |
| BMPR1A | 0.1136 |
| BTF3_3 | 0.1025 |
| C10orf116 | 0.0579 |
| C11orf24 | 0.1872 |
| C11orf49_3 | 0.1148 |
| C14orf102_2 | 0.0905 |
| C14orf109_2 | 0.1288 |
| C17orf106 | 0.1772 |
| C17orf58_2 | 0.0491 |
| C17orf58_3 | 0.0249 |
| C18orf56 | 0.0047 |
| C1orf168 | 0.0462 |
| C1orf64 | 0.1187 |
| C8orf79_1 | 0.039 |
| CALD1_2 | 0.1237 |

TABLE 46-continued

| | |
|---|---|
| CASP8AP2 | 0.1133 |
| CCL13 | 0.1257 |
| CCR2_3 | 0.0405 |
| CD34_1 | 0.015 |
| CDC42BPA_2 | 0.0125 |
| CDC42SE2_2 | 0.012 |
| CLDN6 | 0.1194 |
| CREB5_2 | 0.0186 |
| CRYBA1 | 0.0195 |
| CXCL13 | 0.0646 |
| CYB5R3_2 | 0.1744 |
| CYP1A2 | 0.0928 |
| DBNDD2 | 0.1202 |
| DNAH11 | 0.0329 |
| DNMT3L_2 | 0.03 |
| DOCK7_1 | 0.1428 |
| DSC3_1 | 0.0499 |
| DUT_3 | 0.1323 |
| EEF1E1_1 | 0.1166 |
| ELN_2 | 0.1113 |
| EMP1 | 0.2114 |
| ENO1 | 0.1618 |
| ENPEP_2 | 0.0575 |
| EPHB1 | 0.0325 |
| EPYC | 0.0368 |
| ERI2_2 | 0.2801 |
| ESPNL | 0.0762 |
| EZH2_1 | 0.026 |
| FAM13AOS | 0.0738 |
| FAM187B_2 | 0.0162 |
| FAM70A_1 | 0.0679 |
| FBXO48_2 | 0.2354 |
| FKBP10 | 0.0781 |
| FLJ33360 | 0.0098 |
| FLJ43752 | 0.2543 |
| FMNL3_2 | 0.0068 |
| FOSB | 0.2374 |
| FOSL2 | 0.0174 |
| FOXN1 | 0.2537 |
| GAD1_2 | 0.0135 |
| GBE1 | 0.069 |
| GBP7 | 0.1605 |
| GJA5_1 | 0.0438 |
| GMNN | 0.0875 |
| GSR_2 | 0.019 |
| HBA2 | 0.198 |
| HCFC1R1_1 | 0.0729 |
| HDAC7_2 | 0.003 |
| HDLBP_3 | 0.1117 |
| HIC1 | 0.0219 |
| HPRT1_1 | 0.1409 |
| HPS4_1 | 0.0314 |
| HR_1 | 0.0314 |
| HSD11B1_1 | 0.0913 |
| ICAM2 | 0.0295 |
| ICAM4_1 | 0.2782 |
| IL1RAP_2 | 0.089 |
| IQCA1_2 | 0.051 |
| KCNIP3_1 | 0.0995 |
| KCNQ2_1 | 0.1115 |
| KIF3C | 0.1872 |
| KRT80_2 | 0.1091 |
| KRTAP10.10_2 | 0.0099 |
| L3MBTL2_3 | 0.0423 |
| LBH_2 | 0.087 |
| LENEP | 0.2226 |
| LGI3 | 0.0909 |
| LOC492303 | 0.0523 |
| LRRC14B | 0.0181 |
| LRRC37A4_2 | 0.095 |
| LRRTM4 | 0.192 |
| MACC1 | 0.1756 |
| MANSC1_1 | 0.1191 |
| MCAM | 0.0035 |
| MCART6_1 | 0.1239 |
| MFRP | 0.2181 |
| MIDN | 0.0112 |
| MIR1914 | 0.0735 |
| MIR212 | 0.0953 |
| MIR571 | 0.0131 |
| MIR576 | 0.1188 |
| MIR654 | 0.0263 |
| MIR942 | 0.1061 |
| MMP12_1 | 0.1136 |
| MYCN_2 | 0.112 |
| MYOHD1 | 0.1009 |
| NFATC3_5 | 0.0066 |
| NFATC4 | 0.0369 |
| NLRP9 | 0.1847 |
| NOVA2 | 0.0786 |
| NP | 0.0737 |
| NR6A1_2 | 0.1323 |
| NRXN3_3 | 0.1695 |
| NT5DC1_2 | 0.1883 |
| NTRK2_3 | 0.0264 |
| NUP155_1 | 0.0286 |
| NYX | 0.1093 |
| ODF2_3 | 0.0222 |
| ORC1L | 0.0396 |
| OTUD7A_3 | 0.0602 |
| PANK4 | 0.0492 |
| PDLIM2_2 | 0.2233 |
| PDZRN4_2 | 0.213 |
| PHYH_1 | 0.002 |
| PIGA_1 | 0.1049 |
| PITX2_1 | 0.1925 |
| PKN1_3 | 0.0164 |
| PLEKHG5_5 | 0.2641 |
| PLSCR4 | 0.0318 |
| PMEPA1_4 | 0.1339 |
| PNMA5 | 0.1661 |
| PPAPDC1A | 0.1173 |
| PRAMEF5 | 0.0037 |
| PRKAA2 | 0.0845 |
| PSMC6_1 | 0.0092 |
| RAD54B_2 | 0.1734 |
| RAP1A_1 | 0.2019 |
| RARA_3 | 0.0839 |
| RARG | 0.076 |
| RNASEK | 0.0781 |
| RNF7_1 | 0.0092 |
| ROD1_1 | 0.2241 |
| SATB2 | 0.0194 |
| SBSN | 0.0605 |
| SCXB | 0.0084 |
| SEC22C_3 | 0.0984 |
| SELENBP1 | 0.1409 |
| SERPINB2_2 | 0.0099 |
| SERPINB5 | 0.1984 |
| SFN | 0.0117 |
| SFRS4 | 0.062 |
| SHC1_3 | 0.0792 |
| SLC23A1_2 | 0.1285 |
| SLC25A34 | 0.1046 |
| SLC4A5_3 | 0.0784 |
| SLC9A10 | 0.0692 |
| SNORD93 | 0.1354 |
| SOX2_1 | 0.0821 |
| STC1 | 0.0006 |
| STC2 | 0.1069 |
| STYX_2 | 0.0206 |
| SYTL3 | 0.0128 |
| TAF15_1 | 0.0124 |
| TCEAL8_1 | 0.029 |
| THBS3 | 0.0772 |
| TM2D3_2 | 0.0352 |
| TMEM52 | 0.0973 |
| TMEM62 | 0.0099 |
| TNFRSF18_1 | 0.2259 |
| TNNT2_1 | 0.007 |
| TOMM20L | 0.0038 |
| TPM2_2 | 0.1746 |
| TRIM58 | 0.1143 |
| UBR7_1 | 0.0632 |
| UBR7_2 | 0.1372 |
| WARS_2 | 0.1773 |
| XBP1_2 | 0.1536 |
| XRN2_1 | 0.0131 |
| YARS2 | 0.0087 |
| ZNF75D_2 | 0.1157 |

TABLE 46-continued

| | |
|---|---|
| ZSWIM4_2 | 0.1653 |
| figo_numeric | 0.0012 |
| hist_rev_SBOT | 0.0544 |
| surg_outcome | 0.0116 |

TABLE 47

| | |
|---|---|
| ABCC9_3 | 0.0696 |
| ABHD3 | 0.2533 |
| ADAM17_2 | 0.1436 |
| ADAMTS1 | 0.0774 |
| ADAMTS2_1 | 0.0967 |
| ALS2CL_3 | 0.0472 |
| ANO7_3 | 0.0388 |
| ARL6IP1_1 | 0.0119 |
| ARMCX3_2 | 0.0639 |
| ATP2B1_3 | 0.1777 |
| ATXN10_1 | 0.0694 |
| AXL_1 | 0.0588 |
| BAI1_3 | 0.036 |
| BCAS1_1 | 0.3111 |
| BDNF_2 | 0.1004 |
| BMPR1A | 0.1203 |
| BTF3_3 | 0.1159 |
| C10orf116 | 0.0819 |
| C11orf24 | 0.1375 |
| C11orf49_3 | 0.1207 |
| C14orf102_2 | 0.0873 |
| C14orf109_2 | 0.1053 |
| C17orf106 | 0.1659 |
| C17orf58_2 | 0.0033 |
| C17orf58_3 | 0.0289 |
| C18orf56 | 0.0106 |
| C1orf168 | 0.0384 |
| C1orf64 | 0.1093 |
| C8orf79_1 | 0.0444 |
| CALD1_2 | 0.1526 |
| CASP8AP2 | 0.1126 |
| CCL13 | 0.1468 |
| CCR2_3 | 0.0417 |
| CD34_1 | 0.0562 |
| CDC42BPA_2 | 0.0137 |
| CDC42SE2_2 | 0.001 |
| CIDEC_1 | 0.1086 |
| CLDN6 | 0.0248 |
| CREB5_2 | 0.0103 |
| CRYBA1 | 0.0612 |
| CXCL13 | 0.0664 |
| CYB5R3_2 | 0.1655 |
| CYP1A2 | 0.0623 |
| DBNDD2 | 0.1079 |
| DFFB_2 | 0.0435 |
| DNAH11 | 0.0244 |
| DNMT3L_2 | 0.0951 |
| DOCK7_1 | 0.0083 |
| DSC3_1 | 0.0316 |
| DUT_3 | 0.1331 |
| EEF1E1_1 | 0.1018 |
| ELN_2 | 0.1057 |
| EMP1 | 0.1805 |
| ENO1 | 0.1502 |
| ENPEP_2 | 0.0681 |
| EPHB1 | 0.0478 |
| EPYC | 0.0254 |
| ERI2_2 | 0.2725 |
| ESPNL | 0.0803 |
| EZH2_1 | 0.0506 |
| FAM13AOS | 0.046 |
| FAM187B_2 | 0.0052 |
| FAM70A_1 | 0.1008 |
| FBXO48_2 | 0.1965 |
| FKBP10 | 0.0944 |
| FLJ33360 | 0.0228 |
| FLJ43752 | 0.2324 |
| FMNL3_2 | 0.0244 |
| FOSB | 0.1977 |
| FOSL2 | 0.0472 |

TABLE 47-continued

| | |
|---|---|
| FOXN1 | 0.257 |
| GAD1_2 | 0.024 |
| GBE1 | 0.0549 |
| GBP7 | 0.0954 |
| GJA5_1 | 0.0628 |
| GMNN | 0.1071 |
| GSR_2 | 0.0117 |
| GUSBL2 | 0.1966 |
| HBA2 | 0.0512 |
| HDAC7_2 | 0.0281 |
| HDLBP_3 | 0.1796 |
| HIC1 | 0.0794 |
| HPRT1_1 | 0.135 |
| HPS4_1 | 0.0317 |
| HR_1 | 0.0355 |
| HSD11B1_1 | 0.0991 |
| ICAM2 | 0.0086 |
| ICAM4_1 | 0.2797 |
| IL1RAP_2 | 0.0665 |
| IQCA1_2 | 0.005 |
| KCNIP3_1 | 0.0803 |
| KCNQ2_1 | 0.1234 |
| KIF3C | 0.1851 |
| KRT80_2 | 0.0789 |
| KRTAP10.10_2 | 0.0252 |
| L3MBTL2_3 | 0.045 |
| LBH_2 | 0.0781 |
| LENEP | 0.2225 |
| LGI3 | 0.1071 |
| LOC340508 | 0.0427 |
| LOC492303 | 0.0279 |
| LRRC14B | 0.0689 |
| LRRC37A4_2 | 0.0168 |
| LRRTM4 | 0.1666 |
| MACC1 | 0.1672 |
| MANSC1_1 | 0.122 |
| MAPK3_1 | 0.0462 |
| MCAM | 0.093 |
| MCART6_1 | 0.2299 |
| MFRP | 0.0347 |
| MIDN | 0.0306 |
| MIR1914 | 0.0473 |
| MIR212 | 0.0992 |
| MIR571 | 0.0288 |
| MIR576 | 0.0982 |
| MIR654 | 0.0045 |
| MIR942 | 0.0829 |
| MMP12_1 | 0.1251 |
| MYCN_2 | 0.1504 |
| MYOHD1 | 0.0906 |
| NFATC3_5 | 0.0307 |
| NFATC4 | 0.046 |
| NLRP9 | 0.153 |
| NOVA2 | 0.058 |
| NP | 0.081 |
| NR6A1_2 | 0.1229 |
| NRXN3_3 | 0.1365 |
| NT5DC1_2 | 0.1855 |
| NTRK2_3 | 0.0012 |
| NUP155_1 | 0.0212 |
| NYX | 0.0636 |
| ODF2_3 | 0.0254 |
| ORC1L | 0.0528 |
| OTUD7A_3 | 0.0414 |
| PANK4 | 0.0513 |
| PDLIM2_2 | 0.2016 |
| PDZRN4_2 | 0.2334 |
| PHYH_1 | 0.0129 |
| PIGA_1 | 0.0786 |
| PITX2_1 | 0.2039 |
| PKN1_3 | 0.0349 |
| PLEKHG5_5 | 0.2594 |
| PLSCR4 | 0.0257 |
| PMEPA1_4 | 0.1513 |
| PNMA5 | 0.1849 |
| PPAPDC1A | 0.1082 |
| PRAMEF5 | 0.0173 |
| PRKAA2 | 0.1096 |
| PSMC6_1 | 0.022 |
| RAD54B_2 | 0.1948 |

TABLE 47-continued

| | |
|---|---|
| RAP1A__1 | 0.2024 |
| RARA__3 | 0.0887 |
| RARG | 0.0268 |
| RNASEK | 0.0969 |
| RNF7__1 | 0.0546 |
| ROD1__1 | 0.1945 |
| SATB2 | 0.0246 |
| SBSN | 0.0683 |
| SCXB | 0.0162 |
| SEC22C__3 | 0.1006 |
| SELENBP1 | 0.1444 |
| SERPINB2__2 | 0.025 |
| SERPINB5 | 0.1819 |
| SFN | 0.0093 |
| SFRS4 | 0.0715 |
| SHC1__3 | 0.1054 |
| SLC23A1__2 | 0.0915 |
| SLC25A34 | 0.0864 |
| SLC4A5__3 | 0.0891 |
| SLC9A10 | 0.0702 |
| SNORD93 | 0.121 |
| SOX2__1 | 0.0692 |
| STC1 | 0.0048 |
| STC2 | 0.0886 |
| STYX__2 | 0.0307 |
| SYTL3 | 0.0229 |
| TAF15__1 | 0.0307 |
| TCEAL8__1 | 0.0282 |
| THBS3 | 0.0887 |
| TM2D3__2 | 0.0286 |
| TMEM52 | 0.0716 |
| TMEM62 | 0.005 |
| TNFRSF18__1 | 0.2254 |
| TNNT2__1 | 0.0102 |
| TOMM20L | 0.0059 |
| TPM2__2 | 0.1709 |
| TRIM58 | 0.0914 |
| UBR7__1 | 0.063 |
| UBR7__2 | 0.157 |
| WARS__2 | 0.1918 |
| XBP1__2 | 0.1665 |
| XRN2__1 | 0.0272 |
| YARS2 | 0.0296 |
| ZNF75D__2 | 0.1301 |
| ZSWIM4__2 | 0.1703 |
| figo__numeric | 0.025 |
| hist__rev__SBOT | 0.054 |
| surg__outcome | 0.0057 |

TABLE 48

| | |
|---|---|
| ABCC9__3 | 0.0682 |
| ABHD3 | 0.2441 |
| ADAM17__2 | 0.1457 |
| ADAMTS1 | 0.0811 |
| ADAMTS2__1 | 0.1086 |
| ALS2CL__3 | 0.0528 |
| ANO7__3 | 0.04 |
| ARL6IP1__1 | 0.0068 |
| ARMCX3__2 | 0.0617 |
| ATXN10__1 | 0.1738 |
| AXL__1 | 0.0704 |
| BAI1__3 | 0.0552 |
| BCAS1__1 | 0.3069 |
| BDNF__2 | 0.0938 |
| BMPR1A | 0.118 |
| BTF3__3 | 0.1104 |
| C10orf116 | 0.0783 |
| C11orf24 | 0.1293 |
| C11orf49__3 | 0.1112 |
| C14orf102__2 | 0.0893 |
| C14orf109__2 | 0.111 |
| C17orf106 | 0.1548 |
| C17orf58__2 | 0.0048 |
| C17orf58__3 | 0.0282 |
| C18orf56 | 0.005 |
| C1orf168 | 0.0319 |

TABLE 48-continued

| | |
|---|---|
| C1orf64 | 0.1039 |
| C8orf79__1 | 0.0416 |
| CALD1__2 | 0.1521 |
| CASP8AP2 | 0.1191 |
| CCL13 | 0.1516 |
| CCR2__3 | 0.0349 |
| CD34__1 | 0.0491 |
| CDC42BPA__2 | 0.0004 |
| CDC42SE2__2 | 0.0011 |
| CIDEC__1 | 0.1065 |
| CLDN6 | 0.0203 |
| CREB5__2 | 0.019 |
| CREBBP__1 | 0.052 |
| CRYBA1 | 0.0676 |
| CXCL13 | 0.1719 |
| CYB5R3__2 | 0.1607 |
| CYP1A2 | 0.0661 |
| DBNDD2 | 0.1009 |
| DFFB__2 | 0.0413 |
| DNAH11 | 0.0309 |
| DNMT3L__2 | 0.0976 |
| DOCK7__1 | 0.0128 |
| DSC3__1 | 0.0381 |
| DUT__3 | 0.1224 |
| EEF1E1__1 | 0.1055 |
| ELN__2 | 0.109 |
| EMP1 | 0.1793 |
| ENO1 | 0.1425 |
| ENPEP__2 | 0.0593 |
| EPHB1 | 0.0429 |
| EPYC | 0.0307 |
| ERI2__2 | 0.2674 |
| ESPNL | 0.0826 |
| EZH2__1 | 0.0417 |
| FAM13AOS | 0.0552 |
| FAM187B__2 | 0.0099 |
| FAM70A__1 | 0.1014 |
| FBXO48__2 | 0.1886 |
| FKBP10 | 0.1053 |
| FLJ33360 | 0.0252 |
| FLJ43752 | 0.2252 |
| FMNL3__2 | 0.0363 |
| FOSB | 0.1936 |
| FOSL2 | 0.0383 |
| FOXN1 | 0.2519 |
| GAD1__2 | 0.0272 |
| GBE1 | 0.0517 |
| GBP7 | 0.0793 |
| GJA5__1 | 0.063 |
| GMNN | 0.1054 |
| GSR__2 | 0.0101 |
| GUSBL2 | 0.1925 |
| HBA2 | 0.0693 |
| HDAC7__2 | 0.031 |
| HDLBP__3 | 0.1913 |
| HIC1 | 0.0851 |
| HPRT1__1 | 0.1429 |
| HPS4__1 | 0.0271 |
| HR__1 | 0.0393 |
| HSD11B1__1 | 0.105 |
| ICAM2 | 0.01 |
| ICAM4__1 | 0.2753 |
| IL1RAP__2 | 0.0589 |
| IQCA1__2 | 0.0019 |
| KCNIP3__1 | 0.0834 |
| KCNQ2__1 | 0.126 |
| KIF3C | 0.1827 |
| KRT80__2 | 0.0686 |
| KRTAP10.10__2 | 0.0236 |
| L3MBTL2__3 | 0.049 |
| LBH__2 | 0.0793 |
| LENEP | 0.2316 |
| LGI3 | 0.1073 |
| LOC340508 | 0.0423 |
| LOC492303 | 0.0284 |
| LRRC14B | 0.069 |
| LRRC37A4__2 | 0.0079 |
| LRRTM4 | 0.1632 |
| MACC1 | 0.1621 |
| MANSC1__1 | 0.1219 |

TABLE 48-continued

| | |
|---|---|
| MCAM | 0.061 |
| MCART6_1 | 0.1036 |
| MFRP | 0.2262 |
| MIDN | 0.0248 |
| MIR1914 | 0.0427 |
| MIR212 | 0.0933 |
| MIR571 | 0.0368 |
| MIR576 | 0.0928 |
| MIR654 | 0.0014 |
| MIR942 | 0.0824 |
| MMP12_1 | 0.1313 |
| MYCN_2 | 0.1406 |
| MYOHD1 | 0.0937 |
| NFATC3_5 | 0.0264 |
| NFATC4 | 0.0529 |
| NLRP9 | 0.1568 |
| NOVA2 | 0.0576 |
| NP | 0.0796 |
| NR6A1_2 | 0.1199 |
| NRXN3_3 | 0.1311 |
| NT5DC1_2 | 0.1811 |
| NTRK2_3 | 0.0095 |
| NUP155_1 | 0.0292 |
| NYX | 0.0596 |
| ODF2_3 | 0.0253 |
| ORC1L | 0.0455 |
| OTUD7A_3 | 0.053 |
| PANK4 | 0.0516 |
| PDLIM2_2 | 0.1925 |
| PDZRN4_2 | 0.2315 |
| PHYH_1 | 0.0186 |
| PIGA_1 | 0.0884 |
| PITX2_1 | 0.1951 |
| PKN1_3 | 0.0311 |
| PLEKHG5_5 | 0.2597 |
| PLSCR4 | 0.0168 |
| PMEPA1_4 | 0.1388 |
| PNMA5 | 0.1728 |
| PPAPDC1A | 0.0931 |
| PRAMEF5 | 0.0074 |
| PRKAA2 | 0.1125 |
| PSMC6_1 | 0.0175 |
| RAD54B_2 | 0.1883 |
| RAP1A_1 | 0.1955 |
| RARA_3 | 0.0884 |
| RARG | 0.0401 |
| RNASEK | 0.1025 |
| RNF7_1 | 0.0454 |
| ROD1_1 | 0.1921 |
| SATB2 | 0.0273 |
| SBSN | 0.0751 |
| SCXB | 0.0089 |
| SEC22C_3 | 0.0932 |
| SELENBP1 | 0.1484 |
| SERPINB2_2 | 0.0149 |
| SERPINB5 | 0.1863 |
| SFN | 0.0136 |
| SFRS4 | 0.0676 |
| SHC1_3 | 0.0828 |
| SLC23A1_2 | 0.0898 |
| SLC25A34 | 0.0974 |
| SLC4A5_3 | 0.0942 |
| SLC9A10 | 0.0642 |
| SNORD93 | 0.1309 |
| SOX2_1 | 0.0629 |
| STC1 | 0.0078 |
| STC2 | 0.0898 |
| STYX_2 | 0.0328 |
| SYTL3 | 0.0217 |
| TAF15_1 | 0.0082 |
| TCEAL8_1 | 0.0327 |
| THBS3 | 0.0865 |
| TM2D3_2 | 0.0325 |
| TMEM52 | 0.0704 |
| TMEM62 | 0.0053 |
| TNFRSF18_1 | 0.2353 |
| TNNT2_1 | 0.0044 |
| TOMM20L | 0.0053 |
| TPM2_2 | 0.1562 |
| TRIM58 | 0.1017 |
| UBR7_1 | 0.0568 |
| UBR7_2 | 0.1495 |
| WARS_2 | 0.197 |
| XBP1_2 | 0.1608 |
| XRN2_1 | 0.0265 |
| YARS2 | 0.0284 |
| ZNF75D_2 | 0.1311 |
| ZSWIM4_2 | 0.1653 |
| figo_numeric | 0.0216 |
| hist_rev_SBOT | 0.0739 |
| surg_outcome | 0.0005 |

TABLE 49

| | |
|---|---|
| ABCC9_3 | 0.068 |
| ABHD3 | 0.2454 |
| ADAM17_2 | 0.1462 |
| ADAMTS1 | 0.0822 |
| ADAMTS2_1 | 0.1063 |
| ALS2CL_3 | 0.0537 |
| ANO7_3 | 0.04 |
| ARL6IP1_1 | 0.0054 |
| ARMCX3_2 | 0.0611 |
| ATXN10_1 | 0.1742 |
| AXL_1 | 0.0715 |
| BAI1_3 | 0.0543 |
| BCAS1_1 | 0.3087 |
| BDNF_2 | 0.0934 |
| BMPR1A | 0.1199 |
| BTF3_3 | 0.1106 |
| C10orf116 | 0.0796 |
| C11orf24 | 0.1305 |
| C11orf49_3 | 0.1096 |
| C14orf102_2 | 0.0906 |
| C14orf109_2 | 0.1105 |
| C17orf106 | 0.1558 |
| C17orf58_2 | 0.0049 |
| C17orf58_3 | 0.0281 |
| C18orf56 | 0.0053 |
| C1orf168 | 0.032 |
| C1orf64 | 0.1042 |
| C8orf79_1 | 0.0425 |
| CALD1_2 | 0.152 |
| CASP8AP2 | 0.1205 |
| CCL13 | 0.1506 |
| CCR2_3 | 0.035 |
| CD34_1 | 0.0505 |
| CDC42BPA_2 | 0.0004 |
| CDC42SE2_2 | 0.0019 |
| CIDEC_1 | 0.1069 |
| CLDN6 | 0.0196 |
| CREB5_2 | 0.0181 |
| CREBBP_1 | 0.0508 |
| CRYBA1 | 0.069 |
| CXCL13 | 0.1716 |
| CYB5R3_2 | 0.1593 |
| CYP1A2 | 0.0675 |
| DBNDD2 | 0.1017 |
| DNAH11 | 0.0416 |
| DNMT3L_2 | 0.0309 |
| DOCK7_1 | 0.0989 |
| DSC3_1 | 0.0388 |
| DUT_3 | 0.1208 |
| EEF1E1_1 | 0.1035 |
| ELN_2 | 0.1085 |
| EMP1 | 0.179 |
| ENO1 | 0.141 |
| ENPEP_2 | 0.0603 |
| EPHB1 | 0.0428 |
| EPYC | 0.0301 |
| ERI2_2 | 0.2651 |
| ESPNL | 0.0841 |
| EZH2_1 | 0.0416 |
| FAM13AOS | 0.055 |
| FAM187B_2 | 0.0096 |
| FAM70A_1 | 0.1017 |
| FBXO48_2 | 0.1866 |

TABLE 49-continued

| | |
|---|---|
| FKBP10 | 0.1092 |
| FLJ33360 | 0.0249 |
| FLJ43752 | 0.2269 |
| FMNL3_2 | 0.0362 |
| FOSB | 0.1926 |
| FOSL2 | 0.0387 |
| FOXN1 | 0.2483 |
| GAD1_2 | 0.028 |
| GBE1 | 0.0532 |
| GBP7 | 0.0782 |
| GJA5_1 | 0.0632 |
| GMNN | 0.1057 |
| GSR_2 | 0.0095 |
| GUSBL2 | 0.1919 |
| HBA2 | 0.0697 |
| HDAC7_2 | 0.0309 |
| HDLBP_3 | 0.1909 |
| HIC1 | 0.086 |
| HPRT1_1 | 0.1412 |
| HPS4_1 | 0.0263 |
| HR_1 | 0.0418 |
| HSD11B1_1 | 0.1054 |
| ICAM2 | 0.0105 |
| ICAM4_1 | 0.2757 |
| IL1RAP_2 | 0.0591 |
| IQCA1_2 | 0.002 |
| KCNIP3_1 | 0.0836 |
| KCNQ2_1 | 0.1249 |
| KIF3C | 0.1835 |
| KRT80_2 | 0.0706 |
| KRTAP10.10_2 | 0.024 |
| L3MBTL2_3 | 0.0495 |
| LBH_2 | 0.0807 |
| LENEP | 0.2318 |
| LGI3 | 0.1079 |
| LOC340508 | 0.0398 |
| LOC492303 | 0.0303 |
| LRRC14B | 0.0689 |
| LRRC37A4_2 | 0.0073 |
| LRRTM4 | 0.1634 |
| MACC1 | 0.1622 |
| MANSC1_1 | 0.1204 |
| MAPK3_1 | 0.0606 |
| MCAM | 0.1022 |
| MCART6_1 | 0.2249 |
| MFRP | 0.0225 |
| MIDN | 0.0242 |
| MIR1914 | 0.0421 |
| MIR212 | 0.0922 |
| MIR571 | 0.0368 |
| MIR576 | 0.0937 |
| MIR654 | 0.0009 |
| MIR942 | 0.0813 |
| MMP12_1 | 0.1333 |
| MYCN_2 | 0.1392 |
| MYOHD1 | 0.0938 |
| NFATC3_5 | 0.0257 |
| NFATC4 | 0.0529 |
| NLRP9 | 0.1562 |
| NOVA2 | 0.0577 |
| NP | 0.0808 |
| NR6A1_2 | 0.1203 |
| NRXN3_3 | 0.1293 |
| NT5DC1_2 | 0.1823 |
| NTRK2_3 | 0.0102 |
| NUP155_1 | 0.0288 |
| NYX | 0.0597 |
| ODF2_3 | 0.0269 |
| ORC1L | 0.0462 |
| OTUD7A_3 | 0.0519 |
| PANK4 | 0.0511 |
| PDLIM2_2 | 0.1909 |
| PDZRN4_2 | 0.2316 |
| PHYH_1 | 0.0171 |
| PIGA_1 | 0.0902 |
| PITX2_1 | 0.1949 |
| PKN1_3 | 0.0318 |
| PLEKHG5_5 | 0.2619 |
| PLSCR4 | 0.0156 |
| PMEPA1_4 | 0.1371 |
| PNMA5 | 0.1746 |
| PPAPDC1A | 0.0922 |
| PRAMEF5 | 0.008 |
| PRKAA2 | 0.1141 |
| PSMC6_1 | 0.0188 |
| RAD54B_2 | 0.1879 |
| RAP1A_1 | 0.194 |
| RARA_3 | 0.0878 |
| RARG | 0.04 |
| RNASEK | 0.1015 |
| RNF7_1 | 0.0434 |
| ROD1_1 | 0.1918 |
| SATB2 | 0.0277 |
| SBSN | 0.0754 |
| SCXB | 0.0086 |
| SEC22C_3 | 0.0928 |
| SELENBP1 | 0.1495 |
| SERPINB2_2 | 0.0145 |
| SERPINB5 | 0.1864 |
| SFN | 0.0147 |
| SFRS4 | 0.066 |
| SHC1_3 | 0.0846 |
| SLC23A1_2 | 0.0887 |
| SLC25A34 | 0.0976 |
| SLC4A5_3 | 0.0939 |
| SLC9A10 | 0.0629 |
| SNORD93 | 0.1298 |
| SOX2_1 | 0.0601 |
| STC1 | 0.0078 |
| STC2 | 0.0891 |
| STYX_2 | 0.0319 |
| SYTL3 | 0.0197 |
| TAF15_1 | 0.0084 |
| TCEAL8_1 | 0.0332 |
| THBS3 | 0.0887 |
| TM2D3_2 | 0.0318 |
| TMEM52 | 0.0702 |
| TMEM62 | 0.0059 |
| TNFRSF18_1 | 0.236 |
| TNNT2_1 | 0.004 |
| TOMM20L | 0.0018 |
| TPM2_2 | 0.1568 |
| TRIM58 | 0.1038 |
| UBR7_1 | 0.056 |
| UBR7_2 | 0.1506 |
| WARS_2 | 0.1966 |
| XBP1_2 | 0.1608 |
| XRN2_1 | 0.0261 |
| YARS2 | 0.0286 |
| ZNF75D_2 | 0.1319 |
| ZSWIM4_2 | 0.1657 |
| figo_numeric | 0.0198 |
| hist_rev_SBOT | 0.0732 |
| surg_outcome | 0 |

TABLE 50

| | |
|---|---|
| ABCC9_3 | 0.0489 |
| ABHD3 | 0.2344 |
| ADAM17_2 | 0.1438 |
| ADAMTS1 | 0.1209 |
| ADAMTS2_1 | 0.1094 |
| ALS2CL_3 | 0.0592 |
| ANO7_3 | 0.0383 |
| ARL6IP1_1 | 0.0006 |
| ARMCX3_2 | 0.0553 |
| ATXN10_1 | 0.2055 |
| AXL_1 | 0.0807 |
| BAI1_3 | 0.0368 |
| BCAS1_1 | 0.3119 |
| BDNF_2 | 0.1194 |
| BMPR1A | 0.1171 |
| BTF3_3 | 0.0979 |
| C10orf116 | 0.0732 |
| C11orf24 | 0.1901 |
| C11orf49_3 | 0.1068 |
| C14orf102_2 | 0.1094 |

TABLE 50-continued

| | |
|---|---|
| C14orf109_2 | 0.1188 |
| C17orf106 | 0.161 |
| C17orf58_2 | 0.0206 |
| C17orf58_3 | 0.0155 |
| C18orf56 | 0.0044 |
| C1orf168 | 0.0307 |
| C1orf64 | 0.1113 |
| C8orf79_1 | 0.009 |
| CALD1_2 | 0.1443 |
| CASP8AP2 | 0.1307 |
| CCL13 | 0.1388 |
| CCR2_3 | 0.0199 |
| CD34_1 | 0.0238 |
| CDC42BPA_2 | 0.0086 |
| CDC42SE2_2 | 0.02 |
| CIDEC_1 | 0.1064 |
| CLDN6 | 0.0006 |
| CREB5_2 | 0.0093 |
| CREBBP_1 | 0.0493 |
| CRYBA1 | 0.0645 |
| CXCL13 | 0.19 |
| CYB5R3_2 | 0.1335 |
| CYP1A2 | 0.0835 |
| DBNDD2 | 0.1243 |
| DFFB_2 | 0.0369 |
| DNAH11 | 0.0281 |
| DNMT3L_2 | 0.1236 |
| DOCK7_1 | 0.0156 |
| DSC3_1 | 0.0449 |
| DUT_3 | 0.1145 |
| EEF1E1_1 | 0.1242 |
| ELN_2 | 0.1211 |
| EMP1 | 0.2024 |
| ENO1 | 0.1517 |
| ENPEP_2 | 0.0722 |
| EPHB1 | 0.0435 |
| EPYC | 0.039 |
| ERI2_2 | 0.2597 |
| ESPNL | 0.064 |
| EZH2_1 | 0.0284 |
| FAM13AOS | 0.0739 |
| FAM187B_2 | 0.0046 |
| FAM70A_1 | 0.0789 |
| FBXO48_2 | 0.221 |
| FKBP10 | 0.0756 |
| FLJ33360 | 0.0213 |
| FLJ43752 | 0.2432 |
| FMNL3_2 | 0.0217 |
| FOSB | 0.2156 |
| FOSL2 | 0.0239 |
| FOXN1 | 0.2585 |
| GAD1_2 | 0.0256 |
| GBE1 | 0.0465 |
| GBP7 | 0.123 |
| GJA5_1 | 0.0669 |
| GMNN | 0.1039 |
| GSR_2 | 0.0198 |
| HBA2 | 0.2079 |
| HDAC7_2 | 0.0732 |
| HDLBP_3 | 0.0052 |
| HIC1 | 0.1042 |
| HPRT1_1 | 0.134 |
| HPS4_1 | 0.055 |
| HR_1 | 0.0333 |
| HSD11B1_1 | 0.0919 |
| ICAM2 | 0.0185 |
| ICAM4_1 | 0.2905 |
| IL1RAP_2 | 0.0676 |
| IQCA1_2 | 0.0174 |
| KCNIP3_1 | 0.0952 |
| KCNQ2_1 | 0.1018 |
| KIF3C | 0.1764 |
| KRT80_2 | 0.095 |
| KRTAP10.10_2 | 0.0248 |
| L3MBTL2_3 | 0.0482 |
| LBH_2 | 0.0836 |
| LENEP | 0.2374 |
| LGI3 | 0.0934 |
| LOC340508 | 0.0261 |
| LOC492303 | 0.0233 |
| LRRC14B | 0.0775 |
| LRRC37A4_2 | 0.0065 |
| LRRTM4 | 0.1714 |
| MACC1 | 0.165 |
| MANSC1_1 | 0.1128 |
| MAPK3_1 | 0.025 |
| MCAM | 0.1315 |
| MCART6_1 | 0.216 |
| MFRP | 0.0168 |
| MIDN | 0.0071 |
| MIR1914 | 0.047 |
| MIR212 | 0.0885 |
| MIR571 | 0.0024 |
| MIR576 | 0.1147 |
| MIR654 | 0.0368 |
| MIR942 | 0.0979 |
| MMP12_1 | 0.1322 |
| MYCN_2 | 0.1227 |
| MYOHD1 | 0.1099 |
| NFATC3_5 | 0.017 |
| NFATC4 | 0.0421 |
| NLRP9 | 0.1819 |
| NOVA2 | 0.071 |
| NP | 0.077 |
| NR6A1_2 | 0.1303 |
| NRXN3_3 | 0.1619 |
| NT5DC1_2 | 0.1764 |
| NTRK2_3 | 0.0156 |
| NUP155_1 | 0.0311 |
| NYX | 0.1073 |
| ODF2_3 | 0.0177 |
| ORC1L | 0.0254 |
| OTUD7A_3 | 0.059 |
| PANK4 | 0.052 |
| PDLIM2_2 | 0.2051 |
| PDZRN4_2 | 0.2059 |
| PHYH_1 | 0.0161 |
| PIGA_1 | 0.1019 |
| PITX2_1 | 0.199 |
| PKN1_3 | 0.0066 |
| PLEKHG5_5 | 0.2619 |
| PLSCR4 | 0.0134 |
| PMEPA1_4 | 0.1204 |
| PNMA5 | 0.1591 |
| PPAPDC1A | 0.1056 |
| PRAMEF5 | 0.0127 |
| PRKAA2 | 0.1294 |
| PSMC6_1 | 0.0359 |
| RAD54B_2 | 0.1662 |
| RAP1A_1 | 0.1802 |
| RARA_3 | 0.0875 |
| RARG | 0.0924 |
| RNASEK | 0.0892 |
| RNF7_1 | 0.0137 |
| ROD1_1 | 0.1936 |
| SATB2 | 0.0363 |
| SBSN | 0.0821 |
| SCXB | 0.0083 |
| SEC22C_3 | 0.0939 |
| SELENBP1 | 0.1504 |
| SERPINB2_2 | 0.0175 |
| SERPINB5 | 0.176 |
| SFN | 0.0187 |
| SFRS4 | 0.0621 |
| SHC1_3 | 0.0571 |
| SLC23A1_2 | 0.122 |
| SLC25A34 | 0.1242 |
| SLC4A5_3 | 0.0903 |
| SLC9A10 | 0.0593 |
| SNORD93 | 0.1329 |
| SOX2_1 | 0.0728 |
| STC1 | 0.0041 |
| STC2 | 0.1165 |
| STYX_2 | 0.0169 |
| SYTL3 | 0.0257 |
| TAF15_1 | 0.0093 |
| TCEAL8_1 | 0.0123 |
| THBS3 | 0.0978 |
| TM2D3_2 | 0.035 |
| TMEM52 | 0.0986 |

TABLE 50-continued

| | |
|---|---|
| TMEM62 | 0.0011 |
| TNFRSF18__1 | 0.2241 |
| TNNT2__1 | 0.0148 |
| TOMM20L | 0.0028 |
| TPM2__2 | 0.1687 |
| TRIM58 | 0.1228 |
| UBR7__1 | 0.072 |
| UBR7__2 | 0.1404 |
| WARS__2 | 0.1834 |
| XBP1__2 | 0.1409 |
| XRN2__1 | 0.0367 |
| YARS2 | 0.0318 |
| ZNF75D__2 | 0.1337 |
| ZSWIM4__2 | 0.1715 |
| figo__numeric | 0.0098 |
| hist__rev__SBOT | 0.0556 |
| surg__outcome | 0.0089 |

TABLE 51

| | |
|---|---|
| ABHD3 | 0.0895 |
| ADAM17__2 | 0.2342 |
| ADAMTS1 | 0.1789 |
| ALS2CL__3 | 0.1118 |
| ANO7__3 | 0.0427 |
| ARL6IP1__1 | 0.0328 |
| ARMCX3__2 | 0.0876 |
| ATP2B1__3 | 0.1651 |
| ATXN10__1 | 0.0892 |
| AXL__1 | 0.0516 |
| BAI1__3 | 0.0156 |
| BCAS1__1 | 0.3163 |
| BDNF__2 | 0.0983 |
| BMPR1A | 0.1193 |
| BTF3__3 | 0.1194 |
| C10orf116 | 0.0504 |
| C11orf24 | 0.1279 |
| C11orf49__3 | 0.1283 |
| C14orf102__2 | 0.1 |
| C14orf109__2 | 0.0644 |
| C17orf106 | 0.2144 |
| C17orf58__2 | 0.0323 |
| C17orf58__3 | 0.0304 |
| C18orf56 | 0.0422 |
| C1orf168 | 0.0382 |
| C1orf64 | 0.1103 |
| C8orf79__1 | 0.0779 |
| CALD1__2 | 0.1453 |
| CASP8AP2 | 0.1233 |
| CCL13 | 0.1111 |
| CCR2__3 | 0.0465 |
| CD34__1 | 0.0448 |
| CDC42BPA__2 | 0.0278 |
| CDC42SE2__2 | 0.0062 |
| CLDN6 | 0.1165 |
| CREB5__2 | 0.0067 |
| CRYBA1 | 0.0333 |
| CXCL13 | 0.0849 |
| CYB5R3__2 | 0.1675 |
| CYP1A2 | 0.0607 |
| DBNDD2 | 0.0838 |
| DNAH11 | 0.0496 |
| DNMT3L__2 | 0.0335 |
| DOCK7__1 | 0.1066 |
| DSC3__1 | 0.0589 |
| DUT__3 | 0.1352 |
| EEF1E1__1 | 0.0554 |
| EMP1 | 0.1048 |
| ENO1 | 0.1538 |
| ENPEP__2 | 0.1276 |
| EPHB1 | 0.0403 |
| EPYC | 0.0208 |
| ERI2__2 | 0.2871 |
| ESPNL | 0.0816 |
| EZH2__1 | 0.0653 |
| FAM13AOS | 0.032 |
| FAM187B__2 | 0.0262 |

TABLE 51-continued

| | |
|---|---|
| FAM70A__1 | 0.104 |
| FBXO48__2 | 0.2147 |
| FKBP10 | 0.1034 |
| FLJ33360 | 0.0367 |
| FLJ43752 | 0.1831 |
| FMNL3__2 | 0.0158 |
| FOSB | 0.1895 |
| FOSL2 | 0.0208 |
| FOXN1 | 0.2711 |
| GAD1__2 | 0.0091 |
| GBE1 | 0.0599 |
| GBP7 | 0.1071 |
| GJA5__1 | 0.0485 |
| GMNN | 0.0903 |
| GSR__2 | 0.0286 |
| GUSBL2 | 0.2001 |
| HBA2 | 0.0605 |
| HDAC7__2 | 0.0429 |
| HDLBP__3 | 0.2083 |
| HIC1 | 0.0782 |
| HPRT1__1 | 0.1481 |
| HPS4__1 | 0.0398 |
| HR__1 | 0.0544 |
| HSD11B1__1 | 0.0892 |
| ICAM2 | 0.0475 |
| ICAM4__1 | 0.2773 |
| IL1RAP__2 | 0.0595 |
| IQCA1__2 | 0.0233 |
| KCNIP3__1 | 0.0915 |
| KCNQ2__1 | 0.147 |
| KIF3C | 0.191 |
| KRT80__2 | 0.0782 |
| KRTAP10.10__2 | 0.009 |
| L3MBTL2__3 | 0.0308 |
| LBH__2 | 0.112 |
| LENEP | 0.2121 |
| LGI3 | 0.1325 |
| LOC492303 | 0.0493 |
| LRRC14B | 0.0287 |
| LRRC37A4__2 | 0.0699 |
| LRRTM4 | 0.168 |
| MACC1 | 0.1291 |
| MANSC1__1 | 0.128 |
| MAPK3__1 | 0.0622 |
| MCAM | 0.0933 |
| MCART6__1 | 0.2201 |
| MFRP | 0.0321 |
| MIDN | 0.0479 |
| MIR1914 | 0.0663 |
| MIR212 | 0.0968 |
| MIR571 | 0.0034 |
| MIR576 | 0.1 |
| MIR654 | 0.0046 |
| MIR942 | 0.1109 |
| MMP12__1 | 0.1316 |
| MYCN__2 | 0.1557 |
| MYOHD1 | 0.0821 |
| NFATC3__5 | 0.0231 |
| NFATC4 | 0.0519 |
| NLRP9 | 0.1553 |
| NOVA2 | 0.0958 |
| NP | 0.0913 |
| NR6A1__2 | 0.1335 |
| NRXN3__3 | 0.077 |
| NT5DC1__2 | 0.2107 |
| NTRK2__3 | 0.0122 |
| NUP155__1 | 0.0355 |
| NYX | 0.1133 |
| ODF2__3 | 0.0269 |
| ORC1L | 0.0704 |
| OTUD7A__3 | 0.0327 |
| PANK4 | 0.0527 |
| PDLIM2__2 | 0.2236 |
| PHYH__1 | 0.2248 |
| PIGA__1 | 0.0104 |
| PITX2__1 | 0.0894 |
| PKN1__3 | 0.0599 |
| PLAC9 | 0.2574 |
| PLEKHG5__5 | 0.0193 |
| PLSCR4 | 0.1686 |

TABLE 51-continued

| | |
|---|---|
| PMEPA1__4 | 0.1266 |
| PNMA5 | 0.1496 |
| PPAPDC1A | 0.1127 |
| PRAMEF5 | 0.0323 |
| PRKAA2 | 0.1201 |
| PSMC6__1 | 0.0056 |
| RAD54B__2 | 0.1917 |
| RAP1A__1 | 0.2144 |
| RARA__3 | 0.0852 |
| RARG | 0.0034 |
| RNASEK | 0.0584 |
| RNF7__1 | 0.017 |
| ROD1__1 | 0.2164 |
| SATB2 | 0.0525 |
| SBSN | 0.059 |
| SCXB | 0.0053 |
| SEC22C__3 | 0.1068 |
| SELENBP1 | 0.1885 |
| SERPINB2__2 | 0.0096 |
| SERPINB5 | 0.2131 |
| SFN | 0.0104 |
| SFRS4 | 0.0424 |
| SHC1__3 | 0.1055 |
| SLC23A1__2 | 0.0986 |
| SLC25A34 | 0.107 |
| SLC4A5__3 | 0.0793 |
| SLC9A10 | 0.0892 |
| SNORD93 | 0.1501 |
| SOX2__1 | 0.0608 |
| STC1 | 0.0086 |
| STC2 | 0.0905 |
| STYX__2 | 0.0534 |
| SYTL3 | 0.0026 |
| TAF15__1 | 0.0179 |
| TCEAL8__1 | 0.0572 |
| THBS3 | 0.0912 |
| TM2D3__2 | 0.047 |
| TMEM52 | 0.0592 |
| TMEM62 | 0.0063 |
| TNFRSF18__1 | 0.2489 |
| TNNT2__1 | 0.006 |
| TOMM20L | 0.0459 |
| TPM2__2 | 0.1667 |
| TRIM58 | 0.1021 |
| UBR7__1 | 0.034 |
| UBR7__2 | 0.1325 |
| WARS__2 | 0.181 |
| XBP1__2 | 0.164 |
| XRN2__1 | 0.0274 |
| YARS2 | 0.0085 |
| ZNF75D__2 | 0.1447 |
| ZSWIM4__2 | 0.1611 |
| figo__numeric | 0.043 |
| hist__rev__SBOT | 0.045 |
| surg__outcome | 0.0152 |

TABLE 52

| | |
|---|---|
| ABHD3 | 0.0643 |
| ADAM17__2 | 0.2328 |
| ADAMTS1 | 0.1768 |
| ALS2CL__3 | 0.1045 |
| ANO7__3 | 0.0609 |
| ARL6IP1__1 | 0.0303 |
| ARMCX3__2 | 0.0817 |
| ATP2B1__3 | 0.2063 |
| ATXN10__1 | 0.1041 |
| AXL__1 | 0.0323 |
| BAI1__3 | 0.0262 |
| BCAS1__1 | 0.3374 |
| BDNF__2 | 0.1102 |
| BMPR1A | 0.1163 |
| BTF3__3 | 0.098 |
| C10orf116 | 0.0264 |
| C11orf24 | 0.1822 |
| C11orf49__3 | 0.1291 |
| C14orf102__2 | 0.1272 |

TABLE 52-continued

| | |
|---|---|
| C14orf109__2 | 0.0647 |
| C17orf106 | 0.2377 |
| C17orf58__2 | 0.0515 |
| C17orf58__3 | 0.0197 |
| C18orf56 | 0.0336 |
| C1orf168 | 0.0331 |
| C1orf64 | 0.1099 |
| C8orf79__1 | 0.0329 |
| CALD1__2 | 0.1366 |
| CASP8AP2 | 0.1312 |
| CCL13 | 0.0888 |
| CCR2__3 | 0.0211 |
| CD34__1 | 0.0174 |
| CDC42BPA__2 | 0.0304 |
| CDC42SE2__2 | 0.0185 |
| CLDN6 | 0.1143 |
| CREB5__2 | 0.0211 |
| CRYBA1 | 0.0238 |
| CXCL13 | 0.079 |
| CYB5R3__2 | 0.1854 |
| CYP1A2 | 0.0628 |
| DBNDD2 | 0.1096 |
| DFFB__2 | 0.0427 |
| DNAH11 | 0.0251 |
| DNMT3L__2 | 0.1376 |
| DOCK7__1 | 0.0058 |
| DSC3__1 | 0.072 |
| DUT__3 | 0.1169 |
| EEF1E1__1 | 0.0798 |
| EMP1 | 0.1197 |
| ENO1 | 0.1874 |
| ENPEP__2 | 0.141 |
| EPHB1 | 0.0359 |
| EPYC | 0.0339 |
| ERI2__2 | 0.2917 |
| ESPNL | 0.0419 |
| EZH2__1 | 0.0679 |
| FAM13AOS | 0.0482 |
| FAM187B__2 | 0.0133 |
| FAM70A__1 | 0.0779 |
| FBXO48__2 | 0.2662 |
| FKBP10 | 0.0632 |
| FLJ33360 | 0.0563 |
| FLJ43752 | 0.1886 |
| FMNL3__2 | 0.0365 |
| FOSB | 0.2004 |
| FOSL2 | 0.0289 |
| FOXN1 | 0.2707 |
| GAD1__2 | 0.0238 |
| GBE1 | 0.0385 |
| GBP7 | 0.1356 |
| GJA5__1 | 0.0515 |
| GMNN | 0.1019 |
| GSR__2 | 0.0411 |
| HBA2 | 0.2058 |
| HDAC7__2 | 0.0611 |
| HDLBP__3 | 0.0135 |
| HIC1 | 0.1066 |
| HPRT1__1 | 0.154 |
| HPS4__1 | 0.0647 |
| HR__1 | 0.0482 |
| HSD11B1__1 | 0.0797 |
| ICAM2 | 0.0592 |
| ICAM4__1 | 0.2765 |
| IL1RAP__2 | 0.0478 |
| IQCA1__2 | 0.0351 |
| KCNIP3__1 | 0.1017 |
| KCNQ2__1 | 0.1302 |
| KIF3C | 0.1759 |
| KRT80__2 | 0.1134 |
| KRTAP10.10__2 | 0.0208 |
| L3MBTL2__3 | 0.0365 |
| LBH__2 | 0.1019 |
| LENEP | 0.2237 |
| LGI3 | 0.1147 |
| LOC492303 | 0.0255 |
| LRRC14B | 0.0144 |
| LRRC37A4__2 | 0.0611 |
| LRRTM4 | 0.1658 |
| MACC1 | 0.1162 |

TABLE 52-continued

| | |
|---|---|
| MANSC1__1 | 0.1357 |
| MAPK3__1 | 0.0175 |
| MCAM | 0.1341 |
| MCART6__1 | 0.2205 |
| MFRP | 0.0348 |
| MIDN | 0.0477 |
| MIR1914 | 0.0678 |
| MIR212 | 0.1054 |
| MIR571 | 0.0357 |
| MIR576 | 0.1142 |
| MIR654 | 0.0496 |
| MIR942 | 0.1318 |
| MMP12__1 | 0.1354 |
| MYCN__2 | 0.148 |
| MYOHD1 | 0.0953 |
| NFATC3__5 | 0.009 |
| NFATC4 | 0.053 |
| NLRP9 | 0.1774 |
| NOVA2 | 0.1207 |
| NP | 0.0919 |
| NR6A1__2 | 0.1526 |
| NRXN3__3 | 0.1026 |
| NT5DC1__2 | 0.1848 |
| NTRK2__3 | 0.0046 |
| NUP155__1 | 0.0486 |
| NYX | 0.1717 |
| ODF2__3 | 0.0126 |
| ORC1L | 0.0295 |
| OTUD7A__3 | 0.0328 |
| PANK4 | 0.0581 |
| PDLIM2__2 | 0.2394 |
| PHYH__1 | 0.199 |
| PIGA__1 | 0.0002 |
| PITX2__1 | 0.0908 |
| PKN1__3 | 0.0275 |
| PLAC9 | 0.2579 |
| PLEKHG5__5 | 0.0328 |
| PLSCR4 | 0.1771 |
| PMEPA1__4 | 0.1204 |
| PNMA5 | 0.117 |
| PPAPDC1A | 0.1296 |
| PRAMEF5 | 0.0085 |
| PRKAA2 | 0.1345 |
| PSMC6__1 | 0.0021 |
| RAD54B__2 | 0.1782 |
| RAP1A__1 | 0.2125 |
| RARA__3 | 0.0817 |
| RARG | 0.0414 |
| RNASEK | 0.0641 |
| RNF7__1 | 0.0177 |
| ROD1__1 | 0.2177 |
| SATB2 | 0.0616 |
| SBSN | 0.065 |
| SCXB | 0.0009 |
| SEC22C__3 | 0.1165 |
| SELENBP1 | 0.192 |
| SERPINB2__2 | 0.0118 |
| SERPINB5 | 0.1974 |
| SFN | 0.0056 |
| SFRS4 | 0.0285 |
| SHC1__3 | 0.0709 |
| SLC23A1__2 | 0.134 |
| SLC25A34 | 0.155 |
| SLC4A5__3 | 0.0783 |
| SLC9A10 | 0.0821 |
| SNORD93 | 0.1554 |
| SOX2__1 | 0.0805 |
| STC1 | 0.0033 |
| STC2 | 0.1286 |
| STYX__2 | 0.0479 |
| SYTL3 | 0.0047 |
| TAF15__1 | 0.0001 |
| TCEAL8__1 | 0.0337 |
| THBS3 | 0.0996 |
| TM2D3__2 | 0.0554 |
| TMEM52 | 0.0839 |
| TMEM62 | 0.0056 |
| TNFRSF18__1 | 0.2606 |
| TNNT2__1 | 0.0031 |
| TOMM20L | 0.0531 |
| TPM2__2 | 0.1772 |
| TRIM58 | 0.1121 |
| UBR7__1 | 0.0582 |
| UBR7__2 | 0.1274 |
| WARS__2 | 0.1558 |
| XBP1__2 | 0.1344 |
| XRN2__1 | 0.0507 |
| YARS2 | 0.001 |
| ZNF75D__2 | 0.146 |
| ZSWIM4__2 | 0.1652 |
| figo__numeric | 0.0188 |
| hist__rev__SBOT | 0.0573 |
| surg__outcome | 0.0045 |

TABLE 53

| | |
|---|---|
| ABHD3 | 0.0657 |
| ADAM17__2 | 0.2284 |
| ADAMTS1 | 0.1768 |
| ALS2CL__3 | 0.1078 |
| ANO7__3 | 0.0644 |
| ARL6IP1__2 | 0.0333 |
| ARMCX3__2 | 0.0793 |
| ATXN10__1 | 0.2139 |
| AXL__1 | 0.107 |
| BAI1__3 | 0.0256 |
| BCAS1__3 | 0.3393 |
| BDNF__2 | 0.1033 |
| BMPR1A | 0.1185 |
| BTF3__3 | 0.091 |
| C10orf116 | 0.0269 |
| C11orf24 | 0.1846 |
| C11orf49__3 | 0.1241 |
| C14orf102__2 | 0.1332 |
| C14orf109__2 | 0.0686 |
| C17orf106 | 0.2275 |
| C17orf58__2 | 0.052 |
| C17orf58__3 | 0.0232 |
| C18orf56 | 0.0332 |
| C1orf168 | 0.0261 |
| C1orf64 | 0.1053 |
| C8orf79__1 | 0.0308 |
| CALD1__2 | 0.1359 |
| CASP8AP2 | 0.1334 |
| CCL13 | 0.0936 |
| CCR2__3 | 0.0134 |
| CD34__1 | 0.0137 |
| CDC42BPA__2 | 0.0398 |
| CDC42SE2__2 | 0.0157 |
| CLDN6 | 0.115 |
| CREB5__2 | 0.0255 |
| CREBBP__1 | 0.0262 |
| CRYBA1 | 0.0813 |
| CXCL13 | 0.1902 |
| CYB5R3__2 | 0.1199 |
| CYP1A2 | 0.0645 |
| DBNDD2 | 0.1086 |
| DNAH11 | 0.0409 |
| DNMT3L__2 | 0.0275 |
| DOCK7__1 | 0.1407 |
| DSC3__1 | 0.0755 |
| DUT__3 | 0.1117 |
| EEF1E1__1 | 0.0834 |
| EMP1 | 0.1229 |
| ENO1 | 0.1858 |
| ENPEP__2 | 0.1369 |
| EPHB1 | 0.0251 |
| EPYC | 0.0376 |
| ERI2__2 | 0.2825 |
| ESPNL | 0.044 |
| EZH2__1 | 0.064 |
| FAM13AOS | 0.0489 |
| FAM187B__2 | 0.013 |
| FAM70A__1 | 0.076 |
| FBXO48__2 | 0.26 |
| FKBP10 | 0.0638 |
| FLJ33360 | 0.0603 |

TABLE 53-continued

| | |
|---|---|
| FLJ43752 | 0.1886 |
| FMNL3_2 | 0.032 |
| FOSB | 0.1974 |
| FOSL2 | 0.0265 |
| FOXN1 | 0.2699 |
| GAD1_2 | 0.0285 |
| GBE1 | 0.0357 |
| GBP7 | 0.1272 |
| GJA5_1 | 0.0544 |
| GMNN | 0.1028 |
| GSR_2 | 0.0467 |
| HBA2 | 0.2041 |
| HDAC7_2 | 0.0649 |
| HDLBP_3 | 0.0122 |
| HIC1 | 0.1098 |
| HPRT1_1 | 0.1609 |
| HPS4_1 | 0.0654 |
| HR_1 | 0.0532 |
| HSD11B1_1 | 0.0811 |
| ICAM2 | 0.0557 |
| ICAM4_1 | 0.2758 |
| IL1RAP_2 | 0.0428 |
| IQCA1_2 | 0.0281 |
| KCNIP3_1 | 0.1006 |
| KCNQ2_1 | 0.1265 |
| KIF3C | 0.1707 |
| KRT80_2 | 0.111 |
| KRTAP10.10_2 | 0.0202 |
| L3MBTL2_3 | 0.0415 |
| LBH_2 | 0.1027 |
| LENEP | 0.2253 |
| LGI3 | 0.1144 |
| LOC492303 | 0.0253 |
| LRRC14B | 0.0162 |
| LRRC37A4_2 | 0.0579 |
| LRRTM4 | 0.164 |
| MACC1 | 0.1121 |
| MANSC1_1 | 0.135 |
| MAPK3_1 | 0.0256 |
| MCAM | 0.1396 |
| MCART6_1 | 0.2182 |
| MFRP | 0.0284 |
| MIDN | 0.0503 |
| MIR1914 | 0.0648 |
| MIR212 | 0.1032 |
| MIR571 | 0.0362 |
| MIR576 | 0.11 |
| MIR654 | 0.0493 |
| MIR942 | 0.1301 |
| MMP12_1 | 0.1397 |
| MYCN_2 | 0.1467 |
| MYOHD1 | 0.0968 |
| NFATC3_5 | 0.0088 |
| NFATC4 | 0.0519 |
| NLRP9 | 0.1852 |
| NOVA2 | 0.1234 |
| NP | 0.091 |
| NR6A1_2 | 0.1577 |
| NRXN3_3 | 0.1063 |
| NT5DC1_2 | 0.176 |
| NTRK2_3 | 0.003 |
| NUP155_1 | 0.0557 |
| NYX | 0.1725 |
| ODF2_3 | 0.0155 |
| ORC1L | 0.0244 |
| OTUD7A_3 | 0.0379 |
| PANK4 | 0.0597 |
| PDLIM2_2 | 0.2252 |
| PHYH_1 | 0.1951 |
| PIGA_1 | 0.003 |
| PITX2_1 | 0.0961 |
| PKN1_3 | 0.0207 |
| PLAC9 | 0.257 |
| PLEKHG5_5 | 0.0261 |
| PLSCR4 | 0.1668 |
| PMEPA1_4 | 0.1096 |
| PNMA5 | 0.1042 |
| PPAPDC1A | 0.1256 |
| PRAMEF5 | 0.0042 |
| PRKAA2 | 0.1387 |

TABLE 53-continued

| | |
|---|---|
| PSMC6_1 | 0.0044 |
| RAD54B_2 | 0.1772 |
| RAP1A_1 | 0.2049 |
| RARA_3 | 0.078 |
| RARG | 0.047 |
| RNASEK | 0.07 |
| RNF7_1 | 0.0239 |
| ROD1_1 | 0.2187 |
| SATB2 | 0.0632 |
| SBSN | 0.0725 |
| SCXB | 0.0007 |
| SEC22C_3 | 0.1111 |
| SELENBP1 | 0.194 |
| SERPINB2_2 | 0.0258 |
| SERPINB5 | 0.1961 |
| SFN | 0.0096 |
| SFRS4 | 0.0215 |
| SHC1_3 | 0.0541 |
| SLC23A1_2 | 0.1288 |
| SLC25A34 | 0.1621 |
| SLC4A5_3 | 0.0816 |
| SLC9A10 | 0.0744 |
| SNORD93 | 0.1584 |
| SOX2_1 | 0.0751 |
| STC1 | 0.0025 |
| STC2 | 0.1276 |
| STYX_2 | 0.0473 |
| SYTL3 | 0.001 |
| TAF15_1 | 0.0126 |
| TCEAL8_1 | 0.0251 |
| THBS3 | 0.0935 |
| TM2D3_2 | 0.0546 |
| TMEM52 | 0.0831 |
| TMEM62 | 0.0049 |
| TNFRSF18_1 | 0.2694 |
| TNNT2_1 | 0.0099 |
| TOMM20L | 0.053 |
| TPM2_2 | 0.167 |
| TRIM58 | 0.1201 |
| UBR7_1 | 0.0543 |
| UBR7_2 | 0.1156 |
| WARS_2 | 0.1563 |
| XBP1_2 | 0.1348 |
| XRN2_1 | 0.0512 |
| YARS2 | 0.0014 |
| ZNF75D_2 | 0.1477 |
| ZSWIM4_2 | 0.1654 |
| figo_numeric | 0.0092 |
| hist_rev_SBOT | 0.071 |
| surg_outcome | 0.0015 |

TABLE 54

| | |
|---|---|
| ABCC9_3 | 0.0543 |
| ABHD3 | 0.2423 |
| ADAM17_2 | 0.1473 |
| ADAMTS1 | 0.1127 |
| ADAMTS2_1 | 0.1041 |
| ALS2CL_3 | 0.0601 |
| ANO7_3 | 0.0425 |
| ARL6IP1_1 | 0.0019 |
| ARMCX3_2 | 0.0636 |
| ATXN10_1 | 0.2046 |
| AXL_1 | 0.0795 |
| BAI1_3 | 0.0404 |
| BCAS1_1 | 0.3089 |
| BDNF_2 | 0.1255 |
| BMPR1A | 0.1121 |
| BTF3_3 | 0.1063 |
| C10orf116 | 0.0748 |
| C11orf24 | 0.1832 |
| C11orf49_2 | 0.1119 |
| C14orf102_2 | 0.1038 |
| C14orf109_2 | 0.1136 |
| C17orf106 | 0.1626 |
| C17orf58_2 | 0.0122 |
| C17orf58_3 | 0.0168 |

TABLE 54-continued

| | |
|---|---|
| C18orf56 | 0.0024 |
| C1orf168 | 0.0362 |
| C1orf64 | 0.1183 |
| C8orf79__1 | 0.0052 |
| CASP8AP2 | 0.1416 |
| CCL13 | 0.1337 |
| CCR2__3 | 0.1294 |
| CD34__1 | 0.034 |
| CDC42BPA__2 | 0.0047 |
| CDC42SE2__2 | 0.014 |
| CIDEC__1 | 0.1045 |
| CLDN6 | 0.0153 |
| CREB5__2 | 0.0067 |
| CRYBA1 | 0.0575 |
| CXCL13 | 0.0588 |
| CYB5R3__2 | 0.1811 |
| CYP1A2 | 0.0776 |
| DBNDD2 | 0.1256 |
| DNAH11 | 0.0414 |
| DNMT3L__2 | 0.0199 |
| DOCK7__1 | 0.1092 |
| DSC3__1 | 0.0425 |
| DUT__3 | 0.1247 |
| EEF1E1__1 | 0.1296 |
| ELN__2 | 0.1167 |
| EMP1 | 0.2027 |
| ENO1 | 0.1576 |
| ENPEP__2 | 0.0827 |
| EPHB1 | 0.0476 |
| EPYC | 0.0349 |
| ERI2__2 | 0.267 |
| ESPNL | 0.0611 |
| EZH2__1 | 0.0368 |
| FAM13AOS | 0.0656 |
| FAM187B__2 | 0.0044 |
| FAM70A__1 | 0.082 |
| FBXO48__2 | 0.2301 |
| FKBP10 | 0.064 |
| FLJ33360 | 0.0153 |
| FLJ43752 | 0.2483 |
| FMNL3__2 | 0.0121 |
| FOSB | 0.2134 |
| FOSL2 | 0.0284 |
| FOXN1 | 0.2589 |
| GAD1__2 | 0.019 |
| GBE1 | 0.0572 |
| GBP7 | 0.1378 |
| GJA5__1 | 0.0707 |
| GMNN | 0.1035 |
| GSR__2 | 0.0243 |
| HBA2 | 0.2092 |
| HCFC1R1__1 | 0.0666 |
| HDAC7__2 | 0.0093 |
| HDLBP__3 | 0.099 |
| HIC1 | 0.0033 |
| HPRT1__1 | 0.1305 |
| HPS4__1 | 0.0652 |
| HR__1 | 0.0241 |
| HSD11B1__1 | 0.0913 |
| ICAM2 | 0.0133 |
| ICAM4__1 | 0.2949 |
| IL1RAP__2 | 0.0823 |
| IQCA1__2 | 0.0227 |
| KCNIP3__1 | 0.0912 |
| KCNQ2__1 | 0.0999 |
| KIF3C | 0.1819 |
| KRT80__2 | 0.0972 |
| KRTAP10.10__2 | 0.0269 |
| L3MBTL2__3 | 0.0433 |
| LBH__2 | 0.0755 |
| LENEP | 0.2366 |
| LGI3 | 0.0985 |
| LOC340508 | 0.0304 |
| LOC492303 | 0.022 |
| LRRC14B | 0.0718 |
| LRRC37A4__2 | 0.0176 |
| LRRTM4 | 0.1685 |
| MACC1 | 0.1635 |
| MANSC1__1 | 0.1141 |
| MCAM | 0.0229 |
| MCART6__1 | 0.1238 |
| MFRP | 0.2252 |
| MIDN | 0.0077 |
| MIR1914 | 0.0573 |
| MIR212 | 0.0962 |
| MIR571 | 0.0025 |
| MIR576 | 0.108 |
| MIR654 | 0.0409 |
| MIR942 | 0.1074 |
| MMP12__1 | 0.1182 |
| MYCN__2 | 0.1305 |
| MYOHD1 | 0.1036 |
| NFATC3__5 | 0.0218 |
| NFATC4 | 0.0352 |
| NLRP9 | 0.1773 |
| NOVA2 | 0.0688 |
| NP | 0.0758 |
| NR6A1__2 | 0.1264 |
| NRXN3__3 | 0.1707 |
| NT5DC1__2 | 0.1807 |
| NTRK2__3 | 0.0046 |
| NUP155__1 | 0.0259 |
| NYX | 0.1098 |
| ODF2__3 | 0.0179 |
| ORC1L | 0.0388 |
| OTUD7A__3 | 0.0439 |
| PANK4 | 0.0424 |
| PDLIM2__2 | 0.2119 |
| PDZRN4__2 | 0.205 |
| PHYH__1 | 0.0138 |
| PIGA__1 | 0.0917 |
| PITX2__1 | 0.201 |
| PKN1__3 | 0.0078 |
| PLEKHG5__5 | 0.2566 |
| PLSCR4 | 0.0187 |
| PMEPA1__4 | 0.1384 |
| PNMA5 | 0.1752 |
| PPAPDC1A | 0.1216 |
| PRAMEF5 | 0.0036 |
| PRKAA2 | 0.1182 |
| PSMC6__1 | 0.0364 |
| RAD54B__2 | 0.1722 |
| RAP1A__1 | 0.1922 |
| RARA__3 | 0.0942 |
| RARG | 0.0807 |
| RNASEK | 0.0762 |
| RNF7__1 | 0.0257 |
| ROD1__1 | 0.1981 |
| SATB2 | 0.0347 |
| SBSN | 0.0724 |
| SCXB | 0.0142 |
| SEC22C__3 | 0.1071 |
| SELENBP1 | 0.1474 |
| SERPINB2__2 | 0.0165 |
| SERPINB5 | 0.1785 |
| SFN | 0.017 |
| SFRS4 | 0.0654 |
| SHC1__3 | 0.0707 |
| SLC23A1__2 | 0.1276 |
| SLC25A34 | 0.1046 |
| SLC4A5__3 | 0.0855 |
| SLC9A10 | 0.0704 |
| SNORD93 | 0.1306 |
| SOX2__1 | 0.0723 |
| STC1 | 0.0051 |
| STC2 | 0.1139 |
| STYX__2 | 0.0107 |
| SYTL3 | 0.0249 |
| TAF15__1 | 0.0259 |
| TCEAL8__1 | 0.0144 |
| THBS3 | 0.0976 |
| THY1 | 0.0373 |
| TIMP2__2 | 0.0975 |
| TM2D3__2 | 0.0021 |
| TMEM52 | 0.0217 |
| TMEM62 | 0.0646 |
| TNFRSF18__1 | 0.2151 |
| TNNT2__1 | 0.0075 |
| TOMM20L | 0.001 |
| TPM2__2 | 0.181 |

TABLE 54-continued

| | |
|---|---|
| TRIM58 | 0.115 |
| UBR7_1 | 0.0759 |
| UBR7_2 | 0.1396 |
| WARS_2 | 0.1866 |
| XBP1_2 | 0.1516 |
| XRN2_1 | 0.0393 |
| YARS2 | 0.0272 |
| ZNF75D_2 | 0.1344 |
| ZSWIM4_2 | 0.1752 |
| figo_numeric | 0.0248 |
| hist_rev_SBOT | 0.0369 |
| surg_outcome | 0.0132 |

TABLE 55

| | |
|---|---|
| ABCC9_3 | 0.0363 |
| ABHD3 | 0.2308 |
| ADAM17_2 | 0.1354 |
| ADAMTS1 | 0.1016 |
| ADAMTS2_1 | 0.0919 |
| ALS2CL_3 | 0.0595 |
| ANO7_3 | 0.03 |
| ANTXR1_4 | 0.0244 |
| ARL6IP1_1 | 0.0574 |
| ARMCX3_2 | 0.1944 |
| ATXN10_1 | 0.1342 |
| AXL_1 | 0.0759 |
| BAI1_3 | 0.05 |
| BCAS1_1 | 0.3006 |
| BDNF_2 | 0.1243 |
| BMPR1A | 0.1071 |
| BTF3_3 | 0.0955 |
| C10orf116 | 0.0595 |
| C11orf24 | 0.1965 |
| C11orf49_3 | 0.108 |
| C14orf102_2 | 0.0998 |
| C14orf109_2 | 0.1233 |
| C17orf106 | 0.1689 |
| C17orf58_2 | 0.0138 |
| C17orf58_3 | 0.0176 |
| C18orf56 | 0.0039 |
| C1orf168 | 0.0342 |
| C1orf64 | 0.1156 |
| C8orf79_1 | 0.013 |
| CASP8AP2 | 0.1491 |
| CCL13 | 0.1171 |
| CCR2_3 | 0.1276 |
| CD34_1 | 0.0281 |
| CDC42BPA_2 | 0.0118 |
| CDC42SE2_2 | 0.0229 |
| CIDEC_1 | 0.1068 |
| CLDN6 | 0.0049 |
| CREB5_2 | 0.01 |
| CRYBA1 | 0.0522 |
| CXCL13 | 0.0598 |
| CYB5R3_2 | 0.1898 |
| CYP1A2 | 0.071 |
| DBNDD2 | 0.1155 |
| DNAH11 | 0.0315 |
| DNMT3L_2 | 0.0195 |
| DOCK7_1 | 0.1142 |
| DSC3_1 | 0.0334 |
| DUT_3 | 0.1178 |
| EEF1E1_1 | 0.1312 |
| ELN_2 | 0.1075 |
| EMP1 | 0.2007 |
| ENO1 | 0.1647 |
| ENPEP_2 | 0.0593 |
| EPHB1 | 0.0529 |
| EPYC | 0.0509 |
| ERI2_2 | 0.2695 |
| ESPNL | 0.0572 |
| EZH2_1 | 0.0272 |
| FAM13AOS | 0.0728 |
| FAM187B_2 | 0.0049 |
| FAM70A_1 | 0.0742 |
| FBXO48_2 | 0.2335 |

TABLE 55-continued

| | |
|---|---|
| FKBP10 | 0.0731 |
| FLJ33360 | 0.026 |
| FLJ43752 | 0.2477 |
| FMNL3_2 | 0.0087 |
| FOSB | 0.2167 |
| FOSL2 | 0.0267 |
| FOXN1 | 0.2584 |
| GAD1_2 | 0.0243 |
| GBE1 | 0.049 |
| GBP7 | 0.1241 |
| GJA5_1 | 0.062 |
| GMNN | 0.1054 |
| GSR_2 | 0.0152 |
| HBA2 | 0.196 |
| HCFC1R1_1 | 0.06 |
| HDAC7_2 | 0.0029 |
| HDLBP_3 | 0.0906 |
| HIC1 | 0.0135 |
| HPRT1_1 | 0.1236 |
| HPS4_1 | 0.0602 |
| HR_1 | 0.03 |
| HSD11B1_1 | 0.0849 |
| ICAM2 | 0.0189 |
| ICAM4_1 | 0.2914 |
| IL1RAP_2 | 0.0755 |
| IQCA1_2 | 0.0234 |
| KCNIP3_1 | 0.094 |
| KCNQ2_1 | 0.0971 |
| KIF3C | 0.1745 |
| KRT80_2 | 0.1065 |
| KRTAP10.10_2 | 0.0262 |
| L3MBTL2_3 | 0.0598 |
| LBH_2 | 0.0794 |
| LENEP | 0.2337 |
| LGI3 | 0.087 |
| LOC340508 | 0.021 |
| LOC492303 | 0.0229 |
| LRRC14B | 0.0771 |
| LRRC37A4_2 | 0.0118 |
| LRRTM4 | 0.1777 |
| MACC1 | 0.1721 |
| MANSC1_1 | 0.1226 |
| MCAM | 0.0209 |
| MCART6_1 | 0.1277 |
| MFRP | 0.231 |
| MIDN | 0.0025 |
| MIR1914 | 0.0507 |
| MIR212 | 0.0909 |
| MIR571 | 0.0065 |
| MIR576 | 0.1209 |
| MIR654 | 0.0433 |
| MIR942 | 0.0953 |
| MMP12_1 | 0.1149 |
| MYCN_2 | 0.1309 |
| MYL92 | 0.1119 |
| MYOHD1 | 0.0195 |
| NFATC3_5 | 0.0451 |
| NFATC4 | 0.0617 |
| NLRP9 | 0.1733 |
| NOVA2 | 0.0654 |
| NP | 0.0701 |
| NR6A1_2 | 0.1285 |
| NRXN3_3 | 0.1626 |
| NT5DC1_2 | 0.1734 |
| NTRK2_3 | 0.0138 |
| NUP155_1 | 0.0235 |
| NYX | 0.0955 |
| ODF2_3 | 0.0219 |
| ORC1L | 0.0319 |
| OTUD7A_3 | 0.0385 |
| PANK4 | 0.0535 |
| PDLIM2_2 | 0.2298 |
| PDZRN4_2 | 0.2008 |
| PHYH_1 | 0.0124 |
| PIGA_1 | 0.1008 |
| PITX2_1 | 0.2061 |
| PKN1_3 | 0.0009 |
| PLEKHG5_5 | 0.2748 |
| PLSCR4 | 0.0266 |
| PMEPA1_4 | 0.1197 |

TABLE 55-continued

| | |
|---|---|
| PNMA5 | 0.1628 |
| PPAPDC1A | 0.1228 |
| PRAMEF5 | 0.0044 |
| PRKAA2 | 0.1083 |
| PSMC6__1 | 0.0355 |
| RAD54B__2 | 0.1763 |
| RAP1A__1 | 0.2003 |
| RARA__3 | 0.1036 |
| RARG | 0.0831 |
| RNASEK | 0.0789 |
| RNF7__1 | 0.0396 |
| ROD1__1 | 0.1976 |
| SATB2 | 0.0343 |
| SBSN | 0.0729 |
| SCXB | 0.0149 |
| SEC22C__3 | 0.1034 |
| SELENBP1 | 0.1459 |
| SERPINB2__2 | 0.0047 |
| SERPINB5 | 0.1786 |
| SFN | 0.0076 |
| SFRS4 | 0.0701 |
| SHC1__3 | 0.0709 |
| SLC23A1__2 | 0.1308 |
| SLC25A34 | 0.1157 |
| SLC4A5__3 | 0.0848 |
| SLC9A10 | 0.0604 |
| SNORD93 | 0.1387 |
| SOX2__1 | 0.0749 |
| STC1 | 0.0091 |
| STC2 | 0.1176 |
| STYX__2 | 0.0175 |
| SYTL3 | 0.024 |
| TAF15__1 | 0.0479 |
| TCEAL8__1 | 0.0069 |
| THBS3 | 0.0818 |
| THY1 | 0.0363 |
| TM2D3__2 | 0.1158 |
| TMEM52 | 0.0037 |
| TMEM62 | 0.0154 |
| TNFRSF18__1 | 0.209 |
| TNNT2__1 | 0.0064 |
| TOMM20L | 0.0065 |
| TPM2__2 | 0.1722 |
| TRIM58 | 0.1096 |
| UBR7__1 | 0.0847 |
| UBR7__2 | 0.1296 |
| WARS__2 | 0.1734 |
| XBP1__2 | 0.1254 |
| XRN2__1 | 0.0348 |
| YARS2 | 0.022 |
| ZNF75D__2 | 0.1156 |
| ZSWIM4__2 | 0.1692 |
| figo__numeric | 0.0155 |
| hist__rev__SBOT | 0.048 |
| surg__outcome | 0.0067 |

TABLE 56

| | |
|---|---|
| ABCC9__3 | 0.0551 |
| ABHD3 | 0.2421 |
| ADAM17__2 | 0.1462 |
| ADAMTS1 | 0.114 |
| ADAMTS2__1 | 0.1025 |
| ALS2CL__3 | 0.0551 |
| ANO7__3 | 0.0368 |
| ARL6IP1__1 | 0.001 |
| ARMCX3__2 | 0.0618 |
| ATXN10__1 | 0.2041 |
| AXL__1 | 0.0781 |
| BAI1__3 | 0.0391 |
| BCAS1__1 | 0.3072 |
| BDNF__2 | 0.1215 |
| BMPR1A | 0.1145 |
| BTF3__3 | 0.108 |
| C10orf116 | 0.0775 |
| C11orf24 | 0.1816 |
| C11orf49__3 | 0.1111 |

TABLE 56-continued

| | |
|---|---|
| C14orf102__2 | 0.0994 |
| C14orf109__2 | 0.1148 |
| C17orf106 | 0.1615 |
| C17orf58__2 | 0.019 |
| C17orf58__3 | 0.0153 |
| C18orf56 | 0.0018 |
| C1orf168 | 0.0368 |
| C1orf64 | 0.1171 |
| C8orf79__1 | 0.006 |
| CASP8AP2 | 0.1405 |
| CCL13 | 0.123 |
| CCR2__3 | 0.1285 |
| CD34__1 | 0.0266 |
| CDC42BPA__2 | 0.0051 |
| CDC42SE2__2 | 0.0186 |
| CIDEC__1 | 0.1018 |
| CLDN6 | 0.0127 |
| CREB5__2 | 0.015 |
| CRYBA1 | 0.0605 |
| CXCL13 | 0.0588 |
| CYB5R3__2 | 0.184 |
| CYP1A2 | 0.0757 |
| DBNDD2 | 0.1318 |
| DNAH11 | 0.043 |
| DNMT3L__2 | 0.0208 |
| DOCK7__1 | 0.1131 |
| DSC3__1 | 0.0415 |
| DUT__3 | 0.1213 |
| EEF1E1__1 | 0.1344 |
| ELN__2 | 0.1216 |
| EMP1 | 0.2013 |
| ENO1 | 0.1563 |
| ENPEP__2 | 0.0804 |
| EPHB1 | 0.0428 |
| EPYC | 0.0341 |
| ERI2__2 | 0.2708 |
| ESPNL | 0.0577 |
| EZH2__1 | 0.0393 |
| FAM13AOS | 0.0689 |
| FAM187B__2 | 0.0034 |
| FAM70A__1 | 0.0822 |
| FBXO48__2 | 0.2239 |
| FKBP10 | 0.066 |
| FLJ33360 | 0.0157 |
| FLJ43752 | 0.2403 |
| FMNL3__2 | 0.0157 |
| FOSB | 0.2176 |
| FOSL2 | 0.0301 |
| FOXN1 | 0.2623 |
| GAD1__2 | 0.0161 |
| GBE1 | 0.0553 |
| GBP7 | 0.1383 |
| GJA5__1 | 0.0684 |
| GMNN | 0.1055 |
| GSR__2 | 0.0228 |
| HBA2 | 0.205 |
| HCFC1R1__1 | 0.0649 |
| HDAC7__2 | 0.007 |
| HDLBP__3 | 0.0942 |
| HIC1 | 0.0017 |
| HPRT1__1 | 0.1355 |
| HPS4__1 | 0.0621 |
| HR__1 | 0.021 |
| HSD11B1__1 | 0.088 |
| ICAM2 | 0.019 |
| ICAM4__1 | 0.2947 |
| IL1RAP__1 | 0.0794 |
| IQCA1__2 | 0.0196 |
| KCNIP3__1 | 0.0934 |
| KCNQ2__1 | 0.1022 |
| KIF3C | 0.1799 |
| KRT80__2 | 0.0974 |
| KRTAP10.10__2 | 0.0279 |
| L3MBTL2__3 | 0.0415 |
| LBH__2 | 0.0725 |
| LENEP | 0.2404 |
| LGI3 | 0.0883 |
| LOC340508 | 0.0255 |
| LOC492303 | 0.0222 |
| LRRC14B | 0.0768 |

TABLE 56-continued

| | |
|---|---|
| LRRC37A4__2 | 0.0204 |
| LRRTM4 | 0.1667 |
| MACC1 | 0.161 |
| MANSC1__1 | 0.1117 |
| MCAM | 0.017 |
| MCART6__1 | 0.1234 |
| MFRP | 0.2237 |
| MIDN | 0.0021 |
| MIR1914 | 0.0537 |
| MIR212 | 0.0981 |
| MIR571 | 0 |
| MIR576 | 0.1099 |
| MIR654 | 0.0423 |
| MIR942 | 0.0976 |
| MMP12__1 | 0.12 |
| MYCN__2 | 0.1331 |
| MYL92 | 0.1035 |
| MYOHD1 | 0.0219 |
| NFATC3__5 | 0.0381 |
| NFATC4 | 0.0694 |
| NLRP9 | 0.1732 |
| NOVA2 | 0.0704 |
| NP | 0.0733 |
| NR6A1__2 | 0.1291 |
| NRXN3__3 | 0.169 |
| NT5DC1__2 | 0.1829 |
| NTRK2__3 | 0.0051 |
| NUP155__1 | 0.025 |
| NYX | 0.1094 |
| ODF2__3 | 0.0155 |
| ORC1L | 0.0372 |
| OTUD7A__3 | 0.0442 |
| PANK4 | 0.0437 |
| PDLIM2__2 | 0.2169 |
| PDZRN4__2 | 0.2047 |
| PHYH__1 | 0.0101 |
| PIGA__1 | 0.0908 |
| PITX2__1 | 0.2007 |
| PKN1__3 | 0.0052 |
| PLEKHG5__5 | 0.2567 |
| PLSCR4 | 0.0187 |
| PMEPA1__4 | 0.1358 |
| PNMA5 | 0.1706 |
| PPAPDC1A | 0.1242 |
| PRAMEF5 | 0.0092 |
| PRKAA2 | 0.1234 |
| PSMC6__1 | 0.0397 |
| RAD54B__2 | 0.1761 |
| RAP1A__1 | 0.1946 |
| RARA__3 | 0.0955 |
| RARG | 0.0821 |
| RNASEK | 0.0783 |
| RNF7__1 | 0.0237 |
| ROD1__1 | 0.2044 |
| SATB2 | 0.0369 |
| SBSN | 0.0734 |
| SCXB | 0.0138 |
| SEC22C__3 | 0.1017 |
| SELENBP1 | 0.147 |
| SERPINB2__2 | 0.0097 |
| SERPINB5 | 0.1745 |
| SFN | 0.0181 |
| SFRS4 | 0.0693 |
| SHC1__3 | 0.0685 |
| SLC23A1__2 | 0.1277 |
| SLC25A34 | 0.105 |
| SLC4A5__3 | 0.0881 |
| SLC9A10 | 0.0657 |
| SNORD93 | 0.1246 |
| SOX2__1 | 0.0791 |
| STC1 | 0.003 |
| STC2 | 0.1131 |
| STYX__2 | 0.0137 |
| SYTL3 | 0.027 |
| TAF15__1 | 0.0207 |
| TCEAL8__1 | 0.0124 |
| THBS3 | 0.0997 |
| TIMP2__2 | 0.0391 |
| TM2D3__2 | 0.0923 |
| TMEM52 | 0.0006 |

TABLE 56-continued

| | |
|---|---|
| TMEM62 | 0.0672 |
| TNFRSF18__1 | 0.222 |
| TNNT2__1 | 0.0095 |
| TOMM20L | 0.0003 |
| TPM2__2 | 0.178 |
| TRIM58 | 0.115 |
| UBR7__1 | 0.0826 |
| UBR7__2 | 0.1381 |
| WARS__2 | 0.184 |
| XBP1__2 | 0.146 |
| XRN2__1 | 0.044 |
| YARS2 | 0.0299 |
| ZNF75D__2 | 0.1344 |
| ZSWIM4__2 | 0.1743 |
| figo__numeric | 0.0227 |
| hist__rev__SBOT | 0.0382 |
| surg__outcome | 0.0106 |

TABLE 57

| | |
|---|---|
| ABHD3 | 0.0642 |
| ADAM17__2 | 0.2339 |
| ADAMTS1 | 0.1728 |
| ALS2CL__3 | 0.1139 |
| ANO7__3 | 0.0798 |
| ARL6IP1__1 | 0.032 |
| ARMCX3__2 | 0.0865 |
| ATXN10__1 | 0.2036 |
| AXL__1 | 0.1146 |
| BAI1__3 | 0.0421 |
| BCAS1__1 | 0.3262 |
| BDNF__2 | 0.124 |
| BMPR1A | 0.104 |
| BTF3__3 | 0.1055 |
| C10orf116 | 0.0282 |
| C11orf24 | 0.1814 |
| C11orf49__3 | 0.1315 |
| C14orf102__2 | 0.1313 |
| C14orf109__2 | 0.0748 |
| C17orf106 | 0.2458 |
| C17orf58__2 | 0.0334 |
| C17orf58__3 | 0.0243 |
| C18orf56 | 0.0448 |
| C1orf168 | 0.0354 |
| C1orf64 | 0.1116 |
| C8orf79__1 | 0.0063 |
| CASP8AP2 | 0.1353 |
| CCL13 | 0.1464 |
| CCR2__3 | 0.0935 |
| CD34__1 | 0.0084 |
| CDC42BPA__2 | 0.0185 |
| CDC42SE2__2 | 0.0265 |
| CLDN6 | 0.1037 |
| CREB5__2 | 0.0145 |
| CRYBA1 | 0.0178 |
| CXCL13 | 0.0782 |
| CYB5R3__2 | 0.1846 |
| CYP1A2 | 0.0522 |
| DBNDD2 | 0.1019 |
| DNAH11 | 0.0501 |
| DNMT3L__2 | 0.02 |
| DOCK7__1 | 0.127 |
| DSC3__1 | 0.0611 |
| DUT__3 | 0.1237 |
| EEF1E1__1 | 0.1023 |
| EIF4ENIF1 | 0.1116 |
| EMP1 | 0.1674 |
| ENO1 | 0.1366 |
| ENPEP__2 | 0.0131 |
| EPHB1 | 0.0313 |
| EPYC | 0.0352 |
| ERI2__2 | 0.305 |
| ESPNL | 0.0421 |
| EZH2__1 | 0.0741 |
| FAM13AOS | 0.0355 |
| FAM187B__2 | 0.0113 |
| FAM70A__1 | 0.0699 |

TABLE 57-continued

| | |
|---|---|
| FBXO48_2 | 0.2634 |
| FGF51 | 0.0715 |
| FKBP10 | 0.0412 |
| FLJ33360 | 0.2035 |
| FLJ43752 | 0.0711 |
| FMNL3_2 | 0.0407 |
| FMOD | 0.1931 |
| FOSB | 0.0261 |
| FOSL2 | 0.2651 |
| FOXN1 | 0.033 |
| GAD1_2 | 0.0208 |
| GBE1 | 0.0481 |
| GBP7 | 0.13 |
| GJA5_1 | 0.0509 |
| GMNN | 0.0929 |
| GSR_2 | 0.0473 |
| HBA2 | 0.2102 |
| HCFC1R1_1 | 0.0587 |
| HDAC7_2 | 0.0045 |
| HDLBP_3 | 0.1011 |
| HIC1 | 0.038 |
| HPRT1_1 | 0.1484 |
| HPS4_1 | 0.0713 |
| HR_1 | 0.0435 |
| HSD11B1_1 | 0.1011 |
| ICAM2 | 0.0497 |
| ICAM4_1 | 0.2803 |
| IL1RAP_2 | 0.0686 |
| IQCA1_2 | 0.0231 |
| KCNIP3_1 | 0.1037 |
| KCNQ2_1 | 0.1262 |
| KIF3C | 0.1913 |
| KRT80_2 | 0.1143 |
| KRTAP10.10_2 | 0.023 |
| L3MBTL2_3 | 0.0312 |
| LBH_2 | 0.0936 |
| LENEP | 0.2283 |
| LGI3 | 0.1313 |
| LOC492303 | 0.0382 |
| LRRC14B | 0.0225 |
| LRRC37A4_2 | 0.0591 |
| LRRTM4 | 0.1778 |
| MACC1 | 0.1325 |
| MANSC1_1 | 0.1414 |
| MCAM | 0.0258 |
| MCART6_1 | 0.1484 |
| MFRP | 0.2179 |
| MIDN | 0.044 |
| MIR1914 | 0.0668 |
| MIR212 | 0.1071 |
| MIR571 | 0.035 |
| MIR576 | 0.0983 |
| MIR654 | 0.0624 |
| MIR942 | 0.1443 |
| MMP12_1 | 0.126 |
| MYCN_2 | 0.1402 |
| NFATC3_5 | 0.1015 |
| NFATC4 | 0.0053 |
| NLRP9 | 0.054 |
| NOVA2 | 0.12 |
| NP | 0.0786 |
| NR6A1_2 | 0.1481 |
| NRXN3_3 | 0.0994 |
| NT5DC1_2 | 0.1985 |
| NTRK2_3 | 0.0061 |
| NUP155_1 | 0.0626 |
| NYX | 0.1753 |
| ODF2_3 | 0.0161 |
| ORC1L | 0.0257 |
| OTUD7A_3 | 0.0323 |
| PANK4 | 0.0572 |
| PDLIM2_2 | 0.2354 |
| PHYH_1 | 0.1976 |
| PIGA_1 | 0.0094 |
| PITX2_1 | 0.0919 |
| PKN1_3 | 0.017 |
| PLAC9 | 0.2381 |
| PLEKHG5_5 | 0.0243 |
| PLSCR4 | 0.1715 |
| PMEPA1_4 | 0.1272 |
| PNMA5 | 0.121 |
| PPAPDC1A | 0.1269 |
| PRAMEF5 | 0.011 |
| PRKAA2 | 0.1396 |
| PSMC6_1 | 0.0134 |
| RAD54B_2 | 0.184 |
| RAP1A_1 | 0.2177 |
| RARA_3 | 0.0861 |
| RARG | 0.0469 |
| RNASEK | 0.0707 |
| RNF7_1 | 0.0183 |
| ROD1_1 | 0.2173 |
| SATB2 | 0.0599 |
| SBSN | 0.0498 |
| SCXB | 0.009 |
| SEC22C_3 | 0.116 |
| SELENBP1 | 0.1894 |
| SERPINB2_2 | 0.0164 |
| SERPINB5 | 0.2094 |
| SFN | 0.0154 |
| SFRS4 | 0.0376 |
| SHC1_3 | 0.0715 |
| SLC23A1_2 | 0.1364 |
| SLC25A34 | 0.1695 |
| SLC4A5_3 | 0.081 |
| SLC9A10 | 0.0879 |
| SNORD93 | 0.1688 |
| SOX2_1 | 0.0728 |
| STC1 | 0.0127 |
| STC2 | 0.135 |
| STYX_2 | 0.0462 |
| SYTL3 | 0.0117 |
| TAF15_1 | 0.0117 |
| TCEAL8_1 | 0.0445 |
| THBS3 | 0.1055 |
| THY1 | 0.0613 |
| TIMP2_2 | 0.0807 |
| TM2D3_2 | 0.0101 |
| TMEM52 | 0.0357 |
| TMEM62 | 0.0698 |
| TNFRSF18_1 | 0.2592 |
| TNNT2_1 | 0.0071 |
| TOMM20L | 0.0412 |
| TPM2_2 | 0.1777 |
| TRIM58 | 0.1106 |
| UBR7_1 | 0.0689 |
| UBR7_2 | 0.1189 |
| WARS_2 | 0.153 |
| XBP1_2 | 0.1393 |
| XRN2_1 | 0.0533 |
| YARS2 | 0.0008 |
| ZNF75D_2 | 0.1617 |
| ZSWIM4_2 | 0.1597 |
| figo_numeric | 0.0171 |
| hist_rev_SBOT | 0.0582 |
| surg_outcome | 0.002 |

TABLE 58

| | |
|---|---|
| ABHD3 | 0.0552 |
| ADAM17_2 | 0.2207 |
| ADAMTS1 | 0.1613 |
| ALS2CL_3 | 0.1019 |
| ANO7_3 | 0.0683 |
| ANTXR1_4 | 0.0226 |
| ARL6IP1_1 | 0.0916 |
| ARMCX3_2 | 0.1859 |
| ATXN10_1 | 0.1744 |
| AXL_1 | 0.1084 |
| BAI1_3 | 0.0478 |
| BCAS1_1 | 0.3244 |
| BDNF_2 | 0.1137 |
| BMPR1A | 0.0975 |
| BTF3_3 | 0.0978 |
| C10orf116 | 0.0139 |
| C11orf24 | 0.2032 |
| C11orf49_3 | 0.1212 |

TABLE 58-continued

| | |
|---|---|
| C14orf102_2 | 0.1265 |
| C14orf109_2 | 0.077 |
| C17orf106 | 0.2308 |
| C17orf58_2 | 0.0538 |
| C17orf58_3 | 0.0243 |
| C18orf56 | 0.0471 |
| C1orf168 | 0.0387 |
| C1orf64 | 0.115 |
| C8orf79_1 | 0.0134 |
| CASP8AP2 | 0.1576 |
| CCL13 | 0.1309 |
| CCR2_3 | 0.0953 |
| CD34_1 | 0.0008 |
| CDC42BPA_2 | 0.0051 |
| CDC42SE2_2 | 0.0384 |
| CLDN6 | 0.1048 |
| CREB5_2 | 0.0332 |
| CRYBA1 | 0.024 |
| CXCL13 | 0.0799 |
| CYB5R3_2 | 0.1856 |
| CYP1A2 | 0.0556 |
| DBNDD2 | 0.0925 |
| DNAH11 | 0.0398 |
| DNMT3L_2 | 0.0242 |
| DOCK7_1 | 0.1054 |
| DSC3_1 | 0.0675 |
| DUT_3 | 0.1206 |
| EEF1E1_1 | 0.1002 |
| EIF4ENIF1 | 0.1119 |
| EMP1 | 0.1608 |
| ENO1 | 0.1399 |
| ENPEP_2 | 0.0156 |
| EPHB1 | 0.0301 |
| EPYC | 0.048 |
| ERI2_2 | 0.294 |
| ESPNL | 0.0416 |
| EZH2_1 | 0.0526 |
| FAM13AOS | 0.0436 |
| FAM187B_2 | 0.0219 |
| FAM70A_1 | 0.0574 |
| FBXO48_2 | 0.2748 |
| FGF51 | 0.0745 |
| FKBP10 | 0.0583 |
| FLJ33360 | 0.2091 |
| FLJ43752 | 0.0662 |
| FMNL3_2 | 0.0515 |
| FMOD | 0.1923 |
| FOSB | 0.0188 |
| FOSL2 | 0.2826 |
| FOXN1 | 0.033 |
| GAD1_2 | 0.0245 |
| GBE1 | 0.0383 |
| GBP7 | 0.1213 |
| GJA5_1 | 0.0562 |
| GMNN | 0.1037 |
| GSR_2 | 0.0385 |
| HBA2 | 0.204 |
| HCFC1R1_1 | 0.0443 |
| HDAC7_2 | 0.0003 |
| HDLBP_3 | 0.0761 |
| HIC1 | 0.0559 |
| HPRT1_1 | 0.1294 |
| HPS4_1 | 0.0808 |
| HR_1 | 0.0534 |
| HSD11B1_1 | 0.0889 |
| ICAM2 | 0.074 |
| ICAM4_1 | 0.2733 |
| IL1RAP_2 | 0.0561 |
| IQCA1_2 | 0.0292 |
| KCNIP3_1 | 0.0983 |
| KCNQ2_1 | 0.1237 |
| KIF3C | 0.1983 |
| KRT80_2 | 0.1125 |
| KRTAP10.10_2 | 0.0197 |
| L3MBTL2_3 | 0.0379 |
| LBH_2 | 0.1024 |
| LENEP | 0.217 |
| LGI3 | 0.1299 |
| LOC492303 | 0.0227 |
| LRRC14B | 0.0231 |
| LRRC37A4_2 | 0.0695 |
| LRRTM4 | 0.1848 |
| MACC1 | 0.1529 |
| MANSC1_1 | 0.1436 |
| MCAM | 0.0259 |
| MCART6_1 | 0.1532 |
| MFRP | 0.2209 |
| MIDN | 0.0516 |
| MIR1914 | 0.0664 |
| MIR212 | 0.0976 |
| MIR571 | 0.0285 |
| MIR576 | 0.1141 |
| MIR654 | 0.0578 |
| MIR942 | 0.1333 |
| MMP12_1 | 0.1239 |
| MYCN_2 | 0.1592 |
| MYL92 | 0.1096 |
| NFATC3_5 | 0.0169 |
| NFATC4 | 0.0583 |
| NLRP9 | 0.0595 |
| NOVA2 | 0.1183 |
| NP | 0.0793 |
| NR6A1_2 | 0.1497 |
| NRXN3_3 | 0.0907 |
| NT5DC1_2 | 0.1789 |
| NTRK2_3 | 0.0085 |
| NUP155_1 | 0.052 |
| NYX | 0.1468 |
| ODF2_3 | 0.0051 |
| ORC1L | 0.0197 |
| OTUD7A_3 | 0.0222 |
| PANK4 | 0.0714 |
| PDLIM2_2 | 0.2393 |
| PHYH_1 | 0.1915 |
| PIGA_1 | 0.0132 |
| PITX2_1 | 0.0995 |
| PKN1_3 | 0.0029 |
| PLAC9 | 0.2558 |
| PLEKHG5_5 | 0.0321 |
| PLSCR4 | 0.1527 |
| PMEPA1_4 | 0.1445 |
| PNMA5 | 0.1015 |
| PPAPDC1A | 0.1397 |
| PRAMEF5 | 0.0006 |
| PRKAA2 | 0.1222 |
| PSMC6_1 | 0.016 |
| RAD54B_2 | 0.1742 |
| RAP1A_1 | 0.2178 |
| RARA_3 | 0.0956 |
| RARG | 0.048 |
| RNASEK | 0.0568 |
| RNF7_1 | 0.0152 |
| ROD1_1 | 0.2201 |
| SATB2 | 0.0641 |
| SBSN | 0.0558 |
| SCXB | 0.0109 |
| SEC22C_3 | 0.1123 |
| SELENBP1 | 0.1824 |
| SERPINB2_2 | 0.0044 |
| SERPINB5 | 0.1929 |
| SFN | 0.0033 |
| SFRS4 | 0.0215 |
| SHC1_3 | 0.0768 |
| SLC23A1_2 | 0.1304 |
| SLC25A34 | 0.1714 |
| SLC4A5_3 | 0.0737 |
| SLC9A10 | 0.0721 |
| SNORD93 | 0.1695 |
| SOX2_1 | 0.0682 |
| STC1 | 0.0075 |
| STC2 | 0.1235 |
| STYX_2 | 0.0465 |
| SYTL3 | 0.0017 |
| TAF15_1 | 0.0289 |
| TCEAL8_1 | 0.0274 |
| THBS3 | 0.0867 |
| THY1 | 0.0608 |
| TM2D3_2 | 0.105 |
| TMEM52 | 0.0192 |
| TMEM62 | 0.0212 |

TABLE 58-continued

| | |
|---|---|
| TNFRSF18__1 | 0.2602 |
| TNNT2__1 | 0.0012 |
| TOMM20L | 0.0429 |
| TPM2__2 | 0.1662 |
| TRIM58 | 0.0973 |
| UBR7__1 | 0.0728 |
| UBR7__2 | 0.107 |
| WARS__2 | 0.1502 |
| XBP1__2 | 0.1143 |
| XRN2__1 | 0.0323 |
| YARS2 | 0.002 |
| ZNF75D__2 | 0.1377 |
| ZSWIM4__2 | 0.1552 |
| figo__numeric | 0.0113 |
| hist__rev__SBOT | 0.0568 |
| surg__outcome | 0.0124 |

TABLE 59

| | |
|---|---|
| ABHD3 | 0.0671 |
| ADAM17__2 | 0.2292 |
| ADAMTS1 | 0.1692 |
| ALS2CL__3 | 0.1138 |
| ANO7__3 | 0.0731 |
| ARL6IP1__1 | 0.0241 |
| ARMCX3__2 | 0.0864 |
| ATXN10__1 | 0.2052 |
| AXL__1 | 0.116 |
| BAI1__3 | 0.0354 |
| BCAS1__1 | 0.3268 |
| BDNF__2 | 0.1221 |
| BMPR1A | 0.1083 |
| BTF3__3 | 0.105 |
| C10orf116 | 0.0337 |
| C11orf24 | 0.1795 |
| C11orf49__3 | 0.1271 |
| C14orf102__2 | 0.1271 |
| C14orf109__2 | 0.0735 |
| C17orf106 | 0.2415 |
| C17orf58__2 | 0.0464 |
| C17orf58__3 | 0.0237 |
| C18orf56 | 0.0465 |
| C1orf168 | 0.0392 |
| C1orf64 | 0.1124 |
| C8orf79__1 | 0.0158 |
| CASP8AP2 | 0.1323 |
| CCL13 | 0.1413 |
| CCR2__3 | 0.0938 |
| CD34__1 | 0.001 |
| CDC42BPA__2 | 0.0178 |
| CDC42SE2__2 | 0.0288 |
| CLDN6 | 0.1018 |
| CREB5__2 | 0.0178 |
| CRYBA1 | 0.0274 |
| CXCL13 | 0.0787 |
| CYB5R3__2 | 0.1839 |
| CYP1A2 | 0.0569 |
| DBNDD2 | 0.107 |
| DNAH11 | 0.0513 |
| DNMT3L__2 | 0.022 |
| DOCK7__1 | 0.1366 |
| DSC3__1 | 0.071 |
| DUT__3 | 0.1208 |
| EEF1E1__1 | 0.1047 |
| EIF4ENIF1 | 0.1221 |
| EMP1 | 0.1668 |
| ENO1 | 0.1329 |
| ENPEP__2 | 0.016 |
| EPHB1 | 0.0251 |
| EPYC | 0.03 |
| ERI2__2 | 0.3053 |
| ESPNL | 0.041 |
| EZH2__1 | 0.0705 |
| FAM13AOS | 0.0361 |
| FAM187B__2 | 0.0083 |
| FAM70A__1 | 0.0752 |
| FBXO48__2 | 0.2561 |

TABLE 59-continued

| | |
|---|---|
| FGF51 | 0.0735 |
| FKBP10 | 0.0448 |
| FLJ33360 | 0.2023 |
| FLJ43752 | 0.0722 |
| FMNL3__2 | 0.0414 |
| FMOD | 0.2024 |
| FOSB | 0.0221 |
| FOSL2 | 0.2764 |
| FOXN1 | 0.0242 |
| GAD1__2 | 0.0147 |
| GBE1 | 0.0497 |
| GBP7 | 0.1283 |
| GJA5__1 | 0.0489 |
| GMNN | 0.0972 |
| GSR__2 | 0.0458 |
| HBA2 | 0.2029 |
| HCFC1R1__1 | 0.0588 |
| HDAC7__2 | 0.0054 |
| HDLBP__3 | 0.1015 |
| HIC1 | 0.0352 |
| HPRT1__1 | 0.151 |
| HPS4__1 | 0.0687 |
| HR__1 | 0.0415 |
| HSD11B1__1 | 0.1011 |
| ICAM2 | 0.065 |
| ICAM4__1 | 0.2749 |
| IL1RAP__2 | 0.067 |
| IQCA1__2 | 0.0244 |
| KCNIP3__1 | 0.1062 |
| KCNQ2__1 | 0.1353 |
| KIF3C | 0.1922 |
| KRT80__2 | 0.1104 |
| KRTAP10.10__2 | 0.0235 |
| L3MBTL2__3 | 0.0295 |
| LBH__2 | 0.0915 |
| LENEP | 0.2311 |
| LGI3 | 0.1219 |
| LOC492303 | 0.0315 |
| LRRC14B | 0.0189 |
| LRRC37A4__2 | 0.0641 |
| LRRTM4 | 0.1761 |
| MACC1 | 0.1346 |
| MANSC1__1 | 0.1377 |
| MCAM | 0.0211 |
| MCART6__1 | 0.1461 |
| MFRP | 0.2228 |
| MIDN | 0.0404 |
| MIR1914 | 0.0611 |
| MIR212 | 0.1082 |
| MIR571 | 0.0377 |
| MIR576 | 0.1018 |
| MIR654 | 0.0564 |
| MIR942 | 0.1348 |
| MMP12__1 | 0.1289 |
| MYCN__2 | 0.1459 |
| MYL92 | 0.1003 |
| NFATC3__5 | 0.0044 |
| NFATC4 | 0.055 |
| NLRP9 | 0.0689 |
| NOVA2 | 0.125 |
| NP | 0.0783 |
| NR6A1__2 | 0.1526 |
| NRXN3__3 | 0.1 |
| NT5DC1__2 | 0.1983 |
| NTRK2__3 | 0.0012 |
| NUP155__1 | 0.0634 |
| NYX | 0.1807 |
| ODF2__3 | 0.0127 |
| ORC1L | 0.0228 |
| OTUD7A__3 | 0.0361 |
| PANK4 | 0.0586 |
| PDLIM2__2 | 0.2387 |
| PHYH__1 | 0.1982 |
| PIGA__1 | 0.0033 |
| PITX2__1 | 0.0891 |
| PKN1__3 | 0.0161 |
| PLAC9 | 0.2381 |
| PLEKHG5__5 | 0.0151 |
| PLSCR4 | 0.167 |
| PMEPA1__4 | 0.1285 |

TABLE 59-continued

| | |
|---|---|
| PNMA5 | 0.1162 |
| PPAPDC1A | 0.1306 |
| PRAMEF5 | 0.0005 |
| PRKAA2 | 0.1411 |
| PSMC6__1 | 0.0065 |
| RAD54B__2 | 0.1805 |
| RAP1A__1 | 0.2107 |
| RARA__3 | 0.0828 |
| RARG | 0.0461 |
| RNASEK | 0.0717 |
| RNF7__1 | 0.0208 |
| ROD1__1 | 0.2224 |
| SATB2 | 0.0615 |
| SBSN | 0.051 |
| SCXB | 0.0101 |
| SEC22C__3 | 0.1062 |
| SELENBP1 | 0.1861 |
| SERPINB2__2 | 0.0072 |
| SERPINB5 | 0.204 |
| SFN | 0.0179 |
| SFRS4 | 0.0369 |
| SHC1__3 | 0.0687 |
| SLC23A1__2 | 0.1368 |
| SLC25A34 | 0.1721 |
| SLC4A5__3 | 0.0834 |
| SLC9A10 | 0.0815 |
| SNORD93 | 0.1628 |
| SOX2__1 | 0.0745 |
| STC1 | 0.0131 |
| STC2 | 0.1329 |
| STYX__2 | 0.0475 |
| SYTL3 | 0.0072 |
| TAF15__1 | 0.0023 |
| TCEAL8__1 | 0.0422 |
| THBS3 | 0.106 |
| TIMP2__2 | 0.0656 |
| TM2D3__2 | 0.0735 |
| TMEM52 | 0.0094 |
| TMEM62 | 0.066 |
| TNFRSF18__1 | 0.2722 |
| TNNT2__1 | 0.0012 |
| TOMM20L | 0.0411 |
| TPM2__2 | 0.1754 |
| TRIM58 | 0.1096 |
| UBR7__1 | 0.0721 |
| UBR7__2 | 0.1192 |
| WARS__2 | 0.1469 |
| XBP1__2 | 0.1332 |
| XRN2__1 | 0.0532 |
| YARS2 | 0.0016 |
| ZNF75D__2 | 0.1609 |
| ZSWIM4__2 | 0.1604 |
| figo__numeric | 0.0142 |
| hist__rev__SBOT | 0.0611 |
| surg__outcome | 0.0021 |

TABLE 60

| | |
|---|---|
| ABHD3 | 0.0166 |
| ADAM17__2 | 0.2184 |
| ADAMTS1 | 0.1541 |
| ALS2CL__3 | 0.0861 |
| ANO7__3 | 0.0199 |
| ARL6IP1__1 | 0.05 |
| ARMCX3__2 | 0.1112 |
| ATXN10__1 | 0.2216 |
| AURKA__1 | 0.1001 |
| AXL__1 | 0.1 |
| BAI1__3 | 0.2844 |
| BCAS1__1 | 0.1883 |
| BDNF__2 | 0.1269 |
| BMPR1A | 0.0692 |
| BTF3__3 | 0.079 |
| C10orf116 | 0.0448 |
| C11orf24 | 0.1449 |
| C11orf49__3 | 0.1129 |
| C14orf102__2 | 0.0742 |

TABLE 60-continued

| | |
|---|---|
| C14orf109__2 | 0.0939 |
| C17orf106 | 0.218 |
| C17orf58__2 | 0.0564 |
| C17orf58__3 | 0.0299 |
| C18orf56 | 0.0054 |
| C1orf168 | 0.0376 |
| C1orf64 | 0.1066 |
| C8orf79__1 | 0.0136 |
| CASP8AP2 | 0.1435 |
| CCL13 | 0.1199 |
| CCR2__3 | 0.0409 |
| CD34__1 | 0.0011 |
| CDC42BPA__2 | 0.0136 |
| CDC42SE2__2 | 0.0308 |
| CLDN6 | 0.118 |
| CREB5__2 | 0.0002 |
| CRYBA1 | 0.0273 |
| CXCL13 | 0.11 |
| CYB5R3__2 | 0.1351 |
| CYP1A2 | 0.0707 |
| DBNDD2 | 0.0985 |
| DNAH11 | 0.0484 |
| DNMT3L__2 | 0.0068 |
| DOCK7__1 | 0.0862 |
| DSC3__1 | 0.0803 |
| DUT__3 | 0.1208 |
| EEF1E1__1 | 0.1172 |
| EMP1 | 0.0986 |
| ENO1 | 0.2005 |
| ENPEP__2 | 0.1348 |
| EPHB1 | 0.0508 |
| EPYC | 0.0409 |
| ERI2__2 | 0.2472 |
| ESPNL | 0.0142 |
| FAM13AOS | 0.057 |
| FAM187B__2 | 0.0043 |
| FAM70A__1 | 0.0234 |
| FBXO48__2 | 0.2855 |
| FKBP10 | 0.0479 |
| FLJ33360 | 0.0516 |
| FLJ43752 | 0.1867 |
| FMNL3__2 | 0.0112 |
| FOSB | 0.1898 |
| FOSL2 | 0.0578 |
| FOXN1 | 0.2188 |
| GAD1__2 | 0.0242 |
| GBE1 | 0.0438 |
| GBP7 | 0.098 |
| GJA5__1 | 0.0433 |
| GMNN | 0.0788 |
| GSR__2 | 0.0005 |
| HBA2 | 0.1497 |
| HCFC1R1__1 | 0.0365 |
| HDAC7__2 | 0.0183 |
| HDLBP__3 | 0.1032 |
| HIC1 | 0.0324 |
| HPRT1__1 | 0.0847 |
| HPS4__1 | 0.0753 |
| HR__1 | 0.0263 |
| HSD11B1__1 | 0.1211 |
| ICAM2 | 0.0257 |
| ICAM4__1 | 0.2568 |
| IL1RAP__2 | 0.0475 |
| IQCA1__2 | 0.0619 |
| KCNIP3__1 | 0.1159 |
| KCNQ2__1 | 0.142 |
| KIF3C | 0.1898 |
| KRT80__2 | 0.1454 |
| KRTAP10.10__2 | 0.002 |
| L3MBTL2__3 | 0.0268 |
| LBH__2 | 0.1113 |
| LENEP | 0.1991 |
| LGI3 | 0.149 |
| LOC492303 | 0.0476 |
| LRRC14B | 0.0303 |
| LRRC37A4__2 | 0.0563 |
| LRRTM4 | 0.1923 |
| MACC1 | 0.0885 |
| MANSC1__1 | 0.107 |
| MCAM | 0.0052 |

TABLE 60-continued

| | |
|---|---|
| MCART6_1 | 0.1421 |
| MFRP | 0.2159 |
| MIDN | 0.0265 |
| MIR1914 | 0.0817 |
| MIR212 | 0.0836 |
| MIR571 | 0.0287 |
| MIR576 | 0.1125 |
| MIR654 | 0.0204 |
| MIR942 | 0.1756 |
| MMP12_1 | 0.0881 |
| MYCN_2 | 0.0687 |
| MYOHD1 | 0.0827 |
| NFATC3_5 | 0.014 |
| NFATC4 | 0.0691 |
| NLRP9 | 0.1646 |
| NOVA2 | 0.0813 |
| NP | 0.0971 |
| NR6A1_2 | 0.1233 |
| NRXN3_3 | 0.1004 |
| NT5DC1_2 | 0.1871 |
| NTRK2_3 | 0.0063 |
| NUP155_1 | 0.0334 |
| NYX | 0.1428 |
| ODF2_3 | 0.0248 |
| ORC1L | 0.0191 |
| OTUD7A_3 | 0.0018 |
| PANK4 | 0.0478 |
| PDLIM2_2 | 0.2087 |
| PHYH_1 | 0.1765 |
| PIGA_1 | 0.0169 |
| PITX2_1 | 0.1426 |
| PKN1_3 | 0.0452 |
| PLAC9 | 0.1953 |
| PLEKHG5_5 | 0.0013 |
| PLSCR4 | 0.2019 |
| PMEPA1_4 | 0.1591 |
| PNMA5 | 0.1413 |
| PPAPDC1A | 0.1376 |
| PRAMEF5 | 0.0107 |
| PRKAA2 | 0.0698 |
| PSMC6_1 | 0.0067 |
| RAD54B_2 | 0.1857 |
| RAP1A_1 | 0.1932 |
| RARA_3 | 0.0872 |
| RARG | 0.0506 |
| RNASEK | 0.0743 |
| RNF7_1 | 0.0694 |
| ROD1_1 | 0.1608 |
| SATB2 | 0.0437 |
| SBSN | 0.01 |
| SCXB | 0.0204 |
| SEC22C_3 | 0.1159 |
| SELENBP1 | 0.1537 |
| SERPINB2_2 | 0.0366 |
| SERPINB5 | 0.1726 |
| SFN | 0.0182 |
| SFRS4 | 0.0373 |
| SHC1_3 | 0.0643 |
| SLC23A1_2 | 0.0795 |
| SLC25A34 | 0.1679 |
| SLC4A5_3 | 0.0537 |
| SLC9A10 | 0.072 |
| SNORD93 | 0.1594 |
| SOX2_1 | 0.0624 |
| STC1 | 0.0161 |
| STC2 | 0.1199 |
| STYX_2 | 0.046 |
| SYTL3 | 0.0329 |
| TAF15_1 | 0.0232 |
| TCEAL8_1 | 0.0653 |
| THBS3 | 0.0517 |
| THY1 | 0.0583 |
| TIMP2_2 | 0.0906 |
| TM2D3_2 | 0.0318 |
| TMEM52 | 0.039 |
| TMEM62 | 0.0421 |
| TNFRSF18_1 | 0.2005 |
| TNNT2_1 | 0.003 |
| TOMM20L | 0.0199 |
| TPM2_2 | 0.1777 |

TABLE 60-continued

| | |
|---|---|
| TRIM58 | 0.0964 |
| UBR7_1 | 0.051 |
| UBR7_2 | 0.0982 |
| WARS_2 | 0.1452 |
| WDR76 | 0.1101 |
| XBP1_2 | 0.0458 |
| XRN2_1 | 0.0278 |
| YARS2 | 0.2501 |
| ZNF75D_2 | 0.1344 |
| ZSWIM4_2 | 0.1448 |
| figo_numeric | 0.021 |
| hist_rev_SBOT | 0.047 |
| surg_outcome | 0.0123 |

TABLE 61

| | |
|---|---|
| ABHD3 | 0.0019 |
| ADAM17_2 | 0.21 |
| ADAMTS1 | 0.1502 |
| ALS2CL_3 | 0.0705 |
| ANO7_3 | 0.0243 |
| ANTXR1_4 | 0.0354 |
| ARL6IP1_1 | 0.1207 |
| ARMCX3_2 | 0.2073 |
| ATXN10_1 | 0.1486 |
| AURKA_1 | 0.0958 |
| AXL_1 | 0.0891 |
| BAI1_3 | 0.278 |
| BCAS1_1 | 0.1917 |
| BDNF_2 | 0.1205 |
| BMPR1A | 0.0673 |
| BTF3_3 | 0.0601 |
| C10orf116 | 0.0284 |
| C11orf24 | 0.1598 |
| C11orf49_3 | 0.1189 |
| C14orf102_2 | 0.0818 |
| C14orf109_2 | 0.1017 |
| C17orf106 | 0.208 |
| C17orf58_2 | 0.0783 |
| C17orf58_3 | 0.0303 |
| C18orf56 | 0.0029 |
| C1orf168 | 0.0345 |
| C1orf64 | 0.1047 |
| C8orf79_1 | 0.0105 |
| CASP8AP2 | 0.1559 |
| CCL13 | 0.1015 |
| CCR2_3 | 0.033 |
| CD34_1 | 0.0017 |
| CDC42BPA_2 | 0.0244 |
| CDC42SE2_2 | 0.0446 |
| CLDN6 | 0.1185 |
| CREB5_2 | 0.0133 |
| CRYBA1 | 0.0219 |
| CXCL13 | 0.1102 |
| CYB5R3_2 | 0.1396 |
| CYP1A2 | 0.0811 |
| DBNDD2 | 0.0943 |
| DNAH11 | 0.0423 |
| DNMT3L_2 | 0.0153 |
| DOCK7_1 | 0.0719 |
| DSC3_1 | 0.0821 |
| DUT_3 | 0.1249 |
| EEF1E1_1 | 0.1162 |
| EMP1 | 0.0972 |
| ENO1 | 0.189 |
| ENPEP_2 | 0.1375 |
| EPHB1 | 0.051 |
| EPYC | 0.0483 |
| ERI2_2 | 0.2492 |
| ESPNL | 0.0136 |
| FAM13AOS | 0.0489 |
| FAM187B_2 | 0.0017 |
| FAM70A_1 | 0.0127 |
| FBXO48_2 | 0.2818 |
| FKBP10 | 0.0494 |
| FLJ33360 | 0.0529 |
| FLJ43752 | 0.1844 |

TABLE 61-continued

| | |
|---|---|
| FMNL3__2 | 0.0046 |
| FOSB | 0.1927 |
| FOSL2 | 0.0505 |
| FOXN1 | 0.2285 |
| GAD1__2 | 0.0395 |
| GBE1 | 0.0372 |
| GBP7 | 0.0889 |
| GJA5__1 | 0.0431 |
| GMNN | 0.0813 |
| GSR__2 | 0.0019 |
| HBA2 | 0.1452 |
| HCFC1R1__1 | 0.0271 |
| HDAC7__2 | 0.014 |
| HDLBP__3 | 0.0809 |
| HIC1 | 0.0224 |
| HPRT1__1 | 0.0729 |
| HPS4__1 | 0.0911 |
| HR__1 | 0.0354 |
| HSD11B1__1 | 0.1037 |
| ICAM2 | 0.0493 |
| ICAM4__1 | 0.2507 |
| IL1RAP__2 | 0.0403 |
| IQCA1__2 | 0.0654 |
| KCNIP3__1 | 0.1142 |
| KCNQ2__1 | 0.1373 |
| KIF3C | 0.1919 |
| KRT80__2 | 0.134 |
| KRTAP10.10__2 | 0.0076 |
| L3MBTL2__3 | 0.0274 |
| LBH__2 | 0.1174 |
| LENEP | 0.1867 |
| LGI3 | 0.1499 |
| LOC492303 | 0.0439 |
| LRRC14B | 0.0361 |
| LRRC37A4__2 | 0.0698 |
| LRRTM4 | 0.197 |
| MACC1 | 0.0998 |
| MANSC1__1 | 0.1074 |
| MCAM | 0.0015 |
| MCART6__1 | 0.1464 |
| MFRP | 0.2112 |
| MIDN | 0.0338 |
| MIR1914 | 0.0838 |
| MIR212 | 0.0678 |
| MIR571 | 0.0254 |
| MIR576 | 0.1261 |
| MIR654 | 0.0265 |
| MIR942 | 0.1625 |
| MMP12__1 | 0.0955 |
| MYCN__2 | 0.0921 |
| MYL92 | 0.0846 |
| MYOHD1 | 0.0203 |
| NFATC3__5 | 0.0681 |
| NFATC4 | 0.0821 |
| NLRP9 | 0.1625 |
| NOVA2 | 0.082 |
| NP | 0.0841 |
| NR6A1__2 | 0.134 |
| NRXN3__3 | 0.095 |
| NT5DC1__2 | 0.1783 |
| NTRK2__3 | 0.0015 |
| NUP155__1 | 0.0228 |
| NYX | 0.116 |
| ODF2__3 | 0.0384 |
| ORC1L | 0.0208 |
| OTUD7A__3 | 0.0025 |
| PANK4 | 0.0489 |
| PDLIM2__2 | 0.2133 |
| PHYH__1 | 0.1736 |
| PIGA__1 | 0.0214 |
| PITX2__1 | 0.148 |
| PKN1__3 | 0.0458 |
| PLAC9 | 0.1978 |
| PLEKHG5__5 | 0.0069 |
| PLSCR4 | 0.191 |
| PMEPA1__4 | 0.1677 |
| PNMA5 | 0.1276 |
| PPAPDC1A | 0.1399 |
| PRAMEF5 | 0.0059 |
| PRKAA2 | 0.0535 |
| PSMC6__1 | 0.0074 |
| RAD54B__2 | 0.1884 |
| RAP1A__1 | 0.1965 |
| RARA__3 | 0.0943 |
| RARG | 0.0654 |
| RNASEK | 0.0618 |
| RNF7__1 | 0.0415 |
| ROD1__1 | 0.1632 |
| SATB2 | 0.0509 |
| SBSN | 0.0127 |
| SCXB | 0.0194 |
| SEC22C__3 | 0.0991 |
| SELENBP1 | 0.1396 |
| SERPINB2__2 | 0.0221 |
| SERPINB5 | 0.158 |
| SFN | 0.0197 |
| SFRS4 | 0.0417 |
| SHC1__3 | 0.0654 |
| SLC23A1__2 | 0.0641 |
| SLC25A34 | 0.1718 |
| SLC4A5__3 | 0.049 |
| SLC9A10 | 0.0574 |
| SNORD93 | 0.1661 |
| SOX2__1 | 0.071 |
| STC1 | 0.0345 |
| STC2 | 0.1081 |
| STYX__2 | 0.0504 |
| SYTL3 | 0.0159 |
| TAF15__1 | 0.0054 |
| TCEAL8__1 | 0.0537 |
| THBS3 | 0.0349 |
| THY1 | 0.0577 |
| TM2D3__2 | 0.117 |
| TMEM52 | 0.0352 |
| TMEM62 | 0.017 |
| TNFRSF18__1 | 0.1971 |
| TNNT2__1 | 0.0075 |
| TOMM20L | 0.0123 |
| TPM2__2 | 0.1708 |
| TRIM58 | 0.0796 |
| UBR7__1 | 0.063 |
| UBR7__2 | 0.0959 |
| WARS__2 | 0.1386 |
| WDR76 | 0.0986 |
| XBP1__2 | 0.042 |
| XRN2__1 | 0.0299 |
| YARS2 | 0.2416 |
| ZNF75D__2 | 0.1199 |
| ZSWIM4__2 | 0.1456 |
| figo__numeric | 0.0052 |
| hist_rev__SBOT | 0.0335 |
| surg__outcome | 0.0306 |

TABLE 62

| | |
|---|---|
| ABHD3 | 0.017 |
| ADAM17__2 | 0.2176 |
| ADAMTS1 | 0.1527 |
| ALS2CL__3 | 0.0878 |
| ANO7__3 | 0.0094 |
| ARL6IP1__1 | 0.0333 |
| ARMCX3__2 | 0.1124 |
| ATXN10__1 | 0.2223 |
| AURKA__1 | 0.105 |
| AXL__1 | 0.0966 |
| BAI1__3 | 0.2815 |
| BCAS1__1 | 0.1865 |
| BDNF__2 | 0.1256 |
| BMPR1A | 0.0725 |
| BTF3__3 | 0.0713 |
| C10orf116 | 0.0468 |
| C11orf24 | 0.139 |
| C11orf49__3 | 0.1106 |
| C14orf102__2 | 0.0663 |
| C14orf109__2 | 0.0883 |
| C17orf106 | 0.219 |
| C17orf58__2 | 0.066 |

TABLE 62-continued

| | |
|---|---|
| C17orf58_3 | 0.0267 |
| C18orf56 | 0.0012 |
| C1orf168 | 0.0394 |
| C1orf64 | 0.1035 |
| C8orf79_1 | 0.01 |
| CASP8AP2 | 0.1377 |
| CCL13 | 0.1143 |
| CCR2_3 | 0.0434 |
| CD34_1 | 0.0097 |
| CDC42BPA_2 | 0.0176 |
| CDC42SE2_2 | 0.0329 |
| CLDN6 | 0.1121 |
| CREB5_2 | 0.0093 |
| CRYBA1 | 0.0359 |
| CXCL13 | 0.1118 |
| CYB5R3_2 | 0.1345 |
| CYP1A2 | 0.0768 |
| DBNDD2 | 0.1069 |
| DNAH11 | 0.0487 |
| DNMT3L_2 | 0.0094 |
| DOCK7_1 | 0.0986 |
| DSC3_1 | 0.0875 |
| DUT_3 | 0.1196 |
| EEF1E1_1 | 0.1126 |
| EMP1 | 0.1068 |
| ENO1 | 0.2018 |
| ENPEP_2 | 0.1337 |
| EPHB1 | 0.038 |
| EPYC | 0.0354 |
| ERI2_2 | 0.2532 |
| ESPNL | 0.0135 |
| FAM13AOS | 0.0501 |
| FAM187B_2 | 0.0027 |
| FAM70A_1 | 0.023 |
| FBXO48_2 | 0.283 |
| FKBP10 | 0.0465 |
| FLJ33360 | 0.0527 |
| FLJ43752 | 0.1766 |
| FMNL3_2 | 0.0111 |
| FOSB | 0.1968 |
| FOSL2 | 0.0615 |
| FOXN1 | 0.2269 |
| GAD1_2 | 0.0281 |
| GBE1 | 0.0417 |
| GBP7 | 0.099 |
| GJA5_1 | 0.0371 |
| GMNN | 0.0809 |
| GSR_2 | 0.0039 |
| HBA2 | 0.1363 |
| HCFC1R1_1 | 0.0394 |
| HDAC7_2 | 0.0284 |
| HDLBP_3 | 0.1026 |
| HIC1 | 0.0311 |
| HPRT1_1 | 0.089 |
| HPS4_1 | 0.0776 |
| HR_1 | 0.0218 |
| HSD11B1_1 | 0.1165 |
| ICAM2 | 0.0344 |
| ICAM4_1 | 0.2471 |
| IL1RAP_2 | 0.0433 |
| IQCA1_2 | 0.0582 |
| KCNIP3_1 | 0.1157 |
| KCNQ2_1 | 0.1461 |
| KIF3C | 0.1849 |
| KRT80_2 | 0.1425 |
| KRTAP10.10_2 | 0.0006 |
| L3MBTL2_3 | 0.0242 |
| LBH_2 | 0.1077 |
| LENEP | 0.2008 |
| LGI3 | 0.1389 |
| LOC492303 | 0.0514 |
| LRRC14B | 0.0342 |
| LRRC37A4_2 | 0.0647 |
| LRRTM4 | 0.1939 |
| MACC1 | 0.0857 |
| MANSC1_1 | 0.0982 |
| MCAM | 0.0097 |
| MCART6_1 | 0.1422 |
| MFRP | 0.2177 |
| MIDN | 0.0153 |
| MIR1914 | 0.0808 |
| MIR212 | 0.0853 |
| MIR571 | 0.0334 |
| MIR576 | 0.1152 |
| MIR654 | 0.0177 |
| MIR942 | 0.164 |
| MMP12_1 | 0.0916 |
| MYCN_2 | 0.0695 |
| MYL92 | 0.0799 |
| MYOHD1 | 0.0117 |
| NFATC3_5 | 0.0671 |
| NFATC4 | 0.0823 |
| NLRP9 | 0.1661 |
| NOVA2 | 0.0826 |
| NP | 0.1029 |
| NR6A1_2 | 0.1271 |
| NRXN3_3 | 0.1027 |
| NT5DC1_2 | 0.1957 |
| NTRK2_3 | 0.0049 |
| NUP155_1 | 0.0236 |
| NYX | 0.152 |
| ODF2_3 | 0.0297 |
| ORC1L | 0.0228 |
| OTUD7A_3 | 0.0029 |
| PANK4 | 0.0488 |
| PDLIM2_2 | 0.2142 |
| PHYH_1 | 0.1809 |
| PIGA_1 | 0.0139 |
| PITX2_1 | 0.1438 |
| PKN1_3 | 0.0425 |
| PLAC9 | 0.195 |
| PLEKHG5_5 | 0.0082 |
| PLSCR4 | 0.2028 |
| PMEPA1_4 | 0.1561 |
| PNMA5 | 0.139 |
| PPAPDC1A | 0.1385 |
| PRAMEF5 | 0.0036 |
| PRKAA2 | 0.0733 |
| PSMC6_1 | 0.0134 |
| RAD54B_2 | 0.1888 |
| RAP1A_1 | 0.1863 |
| RARA_3 | 0.0858 |
| RARG | 0.0523 |
| RNASEK | 0.0758 |
| RNF7_1 | 0.0728 |
| ROD1_1 | 0.161 |
| SATB2 | 0.0481 |
| SBSN | 0.0085 |
| SCXB | 0.0173 |
| SEC22C_3 | 0.1026 |
| SELENBP1 | 0.1471 |
| SERPINB2_2 | 0.0274 |
| SERPINB5 | 0.1756 |
| SFN | 0.0273 |
| SFRS4 | 0.0366 |
| SHC1_3 | 0.0575 |
| SLC23A1_2 | 0.0786 |
| SLC25A34 | 0.1716 |
| SLC4A5_3 | 0.0558 |
| SLC9A10 | 0.0634 |
| SNORD93 | 0.1581 |
| SOX2_1 | 0.0701 |
| STC1 | 0.0163 |
| STC2 | 0.1143 |
| STYX_2 | 0.046 |
| SYTL3 | 0.0239 |
| TAF15_1 | 0.0431 |
| TCEAL8_1 | 0.0643 |
| THBS3 | 0.0545 |
| TIMP2_2 | 0.0629 |
| TM2D3_2 | 0.0819 |
| TMEM52 | 0.0349 |
| TMEM62 | 0.0479 |
| TNFRSF18_1 | 0.2089 |
| TNNT2_1 | 0.0031 |
| TOMM20L | 0.0204 |
| TPM2_2 | 0.1781 |
| TRIM58 | 0.0987 |
| UBR7_1 | 0.0557 |
| UBR7_2 | 0.0978 |

TABLE 62-continued

| | |
|---|---|
| WARS_2 | 0.1332 |
| WDR76 | 0.1104 |
| XBP1_2 | 0.0486 |
| XRN2_1 | 0.0238 |
| YARS2 | 0.2485 |
| ZNF75D_2 | 0.1364 |
| ZSWIM4_2 | 0.1491 |
| figo_numeric | 0.0153 |
| hist_rev_SBOT | 0.0486 |
| surg_outcome | 0.0178 |

TABLE 63

| | |
|---|---|
| ABHD3 | 0.0521 |
| ADAM17_2 | 0.2213 |
| ADAMTS1 | 0.1658 |
| ALS2CL_3 | 0.0907 |
| ANO7_3 | 0.0587 |
| ANTXR1_4 | 0.0342 |
| ARL6IP1_1 | 0.0856 |
| ARMCX3_2 | 0.1902 |
| ATXN10_1 | 0.169 |
| AXL_1 | 0.1015 |
| BAI1_3 | 0.0418 |
| BCAS1_1 | 0.3217 |
| BDNF_2 | 0.1077 |
| BMPR1A | 0.1048 |
| BTF3_3 | 0.0958 |
| C10orf116 | 0.018 |
| C11orf24 | 0.2043 |
| C11orf49_3 | 0.1259 |
| C14orf102_2 | 0.1233 |
| C14orf109_2 | 0.0707 |
| C17orf106 | 0.2223 |
| C17orf58_2 | 0.0469 |
| C17orf58_3 | 0.0282 |
| C18orf56 | 0.0395 |
| C1orf168 | 0.0333 |
| C1orf64 | 0.1125 |
| C8orf79_1 | 0.0242 |
| CASP8AP2 | 0.1624 |
| CCL13 | 0.1381 |
| CCR2_3 | 0.0827 |
| CD34_1 | 0.0188 |
| CDC42BPA_2 | 0.0152 |
| CDC42SE2_2 | 0.0308 |
| CLDN6 | 0.1201 |
| CREB5_2 | 0.0291 |
| CRYBA1 | 0.0182 |
| CXCL13 | 0.0753 |
| CYB5R3_2 | 0.1815 |
| CYP1A2 | 0.0613 |
| DBNDD2 | 0.097 |
| DNAH11 | 0.0381 |
| DNMT3L_2 | 0.0235 |
| DOCK7_1 | 0.107 |
| DSC3_1 | 0.0715 |
| DUT_3 | 0.1158 |
| EEF1E1_1 | 0.0878 |
| EMP1 | 0.1131 |
| ENO1 | 0.176 |
| ENPEP_2 | 0.135 |
| EPHB1 | 0.049 |
| EPYC | 0.0465 |
| ERI2_2 | 0.2842 |
| ESPNL | 0.0387 |
| EZH2_1 | 0.0596 |
| FAM13AOS | 0.0447 |
| FAM187B_2 | 0.0197 |
| FAM70A_1 | 0.0648 |
| FBXO48_2 | 0.2762 |
| FKBP10 | 0.0741 |
| FLJ33360 | 0.0615 |
| FLJ43752 | 0.2033 |
| FMNL3_2 | 0.0514 |
| FOSB | 0.1914 |
| FOSL2 | 0.019 |

TABLE 63-continued

| | |
|---|---|
| FOXN1 | 0.2729 |
| GAD1_2 | 0.0204 |
| GBE1 | 0.039 |
| GBP7 | 0.1183 |
| GJA5_1 | 0.0613 |
| GMNN | 0.1067 |
| GSR_2 | 0.0344 |
| HBA2 | 0.2027 |
| HCFC1R1_1 | 0.0491 |
| HDAC7_2 | 0.0076 |
| HDLBP_3 | 0.0949 |
| HIC1 | 0.0549 |
| HPRT1_1 | 0.1298 |
| HPS4_1 | 0.0745 |
| HR_1 | 0.0561 |
| HSD11B1_1 | 0.0839 |
| ICAM2 | 0.0668 |
| ICAM4_1 | 0.2766 |
| IL1RAP_2 | 0.0508 |
| IQCA1_2 | 0.035 |
| KCNIP3_1 | 0.0981 |
| KCNQ2_1 | 0.1202 |
| KIF3C | 0.1849 |
| KRT80_2 | 0.1107 |
| KRTAP10.10_2 | 0.0184 |
| L3MBTL2_3 | 0.0377 |
| LBH_2 | 0.1068 |
| LENEP | 0.2203 |
| LGI3 | 0.1224 |
| LOC492303 | 0.016 |
| LRRC14B | 0.0183 |
| LRRC37A4_2 | 0.0651 |
| LRRTM4 | 0.1744 |
| MACC1 | 0.1333 |
| MANSC1_1 | 0.1395 |
| MCAM | 0.0204 |
| MCART6_1 | 0.1343 |
| MFRP | 0.2165 |
| MIDN | 0.0501 |
| MIR1914 | 0.0644 |
| MIR212 | 0.0935 |
| MIR571 | 0.0218 |
| MIR576 | 0.1186 |
| MIR654 | 0.0517 |
| MIR942 | 0.1342 |
| MMP12_1 | 0.1318 |
| MYCN_2 | 0.1544 |
| MYOHD1 | 0.1013 |
| NFATC3_5 | 0.02 |
| NFATC4 | 0.0566 |
| NLRP9 | 0.1726 |
| NOVA2 | 0.1196 |
| NP | 0.0854 |
| NR6A1_2 | 0.1466 |
| NRXN3_3 | 0.0945 |
| NT5DC1_2 | 0.1696 |
| NTRK2_3 | 0.0102 |
| NUP155_1 | 0.0427 |
| NYX | 0.1433 |
| ODF2_3 | 0.0085 |
| ORC1L | 0.0203 |
| OTUD7A_3 | 0.0279 |
| PANK4 | 0.0644 |
| PDLIM2_2 | 0.2384 |
| PHYH_1 | 0.195 |
| PIGA_1 | 0.0055 |
| PITX2_1 | 0.1038 |
| PKN1_3 | 0.0155 |
| PLAC9 | 0.2659 |
| PLEKHG5_5 | 0.0393 |
| PLSCR4 | 0.1544 |
| PMEPA1_4 | 0.1409 |
| PNMA5 | 0.1132 |
| PPAPDC1A | 0.1394 |
| PRAMEF5 | 0.0069 |
| PRKAA2 | 0.114 |
| PSMC6_1 | 0.0056 |
| RAD54B_2 | 0.177 |
| RAP1A_1 | 0.2181 |
| RARA_3 | 0.0911 |

TABLE 63-continued

| | |
|---|---|
| RARG | 0.048 |
| RNASEK | 0.0568 |
| RNF7_1 | 0.0075 |
| ROD1_1 | 0.2206 |
| SATB2 | 0.0553 |
| SBSN | 0.0583 |
| SCXB | 0.0096 |
| SEC22C_3 | 0.1209 |
| SELENBP1 | 0.1867 |
| SERPINB2_2 | 0.002 |
| SERPINB5 | 0.1796 |
| SFN | 0.0009 |
| SFRS4 | 0.0136 |
| SHC1_3 | 0.0791 |
| SLC23A1_2 | 0.1301 |
| SLC25A34 | 0.1559 |
| SLC4A5_3 | 0.0704 |
| SLC9A10 | 0.0729 |
| SNORD93 | 0.168 |
| SOX2_1 | 0.075 |
| STC1 | 0.0108 |
| STC2 | 0.1222 |
| STYX_2 | 0.0447 |
| SYTL3 | 0.0052 |
| TAF15_1 | 0.0316 |
| TCEAL8_1 | 0.0254 |
| THBS3 | 0.087 |
| THY1 | 0.0544 |
| TM2D3_2 | 0.1096 |
| TMEM52 | 0.0147 |
| TMEM62 | 0.0156 |
| TNFRSF18_1 | 0.2511 |
| TNNT2_1 | 0.0045 |
| TOMM20L | 0.0468 |
| TPM2_2 | 0.1701 |
| TRIM58 | 0.1021 |
| UBR7_1 | 0.0619 |
| UBR7_2 | 0.124 |
| WARS_2 | 0.1597 |
| XBP1_2 | 0.1142 |
| XRN2_1 | 0.0237 |
| YARS2 | 0.0143 |
| ZNF75D_2 | 0.1286 |
| ZSWIM4_2 | 0.1584 |
| figo_numeric | 0.0119 |
| hist_rev_SBOT | 0.0486 |
| surg_outcome | 0.0033 |

TABLE 64

| | |
|---|---|
| ABHD3 | 0.0518 |
| ADAM17_2 | 0.2189 |
| ADAMTS1 | 0.1627 |
| ALS2CL_3 | 0.0917 |
| ANO7_3 | 0.0549 |
| ANTXR1_4 | 0.0264 |
| ARL6IP1_1 | 0.0851 |
| ARMCX3_2 | 0.1895 |
| ATXN10_1 | 0.1694 |
| AXL_1 | 0.0998 |
| BAI1_3 | 0.0398 |
| BCAS1_1 | 0.321 |
| BDNF_2 | 0.1038 |
| BMPR1A | 0.1059 |
| BTF3_3 | 0.0957 |
| C10orf116 | 0.0167 |
| C11orf24 | 0.2026 |
| C11orf49_3 | 0.1251 |
| C14orf102_2 | 0.1184 |
| C14orf109_2 | 0.0692 |
| C17orf106 | 0.222 |
| C17orf58_2 | 0.0519 |
| C17orf58_3 | 0.0265 |
| C18orf56 | 0.0411 |
| C1orf168 | 0.0355 |
| C1orf64 | 0.1107 |
| C8orf79_1 | 0.0309 |

TABLE 64-continued

| | |
|---|---|
| CASP8AP2 | 0.1629 |
| CCL13 | 0.1306 |
| CCR2_3 | 0.084 |
| CD34_1 | 0.0134 |
| CDC42BPA_2 | 0.0136 |
| CDC42SE2_2 | 0.0336 |
| CLDN6 | 0.1165 |
| CREB5_2 | 0.0321 |
| CRYBA1 | 0.0272 |
| CXCL13 | 0.0753 |
| CYB5R3_2 | 0.1815 |
| CYP1A2 | 0.0617 |
| DBNDD2 | 0.1013 |
| DNAH11 | 0.0384 |
| DNMT3L_2 | 0.0252 |
| DOCK7_1 | 0.1162 |
| DSC3_1 | 0.0776 |
| DUT_3 | 0.1168 |
| EEF1E1_1 | 0.0889 |
| EMP1 | 0.1167 |
| ENO1 | 0.1741 |
| ENPEP_2 | 0.1352 |
| EPHB1 | 0.0453 |
| EPYC | 0.0446 |
| ERI2_2 | 0.2847 |
| ESPNL | 0.0365 |
| EZH2_1 | 0.0564 |
| FAM13AOS | 0.047 |
| FAM187B_2 | 0.0205 |
| FAM70A_1 | 0.0644 |
| FBXO48_2 | 0.2709 |
| FKBP10 | 0.0741 |
| FLJ33360 | 0.0643 |
| FLJ43752 | 0.1985 |
| FMNL3_2 | 0.0507 |
| FOSB | 0.1971 |
| FOSL2 | 0.0196 |
| FOXN1 | 0.2786 |
| GAD1_2 | 0.0218 |
| GBE1 | 0.0391 |
| GBP7 | 0.1191 |
| GJA5_1 | 0.0582 |
| GMNN | 0.1094 |
| GSR_2 | 0.0327 |
| HBA2 | 0.1975 |
| HCFC1R1_1 | 0.0469 |
| HDAC7_2 | 0.0034 |
| HDLBP_3 | 0.0921 |
| HIC1 | 0.0553 |
| HPRT1_1 | 0.1329 |
| HPS4_1 | 0.0734 |
| HR_1 | 0.0529 |
| HSD11B1_1 | 0.0836 |
| ICAM2 | 0.0729 |
| ICAM4_1 | 0.2734 |
| IL1RAP_2 | 0.0497 |
| IQCA1_2 | 0.0329 |
| KCNIP3_1 | 0.0986 |
| KCNQ2_1 | 0.1228 |
| KIF3C | 0.1861 |
| KRT80_2 | 0.109 |
| KRTAP10.10_2 | 0.0175 |
| L3MBTL2_3 | 0.038 |
| LBH_2 | 0.1054 |
| LENEP | 0.2222 |
| LGI3 | 0.1125 |
| LOC492303 | 0.0128 |
| LRRC14B | 0.0167 |
| LRRC37A4_2 | 0.0674 |
| LRRTM4 | 0.1748 |
| MACC1 | 0.1373 |
| MANSC1_1 | 0.1381 |
| MCAM | 0.0174 |
| MCART6_1 | 0.1343 |
| MFRP | 0.2201 |
| MIDN | 0.0447 |
| MIR1914 | 0.0616 |
| MIR212 | 0.0947 |
| MIR571 | 0.0221 |
| MIR576 | 0.1206 |

TABLE 64-continued

| | |
|---|---|
| MIR654 | 0.0489 |
| MIR942 | 0.1246 |
| MMP12__1 | 0.1311 |
| MYCN__2 | 0.1546 |
| MYL9__2 | 0.1005 |
| MYOHD1 | 0.0188 |
| NFATC3__5 | 0.0576 |
| NFATC4 | 0.0597 |
| NLRP9 | 0.1731 |
| NOVA2 | 0.1204 |
| NP | 0.0871 |
| NR6A1__2 | 0.1488 |
| NRXN3__3 | 0.0968 |
| NT5DC1__2 | 0.1741 |
| NTRK2__3 | 0.0075 |
| NUP155__1 | 0.0426 |
| NYX | 0.1473 |
| ODF2__3 | 0.0072 |
| ORC1L | 0.0217 |
| OTUD7A__3 | 0.0268 |
| PANK4 | 0.0671 |
| PDLIM2__2 | 0.2424 |
| PHYH__1 | 0.1974 |
| PIGA__1 | 0.0054 |
| PITX2__1 | 0.1021 |
| PKN1__3 | 0.0122 |
| PLAC9 | 0.2658 |
| PLEKHG5__5 | 0.0358 |
| PLSCR4 | 0.1513 |
| PMEPA1__4 | 0.1402 |
| PNMA5 | 0.109 |
| PPAPDC1A | 0.143 |
| PRAMEF5 | 0.0032 |
| PRKAA2 | 0.1167 |
| PSMC6__1 | 0.0032 |
| RAD54B__2 | 0.176 |
| RAP1A__1 | 0.2136 |
| RARA__3 | 0.0892 |
| RARG | 0.0474 |
| RNASEK | 0.0544 |
| RNF7__1 | 0.009 |
| ROD1__1 | 0.2245 |
| SATB2 | 0.0589 |
| SBSN | 0.0593 |
| SCXB | 0.0082 |
| SEC22C__3 | 0.1152 |
| SELENBP1 | 0.1838 |
| SERPINB2__2 | 0.0038 |
| SERPINB5 | 0.1773 |
| SFN | 0.0004 |
| SFRS4 | 0.0137 |
| SHC1__3 | 0.0765 |
| SLC23A1__2 | 0.1317 |
| SLC25A34 | 0.1593 |
| SLC4A5__3 | 0.0728 |
| SLC9A10 | 0.0689 |
| SNORD93 | 0.1656 |
| SOX2__1 | 0.076 |
| STC1 | 0.0071 |
| STC2 | 0.121 |
| STYX__2 | 0.047 |
| SYTL3 | 0.0062 |
| TAF15__1 | 0.0216 |
| TCEAL8__1 | 0.0226 |
| THBS3 | 0.0857 |
| TM2D3__2 | 0.0566 |
| TMEM52 | 0.1043 |
| TMEM62 | 0.016 |
| TNFRSF18__1 | 0.2581 |
| TNNT2__1 | 0.0055 |
| TOMM20L | 0.0454 |
| TPM2__2 | 0.1698 |
| TRIM58 | 0.1002 |
| UBR7__1 | 0.0613 |
| UBR7__2 | 0.1191 |
| WARS__2 | 0.1558 |
| XBP1__2 | 0.1152 |
| XRN2__1 | 0.0266 |
| YARS2 | 0.0116 |
| ZNF75D__2 | 0.1286 |
| ZSWIM4__2 | 0.1584 |
| figo__numeric | 0.0112 |
| hist__rev__SBOT | 0.048 |
| surg__outcome | 0.0076 |

TABLE 65

| | |
|---|---|
| ABHD3 | 0.0753 |
| ADAM17__2 | 0.2396 |
| ADAMTS1 | 0.1705 |
| ALS2CL__3 | 0.1143 |
| ANO7__3 | 0.0691 |
| ARL6IP1__1 | 0.0309 |
| ARMCX3__2 | 0.0889 |
| ATXN10__1 | 0.1967 |
| AXL__1 | 0.121 |
| BAI1__3 | 0.0386 |
| BCAS1__1 | 0.3353 |
| BDNF__2 | 0.1212 |
| BMPR1A | 0.1149 |
| BTF3__3 | 0.1092 |
| C10orf116 | 0.0388 |
| C11orf24 | 0.1998 |
| C11orf49__3 | 0.1186 |
| C14orf102__2 | 0.1322 |
| C14orf109__2 | 0.0672 |
| C17orf106 | 0.2476 |
| C17orf58__2 | 0.0327 |
| C17orf58__3 | 0.0286 |
| C18orf56 | 0.0457 |
| C1orf168 | 0.0373 |
| C8orf79__1 | 0.1182 |
| CALD1__2 | 0.0273 |
| CASP8AP2 | 0.1379 |
| CCL13 | 0.0946 |
| CCR2__3 | 0.0303 |
| CD34__1 | 0.0016 |
| CDC42BPA__2 | 0.0235 |
| CDC42SE2__2 | 0.0312 |
| CLDN6 | 0.0946 |
| CREB5__2 | 0.0268 |
| CRYBA1 | 0.0296 |
| CXCL13 | 0.0857 |
| CYB5R3__2 | 0.1914 |
| CYP1A2 | 0.0552 |
| DBNDD2 | 0.1041 |
| DNAH11 | 0.0499 |
| DNMT3L__2 | 0.0189 |
| DOCK7__1 | 0.1343 |
| DSC3__1 | 0.07 |
| DUT__3 | 0.1147 |
| EEF1E1__1 | 0.0886 |
| EIF4ENIF1 | 0.1286 |
| EMP1 | 0.1811 |
| ENO1 | 0.1365 |
| ENPEP__2 | 0.0192 |
| EPHB1 | 0.0149 |
| EPYC | 0.038 |
| ERI2__2 | 0.3036 |
| ESPNL | 0.04 |
| EZH2__1 | 0.0764 |
| FAM13AOS | 0.0466 |
| FAM187B__2 | 0.0017 |
| FAM70A__1 | 0.0953 |
| FBXO48__2 | 0.2665 |
| FGF5__1 | 0.0676 |
| FKBP10 | 0.0396 |
| FLJ33360 | 0.2129 |
| FLJ43752 | 0.0758 |
| FMNL3__2 | 0.0516 |
| FMOD | 0.2045 |
| FOSB | 0.0182 |
| FOSL2 | 0.2805 |
| FOXN1 | 0.0323 |
| GAD1__2 | 0.0022 |
| GBE1 | 0.0459 |
| GBP7 | 0.1193 |

TABLE 65-continued

| | |
|---|---|
| GJA5__1 | 0.0518 |
| GMNN | 0.0993 |
| GSR__2 | 0.0493 |
| HBA2 | 0.2062 |
| HCFC1R1__1 | 0.0488 |
| HDAC7__2 | 0.0028 |
| HDLBP__3 | 0.0961 |
| HIC1 | 0.0421 |
| HPRT1__1 | 0.149 |
| HPS4__1 | 0.071 |
| HR__1 | 0.0428 |
| HSD11B1__1 | 0.1035 |
| ICAM2 | 0.0492 |
| ICAM4__1 | 0.2806 |
| IL1RAP__2 | 0.0593 |
| IQCA1__2 | 0.019 |
| KCNIP3__1 | 0.1084 |
| KCNQ2__1 | 0.1307 |
| KIF3C | 0.1841 |
| KRT80__2 | 0.1226 |
| KRTAP10.10__2 | 0.0244 |
| L3MBTL2__3 | 0.0279 |
| LBH__2 | 0.0923 |
| LENEP | 0.2273 |
| LGI3 | 0.1388 |
| LOC492303 | 0.0409 |
| LRRC14B | 0.0252 |
| LRRC37A4__2 | 0.0573 |
| LRRTM4 | 0.1777 |
| MACC1 | 0.1394 |
| MANSC1__1 | 0.1346 |
| MCAM | 0.0132 |
| MCART6__1 | 0.1464 |
| MFRP | 0.2275 |
| MIDN | 0.0484 |
| MIR1914 | 0.0643 |
| MIR212 | 0.1025 |
| MIR571 | 0.0364 |
| MIR576 | 0.0969 |
| MIR654 | 0.057 |
| MIR942 | 0.1471 |
| MMP12__1 | 0.1336 |
| MYCN__2 | 0.1438 |
| NFATC3__5 | 0.1006 |
| NFATC4 | 0.0092 |
| NLRP9 | 0.0491 |
| NOVA2 | 0.1101 |
| NP | 0.0838 |
| NR6A1__2 | 0.1477 |
| NRXN3__3 | 0.0935 |
| NT5DC1__2 | 0.2034 |
| NTRK2__3 | 0.0026 |
| NUP155__1 | 0.0708 |
| NYX | 0.1845 |
| ODF2__3 | 0.0228 |
| ORC1L | 0.0184 |
| OTUD7A__3 | 0.0362 |
| PANK4 | 0.0621 |
| PDLIM2__2 | 0.2458 |
| PHYH__1 | 0.1966 |
| PIGA__1 | 0.0049 |
| PITX2__1 | 0.0986 |
| PKN1__3 | 0.0131 |
| PLAC9 | 0.2609 |
| PLEKHG5__5 | 0.0169 |
| PLSCR4 | 0.1507 |
| PMEPA1__4 | 0.1306 |
| PNMA5 | 0.1068 |
| PPAPDC1A | 0.1249 |
| PRAMEF5 | 0.0124 |
| PRKAA2 | 0.1392 |
| PSMC6__1 | 0.0212 |
| RAD54B__2 | 0.1797 |
| RAP1A__1 | 0.2124 |
| RARA__3 | 0.0871 |
| RARG | 0.045 |
| RNASEK | 0.071 |
| RNF7__1 | 0.0109 |
| ROD1__1 | 0.2195 |
| SATB2 | 0.0557 |
| SBSN | 0.0468 |
| SCXB | 0.0131 |
| SEC22C__3 | 0.1123 |
| SELENBP1 | 0.1921 |
| SERPINA12 | 0.0305 |
| SERPINB2__2 | 0.2064 |
| SERPINB5 | 0.0096 |
| SFN | 0.0559 |
| SFRS4 | 0.0362 |
| SHC1__3 | 0.0638 |
| SLC23A1__2 | 0.1368 |
| SLC25A34 | 0.1838 |
| SLC4A5__3 | 0.0834 |
| SLC9A10 | 0.0815 |
| SNORD93 | 0.166 |
| SOX2__1 | 0.0836 |
| STC1 | 0.0138 |
| STC2 | 0.1258 |
| STYX__2 | 0.0528 |
| SYTL3 | 0.0215 |
| TAF15__1 | 0.0031 |
| TCEAL8__1 | 0.0381 |
| THBS3 | 0.0936 |
| TM2D3__2 | 0.0623 |
| TMEM52 | 0.0849 |
| TMEM62 | 0.0072 |
| TNFRSF18__1 | 0.2664 |
| TNNT2__1 | 0.0068 |
| TOMM20L | 0.0409 |
| TPM2__2 | 0.1741 |
| TRIM58 | 0.1153 |
| UBR7__1 | 0.0683 |
| UBR7__2 | 0.1266 |
| WARS__2 | 0.1377 |
| XBP1__2 | 0.1186 |
| XRN2__1 | 0.0488 |
| YARS2 | 0.0002 |
| ZNF75D__2 | 0.1579 |
| ZSWIM4__2 | 0.1639 |
| figo__numeric | 0.0091 |
| hist__rev__SBOT | 0.0715 |
| surg__outcome | 0.0105 |

TABLE 66

| | |
|---|---|
| ABHD3 | 0.0813 |
| ADAM17__2 | 0.2417 |
| ADAMTS1 | 0.168 |
| ALS2CL__3 | 0.0825 |
| ANO7__3 | 0.036 |
| ARL6IP1__1 | 0.0313 |
| ARMCX3__2 | 0.0864 |
| ATXN10__1 | 0.1628 |
| AXL__1 | 0.0992 |
| BAI1__3 | 0.0221 |
| BCAS1__2 | 0.3397 |
| BDNF__2 | 0.0781 |
| BMPR1A | 0.1331 |
| BTF3__3 | 0.136 |
| C10orf116 | 0.0124 |
| C11orf24 | 0.2051 |
| C11orf49__3 | 0.1131 |
| C14orf102__2 | 0.1066 |
| C14orf109__2 | 0.0758 |
| C17orf106 | 0.2221 |
| C17orf58__2 | 0.0306 |
| C17orf58__3 | 0.0163 |
| C18orf56 | 0.0649 |
| C1orf168 | 0.0484 |
| C8orf79__1 | 0.1138 |
| CALD1__2 | 0.0301 |
| CASP8AP2 | 0.1358 |
| CCL13 | 0.0983 |
| CCR2__3 | 0.0515 |
| CD34__1 | 0.0251 |
| CDC42BPA__2 | 0.0376 |
| CDC42SE2__2 | 0.0385 |

TABLE 66-continued

| | |
|---|---|
| CLDN6 | 0.1119 |
| CREB5__2 | 0.0019 |
| CRYBA1 | 0.0221 |
| CXCL13 | 0.0917 |
| CYB5R3__2 | 0.1818 |
| CYP1A2 | 0.0482 |
| DBNDD2 | 0.0995 |
| DNAH11 | 0.0463 |
| DNMT3L__2 | 0.0272 |
| DOCK7__1 | 0.1553 |
| DSC3__1 | 0.0949 |
| DUT__3 | 0.1324 |
| EEF1E1__1 | 0.0895 |
| EMP1 | 0.1266 |
| ENO1 | 0.2039 |
| ENPEP__2 | 0.1438 |
| EPHB1 | 0.0327 |
| EPYC | 0.0302 |
| ERI2__2 | 0.3129 |
| ESPNL | 0.0357 |
| EZH2__1 | 0.0926 |
| FAM13AOS | 0.063 |
| FAM187B__2 | 0.0004 |
| FAM70A__1 | 0.0949 |
| FBXO48__2 | 0.2386 |
| FKBP10 | 0.069 |
| FLJ33360 | 0.0282 |
| FLJ43752 | 0.1748 |
| FMNL3__2 | 0.0607 |
| FOSB | 0.1996 |
| FOSL2 | 0.0233 |
| FOXN1 | 0.2601 |
| GAD1__2 | 0.0046 |
| GBE1 | 0.0512 |
| GBP7 | 0.1278 |
| GJA5__1 | 0.0642 |
| GMNN | 0.0978 |
| GSR__2 | 0.0424 |
| HBA2 | 0.1909 |
| HCFC1R1__1 | 0.0432 |
| HDAC7__2 | 0.0172 |
| HDLBP__3 | 0.0735 |
| HIC1 | 0.0085 |
| HPRT1__1 | 0.1391 |
| HPS4__1 | 0.0659 |
| HR__1 | 0.0647 |
| HSD11B1__1 | 0.078 |
| ICAM2 | 0.0414 |
| ICAM4__1 | 0.2728 |
| IL1RAP__2 | 0.0598 |
| IQCA1__2 | 0.0368 |
| KCNIP3__1 | 0.1115 |
| KCNQ2__1 | 0.1224 |
| KIF3C | 0.1817 |
| KRT80__2 | 0.1172 |
| KRTAP10.10__2 | 0.0261 |
| L3MBTL2__3 | 0.0233 |
| LBH__2 | 0.1123 |
| LENEP | 0.2331 |
| LGI3 | 0.105 |
| LOC492303 | 0.0406 |
| LRRC14B | 0.0007 |
| LRRC37A4__2 | 0.0693 |
| LRRTM4 | 0.1472 |
| MACC1 | 0.1316 |
| MANSC1__1 | 0.1065 |
| MCAM | 0.0085 |
| MCART6__1 | 0.1497 |
| MFRP | 0.2506 |
| MIDN | 0.0414 |
| MIR1914 | 0.0747 |
| MIR212 | 0.1086 |
| MIR571 | 0.01 |
| MIR576 | 0.1146 |
| MIR654 | 0.0528 |
| MIR942 | 0.1236 |
| MMP12__1 | 0.1376 |
| MYCN__2 | 0.1554 |
| MYOHD1 | 0.089 |
| NFATC3__5 | 0.0166 |
| NFATC4 | 0.0421 |
| NLRP9 | 0.1783 |
| NOVA2 | 0.1139 |
| NP | 0.1069 |
| NR6A1__2 | 0.134 |
| NRXN3__3 | 0.093 |
| NT5DC1__2 | 0.1888 |
| NTRK2__3 | 0.0016 |
| NUP155__1 | 0.0488 |
| NYX | 0.1773 |
| ODF2__3 | 0.0107 |
| ORC1L | 0.0338 |
| OTUD7A__3 | 0.0255 |
| PANK4 | 0.0548 |
| PDLIM2__2 | 0.2515 |
| PHYH__1 | 0.222 |
| PIGA__1 | 0.0063 |
| PITX2__1 | 0.1173 |
| PKN1__3 | 0.0283 |
| PLAC9 | 0.265 |
| PLEKHG5__5 | 0.0183 |
| PLSCR4 | 0.1345 |
| PMEPA1__4 | 0.1282 |
| PNMA5 | 0.1223 |
| PPAPDC1A | 0.1156 |
| PRAMEF5 | 0.017 |
| PRKAA2 | 0.135 |
| PSMC6__1 | 0.0037 |
| RAD54B__2 | 0.171 |
| RAP1A__1 | 0.2305 |
| RARA__3 | 0.0855 |
| RARG | 0.0603 |
| RNASEK | 0.0682 |
| RNF7__1 | 0.0087 |
| ROD1__1 | 0.2205 |
| SATB2 | 0.0456 |
| SBSN | 0.0511 |
| SCXB | 0.008 |
| SEC22C__3 | 0.119 |
| SELENBP1 | 0.1894 |
| SERPINA12 | 0.0405 |
| SERPINB2__2 | 0.2056 |
| SERPINB5 | 0.0027 |
| SFN | 0.0615 |
| SFRS4 | 0.0519 |
| SHC1__3 | 0.0782 |
| SLC23A1__2 | 0.1363 |
| SLC25A34 | 0.1694 |
| SLC4A5__3 | 0.0799 |
| SLC9A10 | 0.0781 |
| SNORD93 | 0.1573 |
| SOX2__1 | 0.0598 |
| STC1 | 0.012 |
| STC2 | 0.1203 |
| STYX__2 | 0.0493 |
| SYTL3 | 0.0566 |
| TAF15__1 | 0.0065 |
| TCEAL8__1 | 0.0263 |
| THBS3 | 0.0942 |
| TM2D3__2 | 0.0543 |
| TMEM52 | 0.0817 |
| TMEM62 | 0.0063 |
| TNFRSF18__1 | 0.2525 |
| TNNT2__1 | 0.0017 |
| TOMM20L | 0.0423 |
| TPM2__2 | 0.1761 |
| TRIM58 | 0.0982 |
| UBR7__1 | 0.08 |
| UBR7__2 | 0.1363 |
| WARS__2 | 0.1761 |
| XBP1__2 | 0.1363 |
| XRN2__1 | 0.0457 |
| YARS2 | 0.0061 |
| ZNF75D__2 | 0.1561 |
| ZSWIM4__2 | 0.1787 |
| figo__numeric | 0.0268 |
| hist__rev__SBOT | 0.0578 |
| surg__outcome | 0.0025 |

TABLE 67

| | |
|---|---|
| ABHD3 | 0.092 |
| ADAM17_2 | 0.231 |
| ADAMTS1 | 0.1781 |
| ALS2CL_3 | 0.1139 |
| ANO7_3 | 0.0426 |
| ARL6IP1_1 | 0.0235 |
| ARMCX3_2 | 0.0869 |
| ATXN10_1 | 0.1669 |
| AXL_1 | 0.0917 |
| BAI1_3 | 0.0549 |
| BCAS1_1 | 0.3084 |
| BDNF_2 | 0.097 |
| BMPR1A | 0.1162 |
| BTF3_3 | 0.1203 |
| C10orf116 | 0.0551 |
| C11orf24 | 0.1302 |
| C11orf49_3 | 0.1285 |
| C14orf102_2 | 0.095 |
| C14orf109_2 | 0.0665 |
| C17orf106 | 0.2147 |
| C17orf58_2 | 0.0276 |
| C17orf58_3 | 0.0332 |
| C18orf56 | 0.0455 |
| C1orf168 | 0.0363 |
| C1orf64 | 0.1077 |
| C8orf79_1 | 0.0746 |
| CALD1_2 | 0.1468 |
| CASP8AP2 | 0.1247 |
| CCL13 | 0.1081 |
| CCR2_3 | 0.05 |
| CD34_1 | 0.0404 |
| CDC42BPA_2 | 0.0286 |
| CDC42SE2_2 | 0.0053 |
| CLDN6 | 0.1173 |
| CREB5_2 | 0.0098 |
| CRYBA1 | 0.0357 |
| CXCL13 | 0.0825 |
| CYB5R3_2 | 0.1634 |
| CYP1A2 | 0.0648 |
| DBNDD2 | 0.0823 |
| DFFB_2 | 0.0518 |
| DNAH11 | 0.034 |
| DNMT3L_2 | 0.11 |
| DOCK7_1 | 0.0187 |
| DSC3_1 | 0.0559 |
| DUT_3 | 0.1371 |
| EEF1E1_1 | 0.0555 |
| EMP1 | 0.1035 |
| ENO1 | 0.1519 |
| ENPEP_2 | 0.123 |
| EPHB1 | 0.039 |
| EPYC | 0.022 |
| ERI2_2 | 0.2891 |
| ESPNL | 0.0825 |
| EZH2_1 | 0.0708 |
| FAM13AOS | 0.0307 |
| FAM187B_2 | 0.0247 |
| FAM70A_1 | 0.1057 |
| FBXO48_2 | 0.2173 |
| FKBP10 | 0.0998 |
| FLJ33360 | 0.0357 |
| FLJ43752 | 0.1808 |
| FMNL3_2 | 0.0142 |
| FOSB | 0.1906 |
| FOSL2 | 0.0218 |
| FOXN1 | 0.2726 |
| GAD1_2 | 0.0031 |
| GBE1 | 0.0632 |
| GBP7 | 0.1057 |
| GJA5_1 | 0.0456 |
| GMNN | 0.0921 |
| GSR_2 | 0.0269 |
| GUSBL2 | 0.1963 |
| HBA2 | 0.0603 |
| HDAC7_2 | 0.0411 |
| HDLBP_3 | 0.2042 |
| HIC1 | 0.0782 |
| HPRT1_1 | 0.1527 |
| HPS4_1 | 0.0446 |
| HR_1 | 0.0522 |

TABLE 67-continued

| | |
|---|---|
| HSD11B1_1 | 0.0925 |
| ICAM2 | 0.0495 |
| ICAM4_1 | 0.2756 |
| IL1RAP_2 | 0.0619 |
| IQCA1_2 | 0.0244 |
| KCNIP3_1 | 0.0919 |
| KCNQ2_1 | 0.1481 |
| KIF3C | 0.1888 |
| KRT80_2 | 0.0763 |
| KRTAP10.10_2 | 0.0074 |
| L3MBTL2_3 | 0.0295 |
| LBH_2 | 0.104 |
| LENEP | 0.2161 |
| LGI3 | 0.1333 |
| LOC492303 | 0.0501 |
| LRRC14B | 0.0258 |
| LRRC37A4_2 | 0.0699 |
| LRRTM4 | 0.1677 |
| MACC1 | 0.1239 |
| MANSC1_1 | 0.1271 |
| MAPK3_1 | 0.0573 |
| MCAM | 0.0936 |
| MCART6_1 | 0.2165 |
| MFRP | 0.0326 |
| MIDN | 0.0529 |
| MIR1914 | 0.0672 |
| MIR212 | 0.0983 |
| MIR571 | 0.0031 |
| MIR576 | 0.0994 |
| MIR654 | 0.0058 |
| MIR942 | 0.1102 |
| MMP12_1 | 0.1328 |
| MYCN_2 | 0.158 |
| MYOHD1 | 0.0799 |
| NFATC3_5 | 0.0219 |
| NFATC4 | 0.0494 |
| NLRP9 | 0.1568 |
| NOVA2 | 0.0969 |
| NP | 0.0897 |
| NR6A1_2 | 0.1351 |
| NRXN3_3 | 0.0753 |
| NT5DC1_2 | 0.2076 |
| NTRK2_3 | 0.0093 |
| NUP155_1 | 0.0376 |
| NYX | 0.1149 |
| ODF2_3 | 0.0222 |
| ORC1L | 0.0674 |
| OTUD7A_3 | 0.0279 |
| PANK4 | 0.0527 |
| PDLIM2_2 | 0.2283 |
| PHYH_1 | 0.2252 |
| PIGA_1 | 0.0103 |
| PITX2_1 | 0.09 |
| PKN1_3 | 0.0565 |
| PLAC9 | 0.2524 |
| PLEKHG5_5 | 0.0184 |
| PLSCR4 | 0.1682 |
| PMEPA1_4 | 0.1253 |
| PNMA5 | 0.1472 |
| PPAPDC1A | 0.1119 |
| PRAMEF5 | 0.0337 |
| PRKAA2 | 0.1159 |
| PSMC6_1 | 0.008 |
| RAD54B_2 | 0.1972 |
| RAP1A_1 | 0.2178 |
| RARA_3 | 0.0843 |
| RARG | 0.0129 |
| RNASEK | 0.0588 |
| RNF7_1 | 0.0207 |
| ROD1_1 | 0.2203 |
| SATB2 | 0.0515 |
| SBSN | 0.055 |
| SCXB | 0.0067 |
| SEC22C_3 | 0.1065 |
| SELENBP1 | 0.1878 |
| SERPINB2_2 | 0.0114 |
| SERPINB5 | 0.2086 |
| SFN | 0.0129 |
| SFRS4 | 0.0448 |
| SHC1_3 | 0.1023 |

TABLE 67-continued

| | |
|---|---|
| SLC23A1__2 | 0.0999 |
| SLC25A34 | 0.1057 |
| SLC4A5__3 | 0.0804 |
| SLC9A10 | 0.0886 |
| SNORD93 | 0.1509 |
| SOX2__1 | 0.062 |
| STC1 | 0.011 |
| STC2 | 0.0917 |
| STYX__2 | 0.0541 |
| SYTL3 | 0.0019 |
| TAF15__1 | 0.0193 |
| TCEAL8__1 | 0.0543 |
| THBS3 | 0.0886 |
| TM2D3__2 | 0.0481 |
| TM9SF4 | 0.0564 |
| TMEM52 | 0.0012 |
| TMEM62 | 0.2507 |
| TNFRSF18__1 | 0.0635 |
| TNNT2__1 | 0.0045 |
| TOMM20L | 0.0402 |
| TPM2__2 | 0.1653 |
| TRIM58 | 0.1041 |
| UBR7__1 | 0.0374 |
| UBR7__2 | 0.1358 |
| WARS__2 | 0.1819 |
| XBP1__2 | 0.1673 |
| XRN2__1 | 0.0194 |
| YARS2 | 0.002 |
| ZNF75D__2 | 0.1469 |
| ZSWIM4__2 | 0.1592 |
| figo__numeric | 0.0419 |
| hist__rev__SBOT | 0.0451 |
| surg__outcome | 0.017 |

TABLE 68

| | |
|---|---|
| ABHD3 | 0.0643 |
| ADAM17__2 | 0.2333 |
| ADAMTS1 | 0.1738 |
| ALS2CL__3 | 0.1042 |
| ANO7__3 | 0.0661 |
| ARL6IP1__1 | 0.0312 |
| ARMCX3__2 | 0.0817 |
| ATXN10__1 | 0.2039 |
| AXL__1 | 0.1044 |
| BAI1__3 | 0.0254 |
| BCAS1__1 | 0.3278 |
| BDNF__2 | 0.1062 |
| BMPR1A | 0.1109 |
| BTF3__3 | 0.1034 |
| C10orf116 | 0.0285 |
| C11orf24 | 0.1719 |
| C11orf49__3 | 0.1344 |
| C14orf102__2 | 0.1273 |
| C14orf109__2 | 0.0723 |
| C17orf106 | 0.236 |
| C17orf58__2 | 0.039 |
| C17orf58__3 | 0.0258 |
| C18orf56 | 0.0357 |
| C1orf168 | 0.029 |
| C1orf64 | 0.1061 |
| C8orf79__1 | 0.0282 |
| CASP8AP2 | 0.1462 |
| CCL13 | 0.129 |
| CCR2__3 | 0.0868 |
| CD34__1 | 0.015 |
| CDC42BPA__2 | 0.0287 |
| CDC42SE2__2 | 0.0189 |
| CLDN6 | 0.1121 |
| CREB5__2 | 0.0152 |
| CRYBA1 | 0.0211 |
| CXCL13 | 0.0763 |
| CYB5R3__2 | 0.1894 |
| CYP1A2 | 0.0571 |
| DBNDD2 | 0.1074 |
| DNAH11 | 0.0426 |
| DNMT3L__2 | 0.0252 |

TABLE 68-continued

| | |
|---|---|
| DOCK7__1 | 0.1382 |
| DSC3__1 | 0.0691 |
| DUT__3 | 0.1237 |
| EEF1E1__1 | 0.0875 |
| EMP1 | 0.1139 |
| ENO1 | 0.1828 |
| ENPEP__2 | 0.1387 |
| EPHB1 | 0.0428 |
| EPYC | 0.0377 |
| ERI2__2 | 0.2923 |
| ESPNL | 0.0366 |
| EZH2__1 | 0.0721 |
| FAM13AOS | 0.0541 |
| FAM187B__2 | 0.0161 |
| FAM70A__1 | 0.0771 |
| FBXO48__2 | 0.2613 |
| FKBP10 | 0.0654 |
| FLJ33360 | 0.0503 |
| FLJ43752 | 0.1879 |
| FMNL3__2 | 0.0375 |
| FOSB | 0.1977 |
| FOSL2 | 0.0275 |
| FOXN1 | 0.2655 |
| GAD1__2 | 0.0265 |
| GBE1 | 0.0413 |
| GBP7 | 0.1329 |
| GJA5__1 | 0.0497 |
| GMNN | 0.0972 |
| GSR__2 | 0.0357 |
| HBA2 | 0.2004 |
| HCFC1R1__1 | 0.0523 |
| HDAC7__2 | 0.0141 |
| HDLBP__3 | 0.1047 |
| HIC1 | 0.0469 |
| HPRT1__1 | 0.1578 |
| HPS4__1 | 0.0647 |
| HR__1 | 0.0449 |
| HSD11B1__1 | 0.0867 |
| ICAM2 | 0.0554 |
| ICAM4__1 | 0.2771 |
| IL1RAP__2 | 0.0553 |
| IQCA1__2 | 0.0313 |
| KCNIP3__1 | 0.1019 |
| KCNQ2__1 | 0.128 |
| KIF3C | 0.1851 |
| KRT80__2 | 0.1075 |
| KRTAP10.10__2 | 0.0196 |
| L3MBTL2__3 | 0.0353 |
| LBH__2 | 0.0987 |
| LENEP | 0.228 |
| LGI3 | 0.1153 |
| LOC492303 | 0.0278 |
| LRRC14B | 0.0144 |
| LRRC37A4__2 | 0.0612 |
| LRRTM4 | 0.1651 |
| MACC1 | 0.1255 |
| MANSC1__1 | 0.1413 |
| MCAM | 0.0155 |
| MCART6__1 | 0.1327 |
| MFRP | 0.2201 |
| MIDN | 0.0466 |
| MIR1914 | 0.0738 |
| MIR212 | 0.1083 |
| MIR571 | 0.034 |
| MIR576 | 0.1089 |
| MIR654 | 0.0541 |
| MIR942 | 0.1201 |
| MMP12__1 | 0.1355 |
| MYCN__2 | 0.1427 |
| MYL9__2 | 0.0941 |
| MYOHD1 | 0.0068 |
| NFATC3__5 | 0.0528 |
| NFATC4 | 0.0555 |
| NLRP9 | 0.1795 |
| NOVA2 | 0.1188 |
| NP | 0.0934 |
| NR6A1__2 | 0.1526 |
| NRXN3__3 | 0.0987 |
| NT5DC1__2 | 0.1812 |
| NTRK2__3 | 0.001 |

TABLE 68-continued

| | |
|---|---|
| NUP155_1 | 0.0463 |
| NYX | 0.171 |
| ODF2_3 | 0.0045 |
| ORC1L | 0.033 |
| OTUD7A_3 | 0.0278 |
| PANK4 | 0.063 |
| PDLIM2_2 | 0.2405 |
| PHYH_1 | 0.1978 |
| PIGA_1 | 0.0045 |
| PITX2_1 | 0.0862 |
| PKN1_3 | 0.0166 |
| PLAC9 | 0.2593 |
| PLEKHG5_5 | 0.0354 |
| PLSCR4 | 0.1759 |
| PMEPA1_4 | 0.1183 |
| PNMA5 | 0.1235 |
| PPAPDC1A | 0.13 |
| PRAMEF5 | 0.0112 |
| PRKAA2 | 0.1334 |
| PSMC6_1 | 0.0051 |
| RAD54B_2 | 0.1858 |
| RAP1A_1 | 0.2178 |
| RARA_3 | 0.0893 |
| RARG | 0.0478 |
| RNASEK | 0.0584 |
| RNF7_1 | 0.0139 |
| ROD1_1 | 0.2167 |
| SATB2 | 0.0611 |
| SBSN | 0.0707 |
| SCXB | 0.004 |
| SEC22C_3 | 0.1185 |
| SELENBP1 | 0.1939 |
| SERPINB2_2 | 0.0093 |
| SERPINB5 | 0.1987 |
| SFN | 0.0093 |
| SFRS4 | 0.0288 |
| SHC1_3 | 0.0719 |
| SLC23A1_2 | 0.14 |
| SLC25A34 | 0.1602 |
| SLC4A5_3 | 0.084 |
| SLC9A10 | 0.0844 |
| SNORD93 | 0.1626 |
| SOX2_1 | 0.0747 |
| STC1 | 0.0014 |
| STC2 | 0.1297 |
| STYX_2 | 0.0473 |
| SYTL3 | 0.0084 |
| TAF15_1 | 0.0097 |
| TCEAL8_1 | 0.0403 |
| THBS3 | 0.0982 |
| THY1 | 0.056 |
| TM2D3_2 | 0.083 |
| TMEM52 | 0.0074 |
| TMEM62 | 0.0205 |
| TNFRSF18_1 | 0.2618 |
| TNNT2_1 | 0.0032 |
| TOMM20L | 0.0376 |
| TPM2_2 | 0.1788 |
| TRIM58 | 0.1098 |
| UBR7_1 | 0.0567 |
| UBR7_2 | 0.1156 |
| WARS_2 | 0.1603 |
| XBP1_2 | 0.1325 |
| XRN2_1 | 0.0516 |
| YARS2 | 0.0011 |
| ZNF75D_2 | 0.1494 |
| ZSWIM4_2 | 0.1602 |
| figo_numeric | 0.0217 |
| hist_rev_SBOT | 0.0535 |
| surg_outcome | 0.007 |

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method for treating a patient suffering from ovarian cancer following removal of a tumor, the method comprising:
determining whether the patient is predicted to benefit from the administration of bevacizumab, wherein such determination comprises:
determining the patient's gene expression level of microfibril associated protein 2 (MFAP2);
determining the patient's gene expression level of vascular endothelial growth factor A (VEGFA);
determining the size of the tumor tissue remaining post-removal of the tumor;
calculating a recurrence score as follows:
recurrence score=−3.5 surg_outcome+0.23×MFAP2+ 0.19×VEGFA/bevacizumab−0.15×MFAP2/bevacizumab,
wherein surg_outcome is −1 if the surgical outcome was suboptimal; 0 if the surgical outcome was optimal but tumor tissue smaller than 1 cm remained; or +1 if the surgical outcome was optimal and no visible macroscopic tumor tissue remained,
wherein MFAP2=gene expression level of MFAP2, MFAP2/bevacizumab=interaction effect between MFAP2 and bevacizumab, and
VEGFA/bevacizumab=interaction effect between VEGFA and bevacizumab;
calculating the patient's risk of recurrence at time t ($\lambda(t)$) wherein $$\lambda(t)=\lambda_0(t)e^{recurrence\_score}$$

wherein $\lambda_0(t)$ is the baseline hazard function estimated with a non-parametric strategy;
and
administering bevacizumab to a patient having a lower risk of recurrence with administration of bevacizumab than the risk of recurrence score without administration of bevacizumab.

2. The method of claim 1, wherein determining whether the patient is predicted to benefit from the administration of bevacizumab comprises determining whether the patient is predicted to benefit from the administration of bevacizumab in addition to the administration of platinum-based chemotherapy.

3. The method of claim 1, wherein determining whether the patient is predicted to benefit from the administration of bevacizumab further comprises at least one of:
determining the patient's International Federation of Gynecology and Obstetrics (FIGO) stage; or
determining the patient's Eastern Cooperative Oncology Group (ECOG) performance status.

4. The method of claim 3 wherein
a gene expression level of MFAP greater than a threshold gene expression level indicates a decreased likelihood of benefit from platinum-based chemotherapy, wherein the threshold gene expression level is selected based on a clinical outcome;
a gene expression level of VEGFA greater than a threshold gene expression level indicates an increased likelihood of benefit from the administration of platinum-based chemotherapy, wherein the threshold gene expression level is selected based on a clinical outcome;
a FIGO stage greater than 1 indicates a decreased likelihood of benefit from the administration of bevacizumab,
an ECOG performance status greater than 0 indicates an increased likelihood of benefit from the administration of bevacizumab, and
a tumor size smaller than 1 cm indicates an increased likelihood of benefit from the administration of bevacizumab.

5. The method of claim 1, wherein determining whether the patient is predicted to benefit from the administration of bevacizumab further comprises determining the patient's predicted progression-free survival time with the administration of a platinum-based chemotherapy without bevacizumab.

6. The method of claim 5, wherein determining whether the patient is predicted to benefit from a platinum-based chemotherapy without bevacizumab comprises:
determining the patient's gene expression level of microfibril associated protein 2 (MFAP2);
determining the patient's gene expression level of vascular endothelial growth factor A (VEGFA);
determining the patient's International Federation of Gynecology and Obstetrics (FIGO) stage;
determining the patient's Eastern Cooperative Oncology Group (ECOG) performance status; and
determining the size of the tumor tissue remaining post-removal of the tumor.

7. The method of claim 6, wherein
a gene expression level of MFAP greater than a threshold gene expression level indicates a decreased likelihood of benefit from platinum-based chemotherapy, wherein the threshold gene expression level is selected based on a clinical outcome;
a gene expression level of VEGFA greater than a threshold gene expression level indicates an increased likelihood of benefit from the administration of platinum-based chemotherapy, wherein the threshold gene expression level is selected based on a clinical outcome;
a FIGO stage greater than 1 indicates a decreased likelihood of benefit from platinum-based chemotherapy,
an ECOG performance status greater than 0 indicates a decreased likelihood of benefit from platinum-based chemotherapy, and
a tumor size smaller than 1 cm indicates an increased likelihood of benefit from platinum-based chemotherapy.

8. The method of claim 5, wherein determining whether the patient is predicted to benefit from the administration of bevacizumab further comprises determining if the patient's predicted progression-free survival time with the administration of a platinum-based chemotherapy and bevacizumab is greater than the patient's predicted progression-free survival time with the administration of a platinum-based chemotherapy without bevacizumab.

9. The method of claim 1, wherein determining whether the patient is predicted to benefit from the administration of bevacizumab comprises defining a benefit threshold.

10. The method of claim 1, wherein determining whether the patient is predicted to benefit from the administration of bevacizumab comprises applying a Cox model.

11. The method of claim 1, wherein the method comprises administering platinum-based chemotherapy.

12. The method of claim 1, wherein the tumor comprises a primary tumor or a secondary tumor.

13. The method of claim 1, further comprising:
receiving an identified set of biomarkers determined based on a set of predetermined data comprising clinical data, gene expression data, or both, wherein the identified set of biomarkers comprises at least MFAP2 and VEGFA;
identifying other sets of biomarkers based on the identified set of biomarkers and remaining data comprising the set of predetermined data excluding the identified set of biomarkers; and
generating a signature for each set of biomarkers to predict an outcome for a patient having ovarian cancer,
wherein determining whether the patient is predicted to benefit from the administration of bevacizumab is based on an ensemble prediction using a plurality of signatures and patient test data comprising clinical data, gene expression data, or both.

14. The method of claim 3, wherein the recurrence score is calculated as follows:

$$\text{recurrence\_score} = 0.31 \times \text{figo\_numeric} - 0.35 \times \text{surg\_outcome} + 0.23 \times \text{MFAP2} + 0.48 \times \text{ECOG} + 0.19 \times \text{VEGFA/Bevacizumab} - 0.15 \times \text{MFAP2/Bevacizumab} - 0.44 \times \text{ECOG/Bevacizumab}$$

wherein figo_numeric=FIGO stage coded as integers,
wherein surg_outcome is −1 if the surgical outcome was suboptimal; 0 if the surgical outcome was optimal but tumor tissue smaller than 1 cm remained; or +1 if the surgical outcome was optimal and no visible macroscopic tumor tissue remained;
wherein MFAP2=gene expression level of MFAP2;
wherein ECOG=ECOG performance status;
wherein VEGFA/Bevacizumab=interaction effects between VEGFA and bevacizumab;
wherein MFAP2/Bevacizumab=interaction effects between MFAP2 and bevacizumab; and
wherein ECOG/Bevacizumab=interaction effects between ECOG and bevacizumab.

15. The method of claim 3, wherein the method further comprises computing the patient's risk of recurrence at time t if the patient receives platinum-based therapy.

16. The method of claim 3, wherein the method further comprises computing the patient's risk of recurrence at time t if the patient receives bevacizumab.

17. The method of claim 16, wherein the method comprises calculating the benefit of the patient receiving bevacizumab and platinum-based therapy versus platinum-based therapy without bevacizumab.

18. The method of claim 3, wherein the method further comprises administering platinum-based therapy.

* * * * *